(12) United States Patent
Lander et al.

(10) Patent No.: US 11,324,719 B2
(45) Date of Patent: May 10, 2022

(54) SMALL MOLECULE AGONISTS AND ANTAGONISTS OF NR2F6 ACTIVITY IN HUMANS

(71) Applicant: KCL THERAPEUTICS, INC, La Mesa, CA (US)

(72) Inventors: Harry M. Lander, La Mesa, CA (US); David R. Koos, La Mesa, CA (US)

(73) Assignee: KCL Therapeutics, Inc., La Mesa, CA (US)

( * ) Notice: Subject to any disclaimer, the term of this patent is extended or adjusted under 35 U.S.C. 154(b) by 0 days.

(21) Appl. No.: 15/820,324

(22) Filed: Nov. 21, 2017

(65) Prior Publication Data

US 2018/0214413 A1    Aug. 2, 2018

Related U.S. Application Data

(63) Continuation-in-part of application No. 15/652,967, filed on Jul. 18, 2017, now abandoned.

(60) Provisional application No. 62/363,588, filed on Jul. 18, 2016.

(51) Int. Cl.

| | |
|---|---|
| *C07D 311/08* | (2006.01) |
| *C07D 311/12* | (2006.01) |
| *A61K 31/366* | (2006.01) |
| *A61K 31/4706* | (2006.01) |
| *A61K 31/506* | (2006.01) |
| *A61P 35/00* | (2006.01) |
| *A61K 31/4245* | (2006.01) |
| *A61K 31/496* | (2006.01) |
| *A61K 45/06* | (2006.01) |
| *A61K 31/5377* | (2006.01) |
| *A61P 37/06* | (2006.01) |
| *A61K 35/17* | (2015.01) |

(52) U.S. Cl.
CPC ........ *A61K 31/366* (2013.01); *A61K 31/4245* (2013.01); *A61K 31/4706* (2013.01); *A61K 31/496* (2013.01); *A61K 31/506* (2013.01); *A61K 31/5377* (2013.01); *A61K 35/17* (2013.01); *A61K 45/06* (2013.01); *A61P 35/00* (2018.01); *A61P 37/06* (2018.01); *C07D 311/08* (2013.01); *C07D 311/12* (2013.01)

(58) Field of Classification Search
CPC .............................. C07D 311/08; C07D 311/12
See application file for complete search history.

(56) References Cited

U.S. PATENT DOCUMENTS

| | | | |
|---|---|---|---|
| 2014/0296232 A1* | 10/2014 | Hung ................... | A61K 31/453 514/233.5 |
| 2019/0054118 A1* | 2/2019 | Lander ................. | A61K 35/17 |

OTHER PUBLICATIONS

Chemical Abstract 904432-60-6, indexed in the Registry file on STN CAS Online, Aug. 25, 2006 (Year: 2006).*
Chemical Abstract 904438-80-8, indexed in the Registry file on STN CAS Online, Aug. 25, 2006 (Year: 2006).*
Dias et al., Tetrahedron Letters, 53(39), 2012, pp. 5235-5237 (Year: 2012).*
Edayadulla et al., Indian Journal of Heterocyclic Chemistry, vol. 22, No. 1, Jul.-Sep. 2012, pp. 1-4. (Year: 2012).*
Sahoo et al., European Journal of Experimental Biology, 2012, 2(4), pp. 899-908. (Year: 2012).*
Merchant et al., Chemistry and Industry, Oct. 4, 1980, 19, pp. 791-792. (Year: 1980).*
Merchant et al., Journal of Heterocyclic Chemistry, 1981, 18(2), pp. 441-442. (Year: 1981).*
Goldfarb, Chemical Abstracts 151:92844, 2009. (Year: 2009).*
PubChem CID 2134374, National Center for Biotechnology Information. "PubChem Compound Summary for CID 2134374" PubChem, https://pubchem.ncbi.nlm.nih.gov/compound/2134374. Accessed May 11, 2021, create date Jul. 14, 2005. (Year: 2005).*
PubChem SID 17515642, National Center for Biotechnology Information. PubChem Substance Record for SID 17515642, MLS000722116, Source: MLSMR. https://pubchem.ncbi.nlm.nih.gov/substance/17515642. Accessed May 11, 2021, deposited Feb. 6, 2007. (Year: 2007).*
PubChem BioAssay AID 775, National Center for Biotechnology Information. PubChem Bioassay Record for AID 775, Screen for Chemicals that Extend Yeast Lifespan, Source: SRMLSC. https://pubchem.ncbi.nlm.nih.gov/bioassay/775. Accessed May 11, 2021, deposited Jul. 12, 2007. (Year: 2007).*
Rowe, Raymond C, Paul J. Sheskey, and Marian E Quinn., Handbook of Pharmaceutical Excipients. London: Pharmaceutical Press, 6th Edition, 2009, pp. 238-240 and 766-770. (Year: 2009).*

* cited by examiner

*Primary Examiner* — Laura L Stockton
(74) *Attorney, Agent, or Firm* — Baumgartner Patent Law; Marc Baumgartner

(57) ABSTRACT

The present technology is directed to modulators of nuclear receptor activity, specifically to the modulation of NR2F6 activity and NR2F6 utilizing compounds, and the immune modulation and modulation of cancer stem cell activity through administration of compounds described herein to humans.

3 Claims, 68 Drawing Sheets

Specification includes a Sequence Listing.

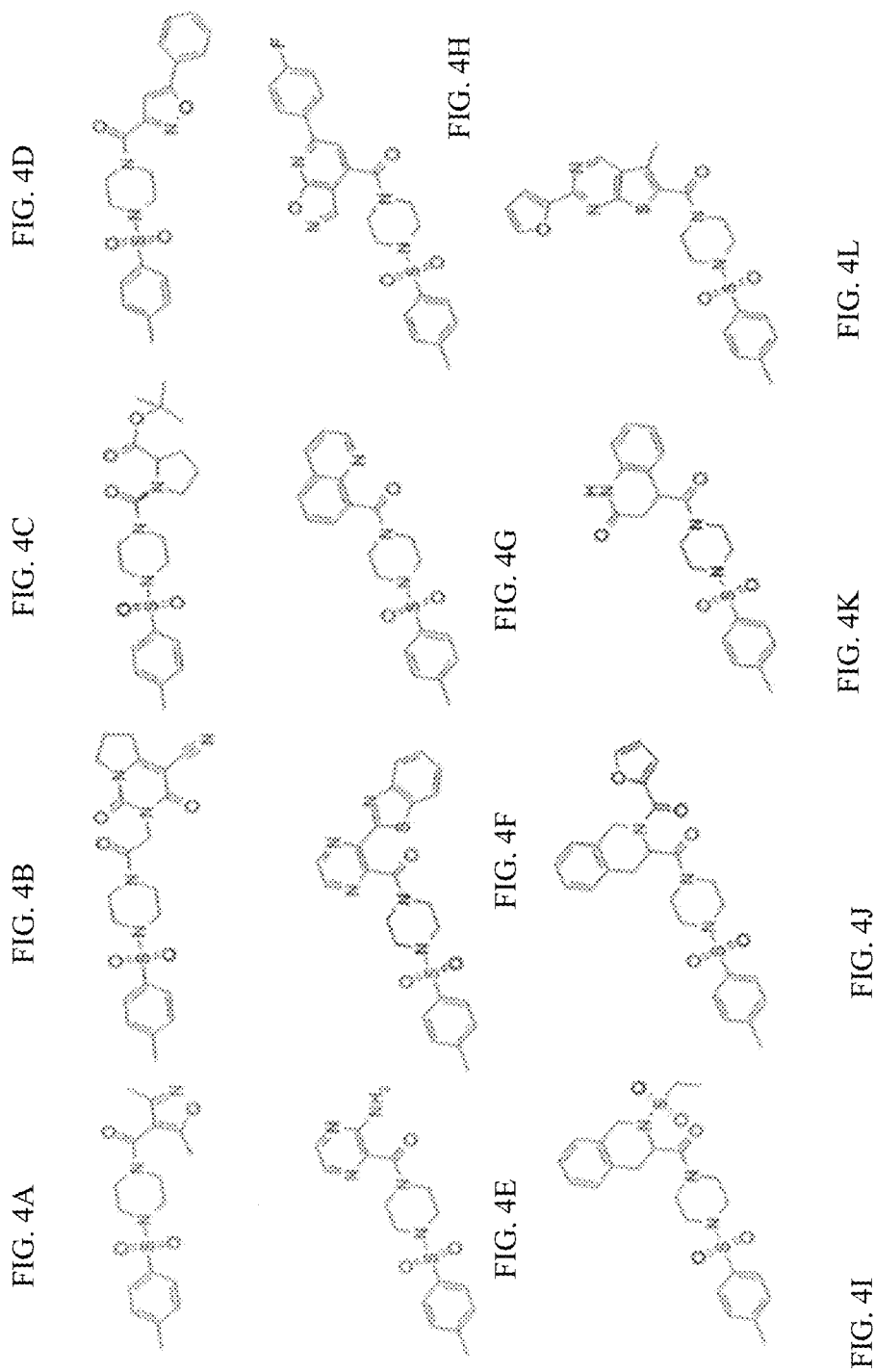

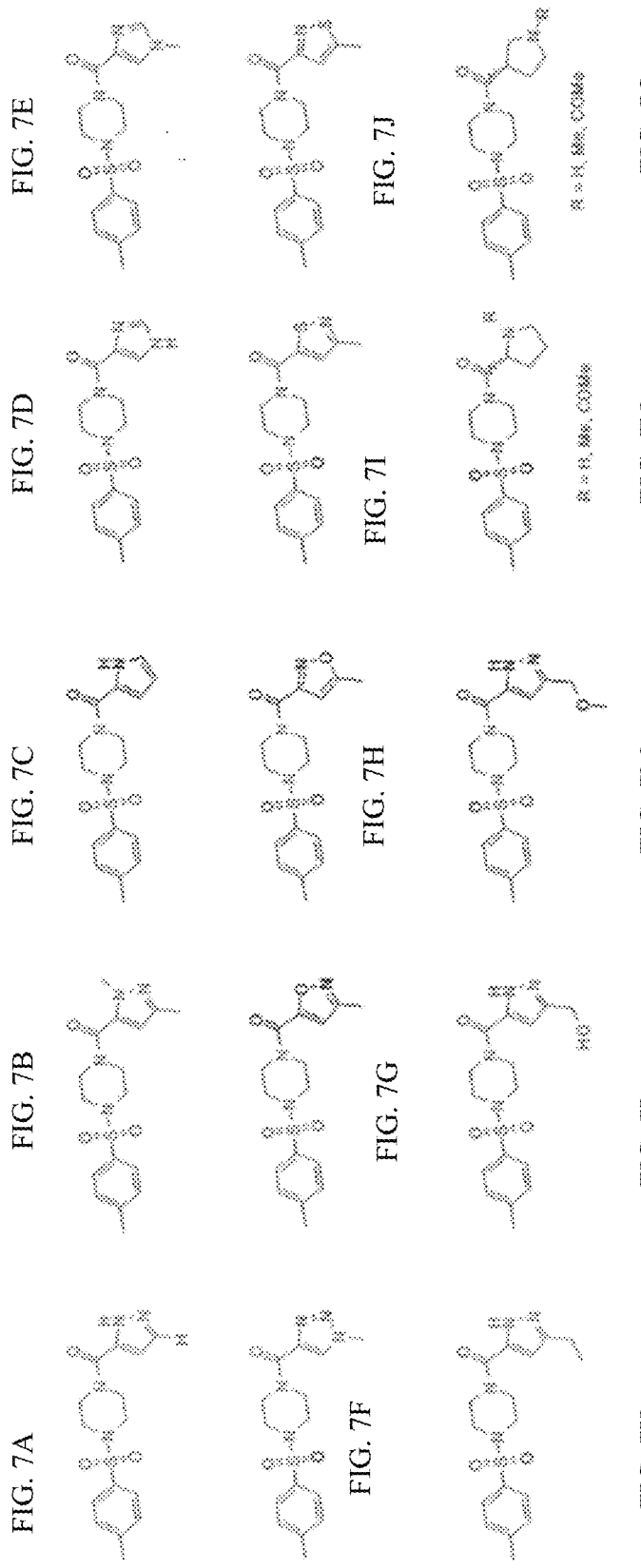

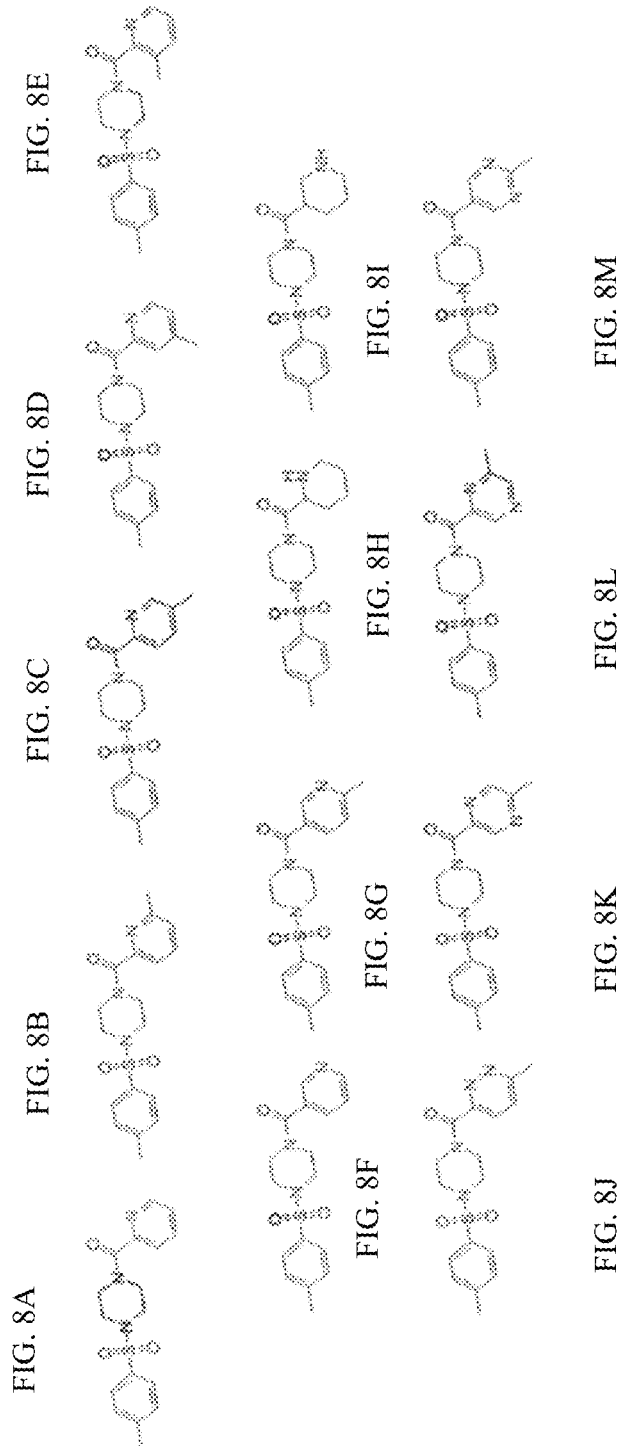

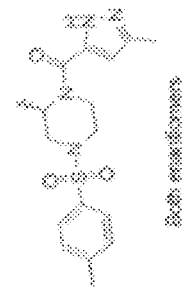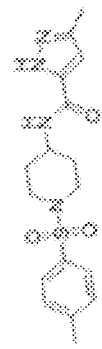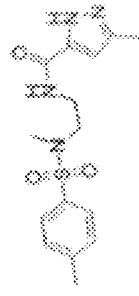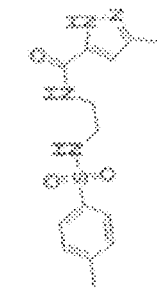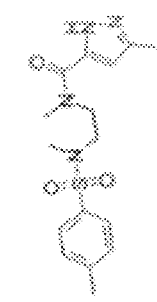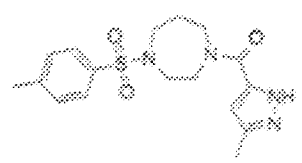
FIG. 9A  FIG. 9B  FIG. 9C  FIG. 9D
FIG. 9E  FIG. 9F
FIG. 9G  FIG. 9H  FIG. 9I  FIG. 9J

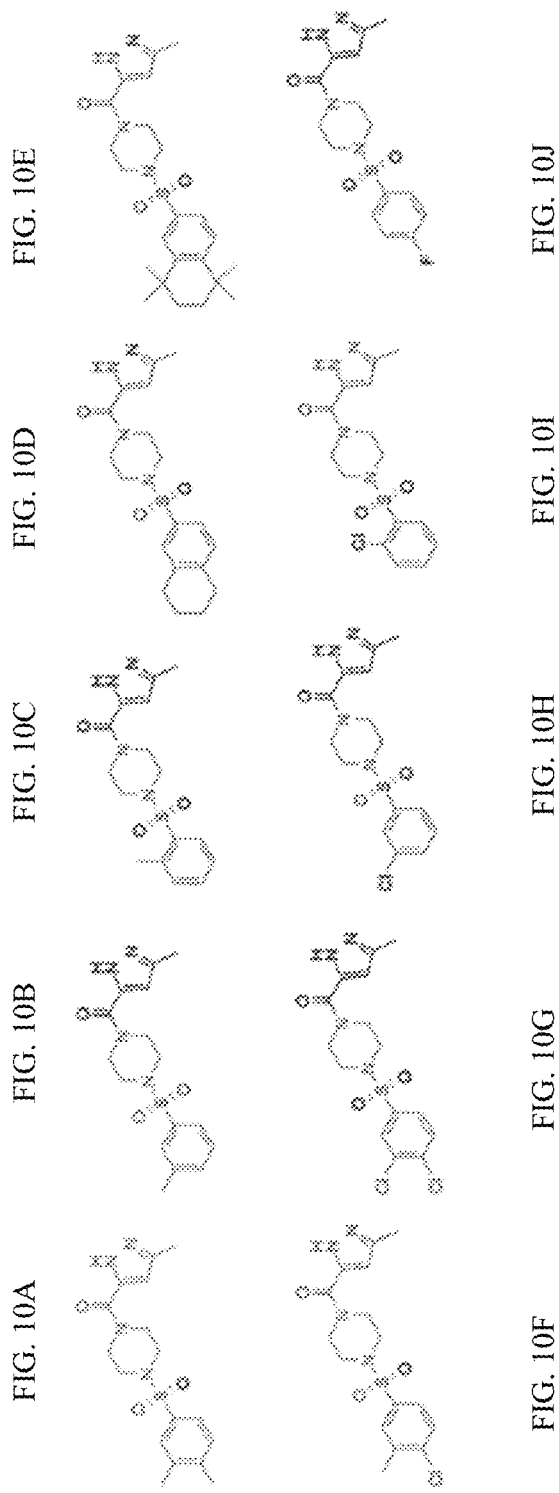

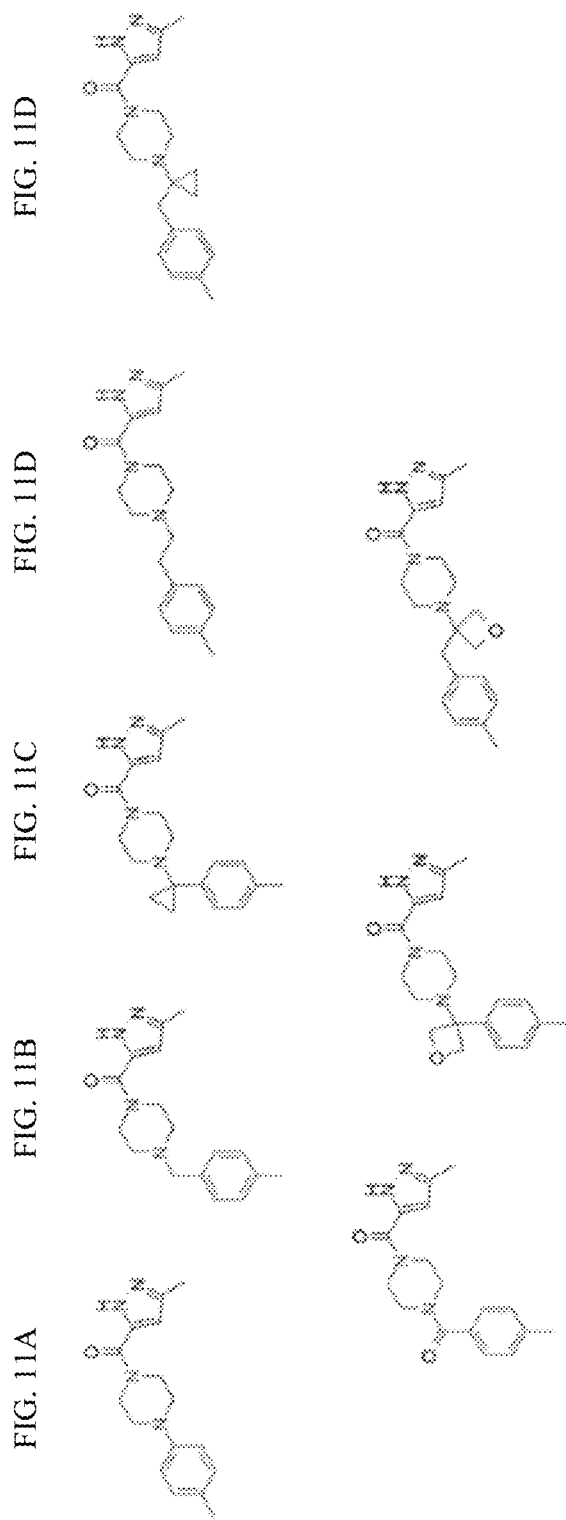

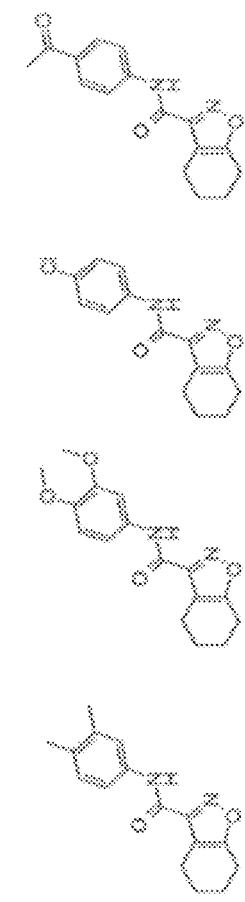
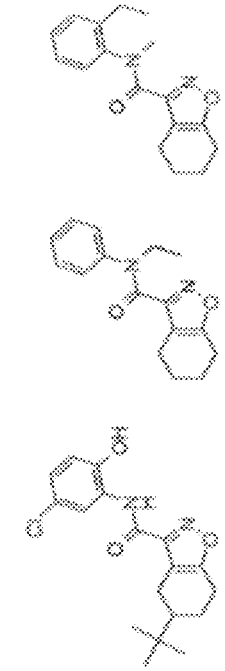
FIG. 13A FIG. 13B FIG. 13C FIG. 13D FIG. 13E FIG. 13F FIG. 13G FIG. 13H

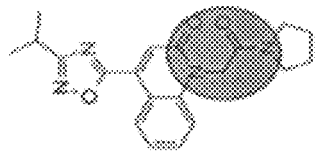
FIG. 15A  FIG. 15B  FIG. 15C
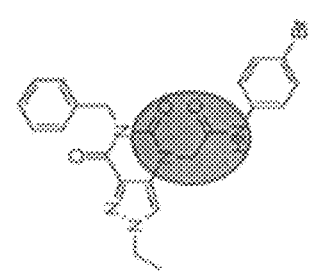
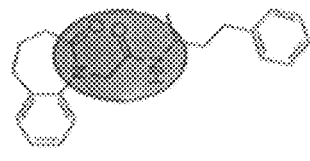
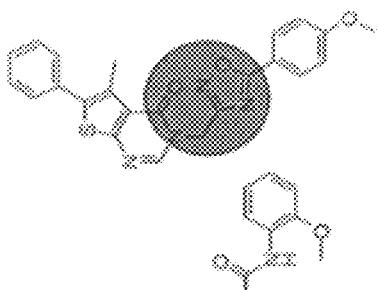
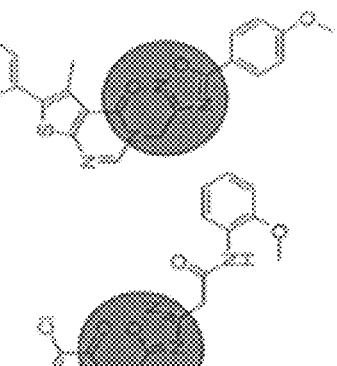
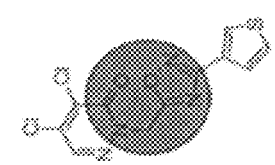
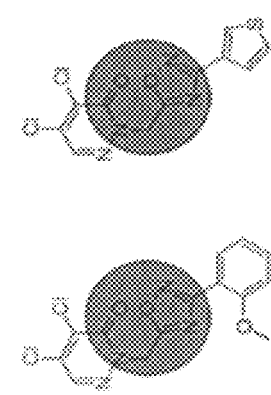
FIG. 15D  FIG. 15E  FIG. 15F  FIG. 15G

Cytokines Release by hPBMC and Cytotox Compound C11

FIG. 17: Analogs of Compound C11

| | EC50 |
|---|---|
| Compound F1 | 3.614e-005 |

Testing of Compound D28

NR2F6 Transient Transfection

LBD Transient Transfection

Compound D28 Activity: LBD Transfection

Compound D28 Toxicity

Compound D28 Cytokine Release Experiment Dogs and Human PBMC

|  | EC50 |
|---|---|
| Compound F1 | 3.614e-005 |

| | EC50 |
|---|---|
| Compound F1 | 2.683e-005 |
| Compound D28 | 1.025e-005 |
| Compound E21 | ~5.317e-005 |

Testing of Compound E21

**Compound E21 Cytokine Release Experiment
Dogs and Human PBMC**

|   | EC50 |
|---|---|
| Compound F1 | 2.683e-005 |
| Compound D28 | 1.025e-005 |
| Compound E21 | ~5.317e-005 |

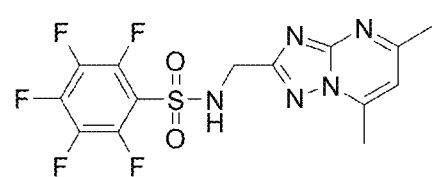
Compound E21
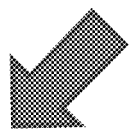 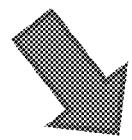
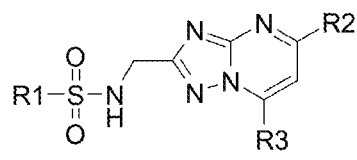 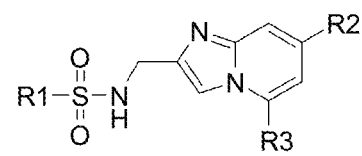
FIG. 36

Testing of Compound F1

NR2F6 Transient Transfection

LBD Transient Transfection

Testing of Compound F1

Testing of Compound F1

Testing of Compound F1

F1 cytokines release inhibition (stimulated by PMA + Ionomycin PBMC)

Testing of Compound F1

Z56 (F1) cytokines release inhibition (stimulated by PMA + Ionomycin hPBMC)

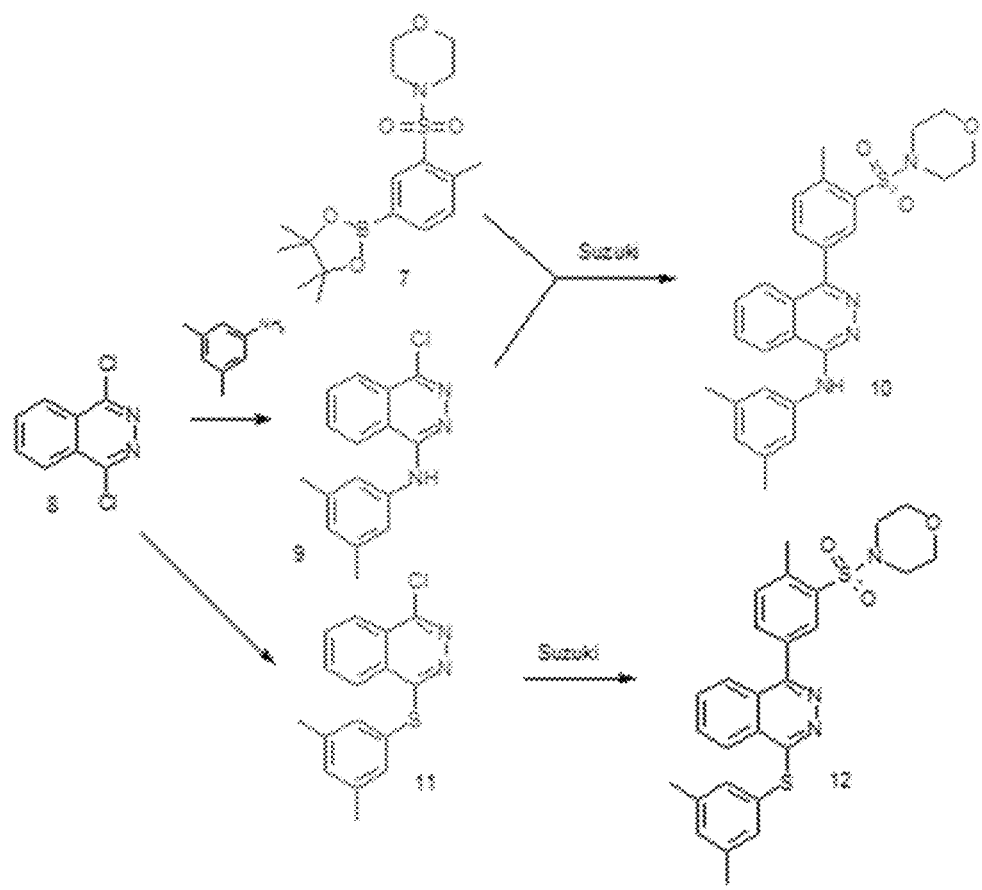
FIG. 43

Compound P1 –
NR2F6 (left) and LBD (right) transient transfection

Compound P1 – Cytokine Release Experiment Dog's PBMC

Compound 1 cytokines release inhibition (simulated by PMA + Ionomycin PMBC)

SEQUENCE LISTING

<160> NUMBER OF SEQ ID NOS: 1

<210> SEQ ID NO 1
<211> LENGTH: 1803
<212> TYPE: DNA
<213> ORGANISM: Homo Sapiens

<400> SEQUENCE: 1

```
gtgcagcccg tgcccccgc gcgccgggc cgaatgcgcg ccgcgtaggg tccccgggc        60 cgagagggt gcccggaggg aagagcgcgg tgggggcgcc ccggccccgc tgccctgggg      120
ctatggccat ggtgaccggc ggctggggcg gccccggcgg cgacacgaac ggcgtggaca      180
aggcgggcgg ctaccgcgc gcggccgagg acgactcggc ctcgccccc ggtgccgcca       240 gcgacgccga gccgggcgac gaggagcggc cggggctgca ggtggactgc gtggtgtgcg      300
gggacaagtc gagcggcaag cattacggtg tcttcacctg cgagggctgc aagagctttt      360
tcaagcgaag catccgccgc aacctcagct acacctgccg gtccaaccgt gactgccaga      420
tcgaccagca ccaccggaac cagtgccagt actgccgtct caagaagtgc ttccgggtgg      480
gcatgaggaa ggaggcggtg cagcgcggcc gcatcccgca ctcgctgcct ggtgccgtgg      540
ccgcctcctc gggcagcccc ccgggctcgg cgctggcggc agtggcgagc ggcggagacc      600
tcttcccggg gcagccggtg tccgaactga tcgcgcagct gctgcgcgct gagccctacc      660
ctgcggcggc cggacgcttc ggcgcagggg gcggcgcggc gggcgcggtg ctgggcatcg      720
acaacgtgtg cgagctggcg gcgcggctgc tcttcagcac cgtggagtgg gcgcgccacg      780 cgccttctt ccccgagctg ccggtggccg accaggtggc gctgctgcgc ctgagctgga      840
gcgagctctt cgtgctgaac gcggcgcagg cggcgctgcc cctgcacacg cgcccgctac      900
tggccgccgc cggcctccac gccgcgccta tggccgccga gcgcgccgtg gctttcatgg      960
accaggtgcg cgccttccag gaggaggtgg acaagctggg ccgcctgcag gtcgactcgg     1020
ccgagtatgg ctgcctcaag gccatcgcgc tttcacgccc gacgcctgtg gcctctcaga     1080
cccggcccac gttgagagcc tgcaggagaa ggcgcaggtg gccctcaccg agtatgtgcg     1140
ggcgcagtac ccgtcccagc cccagcgctt cgggcgcctg ctgctgcggc tccccgccct     1200
gcgcgcggtc cctgcctccc tcatctccca gctgttcttc atgcgcctgg tggggaagac     1260
gcccattgag acactgatca gagacatgct gctgtcgggg agtaccttca actggcccta     1320
cggctcgggc cagtgaccat gacggggcca cgtgtgctgt ggccaggcct gcagacagac     1380
ctcaagggac agggaatgct gaggcctcga ggggcctccc ggggcccagg actctggctt     1440
ctctcctcag acttctattt tttaaagact gtgaaatgtt tgtcttttct gttttttaaa     1500
tgatcatgaa accaaaaaga gactgatcat ccaggcctca gcctcatcct ccccaggacc     1560
```

```
cctgtccagg atggagggtc aatcctagg acagccttgt tcctcagcac ccctagcatg    1620
aacttgtggg atggtggggt tggcttccct ggcatgatgg acaaaggcct ggcgtcggcc    1680 agagggctg ctccagtggg caggggtagc tagcgtgtgc caggcagatc ctctggacac    1740
gtaacctatg tcagacacta catgatgact caaggccaat aataaagaca tttcctacct    1800
gca                                                                  1803
```

SMALL MOLECULE AGONISTS AND ANTAGONISTS OF NR2F6 ACTIVITY IN HUMANS

BACKGROUND

The present technology relates to agonists and antagonists of nuclear receptor activity, specifically to the modulation of NR2F6 activity and NR2F6 utilizing compounds, and the immune modulation and modulation of cancer stem cell activity through administration of compounds described herein.

Many drugs administered to treat diseases or conditions are targeted against differences between a diseased cell and a normal cell. T cells of the immune system are known to recognize and interact with specific molecules through receptors (e.g., a T cell receptor in complex with a CD3 dimer) which, upon recognition or interaction with these molecules, result in the activation of the T cell to perform various immune activities. Innate immune cells are cells of the immune system that are known to be activated by one or more agents (e.g., allergens, chemicals produced upon injury (e.g., opioids and alcohols), polymyxins, crosslinked IgE, crosslinked complement proteins, cytokines produced by T cells or other immune cells (e.g., interferon-γ), DAMPs, or PAMPs) that activate downstream signaling pathway(s) in the innate immune cell and result in the activation of one or more immune activities of the innate immune cell.

Both T cells and innate immune cells play a role in a mammal's immune defense. For example, the immune activities of an innate immune cell can protect a mammal against infectious diseases. The immune activities of a T cell can protect a mammal against, for example, infectious diseases and cancer.

Adoptive cell therapy is a method of treatment that includes harvesting one or more different types of immune cells from a mammal, culturing and/or manipulating the harvested immune cells ex vivo, and administering the cultured and/or manipulated immune cells back to the mammal. The manipulating of a harvested immune cell ex vivo can include introducing a recombinant nucleic acid into the immune cell.

Molecularly targeted therapeutics represent a new approach to discovering anti-cancer drugs. Using this approach, small molecules are designed to inhibit directly the very oncogenetic proteins that are mutated or overexpressed in specific tumor cell types. By targeting specific molecular defects or conditions found within tumor cells, this approach can yield therapies tailored to each tumor's genetic makeup. A complementary strategy involves searching for genotype-selective anti-tumor agents that become lethal to tumor cells only in the presence of specific oncoproteins or only in the absence of specific tumor oppressors. Such genotype-selective compounds might target oncoproteins directly, or target other critical proteins involved in oncoprotein-linked signaling networks.

The immune system is comprised of activatory and inhibitory mechanisms that can allow for control of immune responses and subsequent inhibition of responses after clearance of the immune target. The central event stimulating immune responses is the antigen-specific activation of naive $CD4^+$ T cells subsequent to binding antigen presenting cell MHC containing antigenic peptide. The $CD4^+$ T cell, also known as the "helper T cell," helps to coordinate the activation of the adaptive immune response, playing a role in the stimulation of cytotoxic CD8+ T cells, whose role includes destroying host cells affected by cancer, viruses, and intracellular bacteria, as well as stimulating B cell maturation to eventual plasma cell differentiation. Antibodies can be critical molecules in clearance of extracellular pathogens such as various bacteria and parasites.

Under many circumstances, naive $CD4^+$ T cells require two distinct signals to proliferate and differentiate into the armed effector cells that mediate adaptive immunity. Signal 1 of this two-signal model is antigen-specific and is generated by interaction of the TCR with antigenic peptide presented in context with MHC II antigens. This results in transduction of TCR intracellular signals leading to production of IL-2 and T cell activation. Signal 2 is referred to as a "costimulatory" signal because, while essential, it does not necessarily induce any functional response in T cells.

The best characterized costimulatory signal 2 is generated through the T cell surface molecule CD28. CD28 delivers a costimulatory signal upon interaction with CD80 or CD86 present on B cells, macrophages, or dendritic cells. Activation of the TCR in the presence of costimulatory signals leads to T cell clonal expansion and initiation of effector functions such as IL-2 production.

For cancer, immune inhibitory mechanisms, termed "immune checkpoints," are prematurely activated in order for the tumor to escape immune attack. Two immune checkpoints exist: a) CTLA-4, which sends an inhibitory signal to T cells upon binding CD80 or CD86 on antigen presenting cells; and b) PD-1, which binds to PD-1 ligand on tumor cells, stromal cells, or antigen presenting cells.

CTLA-4 is related to CD28, however instead of activating T cells in a co-stimulatory manner, it leads to inhibition or co-inhibition of T cells.

Nuclear receptor subfamily 2, group F, member 6 (NR2F6), also known as nuclear orphan receptor Ear2, is an orphan member of the nuclear receptor (NR) superfamily of ligand-activated receptors, which exhibit a common modular structure and are involved in various homeostatic functions, but also play a role in oncogenesis and cancer propagation. Specifically, studies have shown that members of the NR family regulate development, reproduction, and metabolism of lipids, drugs and energy. The importance of this family of proteins in metabolic disease is exemplified by NR ligands used in the clinic or under exploratory development for the treatment of diabetes mellitus, dyslipidemia, hypercholesterolemia, or other metabolic abnormalities.

Genetic studies in humans and rodents support the notion that NRs control a wide variety of metabolic processes by regulating the expression of genes encoding key enzymes, transporters and other proteins involved in metabolic homeostasis. Genomic sequence availability has led to the identification of 48 NRs encoded by the human genome and 49 NRs encoded by the mouse genome.

The present disclosure is directed to, in certain embodiments, methods of using small molecule compounds as immune modulators; as well as to compounds, solid forms and compositions thereof that are immune modulators and that exhibit desirable characteristics thereof; as well as to methods of making the compounds, solid forms and composition thereof.

SUMMARY OF THE DISCLOSED TECHNOLOGY

In certain embodiments, the present technology is directed compounds discussed and described herein, which compounds have been found to modulate the immune system. These compounds can include any of the following:

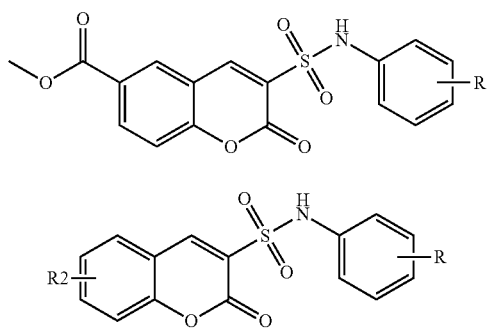
(Ia)
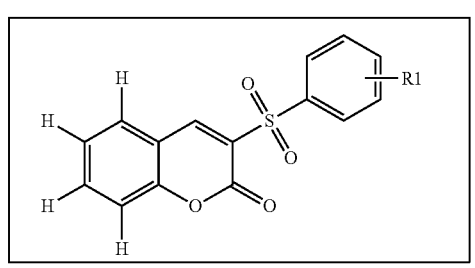
(Ib)
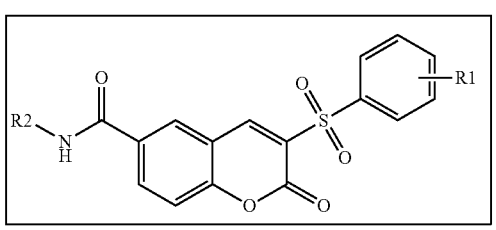
(Ic)
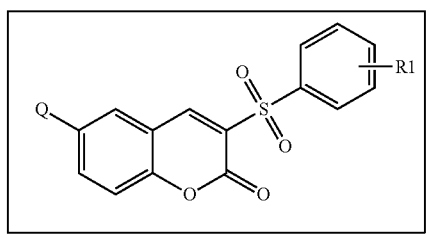
(II)
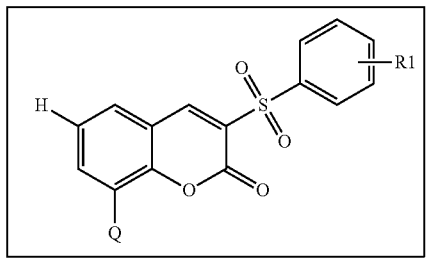
(III)
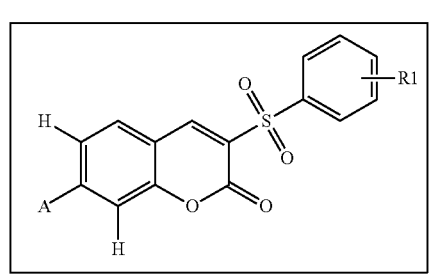
(IV)
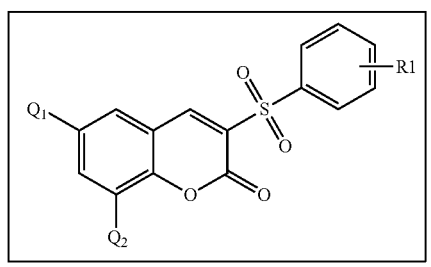
(V)
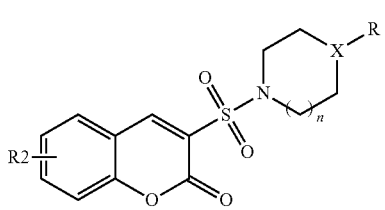
(VI)
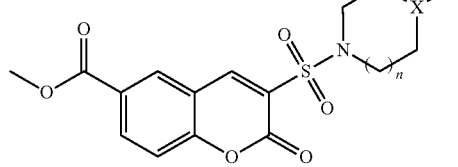
(VII)
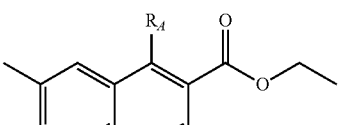
(VIII)
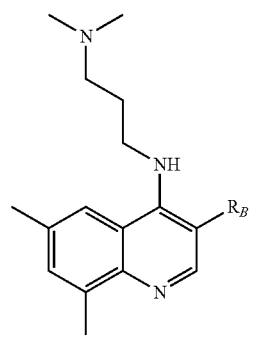
(IX)
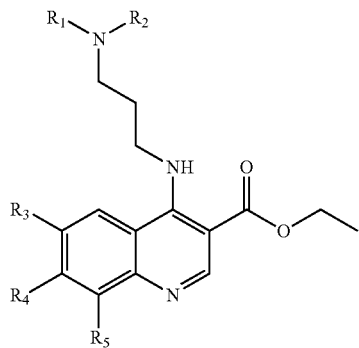
(X)
(XI)

(XII)
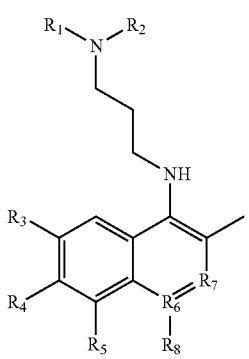

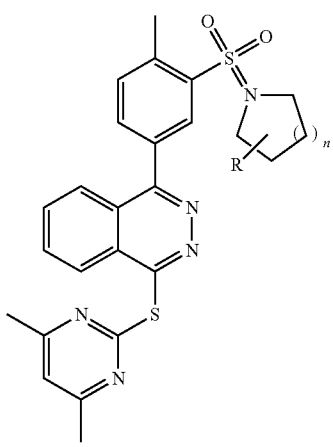

n = 1, 2, 3
R = all available (XIII)

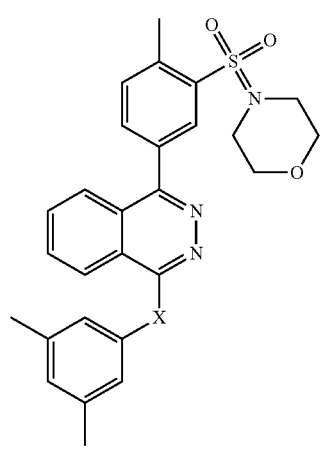

X = any possible (XIV)

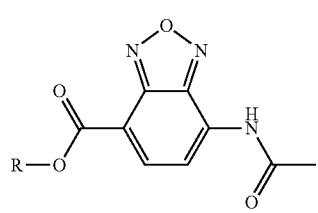

(XV)

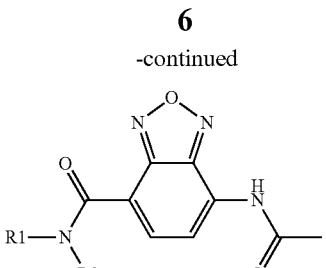

(XVI)

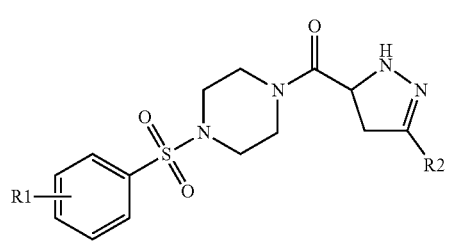

(XVII)

In various embodiments, in any of the above, moieties R, RA, RB, R1-R8, X, Q, Q1, Q2, A can be any of the following: C, H, N, O, S, a halogen, an alkyl group, a substituted alkyl group, a cyclic alkyl group, an aryl group, a substituted aryl group, a heterocyclic group, an ester, an aldehyde, a ketone, a carboxylic acid, an amide, an amine, an ether, a thiol or a nitrile. In various embodiments, in any of the above, n can be an integer 1, 2, 3, 4, 5 or 6.

In various embodiments, any of R, RA, RB, R1-R8, X, Q, Q1, Q2, or A can be any of the following: Me, OMe, Br, N, H, Cl, F or $NO_2$. In certain embodiments, any of R, RA, RB, R1-R8, X, Q, Q1, Q2, or A can be any of the following: 4-Me, 4-OMe, 4-Br, 4-t-Bu, 3,4-di-Me, 4-Cl, 3,4-di-Cl, 3-Cl-4-F, 2-F, 3-Cl, 3-$CH_3$-4-F, a thiazole, an isothiazole or a dithiolane.

In various embodiments, any of R1 and R2 can have the values shown in any of the Figures, for example, FIGS. 1A-1F, FIGS. 3A-3F, FIGS. 4A-4L, FIGS. 5A and 5B, FIGS. 6A-6F, FIGS. 7A-7O, FIGS. 8A-8M, FIGS. 9A-9J, FIGS. 10A-10J or FIGS. 11A-11G.

In certain embodiments, the present technology is directed to a novel compound, any solid form thereof, and any formulation or composition thereof, that is useful as agonists or antagonists of nuclear receptor activity, specifically to the modulation of NR2F6 activity and NR2F6 utilizing compounds.

In certain embodiments, the present technology is directed to methods of modulating the immune system or modulating cancer cell activity using compounds that alter activity of NR2F6.

In certain embodiments, the present technology is directed to methods of "reprogramming" the immune cells in a patient to attack tumors or other invasive cells. Such "reprogramming" can include: (a) extraction of an amount of a patient's cellular material (including, but not limited to: blood, which itself includes blood serum, plasma red blood cells, white blood cells and platelets), (b) isolating specific immune cells from the cellular material; (c) inhibiting or activating the NR2F6 target in the extracted immune cells; and (d) re-administering the immune cells (for example, by injection) to the patient's body.

In certain embodiments, the present technology is directed to methods treating or reducing the effect of an autoimmune response, reaction, disease or disorder, the method comprising any of the steps discussed herein, or activating the NR2F6 target in isolated immune cells by binding them with a compound according to the present technology.

In certain embodiments, the present technology is directed to methods of shrinking a tumor, increasing or decreasing activity of a cell, initiating or inducing an immune response, destroying a cancer cell, reducing the effect of a disease, alleviating a symptom of a disease, as well as methods of inducing a cell in a patient's body to do any of these, the method comprising administering a compound herein to a tumor, contacting a compound herein with a cell, or any other steps discussed herein.

In certain embodiments, the present technology is directed to a pharmaceutical composition comprising a compound described herein, with a pharmaceutically acceptable carrier or excipient.

The methods herein can, in various embodiments, involve humans or non-human mammals as subjects.

BRIEF DESCRIPTION OF THE DRAWINGS

FIGS. 4A-4L show additional compounds that were found to be useful in accordance with the embodiments herein.

FIGS. 7A-7O show additional compounds that were found to be useful in accordance with the embodiments herein.

FIGS. 8A-8M show additional compounds that were found to be useful in accordance with the embodiments herein.

FIGS. 9A-9J show additional compounds that were found to be useful in accordance with the embodiments herein.

FIGS. 10A-10J show additional compounds that were found to be useful in accordance with the embodiments herein.

FIGS. 11A-11G show additional compounds that were found to be useful in accordance with the embodiments herein.

FIG. 13A shows a certain compound that has been found to be effective for the purposes of the present technology. FIGS. 13B-13H show various additional compounds formed from substitution of different moieties.

FIGS. 15A-15G show additional compounds that were found to be useful in accordance with the embodiments herein

FIG. 36 shows additional compounds related to compound E21 that were tested herein.

FIG. 43 shows methods of synthesis of certain compounds found to be useful for the embodiments herein.

DETAILED DESCRIPTION

Figure 1E:
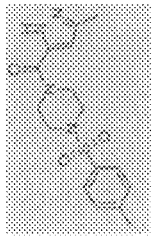
FIGS. 1A-1F show certain compounds that have been found to be effective for the purposes of the present technology.
Figure 1D:
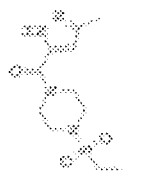
Figure 1C:
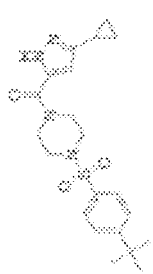
Figure 1F:
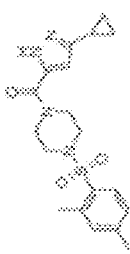
Figure 1B:
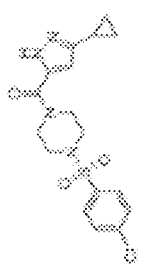
Figure 1A:
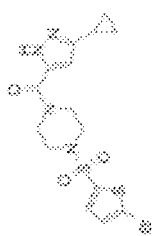
Figure 2B:
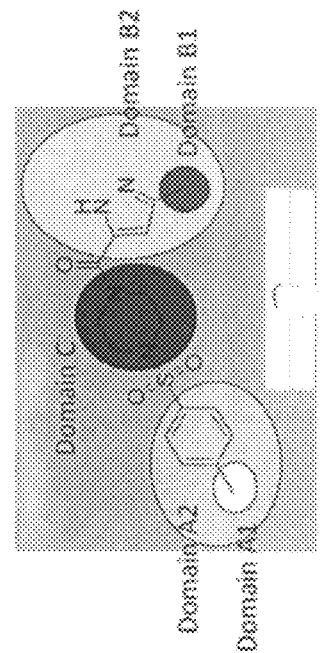
FIG. 2B shows different domains, or portions of a base compound, that were substituted with different moieties to ascertain whether these made a difference in the activity of such compound.
Figure 2A:
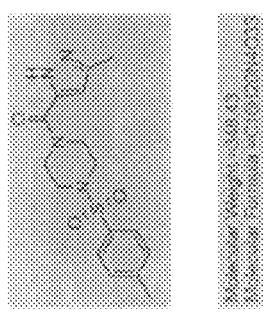
FIG. 2A shows a certain compound that has been found to be effective for the purposes of the present technology.
Figures 3A, 3B, 3C, 3D, 3E, 3F:
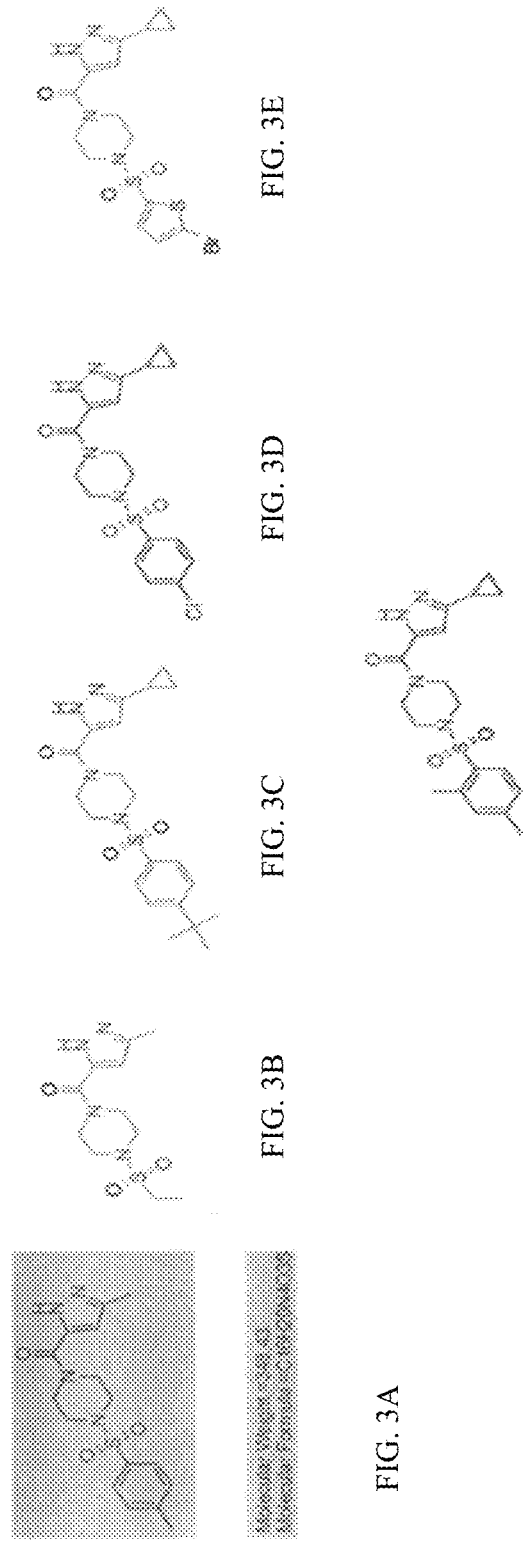
FIG. 3A shows a certain compound that has been found to be effective for the purposes of the present technology.
FIGS. 3B-3F show various additional compounds formed from substitution of different moieties.
Figure 5A:
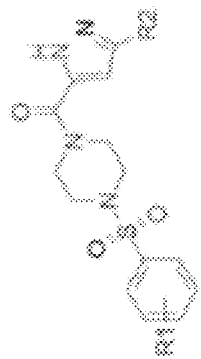
FIGS. 5A and 5B show additional embodiments of compounds, along with (in the case of FIG. 5A) different values of moieties R1 and R2.
Figure 5B:
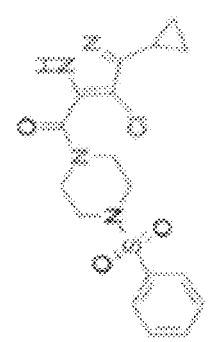
Figure 6A:
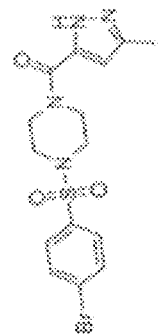
FIGS. 6A-6F show additional compounds that were found to be useful in accordance with the embodiments herein.
Figure 6B:
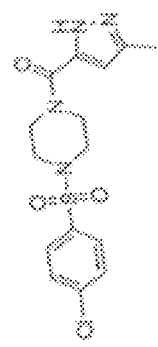
Figure 6C:
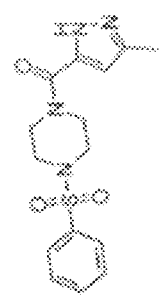
Figure 6D:
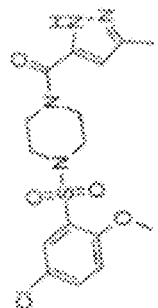
Figure 6E:
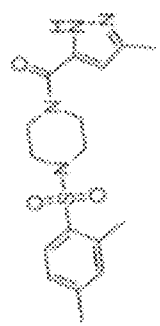
Figure 6F:
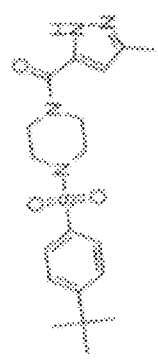
Figure 12:
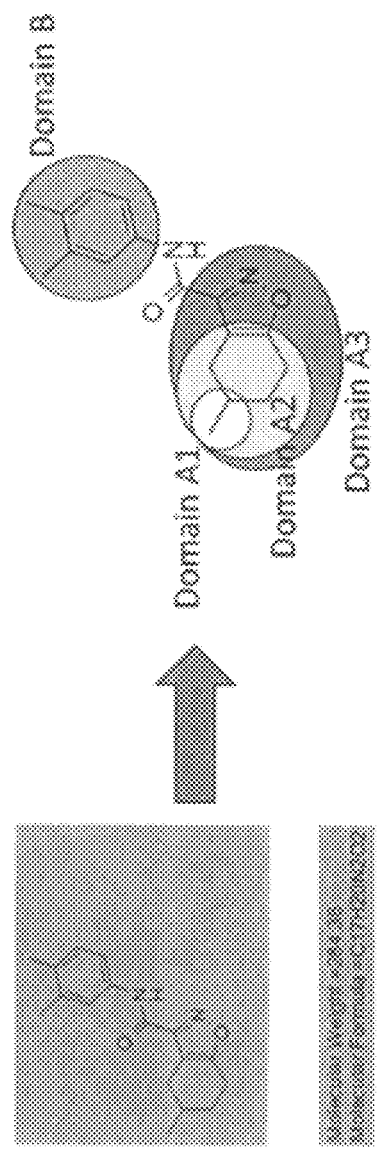
FIG. 12 shows a certain compound that has been found to be effective for the purposes of the present technology; and different domains, or portions of a base compound, that were substituted with different moieties to ascertain whether these made a difference in the activity of such compound.
Figure 14D:
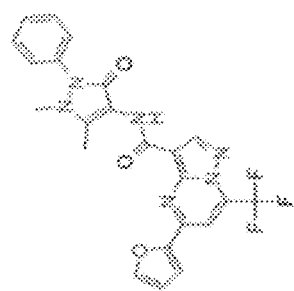
FIGS. 14B-14D show various additional compounds formed from substitution of different moieties.
Figure 14C:
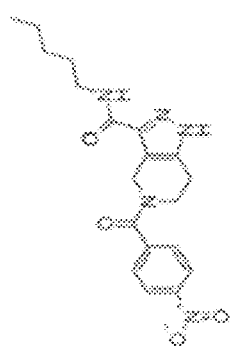
Figure 14B:
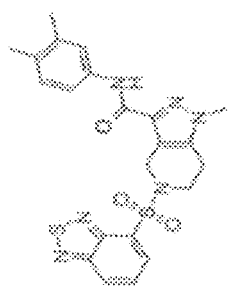
Figure 14A:
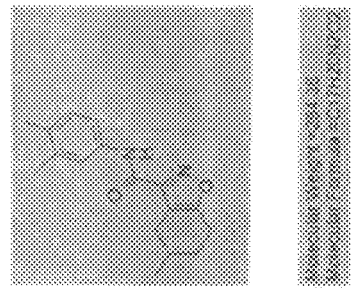
FIG. 14A shows a certain compound that has been found to be effective for the purposes of the present technology.

As used herein, "disease" or "disorder" are used interchangeably and mean a disorder of structure or function in any living thing (including but not limited to a human, animal, or plant), especially one that produces specific signs or symptoms or that affects a specific location and is not simply a direct result of physical injury.

As used herein, "mammal" means a warm-blooded vertebrate animal of a class that is distinguished by the possession of hair or fur, the secretion of milk by females for the nourishment of the young, and (typically) the birth of live young. As used herein, "human" means a person. As used herein, "animal" or "non-human mammal" means any non-human animal, including but not limited to: a canine (e.g., a dog), a feline (e.g., a cat), a rodent, an ungulate (e.g., a cow or ox), an equine (e.g., a horse), or a primate.

As used herein, "modulator" means a molecule that alters the basal activity of NR2F6 either positively (activates it or increases it) or negatively (represses, suppresses or decreases it). "Modulating" means the act of the modulator, either positive or negative. A compound of the technology herein can be, in various embodiments, a modulator of NR2F6, for example, at an effective concentration or in an effective amount, but not be a modulator of any other receptor, or not a modulator at any other amount of NR2F6 or any other receptor. This can provide selectivity of effect of a compound of the technology herein when administered to a patient for treatment of any disease.

In certain embodiments, one diastereomer or one enantiomer of a compound of the present technology can display superior biological activity compared with the other. When required, separation of the diastereomeric mixture or the racemic material can be achieved by HPLC, optionally using a chiral column or by using a resolving agent such as camphonic chloride for the resolution of enantiomers. A chiral compound described herein can also be directly synthesized using a chiral catalyst or a chiral ligand.

In certain embodiments, one deuterated or tritiated compound of the present technology can display superior biological activity compared with one or more others. When required, separation of the material can be achieved by one of ordinary skill in the art.

In certain embodiments, the present technology is directed to methods of modulating the immune system using compounds that alter activity of NR2F6.

In certain embodiments, compounds herein can be utilized for stimulation of NR2F6 activity, alone, or in combination with, for example, PKC activation. In certain embodiments, the compounds herein can be utilized for inhibition of NR2F6 activity, alone or in combination with, for example, anti-PD1, anti-PDL1 or anti-CTLA4 antibodies.

In other embodiments, the methods are directed to the stimulation of NR2F6 for, e.g., induction of immune inhibition, or stimulation of cellular proliferation without significant induction of differentiation. Inhibition of NR2F6 can be desirable in situations where a clinician seeks to augment immune response, or induce cellular differentiation.

In other embodiments, inhibition of NR2F6 expression can be desirable in situations where inhibition of cancer or cancer stem cells is desired.

In certain embodiments, activation of NR2F6 expression can be desirable in situations where inhibition of the immune system is desired, for example, in connection with autoimmune disorders.

The interplay between the activation or deactivation of NRs by different structural classes of endogenous ligands, such as the steroid and thyroid hormones, lipids, vitamins and other biochemicals, is an important part of their function. The 48 NR family members are classified into subgroups based on the identification of endogenous ligands for each receptor. The endocrine receptors include the steroid hormone receptors that bind steroid hormones and the heterodimeric receptors that partner with the retinoid X receptor and bind thyroid hormones, retinoids, and vitamin D.

The identification of specific endogenous ligands for the endocrine receptors has facilitated the design and development of selective receptor modulators (SRMs) that exhibit tissue-specific agonist or antagonist activities and are used for treatment of hormone-/hormone receptor-dependent diseases. Tamoxifen is one of many selective estrogen receptor (ER) modulators used in endocrine therapies for treating ER-positive breast cancer patients.

Adopted orphan receptors are a subtype of NRs that are subdivided into groups based on their ligands. The lipid sensor receptor subtypes and their ligands include retinoid X receptor (9-cis-retinoic acid), peroxisome proliferator-activated receptors (PPARs) (fatty acids), liver X receptor (oxysterols), farnesoid X receptor (bile acids), and pregnane X receptor, which binds cholesterol derivatives.

Retinoid X receptors have been found in various cancer stem cells and methodologies for their utilization, as well as ligands/synthetic ligands targeting them, have been developed. Any of these can be utilized by one of skill in the art to practice the methods of the present technology, which provides compounds useful for modulating the NR2F6 nuclear receptor. Methods of modulating PPARs are also amenable to utilization in the context of the current technology, whose methodologies can, in various embodiments, be adapted for use with the compounds discussed herein for treatment of cancer or immune modulation.

With regard to PPARs, three subtypes of the PPAR family are PPARα, PPARγ, and PPARδ. PPARγ is abundantly expressed in many cell types, where it regulates lipid metabolism, glucose homeostasis, tumor progression, and inflammation. Polyunsaturated fatty acids, eicosanoids, prostaglandins, and linoleic acid have been identified as endogenous ligands for PPARγ. The thiazolidinedione class of compounds function as high-affinity synthetic agonists for PPARγ subsequent to exposure to specific ligands. PPARγ forms a heterodimer complex with retinoid X receptor, which then mediates the target gene expression. In terms of immune modulation, in certain embodiments, NR2F6 specific compounds can be substituted for those described for PPAR.

The enigmatic orphan receptor subtype can include the constitutive androstane receptor (androstane and many drugs or xenobiotics), hepatocyte nuclear factor-4, and steroidogenic factor-1/liver receptor homolog 1 (LRH-1) (phospholipids), retinoid acid-related orphan receptor (cholesterol and retinoic acids), and estrogen-related receptor (estrogens). These can be useful in methods of performing immunotherapy that include NR2F6 modulators.

The orphan receptors are the third class of NRs. The crystal structure of the ligand-binding domain of the orphan receptor Nurr1 (NR4A2) shows that several hydrophobic residues protrude into the ligand-binding pocket, and a typical coactivator-binding site is lacking, suggesting that some orphan receptors may not bind ligands.

Like other NR classes, the orphan receptors play important roles in cellular homeostasis and diseases including cancer, and several recent reports document the expression and potential functions of orphan receptors in different tumors and cancer cell lines. Breast tumors are routinely classified as $ER^+$ or ER, and expression of ER has prognostic significance that influences selection of therapeutic regimens. However, analysis of $ER^+$ and $ER^-$ tumors for expression (mRNA) of all 48 NRs also demonstrated the important prognostic significance of several orphan receptors. The NR4A (Nur77/TR3, Nurr1, and Nor 1) and NR2F6 [v-erbA-related protein (EAR2)] receptors are uniquely overexpressed in ($ER^+$ and $ER^-$ combined) tumors. Moreover, Nur77, EAR2, and chicken ovalbumin upstream promoter transcription factor II (COUP-TFII) are among a limited group of NRs that are prognostic for breast cancer classification and histologic grade, and COUP-TFII expression was a positive prognostic factor for tamoxifen-treated $ER^+$ breast cancer patients.

Examination of lung tumor and nontumor tissue indicated highly variable NR expression; however, gene combinations and individual receptors, such as the orphan receptor small heterodimer partner (SHP, NR0B2), predicted enhanced survival for early-stage lung cancer patients. Moreover, expression of Nur77 in normal lung epithelium from patients has been shown to be an indicator for good prognosis.

NR profiling of the NCI60 cancer cell panel demonstrated that relative expression levels of some orphan receptors also correlated with drug sensitivity. For example, cancer cell sensitivity to microtubule-disrupting drugs has been found to be enhanced in cells expressing low levels of NR2F6 and COUP-TFII, whereas high levels of the orphan receptor tailless (TLX, NR2E1) correlated with sensitivity to 9-fluoroprednisolone.

As used herein, the term "NR2F6" means "nuclear receptor subfamily 2, group F, member 6" or "Ear2." Nuclear receptors are transcription factors that regulate the expression of specific target genes, thereby orchestrating a wide array of cellular processes including cellular activation, development and disease progression. The nuclear receptor super-family includes receptors that bind to hormones and orphan receptors with yet undefined endogenous ligands. As discussed in the present disclosure, NR2F6 can be a target in cancer immunotherapy or autoimmune suppression.

The COUP-TF orphan receptors are preferentially expressed in the central nervous system and organs that depend on the interaction between mesenchyme and epithelial layers. The three mammalian COUP-TF family members are NR2F1/Ear3, NR2F2/Arp1 and NR2F6. The established target genes of said COUP-TF family members are apolipoproteins and retinoic acid-, peroxisome-, oxytocin-, estrogen- and vitamin D receptors. By yeast 1-hybrid screen and in vitro assays with recombinant NR2F6, it was found that the TGACCT direct-repeat motif is the DNA binding sequence of NR2F6, and that overexpression of NR2F6 induces repression of the renin gene transcription in a DNA-binding-specific manner. Wild type human/animal NR2F6 is known to possess the following nucleotide sequence: 1 gtgcagcccg tgcccccgc gcgccgggc cgaatgcgcg ccgcgtaggg tcccccgggc 61 cgagagggt gcccggaggg aagagcgcgg tgggggcgcc ccggcccgc tgcctgggg 121 ctatggccat ggtgaccggc ggctggggcg gccccggcgg cgacacgaac ggcgtggaca 181 aggcgggcgg ctacccgcgc gcggccgagg acgactcggc ctcgcccccc ggtgccgcca 241 gcgacgccga gccgggcgac gaggagcggc cggggctgca ggtggactgc gtggtgtgcg 301 gggacaagtc gagcggcaag cattacggtg tcttcacctg cgagggctgc aagagctttt 361 tcaagcgaag catccgccgc aacctcagct acacctgccg gtccaaccgt gactgccaga 421 tcgaccagca ccaccggaac cagtgccagt actgccgtct caagaagtgc ttccggtgg 481 gcatgaggaa ggaggcggtg cagcgcggcc gcatcccgca ctcgctgcct ggtgccgtgg 541 ccgcctcctc gggcagcccc ccgggctcgg cgctggcggc agtggcgagc ggcggagacc 601 tcttcccggg gcagccggtg tccgaactga tcgcgcagct gctgcgcgct gagccctacc 661 ctgcggcggc cggacgcttc ggcgcagggg gcggcgcggc gggcgcggtg ctgggcatcg 721 acaacgtgtg cgagctggcg gcgcggctgc tcttcagcac cgtggagtgg gcgcgccacg 781 cgcccttctt ccccgagctg ccggtggccg accaggtggc gctgctgcgc ctgagctgga 841 gcgagctctt cgtgctgaac gcggcgcagg cggcgctgcc cctgcacacg gcgccgctac 901 tggccgccgc cggcctccac gccgcgccta tggccgccga gcgcgccgtg gctttcatgg 961 accaggtgcg cgccttccag gaggaggtgg acaagctggg ccgcctgcag gtcgactcgg 1021 ccgagtatgg ctgcctcaag gccatcgcgc tttcacgcc cgacgcctgt ggcctctcag 1081 acccggccca cgttgagagc ctgcaggaga aggcgcaggt ggccctcacc gagtatgtgc 1141 gggcgcagta cccgtcccag ccccagcgct tcgggcgcct gctgctgcgg ctccccgccc 1201 tgcgcgcggt ccctgcctcc ctcatctccc agctgttctt catgcgcctg gtggggaaga 1261 cgcccattga gacactgatc agagacatgc tgctgtcggg gagtaccttc aactggccct 1321 acggctcggg ccagtgacca tgacggggcc acgtgtgctg tggccaggcc tgcagacaga 1381 cctcaaggga cagggaatgc tgaggcctcg aggggcctcc cggggcccag gactctggct 1441 tctctcctca gacttctatt ttttaaagac tgtgaaatgt ttgtcttttc tgttttttaa 1501 atgatcatga aaccaaaaag agactgatca tccaggcctc agcctcatcc tccccaggac 1561 ccctgtccag gatggagggt ccaatcctag gacagccttg ttcctcagca cccctagcat 1621 gaacttgtgg gatggtgggg ttggcttccc tggcatgatg 20
gacaaaggcc tggcgtcggc 1681 cagaggggct gctccagtgg gcaggggtag ctagcgtgtg ccaggcagat cctctggaca 1741 cgtaacctat gtcagacact acatgatgac tcaaggccaa taataaagac atttcctacc 1801 tgca, which corresponds to the following amino acid sequence: MAMVTGGWGGPGGDTNGVDKAGGY- 25 PRAAEDDSASPPGAASDAEPGD EERPGLQVDCVVCGDKSSGKHYGVFTCEGCK- SFFKRSIRRNLSYTC RSNRDCQIDQHHRNQCQYCRLKKCFRVGMRKEA- VQRGRIPHSLPGA VAASSGSPPGSA- 30 LAAVASGGDLFPGQPVSELIAQLLRAEPYPAAAG RFGAGGGAAGAVLGIDNVCELAARLLFSTVEWAR- HAPFFPELPVAD QVALLRLSWSELFVL- NAAQAALPLHTAPLLAAAGLHAAPMAAERAV AFMDQVRAFQEQVDKLGRLQVDSAEYGCLKA- IALFTPDACGLSDPA HVESLQEKAQVALTEYVRAQYPSQPQRFGRLLLRL- PALRAVPASLI SQLFFMRLVGKTPIETLIRDMLLSG- STFNWPYGSGQ (SEQ ID NO: 1).

Accordingly, in certain embodiments the present technology is directed to compounds that bind to a portion or all of an NR2F6 molecule; or any molecule that is, in various embodiments, at least 60%, at least 70%, at least 80%, at least 90%, at least 95%, at least 96%, at least 97%, at least 98% or at least 99% identical to the amino acid sequence of NR2F6.

As used herein, the terms "agonist" or "activator" are used interchangeably and mean a compound or substance capable of fully or partially stimulating the physiologic activity of one or more specific receptors. In the context of the present disclosure, an agonist can therefore stimulate the physiological activity of a receptor such as NR2F6 upon binding of said compound substance to said receptor. As further discussed herein, an "agonist" or "activator" can be used to "activate," "stimulate" or "increase activity" of a cell.

In certain embodiments, binding of an "agonist" or "activator" to a given receptor, e.g., NR2F6, can mimic the action of an endogenous ligand binding to said receptor. As used herein, accordingly, the term "agonist" also encompasses partial agonists or co-agonists or co-activators. In addition, however, an "agonist" or "activator" of NR2F6 as used herein can also be capable of stimulating the function of a given receptor, such as NR2F6, by inducing or enhancing the expression of the nucleic acid molecule encoding for said receptor. Thus, an agonist or activator of NR2F6 can, in certain embodiments, lead to an increased expression level of NR2F6 (e.g., increased level of NR2F6 mRNA, NR2F6 protein) which is reflected in an increased activity of NR2F6. This increased activity can be measured or detected by the methods herein.

Accordingly, an activator of NR2F6 in accordance with the present technology can, in certain embodiments, also encompass transcriptional activators of NR2F6 expression that are capable of enhancing NR2F6 function. As mentioned above, "agonist" includes a partial agonist. "Partial agonists" mean candidate molecules that behave like agonists, but that, even at high concentrations, cannot activate NR2F6 to the same extent as a full agonist. As described below, the increased expression or activity of NR2F6 by an agonist or activator of NR2F6 can lead to decreased activity (or expression) of components of the NR2F6-dependent signaling pathway; in particular the activity of NF-AT and AP-1 can be decreased. NF-AT/AP-1 regulate transcription/expression of further "downstream" components of the NR2F6-dependent signaling pathway, such as IL-2, IL-17 and/or IFN-gamma. A decrease in NF-AT/AP-1 activity can result in a decreased transcription of these "downstream" components (e.g., IL-2, IL-17 and/or IFN-gamma) which in turn leads to a suppression of an immune response.

In certain embodiments, an agonist or activator of NR2F6 can lead to suppression of an immune response. Hence, the use of potent agonists/activators of NR2F6 can lead to a higher expression or activity of NR2F6.

In certain embodiments NR2F6 can be considered its own "agonist" or "activator." For example, in certain embodiments, overexpression of NR2F6 can lead to enhanced NR2F6 activity, thus agonizing NR2F6 function. Accordingly, NR2F6 as defined herein can, in certain embodiments, be used for the treatment of a disease related to an augmented immune response.

For example, NR2F6 can be used in accordance with certain embodiments of the present technology, wherein NR2F6 is any of the following: (a) a polypeptide comprising an amino acid encoded by a nucleic acid molecule having the nucleic acid sequence of NR2F6; (b) a polypeptide having an amino acid sequence of NR2F6; (c) a polypeptide encoded by a nucleic acid molecule encoding a peptide having an NR2F6 amino acid sequence; (d) a polypeptide comprising an amino acid encoded by a nucleic acid molecule hybridizing to the complementary strand of nucleic acid molecules as defined in (a) or (c) and encoding a NR2F6 or a functional fragment thereof; (e) a polypeptide having at least 60% homology to the polypeptide of any one of (a) to (d), whereby said polypeptide is a NR2F6 or a functional fragment thereof; or (f) a polypeptide comprising an amino acid encoded by a nucleic acid molecule being degenerate as a result of the genetic code to the nucleotide sequence of a nucleic acid molecule as defined in (a), (c) and (d). As described herein, the increase of NR2F6 activity can lead to a decreased activity of NF-AT/AP-1 (and other components of the NR2F6-dependent signaling pathway) which in turn can result in a suppressed immune response.

An exemplary transfection of CD4$^+$ T cells with a construct for the overexpression of NR2F6 is also shown in the appended examples. As demonstrated therein, overexpression (about 5-fold increase over normal expression level) can lead to a diminished IL-2 activity/expression and consequently to a reduced IL-2 amount, resulting in a reduced immune response.

Therefore, agonists/activators of NR2F6 are useful in the treatment of diseases where suppression of the immune response is desired (e.g., diseases with an overstimulated immune response, such as allergies and multiple sclerosis). As used herein, the term "overexpression" means that the NR2F6 activity/expression is, in various embodiments, at least 1-fold, at least 2-fold, at least 3-fold, at least 4-fold, at least 5-fold, at least 6-fold, at least 7-fold, at least 8-fold, at least 9-fold, at least 10-fold, or at least 25-fold increased in comparison to a (control) standard value as defined herein, wherein a value of 25 fold expression level or greater over normal can be considered as a maximum overexpression level.

As used herein, "antagonist" or "inhibitor" are used interchangeably and mean a compound or substance capable of fully or partially suppressing or inhibiting the physiologic activity of one or more specific receptors. In the context of the present disclosure, an antagonist can therefore suppress the physiological activity of a receptor upon binding of said compound substance to said receptor but does not activate the receptor and therefore blocks the activity of other agonists. As further discussed herein, an "antagonist" or "inhibitor" can be used to "deactivate," "inhibit," "suppress" or "decrease activity" of a cell.

As used herein, the terms "immune response" or "immune reaction" are used interchangeably and mean the response or reaction of the immune system to an antigen. In the case of an immune response, immune cells are activated in such way that one or more specific functions of said immune cells can be induced. The "immune cells" can include, but are not limited to, B cells, T cells, neutrophils, eosinophils, basophils, mast cells, macrophages and dendritic cells. In certain embodiments, said "specific function(s) of activated immune cells" can include, but are not limited to, secretion of antibodies, presentation of antigen, proliferation of said immune cells, secretion of cytokines such as interleukin-2 (IL-2), interleukin-17 (IL-17), interleukin-18 (IL-18), or interferon gamma (IFNgamma), expression of regulatory-, activation- or adhesion molecules, and the ability to induce apoptosis or cytolysis.

As used herein, the term "antigen" means any substance capable of inducing an immune response. An antigen typically is associated with a foreign substance (i.e. a "non-self antigen"). However, an own body-derived substance (i.e., a "self antigen") can also induce an immune response.

As used herein, accordingly, the term "immune response" also encompasses autoimmune responses or autoimmune reactions. For example, in certain embodiments, the technology herein is directed to a method of treating or reducing the effect of an autoimmune response, reaction, disease or disorder, the method comprising activating the NR2F6 target in isolated immune cells by binding them with a compound according to the present technology.

As used herein, "treating a cancer," "inhibiting cancer" or "reducing cancer growth" are used interchangeably and mean inhibiting or preventing oncogenic activity of cancer cells. Oncogenic activity can comprise stimulating migration, invasion, drug resistance, cell survival, anchorage-independent growth, non-responsiveness to cell death signals, angiogenesis, or combinations thereof of the cancer cells. In various embodiments, agents suitable for use in treating a cancer or reducing the growth rate of a tumor include, but are not limited to, small organic molecules, peptides, proteins, peptidomimetics, nucleic acids, antibodies and combinations thereof. In various embodiments, such agents can be formulated with a pharmaceutically acceptable carrier, and can be administered: intravenously, orally, buccally, sublingually, parenterally, by inhalation, by nasal administration, by insufflation, by topical application, transdermally, by cutaneous injection, or by local administration. An agent can additionally be administered in conjunction with one or more anti-cancer chemotherapeutic agent in an additive or synergistic manner.

As used herein, "cancer," "cancer cell," "tumor" and "tumor cell" are used interchangeably and mean a group of diseases characterized by uncontrolled, abnormal growth of cells (e.g., a neoplasia). These can include solid tumor cancer, liquid tumor cancer and metastatic disease. In some forms of cancer, the cancer cells can spread locally or through the bloodstream and lymphatic system to other parts of the body ("metastatic cancer"). As used herein, "ex vivo activated lymphocytes," "lymphocytes with enhanced anti-tumor activity" and "dendritic cell cytokine induced killers" are used interchangeably and mean composition of cells that have been activated ex vivo and subsequently reintroduced within the context of the current disclosure. Although the word "lymphocyte" is used, this also includes heterogenous cells that have been expanded during the ex vivo culturing process including dendritic cells, NKT cells, gamma delta T cells, and various other innate and adaptive immune cells.

As used herein, "cancer" means any disease caused by uncontrolled division or growth of abnormal cells, and any malignant growth or tumor resultant from such uncontrolled division or growth. As used herein, "cancer" includes all types of cancer or neoplasm or malignant tumors found in animals, including leukemias, carcinomas and sarcomas. Examples of cancers include, but are not limited to: cancer of the brain, skin (including melanoma), breast, cervix, head and neck, kidney, lung, non-small cell lung, mesothelioma, sarcoma, any internal organ (including bladder, stomach, liver, pancreas, uterus, ovary, prostate, colon) and Medulloblastoma.

As used herein, "leukemia" means a broadly progressive, malignant disease of the hematopoietic organs or systems and is generally characterized by a distorted proliferation and development of leukocytes and their precursors in the blood and bone marrow. Leukemia diseases include, but are not limited to: acute nonlymphocytic leukemia, chronic lymphocytic leukemia, acute granulocytic leukemia, chronic granulocytic leukemia, acute promyelocytic leukemia, adult T-cell leukemia, B cell lymphoma, aleukemic leukemia, a leukocythemic leukemia, basophilic leukemia, blast cell leukemia, bovine leukemia, chronic myelocytic leukemia, leukemia cutis, embryonal leukemia, eosinophilic leukemia, Gross' leukemia, Rieder cell leukemia, Schilling's leukemia, stem cell leukemia, subleukemic leukemia, undifferentiated cell leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, chronic myeloid leukemia, myeloid granulocytic leukemia, myelomonocytic leukemia, Naegeli leukemia, plasma cell leukemia, plasmacytic leukemia, and promyelocytic leukemia.

As used herein, the term "carcinoma" means a malignant new growth made up of epithelial cells tending to infiltrate the surrounding tissues, or resist physiological and non-physiological cell death signals and give rise to metastases. Exemplary carcinomas include, but are not limited to: acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrmcous carcinoma, carcinoma villosum, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, and carcinoma scroti.

As used herein, the term, "sarcoma" means a tumor which is made up of a substance like the embryonic connective tissue and is generally composed of closely packed cells embedded in a fibrillar, heterogeneous, or homogeneous substance. Sarcomas include, but are not limited to: chondrosarcoma, fibrosarcoma, lymphosarcoma, melanosarcoma, myxosarcoma, osteosarcoma, endometrial sarcoma, stromal sarcoma, Ewing's sarcoma, fascial sarcoma, fibroblastic sarcoma, giant cell sarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma. Additional exemplary neoplasias include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, lymphomas, thyroid cancer, neuroblastoma, esophageal cancer, genitourinary tract cancer, malignant hypercalcemia, cervical cancer, endometrial cancer, and adrenal cortical cancer.

In some particular embodiments of the present technology, the cancer treated is a melanoma. As used herein, the term "melanoma" means a tumor arising from the melanocytic system of the skin or other organs. Melanomas include, for example, Harding-Passey melanoma, juvenile melanoma, lentigo maligna melanoma, malignant melanoma, acral-lentiginous melanoma, amelanotic melanoma, benign juvenile melanoma, Cloudman's melanoma, S91 melanoma, nodular melanoma subungual melanoma, and superficial spreading melanoma. As used herein, the term "polypeptide" is used interchangeably with "peptide," "altered peptide ligand" and "fluorocarbonated peptides."

As used herein, the term "pharmaceutically acceptable carrier" means any and all solvents, dispersion media, coatings, antibacterial and antifungal agents, isotonic and absorption delaying agents, and the like. Except insofar as any conventional media or agent is incompatible with the active compound, use thereof in the therapeutic compositions is contemplated. Supplementary active compounds can also be incorporated into the compositions herein.

As used herein, the terms "T cell" or "T lymphocyte" are used interchangeably, and mean a cell derived from thymus among lymphocytes involved in an immune response. In various embodiments a T cell includes any of: a CD8-positive T cell (cytotoxic T cell: CTL), a CD4$^+$ T cell (helper T cell), a suppressor T cell, a regulatory T cell such as a controlling T cell, an effector cell, a naive T cell, a memory T cell, an alpha ($\alpha$) beta ($\beta$) T cell expressing TCR $\alpha$ and $\beta$ chains, and a gamma ($\gamma$) delta ($\delta$) T cell expressing TCR $\gamma$ and $\delta$ chains.

In certain embodiments, the T cell includes a precursor cell of a T cell in which differentiation into a T cell is directed. Examples of "cell populations containing T cells" include, in addition to body fluids such as blood (peripheral blood, umbilical blood etc.) and bone marrow fluids, cell populations containing peripheral blood mononuclear cells (PBMC), hematopoietic cells, hematopoietic stem cells, umbilical blood mononuclear cells etc., which have been collected, isolated, purified or induced from the body fluids.

Further, a variety of cell populations containing T cells and derived from hematopoietic cells can be used in connection with the embodiments of the present technology. These cells may have been activated by cytokine such as IL-2 in vivo or ex vivo, and can be collected in any known way, for example, collected from a living body; obtained via ex vivo culture, for example, a T cell population obtained by a method herein; or obtained by freeze preservation.

As used herein, the term "antibody" means both intact molecules as well as fragments thereof that include the antigen-binding site. Whole antibody structure is often given as $H_2L_2$ and refers to the fact that antibodies commonly comprise 2 light (L) amino acid chains and 2 heavy (H) amino acid chains. Both chains have regions capable of interacting with a structurally complementary antigenic target. The regions interacting with the target are referred to as "variable" or "V" regions and are characterized by differences in amino acid sequence from antibodies of different antigenic specificity. The variable regions of either H or L chains contain the amino acid sequences capable of specifically binding to antigenic targets. Within these sequences are smaller sequences dubbed "hypervariable" because of their extreme variability between antibodies of differing specificity. Such hypervariable regions are also referred to as "complementarity determining regions" or "CDR" regions.

These CDR regions account for the basic specificity of the antibody for a particular antigenic determinant structure. The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all antibodies each have 3 CDR regions, each non-contiguous with the others (termed L1, L2, L3, H1, H2, H3) for the respective light (L) and heavy (H) chains.

In various embodiments, the antibodies discussed herein can also be wholly synthetic, wherein the polypeptide chains of the antibodies are synthesized and, possibly, optimized for binding to the polypeptides disclosed herein as being receptors. Such antibodies can be, in various embodiments, chimeric or humanized antibodies, and can be fully tetrameric in structure, or can be dimeric and comprise only a single heavy and a single light chain.

As used herein, the terms "effective amount" or "therapeutically effective amount" are used interchangeably and mean a dosage sufficient to treat, inhibit, or alleviate one or more symptoms of a disease state being treated or to otherwise provide a desired pharmacologic or physiologic effect, especially enhancing T cell response to a selected antigen. The precise dosage in any given embodiment can vary according to a variety of factors such as subject-dependent variables (e.g., age, immune system health, etc.), the disease, and the treatment being administered.

As used herein, the terms "individual," "host," "subject" and "patient" are used interchangeably and mean a mammal, including, but not limited to, primates, for example, human beings, as well as rodents, such as mice and rats, and other laboratory animals or any other animals mentioned herein.

As used herein, "treat," "treating" or "treatment" means an alleviation of symptoms associated with a disorder or disease, or inhibition of further progression or worsening of those symptoms, or prevention or prophylaxis of the disease or disorder; and includes: (i) preventing a pathologic condition from occurring (e.g., prophylaxis); (ii) inhibiting the pathologic condition or arresting its development (e.g., slowing or stopping proliferation of cancer cells or tumor growth); (iii) relieving the pathologic condition; or (iv) diminishing symptoms associated with the pathologic condition.

As used herein, the term "treatment regimen" means a treatment of a disease or a method for achieving a desired physiological change, such as increased or decreased response of the immune system to an antigen or immunogen, such as an increase or decrease in the number or activity of one or more cells, or cell types, that are involved in such response. In various embodiments discussed herein, the treatment or method comprises administering to an animal, such as a mammal, a sufficient amount of one or more (in certain embodiments two or more) chemical agents or components of said regimen to effectively treat a disease or to produce said physiological change. In certain embodiments, the two or more agents or components are administered together, such as part of the same composition, or administered separately and independently at the same time or at different times (i.e., administration of each agent or component is separated by a finite period of time from one or more of the agents or components). In certain embodiments, administration of said one or more agents or components achieves a result greater than that of any of said agents or components when administered alone or in isolation.

As used herein, the terms "anergy" or "unresponsiveness" are used interchangeably and include unresponsiveness to an immune cell to stimulation, for example, stimulation by an activation receptor or cytokine. Anergy can occur due to, for example, exposure to an immune suppressor or exposure to an antigen in a high dose. Such anergy is generally antigen-specific, and can continue even after completion of exposure to a tolerized antigen. For example, the anergy in a T cell and/or NK cell can be characterized by failure of production of cytokine, e.g., interleukin (IL)-2. The T cell anergy and/or NK cell anergy can occur in part when a first signal (signal via TCR or CD-3) is received in the absence of a second signal (costimulatory signal) upon exposure of a T cell and/or NK cell to an antigen.

As used herein, the terms "enhanced function of a T cell," "enhanced cytotoxicity" and "augmented activity" are used interchangeably and mean that the effector function of the T cell or NK cell is improved. In certain embodiments, the enhanced function of the T cell or NK cell can include any of the following: an improvement in the proliferation rate of the T cell or NK cell, an increase in the production amount of cytokine, or an improvement in cytotoxity. Further, in certain embodiments the enhanced function of the T cell or NK cell includes cancellation or suppression of tolerance of the T cell or NK cell in the suppressed state such as the anergy (unresponsive) state, or the rest state, that is, transfer of the T cell or NK cell from the suppressed state into the state where the T cell or NK cell responds to stimulation from the outside.

As used herein, "expression" means generation of mRNA by transcription from nucleic acids such as genes, polynucleotides, and oligonucleotides, or generation of a protein or a polypeptide by transcription from mRNA. Expression can be detected by any method including RT-PCR, Northern Blot, or in situ hybridization. As used herein, "suppression of expression" means a decrease of a transcription product or a translation product in a significant amount as compared with the case of no suppression. The suppression of expression herein shows, in various embodiments, a decrease of a transcription product or a translation product in amounts of 30% or more, 50% or more, 70% or more, or 90% or more.

As used herein, "augmented immune response" means characterized by a particularly strong response or reaction of the immune system to the presence of an antigen. Under normal, non-pathological conditions, immune responses are regulated in a tightly controlled fashion. Moreover, immune responses are self-limiting and decline in time after exposure to the antigen. In case of an "augmented immune response" however, the immune response can be hypersensitive, i.e., the immune response can cause damage to the organism's own cells or tissue in presence of an antigen. Furthermore, in some cases of an "augmented immune response," for example in auto-immune diseases or disorders or in transplant rejects (and the like), the immune system can fail to distinguish between self and non-self substances. As used herein, "disease related to an augmented immune response" accordingly relates to any disease or disorder in which an augmented immune response is etiological for, associated with, secondary to or the resultant of said disorder.

In certain embodiments, an augmented immune response can be determined by directly or indirectly measuring parameters that are indicative for the magnitude of the immune response or reaction to an antigen, and comparing the outcome of said measurement with the outcome of the same test in a physiologically normal subject. Parameters indicative for the magnitude of the immune response/reaction can include, but are not limited to: the presence or quantity of (specific) antibodies; the presence or quantity of (specific) immune cells; the presence or quantity of (specific) cytokines; or the presence or quantity of (specific) regulatory-, activation- or adhesion molecules.

For a disease to be related to an augmented immune response, accordingly, said augmented immune response can be detectable preceding, during or following said disease. In certain embodiments, the disease related to an augmented immune response is any of the following:

an acute or chronic transplant rejection, including septic shock, infections caused by bacteria including MRSA and viruses;

a dermatological disease, for example, psoriasis, atopic dermatitis or contact allergy;

T- and B-cell-mediated inflammatory disease, for example, asthma or chronic obstructive pulmonary disease (COPD);

graft-versus-host disease, for example, acute (or fulminant) graft-versus-host disease or chronic graft-versus-host disease; or auto-immune disease, for example, multiple sclerosis, inflammatory bowel disease, like ulcerative colitis or Behcet's disease; vasculitis, lupus erythematosus, pemphigus vulgaris, pemphigus foliaceus, myasthenia gravis, polymyositis, mixed collective tissue disease (MCTD) rheumatoid arthritis, diabetes mellitus (whether Type 1 or Type 2), celiac disease, celiac sprue disease, atherosclerosis, Goodpasture's syndrome, Grave's disease, autoimmune hepatitis/ hepatic autoimmune diseases, autoimmune thrombocytopenic purpura, granulomatosis (e.g., morbus Wegener), Sjogren's Syndrome, scleroderma, alopecia areata or autoimmune hemolytic anemia.

Immune responses can be exquisitely controlled, requiring multiple finely tuned levels of activation as well as inactivation signals. In T lymphocytes among these signaling networks, T cell receptor (TCR) stimulation activates NF-AT/AP-1, a family of transcription factors that is of particular importance during immune cell activation. NF-AT mediates the transcriptional induction of "cell fate-determining genes," which govern as diverse outcomes as activation, anergy or apoptosis. Mechanistically, the rise of intracellular $Ca^{2+}$ triggered by antigen binding to the TCR can lead to the activation of calcineurin's phosphatase activity. This leads to dephosphorylation of phospho-sites within the N-terminal regulatory domain on NF-AT and, subsequently, nuclear import of NF-AT. Upon transient stimuli, however, feedback inhibition, mediated via GSK3 (glycogen synthase kinase 3), CK1 (casein kinase 1) and DYRK (dual-specificity tyrosine phosphorylation-regulated kinase) protein kinases can counter-regulate NF-AT nuclear occupancy by rephosphorylation, which induces the nuclear export of NF-AT and the abort of immune activation-associated gene transcription. NF-AT family members are also subject to regulation in the nucleus through their ability to directly interact with other transcriptional regulatory factors. NF-AT requires a protein partner for high-affinity binding at most DNA sites. NF-AT complexes mostly contain cell type- or cell lineage—specific protein binding partners. In cardiac, skeletal, and smooth muscle cells, NF-AT forms complexes with GATA proteins.

Accordingly, in certain embodiments the present technology is directed to agonists or activators of NR2F6 for the treatment of a disease related to an augmented immune response. In other embodiments, the present technology is directed to the use of an agonist or activator of NR2F6 for the preparation of a medicament for the treatment of a disease related to an augmented immune response. The utilization of NR2F6 modulating compounds for alteration of immune response can be utilized by administering in patients suffering from cancer in which increased efficacy of a cancer vaccine is desired. In these situations, inhibition of NR2F6 is desirable, optionally in addition to immune stimulation. Thus, in various embodiments, the compositions herein can comprise any of the following:

(a) agonists/activators of NR2F6;

(b) antagonists/inhibitors of NR2F6;

(c) agonists/activators of NR2F6 in combination with: (i) one or more additional immune enhancers (ii) CAR-T cell therapy (which can reduce side effects); or (iii) autologous cell therapies, e.g., dendritic cells, anti-PD1 and antiCTLA4 antibodies, PMBC, or umbilical vein cord blood-derived cells.

(d) antagonists/inhibitors of NR2F6 in combination with: (i) one or more additional immune suppressants; (ii) CAR-T cell therapy (which can reduce side effects); or (iii) autologous cell therapies, e.g., dendritic cells, anti-PD1 and anti-CTLA4 antibodies, PMBC, or umbilical vein cord blood-derived cells.

Accordingly, in certain embodiments, inhibitor compounds of NR2F6 are administered with a cancer antigen, said cancer antigens include ROBO-4. In certain embodiments, the antigens can be used to replace ROBO-4. These can include any of the following: a) Fos-related antigen 1; b) LCK; c) FAP; d) VEGFR2; e) NA17; f) PDGFR-beta; g) PAP; h) MAD-CT-2; i) Tie-2; j) PSA; k) protamine 2; l) legumain; m) endosialin; n) prostate stem cell antigen; o)carbonic anhydrase IX; p) STn; q) Page 4; r) proteinase 3; s) GM3 ganglioside; t) tyrosinase; u) MART1; v) gp100; w) SART3; x) RGS5; y) SSX2; z) Globo1; aa) Tn; ab) CEA; ac) hCG; ad) PRAME; ae) XAGE-1; af) AKAP-4; ag) TRP-2; ah) B7H3; ai) sperm fibrous sheath protein; aj) CYP1B1; ak) HMWMAA; al) sLe(a); am) MAGE A1; an) GD2; ao) PSMA; ap) mesothelin; aq) fucosyl GM1; ar) GD3; as) sperm protein 17; at) NY-ESO-1; au) PAX5; av) AFP; aw) polysialic acid; ax) EpCAM; ay) MAGE-A3; az) mutant p53; ba) ras; bb) mutant ras; bc) NY-BR1; bd) PAX3; be) HER2/neu; bf) OY-TES1; bg) HPV E6 E7; bh) PLAC1; bi) hTERT; bj) BORIS; bk) ML-IAP; bl) idiotype of b cell lymphoma or multiple myeloma; bm) EphA2; bn) EGFRvIII; bo) cyclin Bl; bp) RhoC; bq) androgen receptor; br) surviving; bs) MYCN; bt) wildtype p53; bu) LMP2; by) ETV6-AML; bw) MUC1; bx) BCR-ABL; by) ALK; bz) WT1; ca) ERG (TMPRSS2 ETS fusion gene); cb) sarcoma translocation breakpoint; cc) STEAP; cd) OFA/iLRP; and ce) Chondroitin sulfate proteoglycan 4 (CSPG4).

In certain embodiments, the assessment of compounds for NR2F6 modulating activity is performed utilizing means known in the art, such as described in U.S. Pat. No. 9,091,696. Compounds useful for the screening and modification for enhanced NR2F6 modulatory activity include: CAR Agonists such as 5β-Dihydroprogesterone, 6,7-Dimethylesculetin, Amiodarone, Artemisinin, Benfuracarb, Carbamazepine, Carvedilol, Chlorpromazine, Chrysin, CITCO, Clotrimazole, Cyclophosphamide, Cypermethrin, DHEA, Efavirenz, Ellagic acid, Griseofulvin, Methoxychlor, Mifepristone, Nefazodone, Nevirapine, Nicardipine, Octicizer, Permethrin, Phenobarbital, Phenytoin, Reserpine, TCPOBOP, Telmisartan, Tolnaftate, Troglitazone, Valproic acid. CAR Antagonists such as 3,17β-Estradiol, 3α-Androstanol, 3α-Androstenol, 3β-Androstanol, 17-Androstanol, AITC, Ethinyl estradiol, Meclizine, Nigramide J, Okadaic acid, PK-11195, S-07662, T-0901317. FXR Agonists such as Bile acids, Cafestol, Chenodeoxycholic acid, Fexaramine, GW-4064, Obeticholic acid. FXR Antagonists such as Guggulsterone. LXR Agonists such as 22R-Hydroxycholesterol, 24S-Hydroxycholesterol, 27-Hydroxycholesterol, Cholestenoic acid, DMHCA, GW-3965, Hypocholamide, T-0901317. PPAR-alpha Agonists such as 15-HETE, 15-HpETE, Aleglitazar, Aluminum clofibrate, Arachidonic acid, Bezafibrate, Clofibrate, CP-775146, DHEA, Elafibranor, Fenofibrate, Gemfibrozil, GW-7647, Leukotriene B4, LG-101506, LG-100754, Lobeglitazone, Muraglitazar, Oleylethanolamide, Palmitoylethanolamide, Pemafibrate, Perfluorononanoic acid, Perfluorooctanoic acid, Pioglitazone, Saroglitazar, Sodelglitazar, Tesaglitazar, Tetradecylthioacetic acid, Troglitazone, WY-14643. PPAR-alpha Antagonists such as GW-6471, MK-886. PPAR-delta Agonists such as 15-HETE, 15-HpETE, Arachidonic acid, Bezafibrate, Elafibranor, GW-0742, GW-501516, L-165,041, LG-101506, MBX-8025, Sodelglitazar, Tetradecylthioacetic acid. PPAR-delta Antagonists such as FH-535, GSK-0660, GSK-3787. PPAR gamma agonists such as 5-Oxo-ETE, 5-Oxo-15-hydroxy-ETE, 15-Deoxy-Δ12,14-prostaglandin J2, 15-HETE, 15-HpETE, Aleglitazar, Arachidonic acid, Berberine, Bezafibrate, Ciglitazone, Darglitazone, Edaglitazone, Etalocib, GW-1929, Ibuprofen, LG-100268, LG-100754, LG-101506, Lobeglitazone, Muraglitazar, nTZDpa, Perfluorononanoic, acid, Pioglitazone, Prostaglandin J2, Rosiglitazone, RS5444, Saroglitazar, Sodelglitazar, Telmisartan, Tesaglitazar, Troglitazone. SSPARMS such as BADGE, EPI-001, INT-131, MK-0533, S26948. PPAR gamma antagonists such as FH-535, GW-9662, SR-202, T-0070907. PPAR nonselective agonists such as Ciprofibrate, Clinofibrate, Clofibride, Englitazone, Etofibrate, Farglitazar, Netoglitazone, Ronifibrate, Rivoglitazone, Simfibrate. PXR Agonists such as 5α-Dihydroprogesterone, 5β-Dihydroprogesterone, 17α-Hydroxypregnenolone, 17α-Hydroxyprogesterone, Δ4-Androstenedione, Δ5-Androstenediol, Δ5-Androstenedione, AA-861, Allopregnanolone, Alpha-Lipoic acid, Ambrisentan, AMI-193, Amlodipine besylate, Antimycotics, Artemisinin, Aurothioglucose, Bile acids, Bithionol, Bosentan, Bumecaine, Cafestol, Cephaloridine, Cephradine, Chlorpromazine, Ciglitazone, Clindamycin, Clofenvinfos, Chloroxine, Clotrimazole, Colforsin, Corticosterone, Cyclophosphamide, Cyproterone acetate, Demecolcine, Dexamethasone, DHEA, DHEA-S, Dibunate sodium, Diclazuril, Dicloxacillin, Dimercaprol, Dinaline, Docetaxel, Docusate calcium, Dodecylbenzenesulfonic acid, Dronabinol, Droxidopa, Eburnamonine, Ecopipam, Enzacamene, Epothilone B, Erythromycin, Famprofazone, Febantel, Felodipine, Fenbendazole, Fentanyl, Flucloxacillin, Fluorometholone, Griseofulvin, Haloprogin, Hetacillin potassium, Hyperforin (Hypericum perforatum), Indinavir sulfate, Lasalocid sodium, Levothyroxine, Linolenic acid, LOE-908, Loratadine, Lovastatin, Meclizine, Methacycline, Methylprednisolone, Metyrapone, Mevastatin, Mifepristone, Nafcillin, Nicardipine, Nicotine, Nifedipine, Nilvadipine, Nisoldipine, Norelgestromin, Omeprazole, Orlistat, Oxatomide, Paclitaxel, Phenobarbital, Plicamycin, Prednisolone, Pregnanolone, Pregnenolone, Pregnenolone 16α-carbonitrile, Proadifen, Progesterone, Reserpine, Reverse triiodothyronine Rifampicin, Rifaximin, Rimexolone, Riodipine, Ritonavir, Simvastatin, Sirolimus, Spironolactone, Spiroxatrine, SR-12813, Suberoylanilide, Sulfisoxazole, Suramin, Tacrolimus, Tenylidone, Terconazole, Testosterone isocaproate, Tetracycline, Thiamylal sodium, Thiothixene, Thonzonium bromide, Tianeptine, Troglitazone, Troleandomycin, Tropanyl 3,5-dimethulbenzoate, Zafirlukast, Zearalanol. PXR Antagonist such as Ketoconazole. RAR Agonists such as 9CDHRA, 9-cis-Retinoic acid (alitretinoin), AC-261066, AC-55649, Acitretin, Adapalene, all-trans-Retinoic acid (tretinoin), AM-580, BMS-493, BMS-753, BMS-961, CD-1530, CD-2314, CD-437, Ch-55, EC 23, Etretinate, Fenretinide, Isotretinoin, Palovarotene, Retinoic acid, Retinol (vitamin A), Tamibarotene, Tazarotene, Tazarotenic acid, TTNPB. RAR Antagonists such as BMS-195614, BMS-493, CD-2665, ER-50891, LE-135, MM-11253. RXR Agonists such as 9CDHRA, 9-cis-Retinoic acid (alitretinoin), all-trans-Retinoic acid (tretinoin), Bexarotene, CD 3254, Docosahexaenoic acid, Fluorobexarotene, Isotretinoin, LG-100268, LG-101506, LG-100754, Retinoic acid, Retinol (vitamin A), SR-11237. RXR Antagonists such as HX-531, HX-630, LG-100754, PA-452, UVI-3003. TR Agonists such as Dextrothyroxine, GC-1, Levothyroxine, Liothyronine, Thyroxine, Tiatricol, Triiodothyronine.

Other compounds useful for modulation of NR2F6 activity include: 5-tert-butyl-N-[(6-fluoro-4H-1,3-benzodioxin-8-yl)methyl]-2-methylpyrazole-3-carboxamide, ST50775950, ethyl 4-(cyclohexylamino)-2-(3,5-dimethylpyrazol-1-yl)pyrimidine-5-carboxylate, ethyl 4-(cyclopentylamino)-2-(3,5-dimethylpyrazol-1-yl)pyrimidine-5-carboxylate, AGN-PC-09SAX3, SMR000064686, AGN-PC-0NLTEQ, T6090485, MLS002548992, 5,6-dimethyl-4-[4-[4-[2-(4-methylphenoxy)ethyl]piperazin-1-yl]thieno[2,3-d]pyrimidine, MLS002473459, MLS001030349, 4-(3,4-dihydro-1H-isoquinolin-2-yl)-5H-pyrimido[5,4-b]indole, 4-(3,4-Dihydro-1H-isoquinolin-2-yl)-8-fluoro-5H-pyrimido[5,4-b]indole, 4-[4-(4-methoxyphenyl)piperazino]-5H-pyrimido[5,4-b]indole, 4-[4-(1,3-benzodioxol-5-ylmethyl)piperazin-1-yl]-7-methoxy-5H-pyrimido[5,4-b]indole, SMR000044829,8-fluoro-N-(3-propan-2-yloxypropyl)-5H-pyrimido[5,4-b]indol-4-amine, GNF-Pf-1678, MLS003116118, 2-[4-(5-methyl[1,2,4]triazolo[1,5-a]pyrimidin-7-yl)piperazin-1-yl]-1,3-benzothiazole, 5-methyl-3,6-diphenylpyrazolo[1,5-a]pyrimidin-7-amine, 4-[4-[(4-chlorophenyl)methyl]piperazin-1-yl]-1-[(4-methylphenyl)methyl]pyrazolo[3,4-d]pyrimidine, MLS002632722, MLS002477203, MLS003120814, AGN-PC-07AHX3, MLS003120821, MLS003120807, MLS003120811, MLS003120820, ethyl 4-[[1-(2,4-dimethylphenyl)pyrazolo[3,4-d]pyrimidin-4-yl]amino]piperidine-1-carboxylate, N-[2-(3,4-dimethoxyphenyl)ethyl]thieno[2,3-d]pyrimidin-4-amine, N-[2-(3,4-dimethoxyphenyl)ethyl]-6-methylthieno[2,3-d]pyrimidin-4-amine hydrochloride, N-(1-phenylethyl)quinazolin-4-amine, AG-F-87638, ZINC03428816, CHEMBL493153, ST50323391, N-Benzylquinazolin-4-amine, ST50483228, N-[4-(2-methyl-1-methylsulfonyl-2,3-dihydroindol-5-yl)-1,3-thiazol-2-yl]-2-thiophen-2-ylacetamide, F0558-0175, AC1MLRO7, 4-(2-methylimidazo[1,2-a]pyridin-3-yl)-N-(3-methylphenyl)-1,3-thiazol-2-amine, AGN-PC-09PPXW, Compound 15Jf, AC1MEEXM, ST50941838, [2-[3-carbamoylthiophen-2-yl)amino]-2-oxoethyl] 2-naphthalen-1-ylacetate, F0239-0029, AC1OBZ0O, ST4126227, 1-[(4-bromophenyl)methyl]-2-methylbenzimidazole, SMR000718391, MLS002694437, Chlormidazole, 2-methyl-1-(2-methylbenzyl)-1H-benzimidazole, MLS003119103, Ambcb90456311, AGN-PC-04RX4B, MLS001122505, Ambcb81049924, AGN-PC-04RX7E, Ambcb42757923, MLS001124721, 7-benzyl-4-chloro-5,6-dimethyl-7H-pyrrolo[2,3-d]pyrimidine, AGN-PC-04V4GP, MLS000562030, AGN-PC-00YPMB, T5400648, MLS003107990, AC1NUNJE, MLS002701851, SMR000185185, STK850401, [(3-bromobenzyl)sulfanyl][(4-fluorophenyl)amino]methylidene, propanedinitrile, AC1NXBLH, CAS-66-81-9, Cycloheximide, ACTIPHENOL, MLS001032885, MLS000553012, SMR000285129, MLS000688479, MLS002702480, GNF-Pf-4659, MLS002702449, T0501-4035, MLS000712179, AGN-PC-00MQWB, AGN-PC-0NKU3S, T0503-0850, T0501-5798, SMR000212173, 3,3'-Diethylthiazolinocarbocyanine iodide, 2-methyl-3,5-bis(4-methylphenyl)isoxazol-2-ium, MLS000705900, SMR000211540, AGN-PC-00PL3I, AGN-PC-0NJNZK, SMR000354849, T0503-1204, MLS000688685, GNF-Pf-4078, T0503-3525, T0503-4982, T0501-7391, GNF-Pf-3268, TCMDC-125620, 1-[1,1'-Biphenyl]-4-yl-2-(4-imino-1(4H)-pyridinyl)ethanone, SMR000036350, MLS000080109, MLS000080126, Ambcb40308772, MLS000733369, Ambcb20390854, MLS000732313, AGN-PC-04RYS6, Ambcb33735952, AGN-PC-04RYKA, MLS000733096, Ambcb63657849, MLS001090213, T6132867, MLS003678910, AC1OXF5M, SMR000218920, MLS000037490, Boc-KS, MLS000734694, AGN-PC-087SDW, ISUPSL100073, 4-{[5,7-bis(trifluoromethyl) benzenol, BAS 07204618, MLS001144057, MLS001250118, SMR000041809, SMR000635220, MLS003120011, T5546966, 4-chloro-N-(4-chlorobenzyl)-1,3-dimethyl-1H-pyrazole-5-carboxamide, 3-(Toluene-4-sulfonylmethyl)-2,3-dihydro-benzo[4,5]imidazo[2,1-b]thiazole, T0508-0735, Carboxyamidotriazole, MLS003116132, F0850-5968, Verrucarin A 9,10-epoxide, MLS002702133, Ossamycin, MLS002702060, Dihydrorotenone, SMR000623161, Pyridaben, ASN 09858385, T6069554, T6302989, SMR000629820, SMR000629835, MLS001028777, MLS001028747, MLS001028806, SMR000625125, T5403634, T5459762, T5626573, T5337170, SMR000093473, T6120097, N-[2-[2-[2,5-dimethyl-1-(thiophen-2-ylmethyl)pyrrol-3-yl]-2-oxoethoxy]phenyl]acetamide, MLS000575323, N-[4-[2-[2,5-dimethyl-1-(thiophen-2-ylmethyl)pyrrol-3-yl]-2-oxoethyl]sulfanylphenyl]acetamide, SMR000274842, T5565081, 6-chloro-N-[3-[(4-methoxyphenyl)sulfamoyl]phenyl]pyridine-3-carboxamide, N-methyl-N-[(1,3,5-trimethylpyrazol-4-yl)methyl]naphthalene-2-sulfonamide, T6099016, T6094971, ASN 04448329, SMR000241542, AGN-PC-03RL0E, AGN-PC-080KFN, T6151837, AGN-PC-0KIUAY, N-[4-(4-methylphenyl)-1,3-thiazol-2-yl]-1-thiophen-2-ylsulfonylpiperidine-4-carboxamide, 5-(3,5-dimethylpiperidin-1-yl)sulfonyl-N,N-diethyl-3-methyl-1-benzofuran-2-carboxamide, SMR000124769, N-(1-benzylpiperidin-4-yl)-1-(5-chloro-2-methylphenyl)sulfonylpiperidine-4-carboxamide, MLS001095722, 4-ethoxy-N-(pyridin-4-ylmethyl)benzenesulfonamide, 4-chloro-3-ethoxy-N-(pyridin-4-ylmethyl)benzenesulfonamide, 2,4,6-trimethyl-N-(pyridin-4-ylmethyl)benzenesulfonamide, BAS 05598377, 4-bromo-2,5-dimethyl-N-(pyridin-4-ylmethyl)benzenesulfonamide, MLS000735463, MLS000687652, AGN-PC-093SBW, AG-401/42008258, 5L-526S, 2-[[5-(3-chloro-1-benzothiophen-2-yl)-1,3,4-oxadiazol-2-yl]sulfanyl]acetonitrile, 2-(5-Pyridin-3-yl-[1,3,4]thiadiazol-2-ylsulfanyl)-N-quinolin-4-yl-acetamide, 2-[[5-(benzotriazol-1-ylmethyl)-1,3,4-oxadiazol-2-yl]sulfanyl]-N-[(4-chlorophenyl)methyl]-N-phenylacetamide, 2-[[5-(benzotriazol-1-ylmethyl)-1,3,4-oxadiazol-2-yl]sulfanyl]-N-[(4-fluorophenyl)methyl]-N-phenylacetamide, SR-01000288264, 2-(1-cyclopropyltetrazol-5-yl)sulfanyl-1-[4-[(4-propan-2-ylphenyl)methyl]piperazin-1-yl]ethanone, N-(2,4-difluorophenyl)-4-[5-(trifluoromethyl)pyridin-2-yl]-1,4-diazepane-1-carbothioamide, T0512-9975, [[2,7-bis(2-morpholin-4-ylethoxy)fluoren-9-ylidene]amino]thiourea, MLS001018548, T0507-0244, 4-(4-acetylphenyl)-N-(4-phenoxyphenyl)piperazine-1-carbothioamide, N-(3-ethoxypropyl)-4-[4-(4-fluorophenyl)-1,3-thiazol-2-yl]piperazine-1-carbothioamide, (+)-Emetine dihydrochloride hydrate, MLS002302684, 4-(6-chloro-1,3-benzothiazol-2-yl)-N-(2-chloro-6-methylphenyl)-1,4-diazepane-1-carboxamide, N-(3-chloro-2-methylphenyl)-4-(3-phenyl-1,2,4-thiadiazol-5-yl)-1,4-diazepane-1-carboxamide, MLS000692856, bjm-csc-19, MLS002701991, and MLS000586514. Additional compounds include 6-formylindolo (3,2-B) carbazole, 4-hydroxyphenylretinamide, 3,5-Dilodo-L-tyrosine, Rifampicin, and Z30972355.

Another aspect of the present disclosure is a pharmaceutical composition comprising a NR2F6 modulator, such as a NR2F6 inhibitor or NR2F6 activator, for use in the methods described herein. Accordingly, in certain embodiments, the present technology provides a pharmaceutical composition comprising an effective amount of a NR2F6 inhibitor or NR2F6 activator in admixture with a pharmaceutically acceptable carrier, excipient or diluent.

In various embodiments, the pharmaceutical compositions herein can be used to inhibit NR2F6; or to activate NR2F6.

In certain embodiments, the pharmaceutical composition is used to treat a disease or a hematopoietic condition as described herein. The NR2F6 inhibitors or NR2F6 activators can be formulated into pharmaceutical compositions for administration to subjects in a biologically compatible form suitable for administration in vivo.

As used herein, "biologically compatible form suitable for administration in vivo" means a form of the substance to be administered in which any toxic effects are outweighed by the therapeutic effects. In various embodiments, the substances herein can be administered to living organisms including humans, and animals. Administration of a therapeutically active amount of the pharmaceutical compositions of the present disclosure is defined as an amount effective, at dosages and for periods of time necessary to achieve the desired result. For example, a therapeutically active amount of a substance can vary according to factors such as the disease state, age, sex, and weight of the individual, and the ability of inhibitor to elicit a desired response in the individual. Dosage regime can be adjusted to provide the optimum therapeutic response. For example, several divided doses can be administered daily or the dose can be proportionally reduced as indicated by the exigencies of the therapeutic situation.

In various embodiments, the active substance can be administered by, e.g., injection (subcutaneous, intravenous, intramuscular, etc.), oral administration, inhalation, intranasal, transdermal or topical administration (such as topical cream or ointment, salve, paste or the like), pulmonary, buccal, subdermal, intradermal, transdermal or parenteral, rectal, subcutaneous, intravenous, intraurethral, intramuscular, ophthalmic or suppository administration. Depending on the route of administration, the active substance can, in certain embodiments, be coated in a material to protect the compound from the action of enzymes, acids and other natural conditions which could inactivate the compound.

In certain embodiments, the active substance can be formulated into delayed release formulations such that NR2F6 can be inhibited or activated for longer periods of time than a conventional formulation.

In certain embodiments, a method herein includes the following steps: (a) extraction of an amount of a patient's cellular material, including, but not limited to: blood, saliva, sweat, or any portion of a tumor known or believed to be in a diseased state; (b) isolating immune cells from the cellular material; (c) inhibiting or activating the NR2F6 target in the extracted immune cells; and (d) re-administering the immune cells (for example, by injection) to the patient's body. This can have the effect of "reprogramming" the immune cells to attack tumors or other invasive cells.

In certain embodiments, other types of a patient's cellular material can also be extracted. These include, for example, any part of the blood (blood serum, red blood cells, white blood cells, plasma, platelets), any other material from the body that includes the patient's cells (for example, skin, hair, nails, saliva, cerebrospinal fluid, intracellular fluid, extracellular fluid, intravascular fluid, interstitial fluid, lymphatic fluid, transcellular fluid, exudates, lymph, sweat, sebum or serous fluid). In certain embodiments, the re-administering of the immune cells to the patient's body can be done by injection, introduction through the nose or mouth (for example, inhalation), skin or mucous membranes.

In certain embodiments, the present technology is directed to compounds alone or in combination with another medicament. As set forth herein, compounds herein include stereoisomers (including, e.g., enantiomers, diastereomers, cis-trans and E-Z isomers, conformers and atropisomers), tautomers, solvates, prodrugs, metabolites, pharmaceutically acceptable salts and mixtures thereof. Compositions containing a compound herein can be prepared by conventional techniques, and can appear in conventional forms, for example, oral dosage forms; or any ingestible, inhalable (e.g., through the mouth, nose or mucosa); or topical applications, e.g., applicable to the skin, nails, eyes or the like. These can include, in various embodiments, capsules, tablets, pills, cachets, dispersible granules, lozenges, aerosols, solutions, powders, suspensions, emulsions, gels, mousses, foams, drops, lotions, creams, paste, dragees, suppositories and any application deliverable to the body of a user.

In various embodiments, dosages and compounds herein can be prepared and administered in a wide variety of oral, parenteral, and topical dosage forms, including, but not limited to, by injection (e.g., intravenously, intramuscularly, intracutaneously, subcutaneously, intraduodenally, or intraperitoneally); by inhalation (e.g., intranasally); or transdermally. In certain embodiments, multiple routes of administration can be used to optimize delivery of the compounds herein.

In various embodiments, the compositions described herein can be prepared by known methods for the preparation of pharmaceutically acceptable compositions which can be administered to subjects, such that an effective quantity of the active substance is combined in a mixture with a pharmaceutically acceptable vehicle. On this basis, the compositions can include, albeit not exclusively, solutions of the substances in association with one or more pharmaceutically acceptable vehicles or diluents, and contained in buffered solutions with a suitable pH and iso-osmotic with the physiological fluids.

In certain embodiments, a powder or tablet according to a dosage form herein can contain about 5 to about 75%, about 10 to about 70%, or about 15 to about 65% of the active compound. Suitable carriers include, but are not limited to: magnesium carbonate, magnesium stearate, talc, sugar, lactose, pectin, dextrin, starch, gelatin, tragacanth, methylcellulose, sodium carboxymethylcellulose, a low melting wax, cocoa butter, and the like.

In various embodiments, carriers for certain dosages can include aqueous solutions of dextrose, saline, water, organic solvents including ethanol, glycerol, propylene glycol, oils including peanut oil or sesame oil; or polyoxyethylene-block polymers. Aqueous solutions or suspensions can be made by dispersing the finely divided active component in water or another solvent with viscous material, such as natural or synthetic gums, resins, methylcellulose, sodium carboxymethylcellulose, and other suspending agents.

In various embodiments, the compounds or dosages herein can also be incorporated into liposomes or micelles, or administered via transdermal pumps or patches.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil; and in various embodiments, are present in amounts of about 0.01 to about 10%, about 0.05 to about 5% or about 0.1 to about 3% by weight.

In certain embodiments, it may be desirable to increase the viscosity of the dosage forms herein for ease in dispensing or delivery. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing; and in various embodiments, are present in amounts of about 0.01 to about 10%, about 0.05 to about 5% or about 0.1 to about 3% by weight.

The compositions herein can, in certain embodiments, additionally include components to provide sustained release or comfort. Such components include, but are not limited to, high molecular weight, anionic mucomimetic polymers, gelling polysaccharides, finely-divided drug carrier substrates, emollients, humectants, moisturizers, essential oils, oils, lipids, fatty acids, glycerides, extracts of natural ingredients, soaps and waxes.

Useful Compounds

The present disclosure includes various compounds that were found to be modulators of NR2F6 activity and NR2F6 utilizing compounds, and the immune modulation and modulation of cancer stem cell activity. Exemplary compounds and methods are shown in the attached FIGS. 1-58. These compounds were initially found to be modulators of NR2F6 activity and NR2F6 utilizing compounds, and the immune modulation and modulation of cancer stem cell activity. In various embodiments, the compounds comprise one or more of the following functional groups: a sulfonyl group, a sulfone group R—S(=O)2-R' where R and R' are any organic functional groups, a pyrazine group, any phenyl substituted with one or more halogens including chlorine or fluorine; or any composition comprising two or more phenyl constituents. In certain embodiments, a compound herein can be in amorphous form, crystalline form, or a mixture thereof; as well as any polymorph or amorphous form, a solvate, a hydrate or an unsolvated form.

EXAMPLE 1

The methodology for screening candidate compounds as NR2F6 agonists was as follows: For primary screening, hit criteria was ACT %>DMSO control+5*SD (DSO control) at 10 µM, or any compound with S/B>2. For rescreening, hit criteria was ACT %>DMSO control+3*SD (DSO control) in each replicate at 10 µM. For counterscreening, hit criteria was mean ACT<DMSO control+3*SD (DMSO control) with ERα transient transfection in duplicate at 10 µM.

Table 1 shows screening results from a first set of compounds.

TABLE 1

| Compound I.D. | Firefly, cmpd/DMSO repeat 1 | Firefly, cmpd/DMSO repeat 2 | Firefly_ERa, cmpd/DMSO repeat 1 | Firefly_ERa, cmpd/DMSO repeat 2 | Renilla, cmpd/DMSO repeat 1 | Renilla, cmpd/DMSO repeat 2 | Renilla_ERa, cmpd/DMSO repeat 1 | Renilla_ERa, cmpd/DMSO repeat 2 |
|---|---|---|---|---|---|---|---|---|
| 17 | 2.2 | 2.4 | 2.5 | 2.2 | 1.3 | 1.4 | 1.3 | 1.0 |
| 18 | 3.8 | 3.8 | 2.5 | 1.9 | 3.3 | 4.2 | 0.8 | 0.9 |
| 19 | 2.2 | 1.7 | 2.3 | 2.4 | 1.6 | 1.7 | 1.2 | 1.0 |
| 20 | 2.2 | 2.1 | 1.5 | 1.7 | 4.4 | 4.8 | 1.1 | 0.9 |
| 21 | 2.4 | 2.2 | 1.1 | 1.0 | 3.8 | 3.0 | 1.1 | 0.9 |
| 22 | 2.1 | 2.9 | 1.5 | 2.2 | 1.1 | 1.3 | 0.8 | 1.1 |
| 23 | 3.0 | 1.9 | 1.8 | 1.8 | 4.6 | 3.4 | 1.1 | 1.2 |
| 24 | 2.0 | 2.3 | 1.3 | 1.6 | 2.4 | 2.2 | 0.9 | 1.0 |
| 25 | 2.4 | 1.9 | 1.3 | 0.7 | 3.1 | 2.1 | 0.9 | 1.0 |
| C1 | 3.4 | 4.1 | 1.0 | 1.0 | 4.1 | 1.5 | 1.3 | 1.2 |
| C2 | 2.7 | 2.2 | 1.0 | 0.8 | 6.0 | 5.3 | 1.7 | 1.6 |
| C3 | 2.0 | 2.0 | 1.8 | 1.9 | 1.6 | 1.2 | 1.1 | 1.2 |
| C4 | 2.5 | 2.5 | 1.6 | 1.7 | 1.6 | 1.5 | 1.1 | 1.2 |
| C5 | 2.2 | 1.7 | 1.6 | 2.0 | 1.3 | 1.4 | 1.2 | 1.0 |
| C6 | 2.6 | 1.9 | 2.2 | 1.4 | 1.2 | 0.9 | 1.0 | 1.0 |
| C7 | 2.1 | 2.1 | 0.8 | 0.5 | 1.1 | 1.4 | 0.8 | 0.8 |
| C8 | 2.1 | 2.8 | 1.2 | 1.2 | 3.4 | 3.1 | 1.0 | 1.1 |
| C9 | 2.7 | 1.9 | 2.5 | 2.4 | 2.4 | 2.5 | 0.9 | 1.0 |
| C10 | 2.1 | 2.6 | 1.0 | 1.3 | 3.1 | 1.6 | 0.7 | 0.8 |
| C11 | 13.5 | 12.6 | 1.7 | 1.7 | 3.8 | 3.3 | 1.3 | 1.2 |
| C16 | 2.7 | 2.3 | 1.0 | 0.9 | 3.9 | 3.2 | 0.9 | 1.1 |

C1, C7 and C11 were found to have particularly good activity:

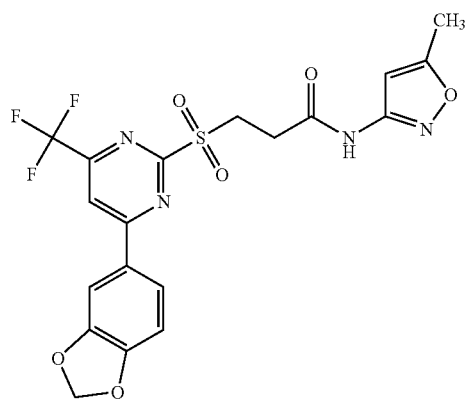

Compound C1

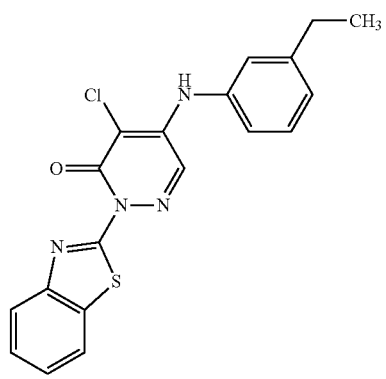

Compound C7

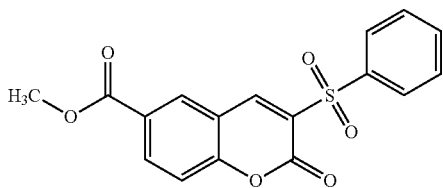

Compound C11

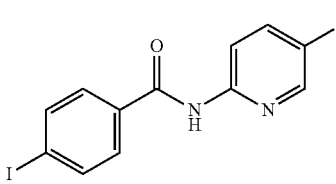

Compound C18

Additional compounds included the following:

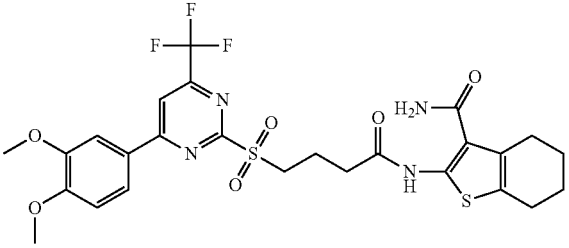

Compound C2

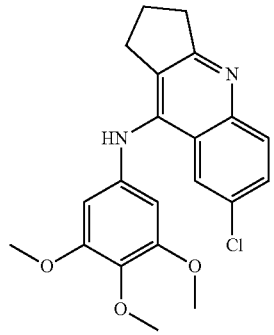

Compound C10

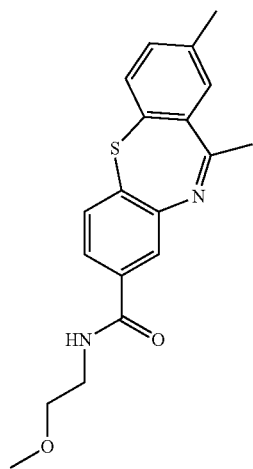

Compound C8

-continued

Compound C9

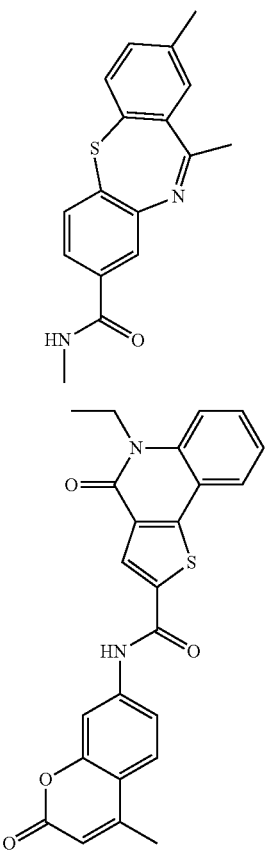

Compound C16

Compound C3

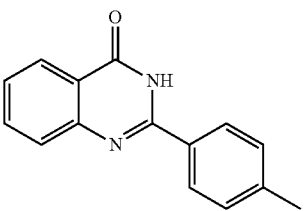

Compound 22

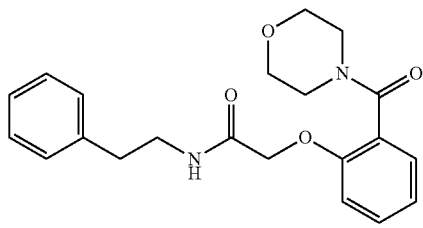

Compound C5

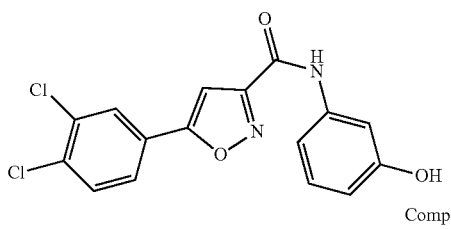

Compound C6

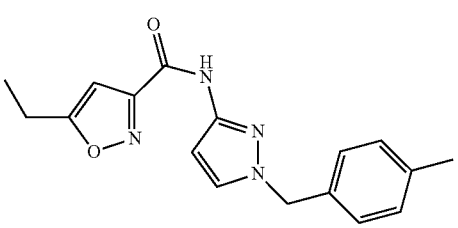

Yet additional compounds tested included Compounds 17, 19, 22 and C3-C6:

Compound 17

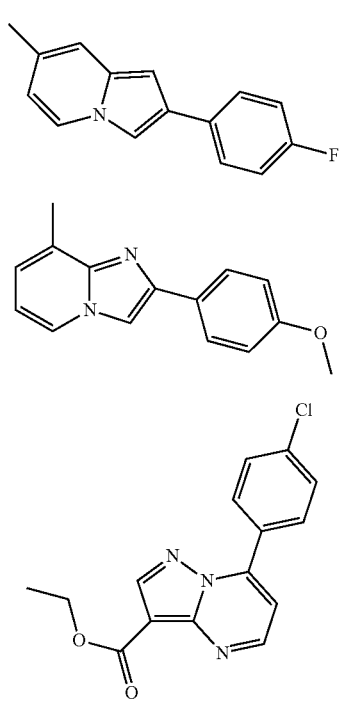

Compound 19

Compound C4

Figure 16A:
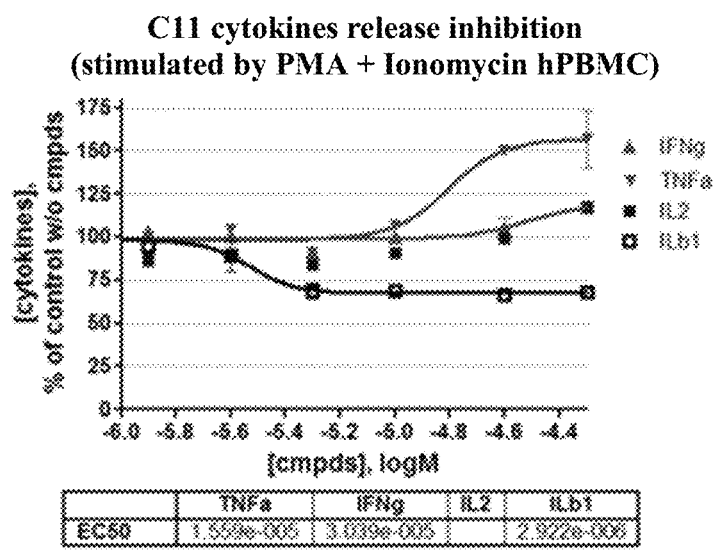
FIGS. 16A and 16B show charts of cytokines release by hPBMC and cytotox for Compound C11, which was identified as a useful compound in accordance with the embodiments herein. Results were repeated in follow set screen from fresh powder. 5 direct analogs were available (top structure in FIG. 16A).
Figure 16B:
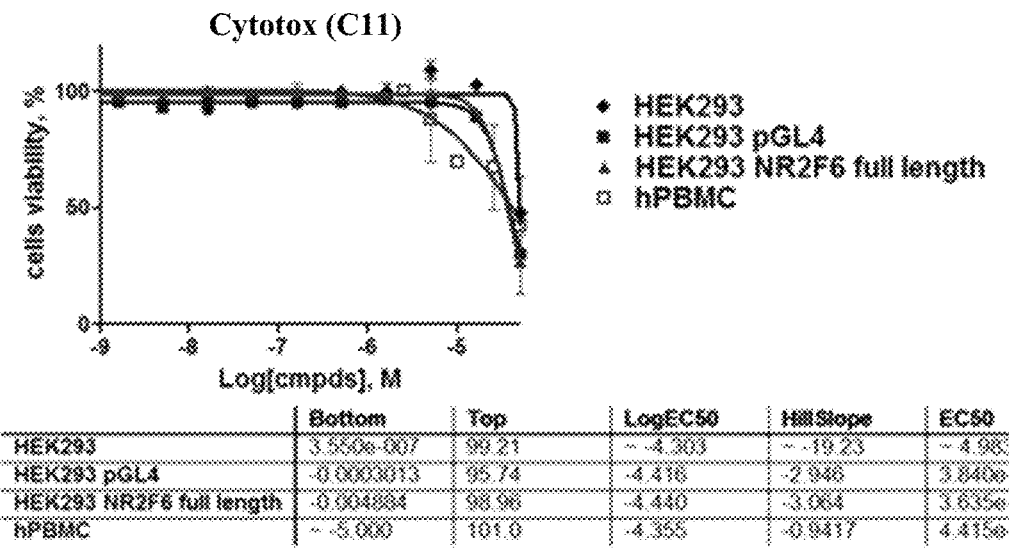

Compound C11 was found to be particularly promising. FIGS. 16A and 16B show results of cytokins release by hPBMC and cytotox for Compound C11. For cytokines release and cytotox on hPBMCs, the Compound was tested at 1.25, 2.5, 5, 10, 25 and 50 uM in duplicates. For cytotox on HEK293, HEK293 pGL4 and HEK293 NR2F6 (full length) cmpd was tested from 50 uM with dilution step 3.16 in duplicates.

The human PBMC were activated by 10 ng/mL PMA+ 500 ng/mL ionomycin. Data were normalized to controls with (100%) w/o compounds.

Compounds related to Compound C11 were further explored, and in particular, Compound C11 was substituted with various moieties to test how this affected its activity.

In certain embodiments, the present technology is directed to compounds of Formula (Ia), (Ib) or (Ic):

(Ia)

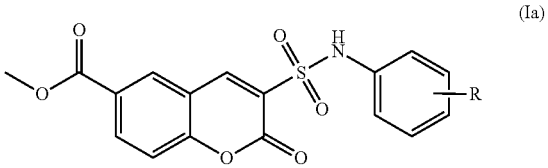

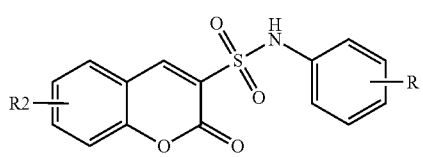

(Ib)

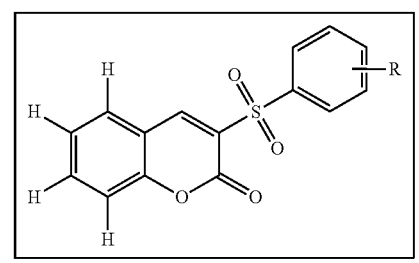

(Ic)

wherein any of R, R1 and R2 are C, H, N, O, S, a halogen, an alkyl group, a substituted alkyl group, a cyclic alkyl group, an aryl group, a substituted aryl group, a heterocyclic group, an ester, an aldehyde, a ketone, a carboxylic acid, an amide, an amine, an ether, a thiol or a nitrile.

In certain embodiments of any of the Formulas (I through XVII) herein, any of R, RA, RB, R1-R8, X, Q, Q1, Q2, or A can be any of the following: Me, OMe, Br, N, H, Cl, F or $NO_2$. In certain embodiments, any of R, RA, RB, R1-R8, X, Q, Q1, Q2, or A can be any of the following: 4-Me, 4-OMe, 4-Br, 4-t-Bu, 3,4-di-Me, 4-Cl, 3,4-di-Cl, 3-Cl-4-F, 2-F, 3-Cl, 3-$CH_3$-4-F, 4-iPr, Ph, 4-MeO—C6H4, 4-tBu, 2, 4-diMe, 2-thienyl, 2-MeO-4-Cl, 4-Cl, 2-furayl, 4-F—C6H4, 2,4-diMeC6H3, 3-Me-4-F or 4-Cl—C6H4.

Figure 17A:
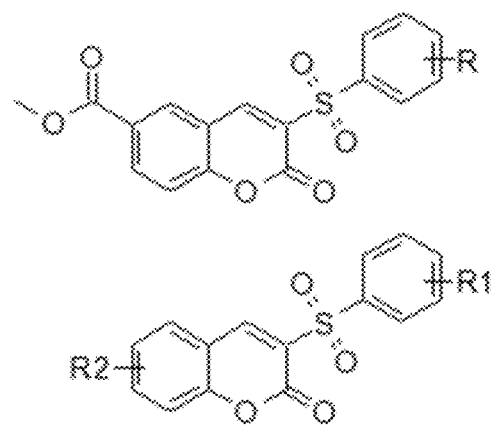
FIGS. 17A and 17B show analogues and other related compounds to Compound C11.
Figure 17B:
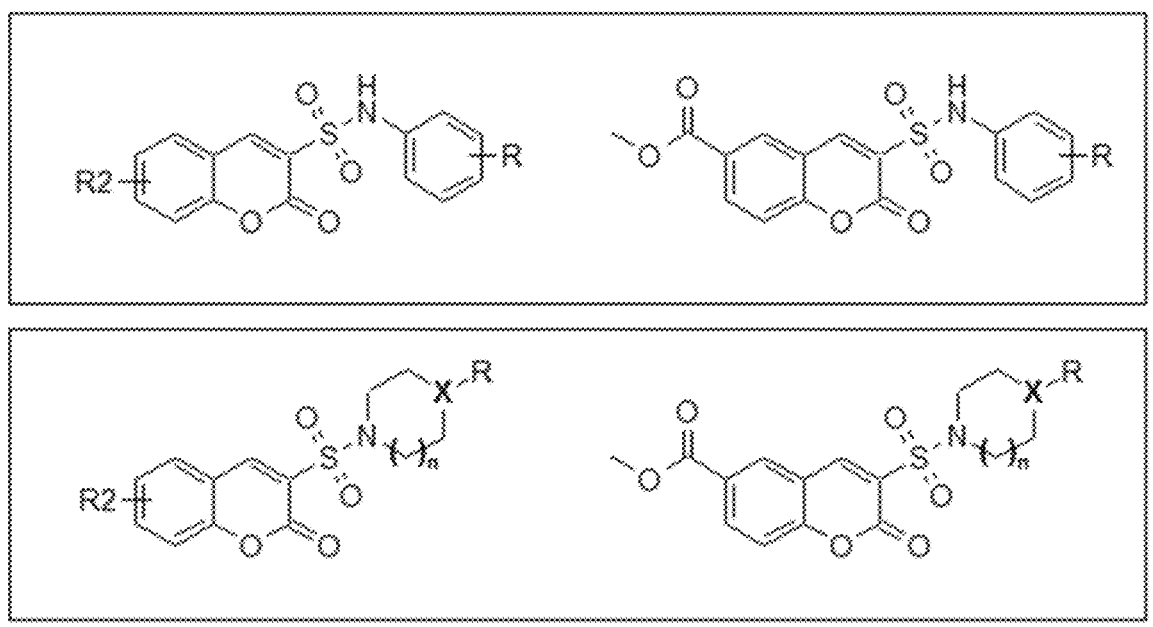
Figure 18A:
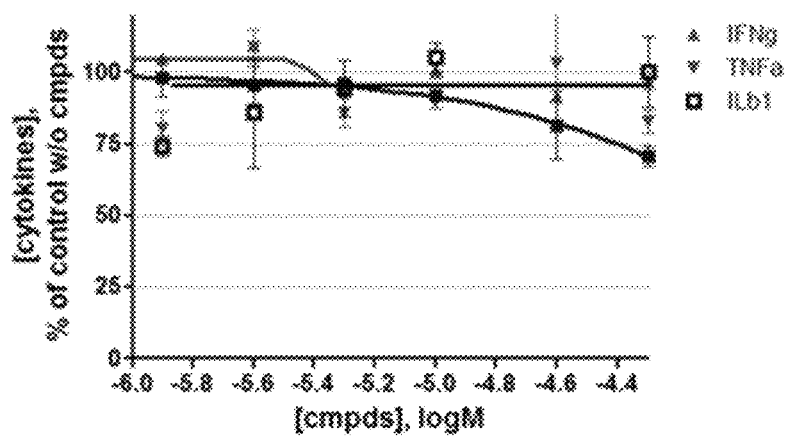
FIGS. 18A and 18B show charts of cytokines release by hPBMC and cytotox for Compound 18. For cytokines release and cytotox on hPBMCs compound was tested at 1.25, 2.5, 5, 10, 25 and 50 uM in duplicates. For cytotox on HEK293, HEK293 pGL4 and HEK293 NR2F6 (full length) compound was tested from 50 uM with dilution step 3.16 in duplicates. Human PBMC were activated by 10 ng/mL PMA+500 ng/mL ionomycin. Data were normalized to controls with (100%) w/o compounds.
Figure 18B:
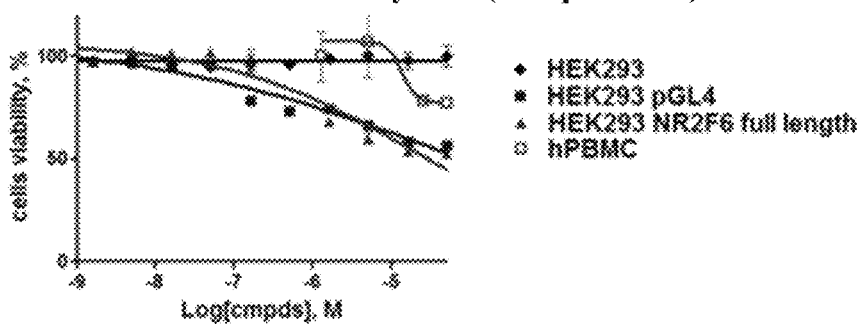

Compounds of Formulas I(a) and I(b) were rescreened in multiple assays to acquire statistical confidence in the results. Results were repeated in follow set screens from fresh powder. Analogs obtained are shown in FIG. 17B.

Four particularly useful compounds that were all based on C11 (Compounds C12 through C15) were identified as follows:

C12

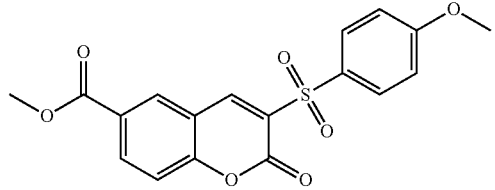

C13

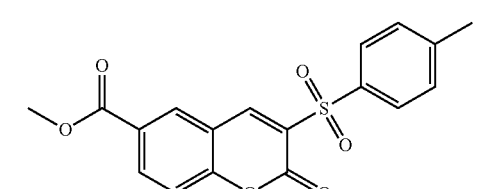

C14

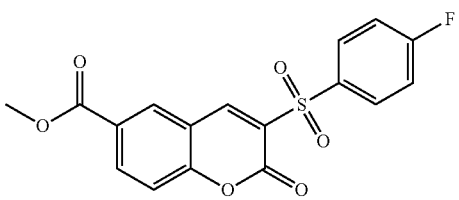

C15

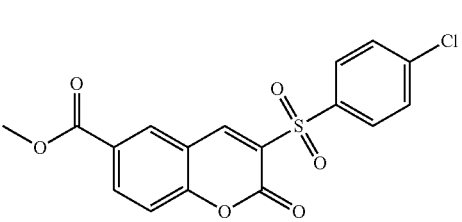

Activity of the above compounds (C12 through C15) is shown in Table 2:

TABLE 2

| IDNUMBER | Firefly, cmpd/DMSO | | Renilla, cmpd/DMSO | | Firefly_pGL, cmpd/DMSO | |
|---|---|---|---|---|---|---|
| | repeat 1 | repeat 2 | repeat 1 | repeat 2 | repeat 1 | repeat 2 |
| C12 | 20.0 | 16.7 | 4.5 | 9.4 | 2.6 | 2.9 |
| C11 | 24.6 | 21.3 | 13.9 | 12.3 | 3.3 | 3.3 |
| C13 | 14.0 | 12.9 | 6.4 | 8.2 | 3.2 | 3.2 |
| C14 | 22.3 | 20.0 | 12.1 | 15.2 | 2.9 | 2.6 |
| C15 | 0.9 | 1.7 | 5.8 | 10.7 | 1.2 | 1.7 |

Further compounds related to the Compound C11 and the compound of Formulas (Ia) (Ib) or (Ic) were tested. These include the following:

Compound C101

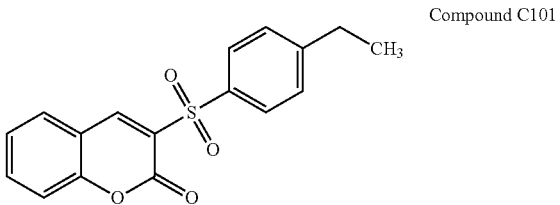

Compound C102

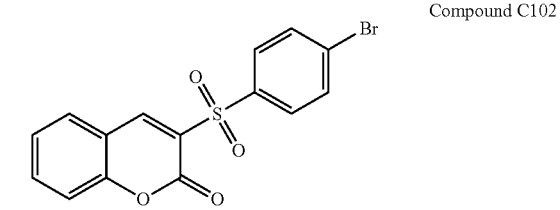

Compound C105

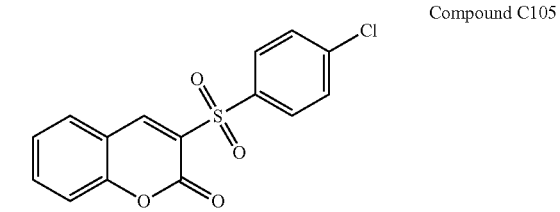

Compound C107
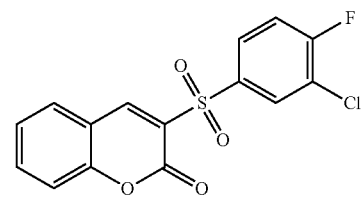
Compound C108
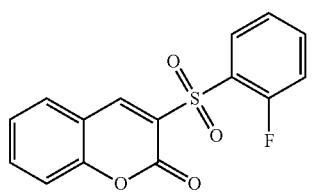
Compound C109
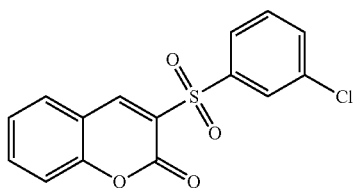
Compound C110
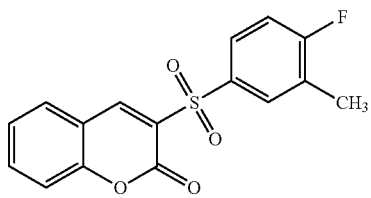
Compound C111
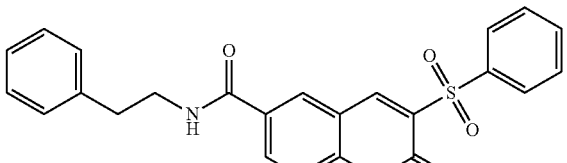
Compound C112
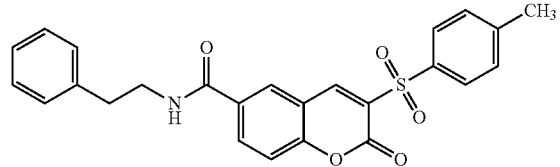
Compound C118
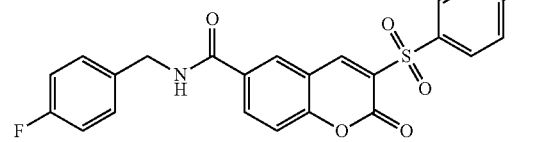
Compound C126
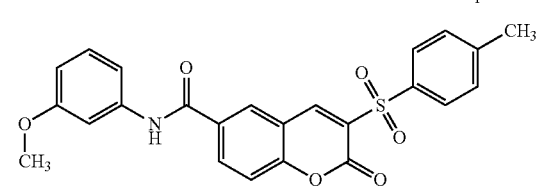
Compound C127
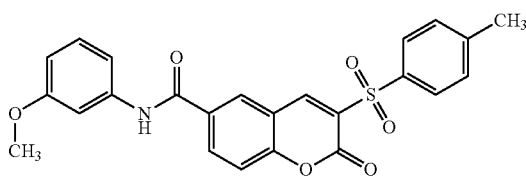
Compound C134
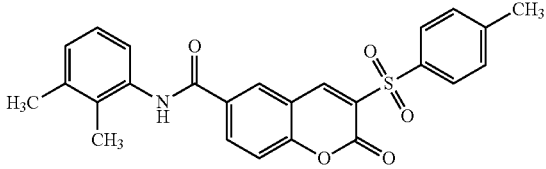
Compound C136
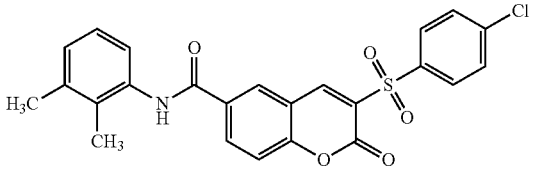
Compound C137
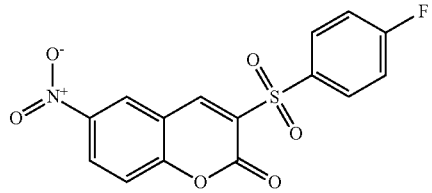
Compound C154
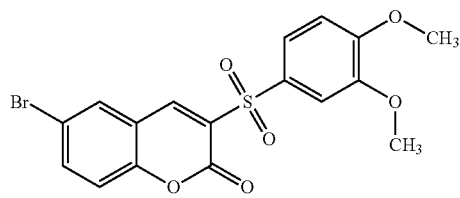
Compound C155
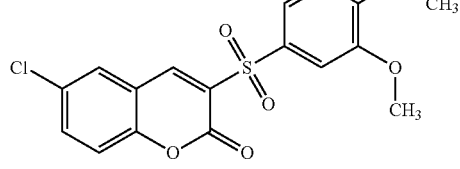
Compound C160
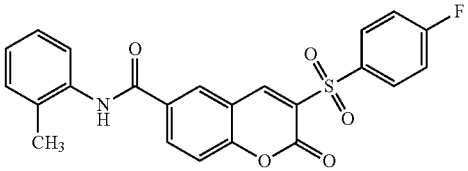

-continued

Compound C161
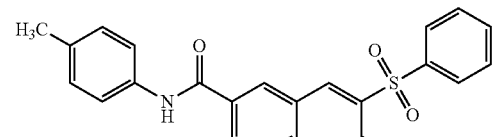

Compound C164
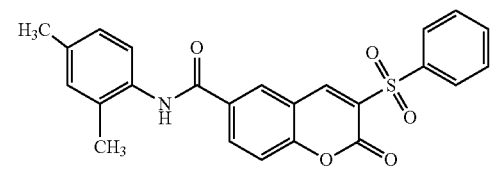

Compound C175
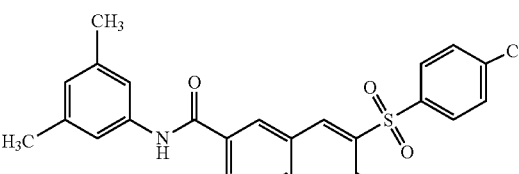

Compound C177
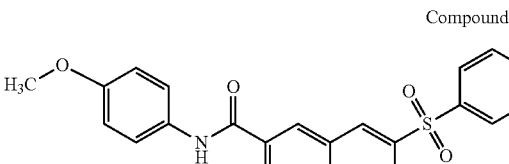

Compound C180
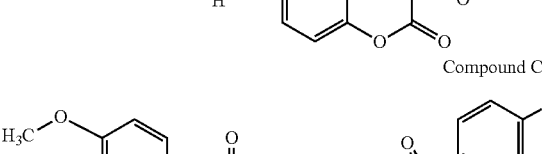

Further results of the testing of these compounds are shown in the tables below. Each compound shows results based on the different identities of the R1 moiety.

For example, compounds of Formula (Ia) and (Ib) were tested with different moieties as R1, and the results are shown below in Table 3:

TABLE 3

| ID NUMBER | R1 | Firefly, cmpd/DMSO | | Renilla, cmpd/DMSO | | Firefly_pGL, cmpd/DMSO | |
| --- | --- | --- | --- | --- | --- | --- | --- |
| | | repeat 1 | repeat 2 | repeat 1 | repeat 2 | repeat 1 | repeat 2 |
| C100 | 4-CH3 | 2.0 | 1.9 | 1.6 | 1.3 | 1.3 | 1.1 |
| C101 | 4-OMe | 4.5 | 4.7 | 1.8 | 2.0 | 1.2 | 1.3 |
| C102 | 4-Br | 13.0 | 15.3 | 5.8 | 6.1 | 2.3 | 2.5 |
| C103 | 4-t-Bu | 2.8 | 1.4 | 1.9 | 1.7 | 1.3 | 1.4 |
| C104 | 3,4-di-Me | 3.1 | 4.4 | 1.7 | 1.8 | 2.3 | 1.2 |
| C105 | 4-Cl | 5.7 | 4.8 | 1.7 | 2.3 | 1.5 | 1.8 |
| C106 | 3,4-di-Cl | 1.4 | 1.3 | 1.8 | 5.8 | 1.0 | 1.1 |
| C107 | 3-Cl-4-F | 11.0 | 11.0 | 8.7 | 6.5 | 1.7 | 2.1 |
| C108 | 2-F | 7.9 | 7.3 | 3.0 | 2.8 | 1.3 | 1.5 |
| C109 | 3-Cl | 9.2 | 10.3 | 3.4 | 3.3 | 3.5 | 3.4 |
| C110 | 3-CH3-4-F | 7.6 | 7.2 | 2.3 | 2.1 | 1.7 | 2.0 |

In further embodiments, the present technology is directed to compounds of Formula (II):

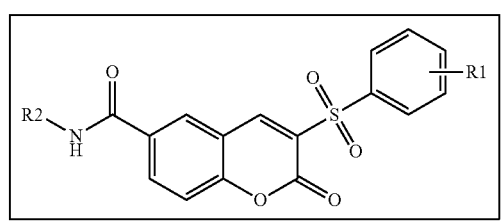

(II)

wherein any of R1 and R2 are C, H, N, O, S, a halogen, an alkyl group, a substituted alkyl group, a cyclic alkyl group, an aryl group, a substituted aryl group, a heterocyclic group, an ester, an aldehyde, a ketone, a carboxylic acid, an amide, an amine, an ether, a thiol or a nitrile.

In certain embodiments, any of R1 and R2 can be any of the moieties listed below in Tables 4 and 5. Various compounds of Formula (II) were tested with different moieties as R1 and R2, and the results are shown below in Tables 4 and 5:

TABLE 4

| ID NUMBER | R2 | R1 | Firefly, cmpd/DMSO | | Renilla, cmpd/DMSO | | Firefly_pGL, cmpd/DMSO | |
| --- | --- | --- | --- | --- | --- | --- | --- | --- |
| | | | repeat 1 | repeat 2 | repeat 1 | repeat 2 | repeat 1 | repeat 2 |
| C111 | PhCH2CH2 | H | 29.8 | 35.9 | 29.4 | 30.8 | 3.7 | 3.9 |
| C112 | PhCH2CH2 | 4-CH3 | 11.7 | 10.1 | 5.6 | 5.1 | 2.5 | 2.8 |
| C113 | PhCH2CH2 | 4-F | 5.8 | 7.0 | 10.2 | 10.8 | 2.2 | 3.2 |
| C114 | PhCH2Ch2 | 4-Cl | 4.5 | 4.7 | 4.0 | 2.9 | 2.3 | 1.6 |
| C115 | PhCH2 | H | 6.8 | 21.9 | 4.8 | 10.9 | 6.2 | 7.2 |
| C116 | 4-CH3C6H4CH2 | 4-Cl | 8.6 | 9.0 | 9.8 | 9.9 | 2.1 | 2.0 |
| C117 | 4-OMeC6H4CH2 | 4-F | 17.3 | 24.1 | 28.1 | 35.6 | 3.9 | 4.5 |
| C118 | 4-F-C6H4CH2 | 4-F | 13.5 | 17.1 | 11.8 | 14.8 | 2.4 | 2.7 |
| C119 | 4-F-C6H4CH2 | 4-Cl | 18.4 | 16.2 | 27.8 | 27.6 | 2.0 | 2.2 |
| C120 | 2-CF3C6H4 | 4-F | 4.5 | 6.3 | 15.2 | 18.6 | 2.9 | 3.3 |
| C121 | 3,4-di-MeO-C6H3 | 4-CH3 | 9.0 | 21.5 | 18.6 | 40.1 | 9.1 | 8.8 |
| C122 | 3,4-di-MeO-C6H3 | 4-Cl | 4.4 | 5.7 | 14.8 | 12.8 | 5.3 | 4.8 |
| C123 | 2-MeO-C6H4 | H | 17.7 | 16.8 | 31.9 | 31.7 | 8.2 | 10.6 |
| C124 | 2-MeO-C6H4 | 4-F | 25.5 | 29.8 | 50.0 | 51.4 | 6.6 | 6.7 |
| C125 | 2-MeO-C6H4 | 4-Cl | 28.0 | 24.5 | 30.4 | 33.8 | 2.5 | 2.7 |
| C126 | 3-MeO-C6H4 | 4-CH3 | 45.1 | 44.8 | 43.5 | 42.2 | 4.8 | 4.3 |

TABLE 4-continued

| ID NUMBER | R2 | R1 | Firefly, cmpd/DMSO repeat 1 | repeat 2 | Renilla, cmpd/DMSO repeat 1 | repeat 2 | Firefly_pGL, cmpd/DMSO repeat 1 | repeat 2 |
|---|---|---|---|---|---|---|---|---|
| C127 | 3-MeO-C6H4 | 4-F | 36.7 | 56.2 | 43.1 | 43.5 | 8.3 | 8.0 |
| C128 | 3-Cl-C6H4 | 4-F | 1.7 | 5.2 | 1.7 | 10.1 | 4.4 | 5.4 |
| C129 | 4-Cl-C6H4 | 4-F | 0.9 | 1.2 | 1.0 | 0.7 | 3.3 | 4.5 |
| C130 | 3.5-di-MeO-C6H3 | H | 2.3 | 3.4 | 2.2 | 6.4 | 6.4 | 10.2 |
| C131 | 3.5-di-MeO-C6H3 | 4-CH3 | 9.5 | 15.3 | 30.8 | 38.2 | 4.8 | 4.7 |
| C132 | 3.5-di-MeO-C6H3 | 4-F | 1.4 | 1.4 | 6.7 | 2.4 | 4.3 | 6.8 |
| C133 | 3.5-di-MeO-C6H3 | 4-Cl | 2.1 | 4.3 | 9.9 | 12.6 | 3.2 | 2.6 |
| C134 | 2,3-di-MeC6H3 | 4-CH3 | 38.1 | 31.9 | 21.0 | 18.9 | 3.7 | 5.4 |
| C135 | 2,3-di-MeC6H3 | 4-F | 5.6 | 4.9 | 19.8 | 18.6 | 1.9 | 3.1 |
| C136 | 2,3-di-MeC6H3 | 4-Cl | 22.1 | 25.8 | 12.5 | 14.9 | 2.9 | 3.0 |

TABLE 5

| ID NUMBER | R2 | R1 | Firefly, cmpd/DMSO repeat 1 | repeat 2 | Renilla, cmpd/DMSO repeat 1 | repeat 2 | Firefly_pGL, cmpd/DMSO repeat 1 | repeat 2 |
|---|---|---|---|---|---|---|---|---|
| C159 | 4-F-C6H4 | 4-F | 0.9 | 1.2 | 0.1 | 0.3 | 1.8 | 2.4 |
| C160 | 2-me-C6H4 | 4-F | 22.9 | 20.2 | 9.5 | 8.2 | 3.2 | 2.7 |
| C161 | 4-Me-C6H4 | H | 35.4 | 39.0 | 28.6 | 27.7 | 4.0 | 5.1 |
| C162 | 4-Me-C6H4 | 4-CH3 | 20.9 | 20.6 | 37.9 | 35.8 | 3.7 | 4.1 |
| C163 | 4-Me-C6H4 | 4-F | 2.0 | 5.2 | 6.9 | 15.8 | 5.5 | 5.0 |
| C164 | 2,4-di-MeC6H3 | H | 29.3 | 19.6 | 13.8 | 8.9 | 3.1 | 2.8 |
| C165 | 2,4-di-MeC6H3 | 4-CH3 | 4.2 | 4.0 | 4.7 | 4.6 | 1.4 | 1.4 |
| C166 | 2,4-di-MeC6H3 | 4-Cl | 3.4 | 4.2 | 2.9 | 2.9 | 1.4 | 1.7 |
| C167 | 3,4-di-MeC6H3 | H | 1.0 | 0.7 | 0.2 | 0.2 | 0.9 | 0.9 |
| C168 | 3,4-di-MeC6H3 | 4-CH3 | 11.8 | 11.4 | 14.8 | 14.0 | 2.4 | 1.6 |
| C169 | 3,4-di-MeC6H3 | 4-F | 8.8 | 10.6 | 9.9 | 10.9 | 2.0 | 1.9 |
| C170 | 3,4-di-MeC6H3 | 4-Cl | 1.7 | 1.6 | 0.2 | 0.3 | 0.7 | 1.0 |
| C171 | 3-MeC6H4 | 4-CH3 | 6.4 | 4.2 | 15.4 | 9.8 | 2.0 | 2.3 |
| C172 | 3-MeC6H4 | 4-F | 30.4 | 32.8 | 44.9 | 37.0 | 3.5 | 4.7 |
| C173 | 3-MeC6H4 | 4-Cl | 9.8 | 6.9 | 19.8 | 19.5 | 2.3 | 2.4 |
| C174 | 3,5-di-MeC6H3 | H | 5.8 | 14.3 | 16.0 | 28.3 | 4.3 | 6.0 |
| C175 | 3,5-di-MeC6H3 | 4-CH3 | 13.2 | 11.9 | 10.5 | 12.0 | 2.5 | 1.9 |
| C176 | 3,5-di-MeC6H3 | 4-F | 3.7 | 9.6 | 19.0 | 29.1 | 3.9 | 3.8 |
| C177 | 4-MeOC6H4 | H | 17.4 | 8.2 | 6.7 | 4.6 | 1.7 | 1.3 |
| C178 | 4-MeOC6H4 | 4-CH3 | 15.2 | 16.9 | 27.7 | 28.2 | 3.5 | 4.4 |
| C179 | 4-MeOC6H4 | 4-F | 8.7 | 10.1 | 11.9 | 10.5 | 2.4 | 2.5 |
| C180 | 4-MeOC6H4 | 4-Cl | 34.0 | 34.5 | 30.9 | 30.0 | 2.5 | 2.7 |
| C181 | 2-EtOC6H4 | 4-F | 10.4 | 13.5 | 14.6 | 21.4 | 2.2 | 1.7 |

In further embodiments, the present technology is direct to compounds of Formula (III):

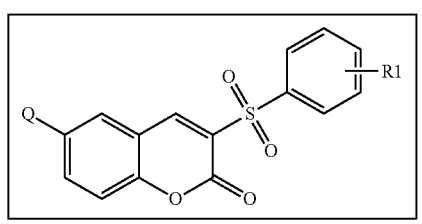

(III)

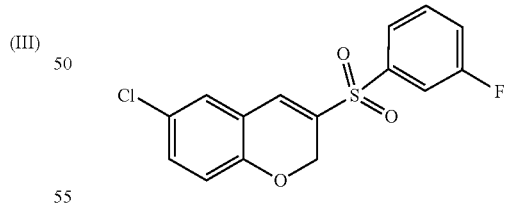

Compound C182 wherein any of Q and R1 are C, H, N, O, S, a halogen, an alkyl group, a substituted alkyl group, a cyclic alkyl group, an aryl group, a substituted aryl group, a heterocyclic group, an ester, an aldehyde, a ketone, a carboxylic acid, an amide, an amine, an ether, a thiol or a nitrile.

Various compounds of Formula (III) were tested with different moieties as R1 and Q, and t. These include the following:

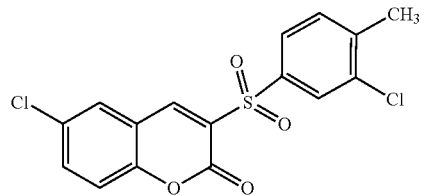

Compound C188

Compound C194
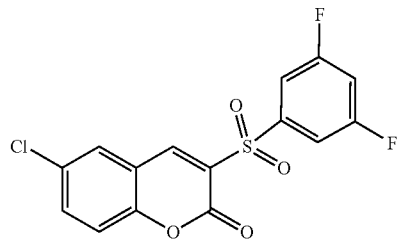

Compound C195
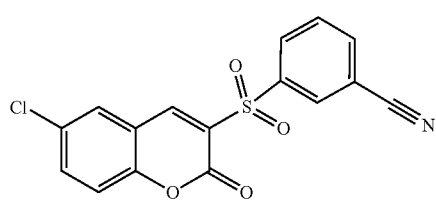

Compound C197
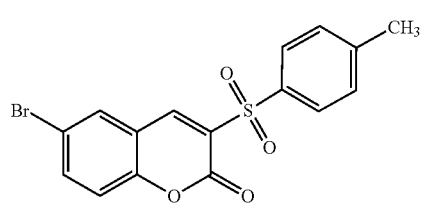

Compound C200
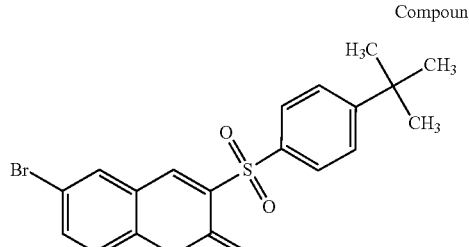

Compound C202
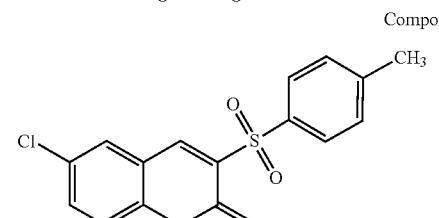

Compound C209
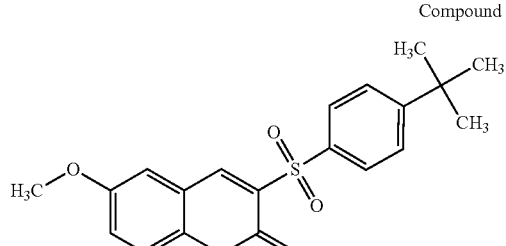

Compound C210
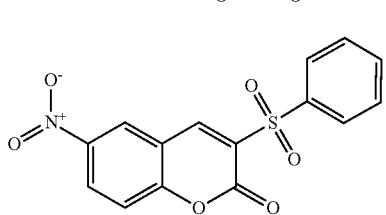

Compound C213
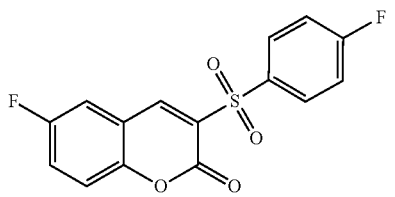

Compound C218
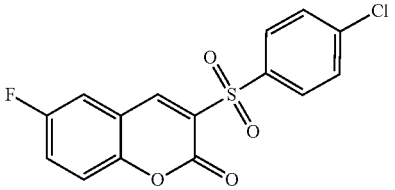

Compound C220
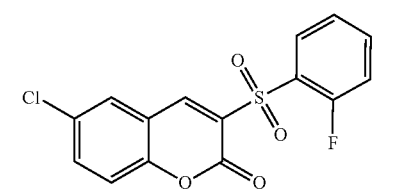

Compound C222
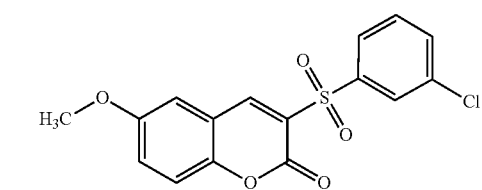

The results of the tests are shown below in Tables 6-8:

TABLE 6

| ID | | | Firefly, cmpd/ DMSO | | Renilla, cmpd/ DMSO | | Firefly_pGL, cmpd/ DMSO | |
|---|---|---|---|---|---|---|---|---|
| NUMBER | Q | R1 | repeat 1 | repeat 2 | repeat 1 | repeat 2 | repeat 1 | repeat 2 |
| C182 | Cl | 3-F | 16.2 | 17.3 | 15.1 | 13.2 | 2.0 | 2.1 |
| C183 | Br | 3-F | 1.2 | 1.2 | 3.1 | 2.4 | 1.1 | 1.2 |
| C184 | Cl | 3-MeO | 1.1 | 1.4 | 1.2 | 1.8 | 0.9 | 1.1 |
| C185 | Br | 3-MeO | 2.6 | 2.4 | 0.1 | 0.3 | 0.8 | 1.2 |
| C186 | Cl | 3,5-diMe | 1.0 | 6.9 | 0.4 | 18.8 | 1.2 | 1.7 |
| C187 | Br | 3,5-diMe | 0.8 | 0.7 | 1.0 | 0.8 | 0.9 | 1.1 |
| C188 | Cl | 3-Cl-4-Me | 9.4 | 8.7 | 7.6 | 6.9 | 1.8 | 1.8 |
| C189 | Br | 3-Cl-4-Me | 2.8 | 2.2 | 2.7 | 2.4 | 1.2 | 1.1 |
| C190 | F | 3,5-diMe | 2.1 | 2.5 | 1.4 | 1.4 | 1.3 | 1.1 |
| C191 | Cl | 3-Cl | 8.6 | 12.8 | 35.8 | 30.6 | 1.7 | 2.2 |
| C192 | Br | 3-Cl | 1.8 | 2.4 | 9.6 | 9.5 | 1.7 | 2.0 |
| C193 | Br | 3,5-diF | 1.8 | 1.9 | 6.5 | 14.6 | 1.5 | 1.8 |
| C194 | Cl | 3,5-diF | 10.6 | 6.3 | 7.2 | 6.2 | 1.3 | 1.3 |
| C195 | Cl | 3-CN | 38.7 | 29.4 | 22.8 | 10.1 | 3.7 | 5.1 |
| C196 | Br | 3-CN | 3.8 | 3.4 | 13.6 | 18.8 | 2.3 | 2.9 |
| C197 | Br | 4-Me | 17.6 | 14.8 | 16.1 | 13.7 | 2.6 | 2.5 |
| C198 | Br | 4-F | 1.0 | 0.8 | 8.8 | 5.3 | 1.2 | 1.1 |
| C199 | Br | 4-MeO | 19.3 | 16.1 | 25.9 | 23.2 | 2.2 | 2.9 |
| C200 | Br | 4-t-Bu | 11.0 | 8.1 | 5.8 | 10.4 | 1.6 | 1.9 |
| C201 | Cl | H | 6.1 | 5.3 | 8.8 | 8.2 | 1.8 | 2.4 |
| C202 | Cl | 4-Me | 15.7 | 14.1 | 8.3 | 8.9 | 2.6 | 2.3 |
| C203 | Cl | 4-MeO | 9.5 | 15.5 | 20.2 | 22.8 | 2.1 | 2.7 |
| C204 | Cl | 4-Br | 5.0 | 5.8 | 28.9 | 27.9 | 1.5 | 1.8 |
| C205 | Cl | 4-t-Bu | 6.9 | 6.0 | 9.7 | 8.8 | 1.5 | 1.4 |
| C206 | MeO | H | 2.1 | 1.8 | 1.1 | 1.1 | 1.2 | 1.4 |
| C207 | MeO | 4-MeO | 2.5 | 2.8 | 1.2 | 0.7 | 1.5 | 1.4 |

TABLE 6-continued

| ID NUMBER | Q | R1 | Firefly, cmpd/DMSO repeat 1 | Firefly, cmpd/DMSO repeat 2 | Renilla, cmpd/DMSO repeat 1 | Renilla, cmpd/DMSO repeat 2 | Firefly_pGL, cmpd/DMSO repeat 1 | Firefly_pGL, cmpd/DMSO repeat 2 |
|---|---|---|---|---|---|---|---|---|
| C208 | MeO | 4-Br | 0.8 | 0.9 | 1.0 | 1.1 | 1.1 | 1.0 |
| C209 | MeO | 4-t-Bu | 3.1 | 4.2 | 0.9 | 1.1 | 1.3 | 1.1 |
| C210 | NO2 | H | 22.8 | 14.3 | 15.0 | 9.8 | 2.4 | 2.1 |
| C211 | NO2 | 4-Me | 5.8 | 17.7 | 18.1 | 18.9 | 3.3 | 4.0 |

TABLE 7

| ID NUMBER | Q | R1 | Firefly, cmpd/DMSO repeat 1 | Firefly, cmpd/DMSO repeat 2 | Renilla, cmpd/DMSO repeat 1 | Renilla, cmpd/DMSO repeat 2 | Firefly_pGL, cmpd/DMSO repeat 1 | Firefly_pGL, cmpd/DMSO repeat 2 |
|---|---|---|---|---|---|---|---|---|
| C137 | NO2 | 4-F | 22.6 | 23.4 | 17.6 | 15.7 | 2.7 | 2.9 |
| C138 | NO2 | 4-Br | 10.0 | 16.6 | 18.3 | 18.7 | 2.9 | 2.8 |
| C139 | NO2 | 4-t-Bu | 6.6 | 6.4 | 7.0 | 6.7 | 1.4 | 1.8 |
| C140 | Cl | 4-i-Pr | 12.8 | 12.0 | 12.4 | 11.8 | 2.4 | 2.6 |
| C141 | MeO | 4-i-Pr | 1.6 | 1.6 | 1.2 | 1.3 | 1.4 | 1.1 |
| C142 | Br | 3,4-diMe | 1.2 | 1.7 | 1.4 | 9.8 | 1.1 | 1.6 |
| C143 | Cl | 3,4-diMe | 15.2 | 14.5 | 19.0 | 17.7 | 2.6 | 2.4 |
| C144 | MeO | 3,4-diMe | 0.9 | 0.8 | 3.4 | 1.1 | 1.0 | 0.9 |
| C145 | NO2 | 3,4-diMe | 11.2 | 24.4 | 20.5 | 20.5 | 3.3 | 3.5 |
| C146 | Br | 4-Cl | 1.5 | 0.9 | 0.6 | 3.2 | 0.8 | 1.2 |
| C147 | Cl | 4-Cl | 2.6 | 2.9 | 1.8 | 5.0 | 1.5 | 1.4 |
| C148 | MeO | 4-Cl | 1.0 | 0.9 | 0.6 | 1.3 | 1.1 | 1.0 |
| C149 | NO2 | 4-Cl | 7.8 | 15.3 | 15.3 | 19.7 | 2.7 | 2.3 |
| C150 | Br | 3,4-diCl | 8.5 | 7.9 | 12.2 | 11.5 | 1.7 | 1.7 |
| C151 | Cl | 3,4-diCl | 3.6 | 5.5 | 15.1 | 15.3 | 1.1 | 1.3 |
| C152 | OMe | 3,4-di-Cl | 4.5 | 3.1 | 4.4 | 4.2 | 1.3 | 1.1 |
| C153 | NO2 | 3,4-diCl | 6.5 | 9.0 | 13.6 | 16.2 | 1.3 | 1.6 |
| C154 | Br | 3,4-diMeO | 35.4 | 35.4 | 25.6 | 19.5 | 4.0 | 3.8 |
| C155 | Cl | 3,4-diMeO | 37.3 | 33.3 | 19.3 | 15.4 | 3.5 | 3.0 |
| C156 | MeO | 3,4-diMeO | 1.0 | 1.0 | 0.9 | 1.0 | 1.0 | 1.0 |
| C157 | NO2 | 3,4-diMeO | 24.9 | 20.4 | 6.9 | 6.0 | 2.3 | 2.1 |
| C158 | MeO | 3-Cl-4-F | 1.5 | 1.2 | 2.7 | 2.4 | 1.1 | 1.2 |

TABLE 8

| ID NUMBER | Q | R1 | Firefly, cmpd/DMSO repeat 1 | Firefly, cmpd/DMSO repeat 2 | Renilla, cmpd/DMSO repeat 1 | Renilla, cmpd/DMSO repeat 2 | Firefly_pGL, cmpd/DMSO repeat 1 | Firefly_pGL, cmpd/DMSO repeat 2 |
|---|---|---|---|---|---|---|---|---|
| C212 | F | H | 1.7 | 1.9 | 1.7 | 1.7 | 1.0 | 1.4 |
| C213 | F | 4-F | 14.0 | 13.6 | 9.0 | 8.1 | 1.2 | 1.7 |
| C214 | F | 4-MeO | 1.9 | 1.9 | 1.7 | 1.7 | 1.0 | 1.4 |
| C215 | F | 4-Br | 11.6 | 13.8 | 14.8 | 15.1 | 2.1 | 2.2 |
| C216 | F | 4-t-Bu | 1.3 | 1.0 | 1.3 | 1.0 | 1.3 | 1.2 |
| C217 | F | 3-CH3-4-F | 1.8 | 1.4 | 1.8 | 1.5 | 0.9 | 1.4 |
| C218 | F | 4-Cl | 18.2 | 19.1 | 11.9 | 10.2 | 1.9 | 2.0 |
| C219 | Br | 2-F | 1.3 | 2.5 | 8.7 | 23.5 | 2.0 | 2.3 |
| C220 | Cl | 2-F | 10.4 | 6.5 | 8.1 | 6.7 | 1.3 | 1.5 |
| C221 | MeO | 2-F | 1.3 | 0.9 | 1.3 | 1.3 | 1.4 | 1.7 |
| C222 | MeO | 3-Cl | 4.5 | 3.7 | 2.3 | 1.8 | 1.0 | 1.3 |
| C223 | Br | 3-CH3-4-F | 4.5 | 5.1 | 3.7 | 5.9 | 1.9 | 1.4 |
| C224 | Cl | 3-CH3-4-F | 6.6 | 11.4 | 18.2 | 26.9 | 2.8 | 3.1 |
| C225 | MeO | 3-CH3-4-F | 1.5 | 3.1 | 1.2 | 1.4 | 1.3 | 1.5 |

In further embodiments, the present technology is directed to compounds of Formula (IV):

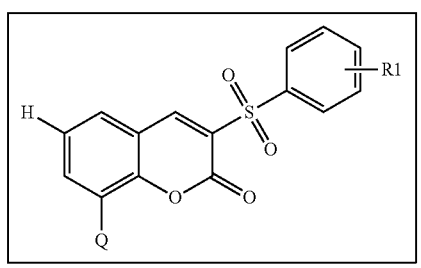

(IV)

wherein any of Q and R1 are C, H, N, O, S, a halogen, an alkyl group, a substituted alkyl group, a cyclic alkyl group, an aryl group, a substituted aryl group, a heterocyclic group, an ester, an aldehyde, a ketone, a carboxylic acid, an amide, an amine, an ether, a thiol or a nitrile.

Various compounds of Formula (IV) were tested with different moieties as Q and R1. These included the following:

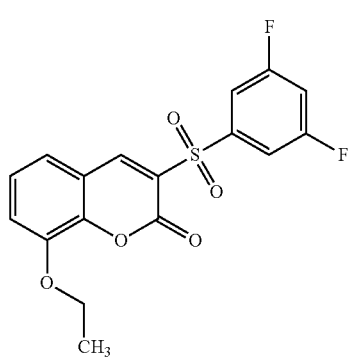

Compound C230

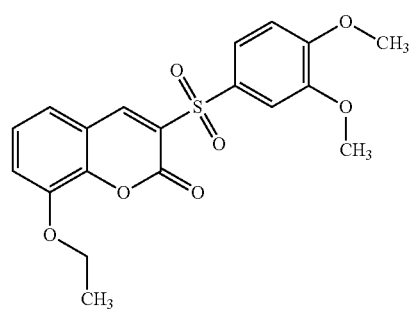

Compound C248

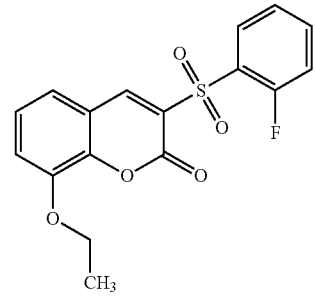

Compound C254

Compound C256

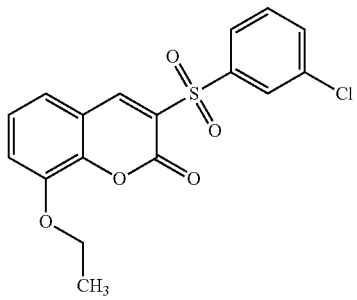

The results are shown below in Table 9:

TABLE 9

| ID NUMBER | Q | R1 | Firefly, cmpd/DMSO repeat 1 | Firefly, cmpd/DMSO repeat 2 | Renilla, cmpd/DMSO repeat 1 | Renilla, cmpd/DMSO repeat 2 | Firefly_pGL, cmpd/DMSO repeat 1 | Firefly_pGL, cmpd/DMSO repeat 2 |
|---|---|---|---|---|---|---|---|---|
| C226 | OMe | 3-OMe | 1.1 | 1.0 | 0.5 | 1.1 | 1.2 | 1.3 |
| C227 | OMe | 3,5-di-Me | 1.0 | 1.3 | 1.1 | 1.1 | 1.0 | 1.1 |
| C228 | OMe | 3-Cl-4-Me | 1.0 | 1.3 | 2.2 | 2.1 | 1.1 | 1.0 |
| C229 | OMe | 3,5-di-F | 2.9 | 1.8 | 1.5 | 1.3 | 1.2 | 0.8 |
| C230 | OEt | 3,5-di-F | 12.5 | 8.3 | 4.5 | 3.8 | 1.8 | 1.5 |
| C231 | OMe | 4-Me | 0.7 | 0.9 | 1.3 | 1.1 | 1.1 | 1.0 |
| C232 | OMe | 4-OMe | 1.0 | 0.9 | 1.0 | 1.0 | 1.0 | 0.9 |
| C233 | OMe | 4-Br | 2.8 | 2.1 | 1.1 | 1.3 | 1.3 | 1.2 |
| C234 | OMe | 4-t-Bu | 2.2 | 1.8 | 4.3 | 2.7 | 1.0 | 1.1 |
| C235 | OMe | H | 1.0 | 1.2 | 1.0 | 1.1 | 1.0 | 0.9 |
| C236 | OEt | CH3 | 4.4 | 4.9 | 3.1 | 3.2 | 1.6 | 1.6 |
| C237 | OEt | 4-F | 3.5 | 2.9 | 1.5 | 1.3 | 1.3 | 1.3 |
| C238 | OEt | 4-OMe | 1.3 | 1.4 | 1.5 | 1.0 | 1.3 | 1.2 |
| C239 | OEt | 4-Br | 1.4 | 2.2 | 8.4 | 17.2 | 1.2 | 1.1 |
| C240 | OEt | 4-t-Bu | 1.5 | 0.9 | 1.5 | 1.5 | 0.9 | 1.1 |
| C241 | OMe | 4-i-Pr | 2.1 | 2.7 | 1.5 | 1.9 | 1.2 | 1.8 |
| C242 | OMe | 3,4-di-Me | 1.1 | 1.1 | 0.9 | 1.1 | 1.1 | 1.1 |
| C243 | OEt | 3,4-di-Me | 2.0 | 3.3 | 2.3 | 2.3 | 1.4 | 1.9 |
| C244 | OEt | 4-Cl | 9.7 | 14.1 | 19.8 | 18.4 | 1.7 | 1.9 |
| C245 | OMe | 3,4-di-Cl | 1.9 | 1.3 | 1.7 | 1.8 | 1.1 | 1.3 |
| C246 | OEt | 3,4-di-Cl | 7.4 | 6.5 | 7.6 | 8.4 | 1.6 | 1.9 |
| C247 | OMe | 3,4-di-OMe | 2.2 | 1.6 | 1.7 | 1.5 | 1.3 | 1.1 |
| C248 | OEt | 3,4-di-OMe | 8.6 | 4.3 | 2.8 | 1.9 | 1.4 | 1.4 |
| C249 | OMe | 2,5-di-OMe | 1.4 | 1.5 | 1.0 | 1.1 | 1.1 | 1.3 |
| C250 | OMe | 3-Cl-4-F | 1.2 | 1.8 | 1.7 | 1.9 | 1.1 | 1.1 |
| C251 | OEt | 3-Cl-4-F | 2.1 | 1.9 | 2.4 | 2.0 | 1.0 | 0.9 |
| C252 | OEt | 4-OEt | 3.2 | 2.4 | 1.4 | 1.6 | 1.4 | 1.3 |
| C253 | OMe | 2-F | 2.5 | 2.7 | 1.5 | 1.2 | 1.3 | 1.2 |
| C254 | OEt | 2-F | 7.6 | 5.1 | 2.7 | 2.5 | 1.5 | 1.4 |
| C255 | OMe | 3-Cl | 1.5 | 1.5 | 1.2 | 1.1 | 1.3 | 1.0 |
| C256 | OEt | 3-Cl | 11.5 | 7.9 | 5.1 | 3.5 | 2.0 | 2.4 |
| C257 | OMe | 3-Me-4-F | 2.1 | 1.6 | 1.2 | 1.1 | 0.8 | 1.0 |
| C258 | OEt | 3-Me-4-F | 1.5 | 1.8 | 1.3 | 1.5 | 1.3 | 1.5 |

In further embodiments, the present technology is directed to compounds of Formula (V):

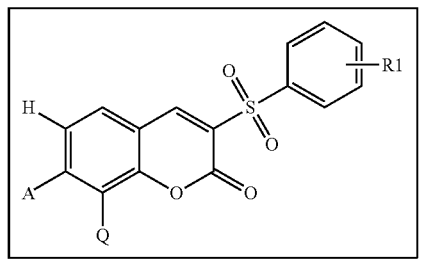

(V)

wherein any of A and R1 are C, H, N, O, S, a halogen, an alkyl group, a substituted alkyl group, a cyclic alkyl group, an aryl group, a substituted aryl group, a heterocyclic group, an ester, an aldehyde, a ketone, a carboxylic acid, an amide, an amine, an ether, a thiol or a nitrile.

Various compounds of Formula (V) were tested with different moieties as A and R1, and the results are shown below in Table 10:

TABLE 10

| ID NUMBER | A | R | Firefly, cmpd/DMSO repeat 1 | Firefly, cmpd/DMSO repeat 2 | Renilla, cmpd/DMSO repeat 1 | Renilla, cmpd/DMSO repeat 2 | Firefly_pGL, cmpd/DMSO repeat 1 | Firefly_pGL, cmpd/DMSO repeat 2 |
|---|---|---|---|---|---|---|---|---|
| C259 | OMe | 3-OMe | 1.3 | 1.9 | 1.2 | 1.2 | 0.9 | 1.1 |
| C260 | OMe | 3,5-di-Me | 1.0 | 1.0 | 1.4 | 1.3 | 1.0 | 1.1 |
| C261 | OMe | 3-Cl-4-CH3 | 2.0 | 1.4 | 1.7 | 1.5 | 0.9 | 1.2 |
| C262 | OMe | 3,5-di-F | 1.8 | 2.2 | 1.4 | 1.2 | 1.4 | 1.3 |
| C263 | OMe | 3-CN | 1.8 | 1.7 | 1.4 | 1.3 | 1.2 | 1.0 |
| C264 | OMe | H | 1.1 | 0.8 | 1.2 | 1.2 | 0.9 | 1.0 |
| C265 | OMe | CH3 | 1.0 | 1.3 | 1.4 | 1.3 | 1.2 | 1.1 |
| C266 | OMe | OMe | 0.9 | 1.2 | 1.4 | 1.3 | 1.0 | 1.0 |
| C267 | OMe | 4-Br | 1.4 | 1.7 | 2.5 | 1.2 | 1.2 | 1.6 |
| C268 | OMe | 4-t-Bu | 2.8 | 3.1 | 1.3 | 2.1 | 0.9 | 1.2 |
| C269 | OMe | 4-t-Pr | 3.0 | 3.0 | 1.5 | 1.4 | 1.2 | 1.0 |
| C270 | OMe | 3,4-di-Me | 3.2 | 3.1 | 2.2 | 1.8 | 1.3 | 1.2 |
| C271 | OMe | 4-Cl | 2.2 | 1.2 | 2.3 | 2.1 | 1.6 | 1.6 |
| C272 | OMe | 3,4-di-Cl | 4.5 | 3.1 | 4.4 | 4.2 | 1.3 | 1.1 |
| C273 | OH | H | 2.0 | 1.5 | 1.6 | 2.0 | 1.0 | 1.2 |
| C274 | OMe | 3,4-di-OMe | 3.3 | 3.5 | 1.2 | 1.5 | 1.6 | 1.2 |
| C275 | OMe | 3-Cl-4-F | 2.6 | 2.5 | 2.3 | 1.9 | 1.2 | 1.3 |
| C276 | OH | 3-Cl-4-F | 1.2 | 1.3 | 2.3 | 1.9 | 0.9 | 1.0 |
| C277 | NEt2 | 4-Me | 3.4 | 2.9 | 1.5 | 0.9 | 1.0 | 1.3 |
| C278 | NEt2 | 4-Br | 2.4 | 3.0 | 1.5 | 1.7 | 1.0 | 1.2 |
| C279 | NEt2 | 4-Cl | 3.9 | 2.1 | 1.4 | 1.6 | 0.9 | 0.9 |
| C280 | OMe | 2-F | 0.6 | 0.6 | 1.4 | 1.4 | 0.9 | 1.2 |
| C281 | OMe | 3-Cl | 3.0 | 4.4 | 1.8 | 1.9 | 1.4 | 1.3 |
| C282 | OMe | 3-CH3-4-F | 0.7 | 1.1 | 1.5 | 1.7 | 1.4 | 2.0 |

In further embodiments, the present technology is directed to compounds of Formula (VI):

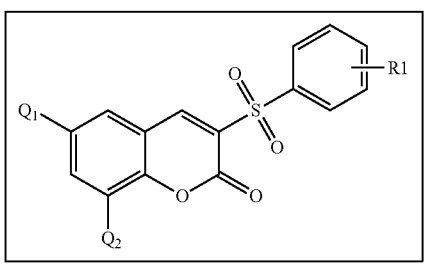

(VI)

wherein any of Q1, Q2 and R1 are C, H, N, O, S, a halogen, an alkyl group, a substituted alkyl group, a cyclic alkyl group, an aryl group, a substituted aryl group, a heterocyclic group, an ester, an aldehyde, a ketone, a carboxylic acid, an amide, an amine, an ether, a thiol or a nitrile.

Various compounds of Formula (VI) were tested with different moieties as Q1 and Q2. These included the following:

Compound C289

Compound C292

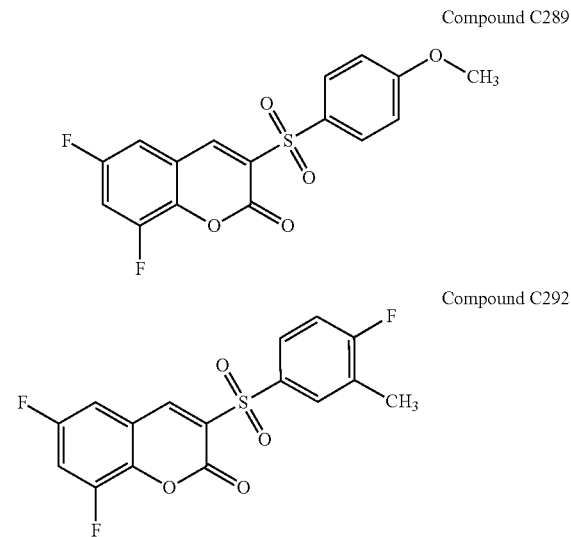

Compound C299

Compound C300

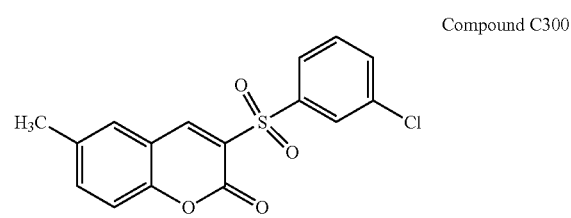

Compound C301

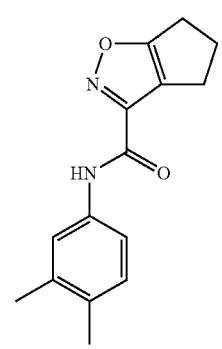

Compound C302

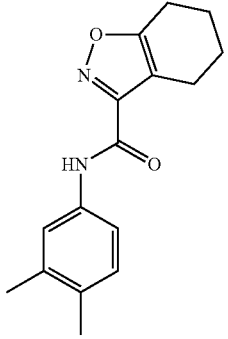

Compound C303

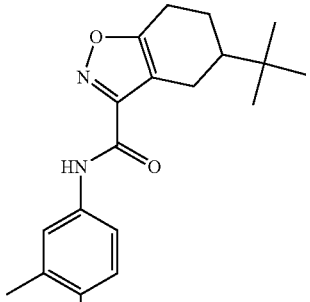

The results are shown below in Table 11:

TABLE 11

| ID | | | | Firefly, cmpd/ DMSO | | Renilla, cmpd/ DMSO | | Firefly_pGL, cmpd/ DMSO | |
|---|---|---|---|---|---|---|---|---|---|
| NUMBER | Q1 | Q2 | R1 | repeat 1 | repeat 2 | repeat 1 | repeat 2 | repeat 1 | repeat 2 |
| C283 | Br | Br | OMe | 1.0 | 1.3 | 0.1 | 0.2 | 1.0 | 0.9 |
| C284 | Br | Br | 4-i-Pr | 2.9 | 2.5 | 0.4 | 0.3 | 0.9 | 1.0 |
| C285 | Br | Br | 3,4-di-Me | 1.0 | 1.0 | 0.1 | 0.6 | 1.0 | 1.2 |
| C286 | Br | Br | 4-Cl | 2.3 | 2.4 | 0.3 | 0.9 | 0.8 | 1.1 |
| C287 | Br | Br | 3,4-di-Cl | 3.0 | 2.6 | 2.9 | 2.5 | 1.1 | 1.5 |
| C288 | F | F | H | 6.8 | 3.3 | 4.4 | 3.3 | 1.6 | 1.4 |
| C289 | F | F | OMe | 31.3 | 15.6 | 13.5 | 10.0 | 1.7 | 1.3 |
| C290 | F | F | 4-Br | 13.8 | 14.6 | 21.6 | 17.1 | 2.0 | 1.8 |
| C291 | F | F | 4-t-Bu | 0.9 | 0.8 | 0.1 | 0.2 | 0.7 | 0.7 |
| C292 | F | F | 3-Me-4-F | 18.3 | 14.8 | 15.6 | 13.4 | 1.7 | 1.7 |
| C293 | F | F | 4-Cl | 8.5 | 11.9 | 27.8 | 21.2 | 2.1 | 1.7 |
| C294 | Br | OMe | H | 16.5 | 16.5 | 36.0 | 27.5 | 2.4 | 2.9 |
| C295 | Br | OMe | 4-F | 4.0 | 4.6 | 4.3 | 3.6 | 1.8 | 1.6 |
| C296 | Br | OMe | 4-OMe | 6.0 | 7.8 | 14.9 | 14.1 | 2.2 | 2.0 |
| C297 | Br | OMe | 4-t-Bu | 1.5 | 2.6 | 2.0 | 6.9 | 1.4 | 1.3 |
| C298 | Br | OMe | 3-Me-4-F | 2.2 | 3.2 | 1.9 | 1.9 | 1.3 | 1.4 |

In certain embodiments, the technology is directed to compounds of Formulas (VII) or (VIII):

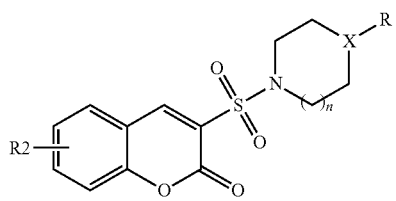

(VII)

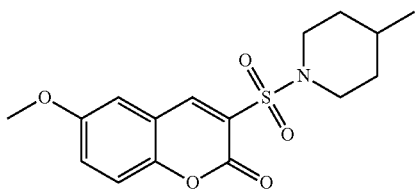

Compound C307

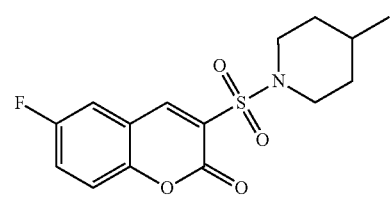

Compound C308

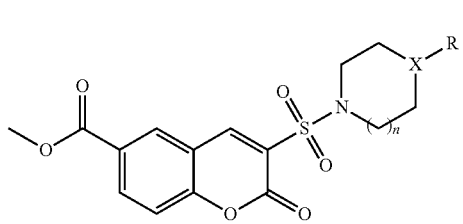

(VIII)

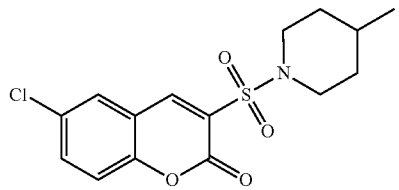

Compound C309

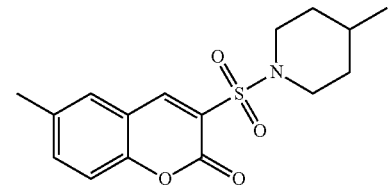

Compound C310 wherein any of X and R is: C, H, N, O, S, a halogen, an alkyl group, a substituted alkyl group, a cyclic alkyl group, an aryl group, a substituted aryl group, a heterocyclic group, an ester, an aldehyde, a ketone, a carboxylic acid, and amide, an amine, an ether, a thiol or a nitrile; and wherein n is an integer 1, 2, 3, 4, 5 or 6. In certain embodiments, the X-R moiety represents a benzene ring fused to the n-membered ring containing the N substitution, to create a bicyclic functional group; see, e.g., Compounds F41 through F47 below.

Exemplary compounds in accordance with these Formulas include the following:

Compound C304

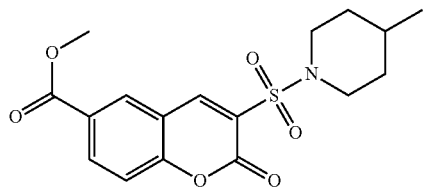

Compound C311

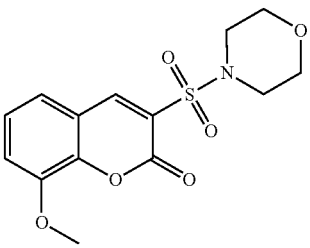

Compound C305

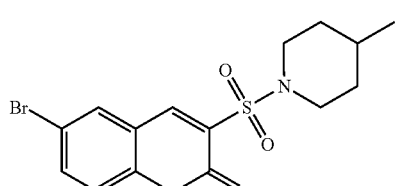

Compound C312

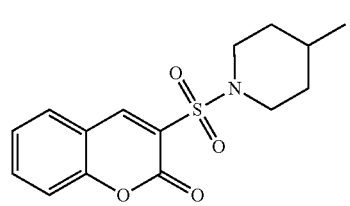

Compound C306

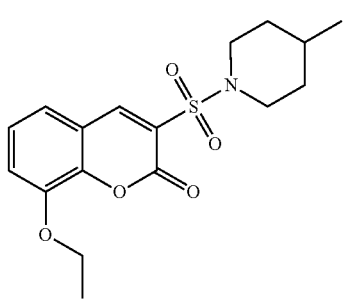

Compound C313

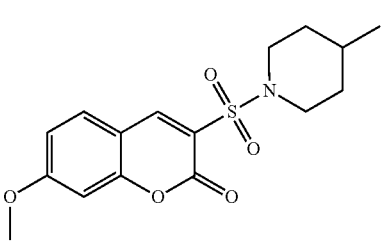

Compound C314
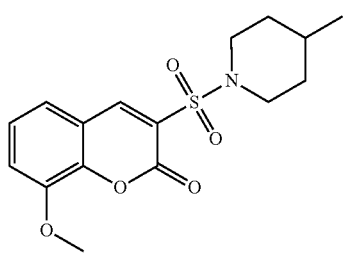
Compound F14
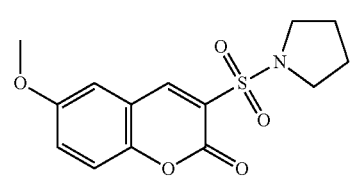
Compound F15
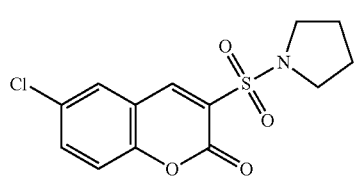
Compound F13
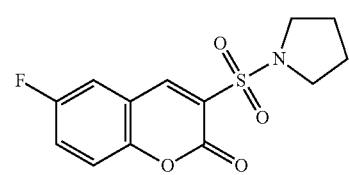
Compound F16
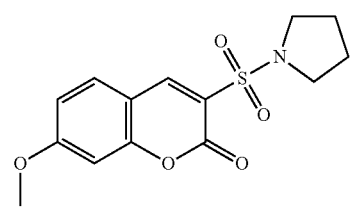
Compound F17
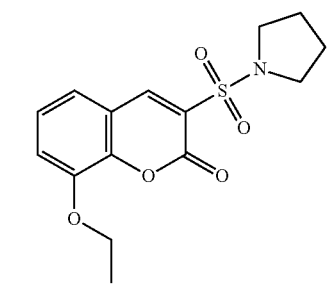
Compound F18
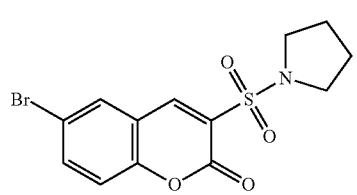
Compound F19
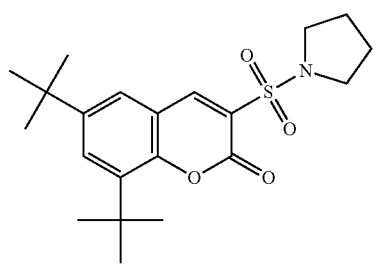
Compound F20
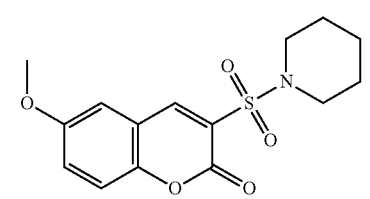
Compound F21
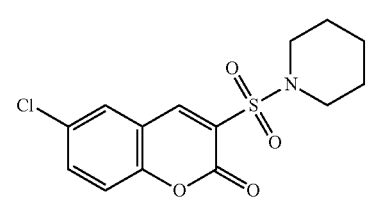
Compound F22
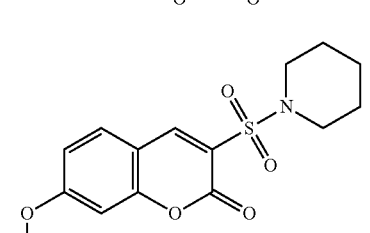
Compound F23
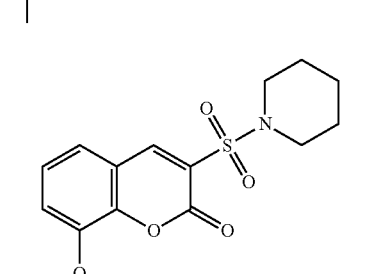
Compound F24
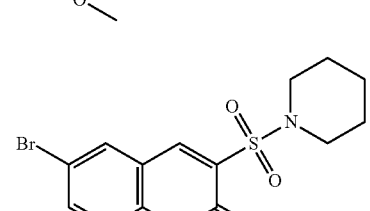
Compound F25
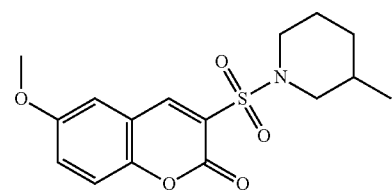

Compound F26
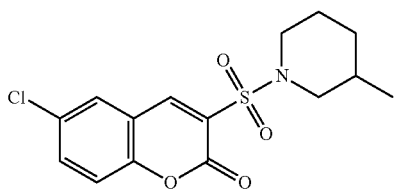
Compound F27
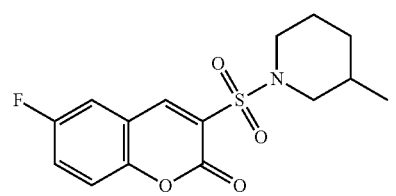
Compound F28
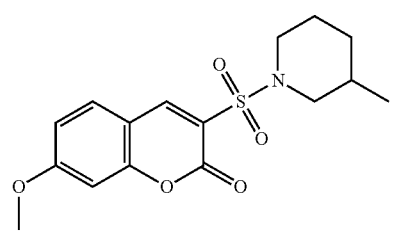
Compound F29
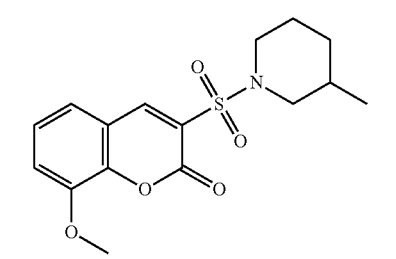
Compound F30
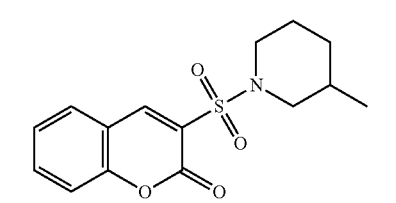
Compound F31
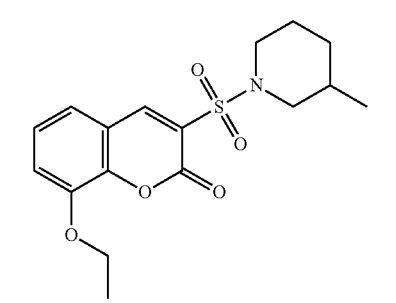
Compound F32
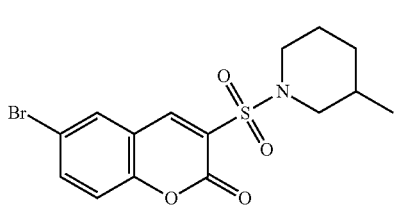
Compound F33
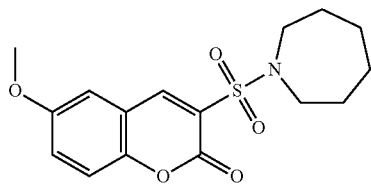
Compound F34
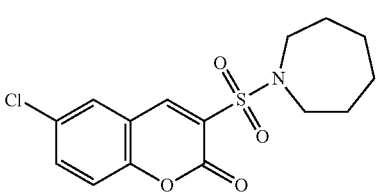
Compound F35
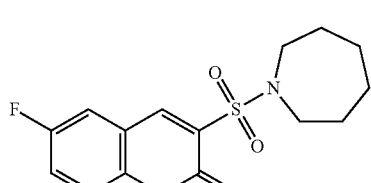
Compound F36
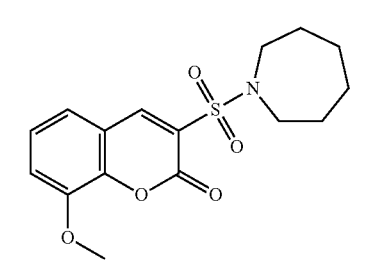
Compound F37
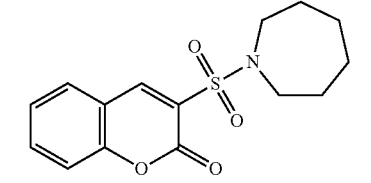
Compound F38
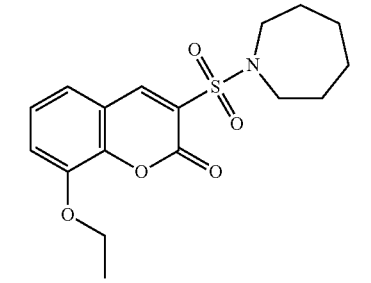
Compound F39
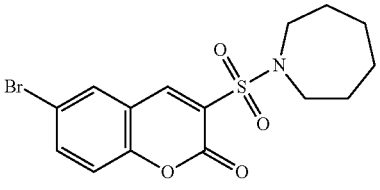

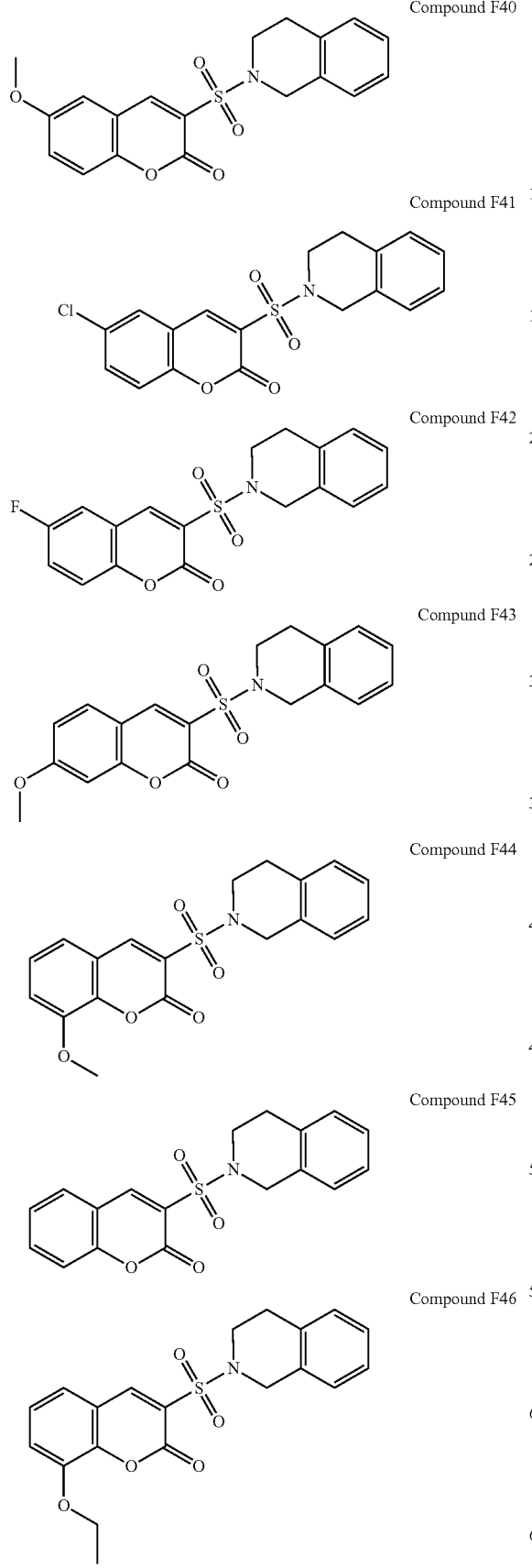
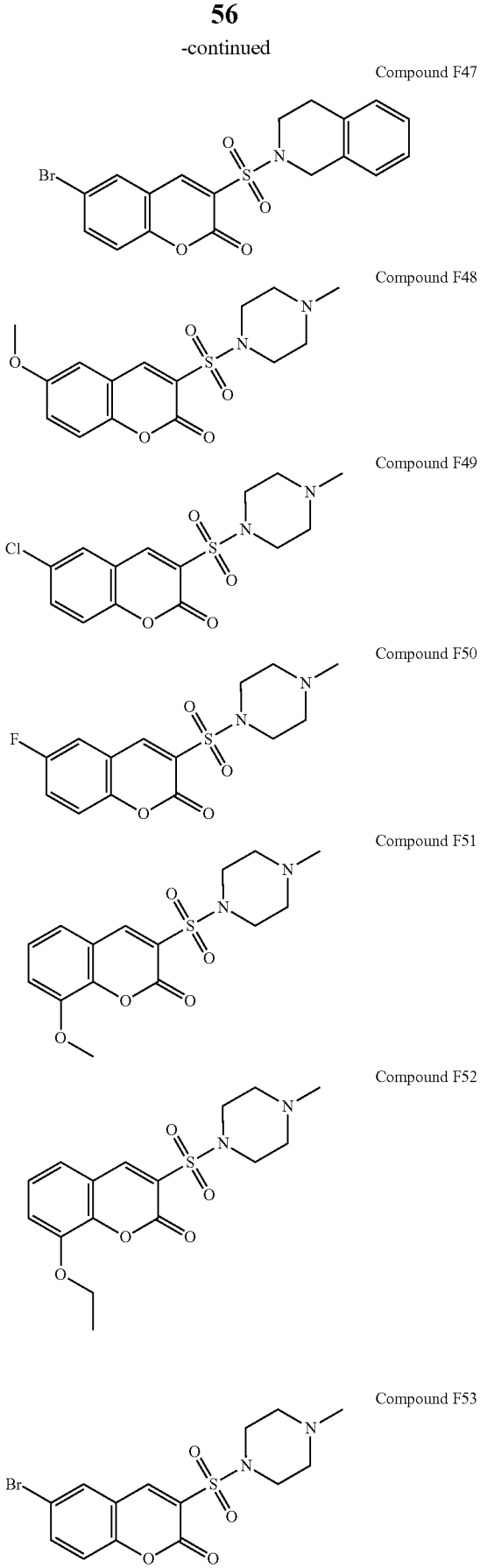

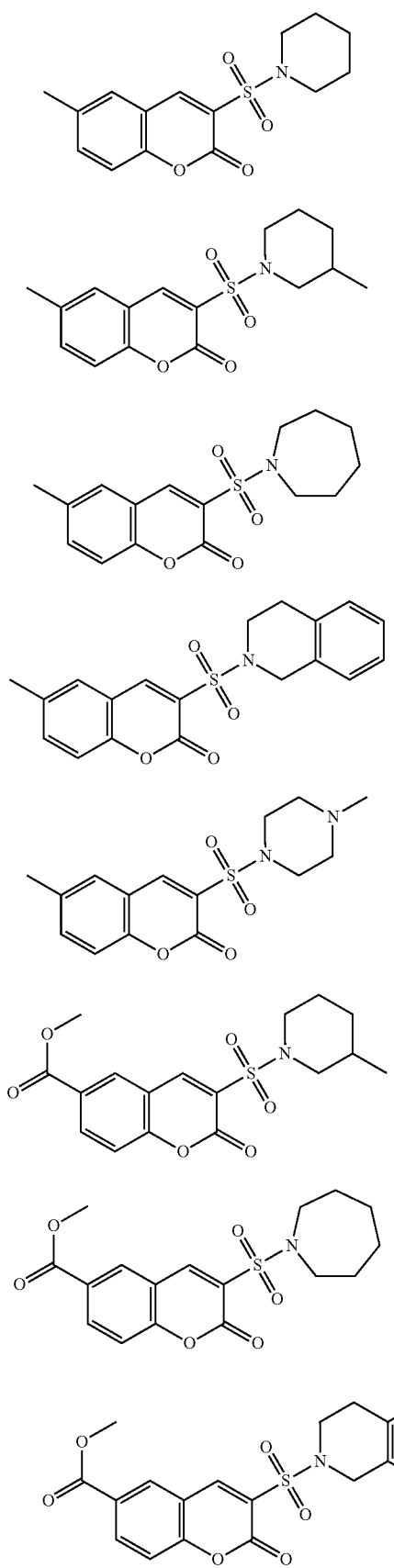
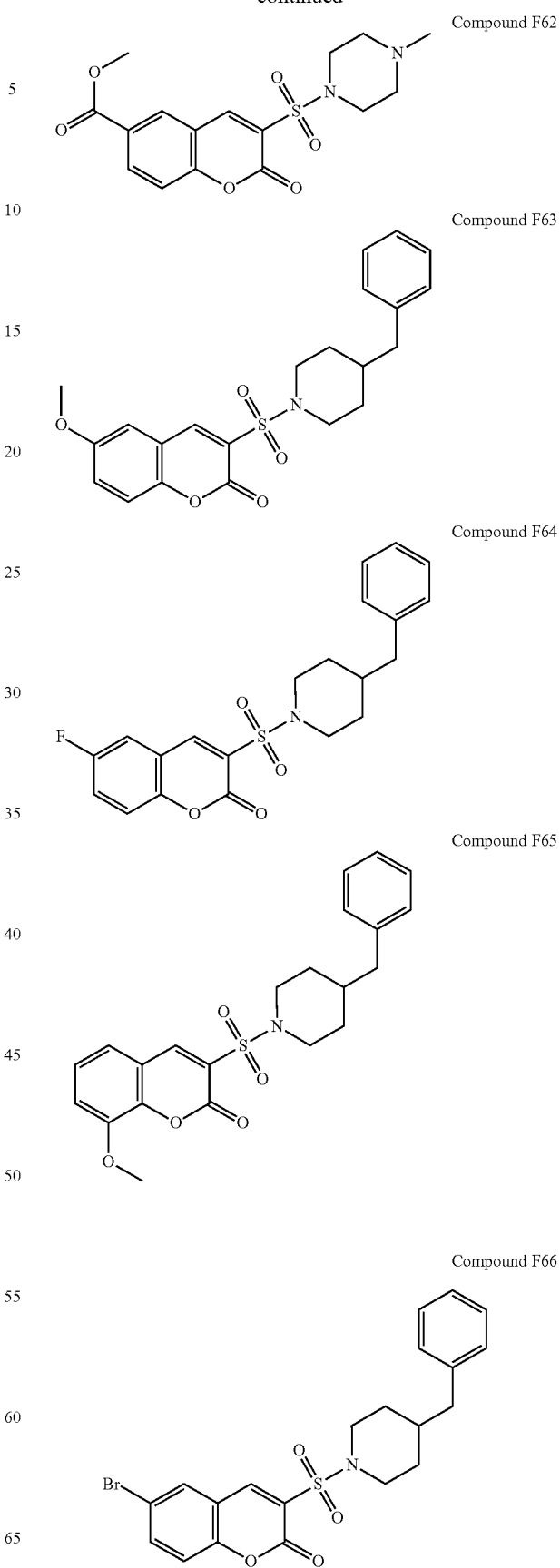

-continued

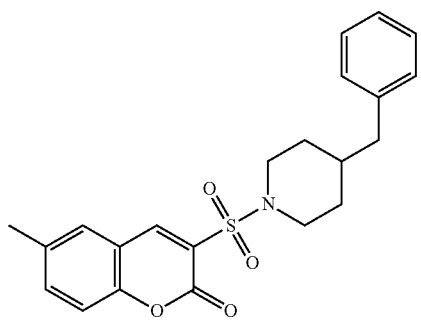
Compound F67

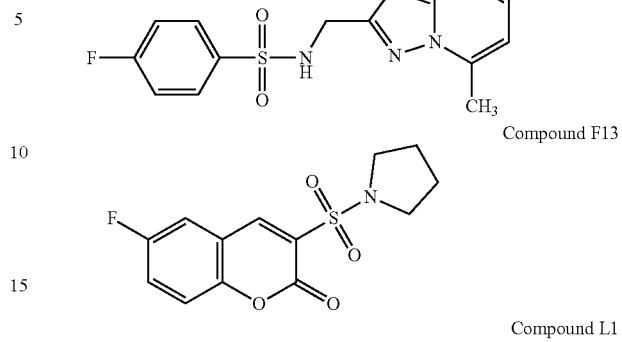
Compound E12

Compound F13

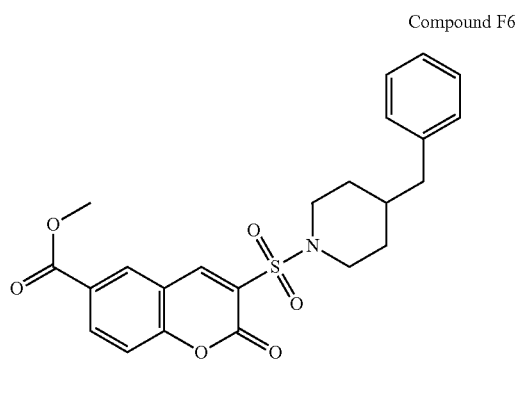
Compound F68

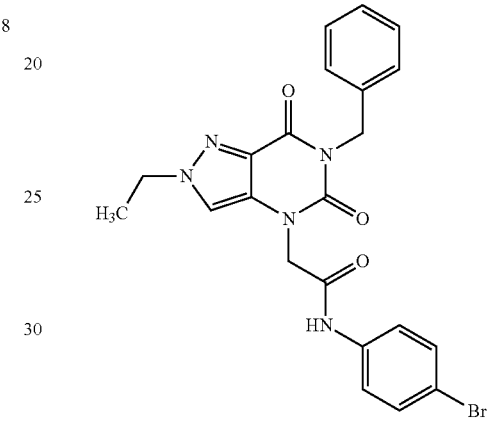
Compound L1

Further exemplary compounds tested in accordance with the various Formulas disclosed herein include the following:

Tables 12 and 13 show a summary of selected compounds for CRC analysis.

TABLE 12

| | Firefly, cmpd/DMSO | | Renilla, cmpd/DMSO | | Firefly_pGL, cmpd/DMSO | | Firefly/Renilla | Firefly, |
|---|---|---|---|---|---|---|---|---|
| ID NUMBER | repeat 1 | repeat 2 | repeat 1 | repeat 2 | repeat 1 | repeat 2 | (NR2F6 stable, clone F4) | NR2F6 stable (clone F4)/pGL4 |
| C289 | 31.3 | 15.6 | 13.5 | 10.0 | 1.7 | 1.3 | 2.0 | 15.3 |
| C155 | 37.3 | 33.3 | 19.3 | 15.4 | 3.5 | 3.0 | 2.0 | 10.9 |
| C157 | 24.9 | 20.4 | 6.9 | 6.0 | 2.3 | 2.1 | 3.5 | 10.2 |
| C299 | 21.5 | 15.2 | 5.5 | 3.8 | 1.8 | 1.8 | 4.0 | 10.1 |
| C218 | 18.2 | 19.1 | 11.9 | 10.2 | 1.9 | 2.0 | 1.7 | 9.5 |
| C177 | 17.4 | 8.2 | 6.7 | 4.6 | 1.7 | 1.3 | 2.3 | 8.5 |
| C164 | 29.3 | 19.6 | 13.8 | 8.9 | 3.1 | 2.8 | 2.1 | 8.2 |
| C136 | 22.1 | 25.8 | 12.5 | 14.9 | 2.9 | 3.0 | 1.7 | 8.1 |
| C134 | 38.1 | 31.9 | 21.0 | 18.9 | 3.7 | 5.4 | 1.8 | 7.7 |
| C195 | 38.7 | 29.4 | 22.8 | 10.1 | 3.7 | 5.1 | 2.1 | 7.7 |
| C160 | 22.9 | 20.2 | 9.5 | 8.2 | 3.2 | 2.7 | 2.4 | 7.2 |
| C11 | 24.6 | 21.3 | 13.9 | 12.3 | 3.3 | 3.3 | 1.8 | 7.0 |
| C12 | 20.0 | 16.7 | 4.5 | 9.4 | 2.6 | 2.9 | 2.6 | 6.6 |
| C230 | 12.5 | 8.3 | 4.5 | 3.8 | 1.8 | 1.5 | 2.5 | 6.5 |
| C202 | 15.7 | 14.1 | 8.3 | 8.9 | 2.6 | 2.3 | 1.7 | 6.1 |
| C102 | 13.0 | 15.3 | 5.8 | 6.1 | 2.3 | 2.5 | 2.4 | 5.9 |
| C108 | 7.9 | 7.3 | 3.0 | 2.8 | 1.3 | 1.5 | 2.6 | 5.5 |
| C248 | 8.6 | 4.3 | 2.8 | 1.9 | 1.4 | 1.4 | 2.8 | 4.6 |
| C256 | 11.5 | 7.9 | 5.1 | 3.5 | 2.0 | 2.4 | 2.3 | 4.5 |
| C254 | 7.6 | 5.1 | 2.7 | 2.5 | 1.5 | 1.4 | 2.4 | 4.4 |
| C13 | 14.0 | 12.9 | 6.4 | 8.2 | 3.2 | 3.2 | 1.8 | 4.2 |
| C112 | 11.7 | 10.1 | 5.6 | 5.1 | 2.5 | 2.8 | 2.0 | 4.1 |
| C110 | 7.6 | 7.2 | 2.3 | 2.1 | 1.7 | 2.0 | 3.3 | 3.9 |
| F312-0003 | 4.6 | 4.2 | 1.1 | 1.1 | 1.1 | 1.3 | 4.0 | 3.7 |
| C101 | 4.5 | 4.7 | 1.8 | 2.0 | 1.2 | 1.3 | 2.4 | 3.6 |

TABLE 13

| ID NUMBER | Firefly, cmpd/DMSO repeat 1 | Firefly, cmpd/DMSO repeat 2 | Renilla, cmpd/DMSO repeat 1 | Renilla, cmpd/DMSO repeat 2 | Firefly_pGL, cmpd/DMSO repeat 1 | Firefly_pGL, cmpd/DMSO repeat 2 | Firefly/Renilla (NR2F6 stable, clone F4) | Firefly, NR2F6 stable (clone F4)/pGL4 |
|---|---|---|---|---|---|---|---|---|
| C222 | 4.5 | 3.7 | 2.3 | 1.8 | 1.0 | 1.3 | 2.0 | 3.6 |
| C105 | 5.7 | 4.8 | 1.7 | 2.3 | 1.5 | 1.8 | 2.6 | 3.1 |
| C209 | 3.1 | 4.2 | 0.9 | 1.1 | 1.3 | 1.1 | 3.6 | 3.1 |
| C109 | 9.2 | 10.3 | 3.4 | 3.3 | 3.5 | 3.4 | 2.9 | 2.9 |
| C213 | 14.0 | 13.6 | 9.0 | 8.1 | 1.2 | 1.7 | 1.6 | 9.6 |
| C300 | 9.8 | 7.4 | 6.2 | 4.7 | 1.7 | 2.3 | 1.6 | 4.3 |
| C154 | 35.4 | 35.4 | 25.6 | 19.5 | 4.0 | 3.8 | 1.6 | 9.1 |
| C14 | 22.3 | 20.0 | 12.1 | 15.2 | 2.9 | 2.6 | 1.5 | 7.6 |
| C210 | 22.8 | 14.3 | 15.0 | 9.8 | 2.4 | 2.1 | 1.5 | 8.2 |
| C107 | 11.0 | 11.0 | 8.7 | 6.5 | 1.7 | 2.1 | 1.4 | 5.8 |
| C137 | 22.6 | 23.4 | 17.6 | 15.7 | 2.7 | 2.9 | 1.4 | 8.4 |
| C161 | 35.4 | 39.0 | 28.6 | 27.7 | 4.0 | 5.1 | 1.3 | 8.1 |
| C194 | 10.6 | 6.3 | 7.2 | 6.2 | 1.3 | 1.3 | 1.3 | 6.6 |
| C188 | 9.4 | 8.7 | 7.6 | 6.9 | 1.8 | 1.8 | 1.2 | 5.0 |
| C182 | 16.2 | 17.3 | 15.1 | 13.2 | 2.0 | 2.1 | 1.2 | 8.2 |
| C200 | 11.0 | 8.1 | 5.8 | 10.4 | 1.6 | 1.9 | 1.2 | 5.4 |
| C220 | 10.4 | 6.5 | 8.1 | 6.7 | 1.3 | 1.5 | 1.1 | 6.2 |
| C118 | 13.5 | 17.1 | 11.8 | 14.8 | 2.4 | 2.7 | 1.1 | 5.9 |
| C292 | 18.3 | 14.8 | 15.6 | 13.4 | 1.7 | 1.7 | 1.1 | 9.7 |
| C180 | 34.0 | 34.5 | 30.9 | 30.0 | 2.5 | 2.7 | 1.1 | 13.1 |
| C175 | 13.2 | 11.9 | 10.5 | 12.0 | 2.5 | 1.9 | 1.1 | 5.7 |
| C111 | 29.8 | 35.9 | 29.4 | 30.8 | 3.7 | 3.9 | 1.1 | 8.7 |
| C197 | 17.6 | 14.8 | 16.1 | 13.7 | 2.6 | 2.5 | 1.1 | 6.3 |
| C127 | 36.7 | 56.2 | 43.1 | 43.5 | 8.3 | 8.0 | 1.1 | 5.7 |
| C126 | 45.1 | 44.8 | 43.5 | 42.2 | 4.8 | 4.3 | 1.0 | 9.9 |

TABLE 14

| Compound ID | Firefly F4, cmpd/DMSO (mean) 40 uM | Firefly F4, cmpd/DMSO (mean) 10 uM | Firefly F4, cmpd/DMSO (mean) 2 uM | Firefly pGL4, cmpd/DMSO (mean) 40 uM | Firefly pGL4, cmpd/DMSO (mean) 10 uM | Firefly pGL4, cmpd/DMSO (mean) 2 uM | Renilla F4, cmpd/DMSO (mean) 40 uM | Renilla F4, cmpd/DMSO (mean) 10 uM | Renilla F4, cmpd/DMSO (mean) 2 uM |
|---|---|---|---|---|---|---|---|---|---|
| 17 | 1.3 | 1.2 | 1.9 | 1.3 | 1.6 | 1.7 | 1.0 | 1.0 | 0.8 |
| 19 | 0.5 | 1.0 | 1.7 | 0.9 | 1.3 | 1.9 | 0.6 | 1.0 | 1.1 |
| 22 | 0.6 | 1.4 | 1.3 | 1.5 | 1.0 | 1.6 | 1.0 | 1.1 | 0.8 |
| C1 | 0.4 | 0.5 | 0.5 | 0.6 | 0.7 | 0.7 | 0.2 | 0.2 | 2.1 |
| C3 | 0.9 | 1.1 | 1.5 | 1.0 | 1.3 | 1.1 | 0.9 | 0.9 | 1.0 |
| C4 | 0.7 | 0.8 | 1.1 | 1.3 | 0.9 | 1.0 | 0.5 | 0.5 | 0.6 |
| C5 | 0.8 | 0.8 | 0.9 | 1.0 | 1.2 | 1.3 | 1.1 | 0.5 | 0.7 |
| C6 | 0.4 | 0.6 | 1.4 | 1.0 | 1.3 | 1.3 | 0.5 | 0.6 | 0.7 |
| C301 | 1.0 | 1.0 | 1.2 | 1.1 | 1.6 | 2.4 | 1.0 | 0.7 | 1.1 |
| C302 | 0.9 | 0.9 | 1.2 | 0.8 | 1.4 | 1.8 | 1.0 | 1.1 | 0.7 |
| C303 | 0.9 | 0.9 | 1.2 | 1.1 | 1.1 | 1.1 | 1.0 | 0.8 | 1.0 |
| C7 | 0.4 | 0.5 | 0.6 | 0.8 | 0.8 | 0.9 | 0.4 | 0.3 | 1.0 |
| C11 | 0.4 | 1.6 | 1.7 | 0.8 | 1.7 | 1.1 | 0.2 | 1.2 | 1.1 |
| E12 | 0.5 | 0.9 | 0.7 | 1.0 | 0.8 | 0.9 | 1.0 | 0.7 | 0.7 |
| E53 | 1.4 | 1.1 | 1.0 | 1.6 | 1.4 | 1.5 | 1.1 | 0.8 | 0.9 |
| L1 | 0.5 | 0.5 | 0.9 | 0.8 | 0.4 | 0.8 | 0.7 | 0.8 | 0.8 |
| Z54 | 0.6 | 1.6 | 0.8 | 0.8 | 1.9 | 1.1 | 0.2 | 0.3 | 0.7 |
| Z55 | 2.0 | 0.8 | 1.1 | 2.3 | 0.7 | 0.8 | 0.1 | 0.3 | 0.8 |
| Z56 | 0.5 | 2.1 | 1.2 | 1.2 | 8.9 | 1.2 | 0.2 | 0.3 | 0.9 |
| Z74 | 0.7 | 0.5 | 0.7 | 0.7 | 0.6 | 0.7 | 0.3 | 0.2 | 0.8 |
| Z79 | 0.3 | 0.5 | 0.9 | 0.8 | 0.5 | 0.8 | 0.2 | 0.6 | 0.9 |
| Z81 | 0.4 | 0.7 | 2.4 | 0.7 | 0.9 | 1.4 | 0.3 | 0.3 | 1.1 |
| Z83 | 0.7 | 0.6 | 1.2 | 0.5 | 0.9 | 1.0 | 0.3 | 0.8 | 1.0 |
| Z90 | 0.4 | 2.5 | 0.7 | 0.7 | 2.4 | 0.7 | 0.1 | 0.2 | 0.9 |
| Z91 | 1.3 | 1.1 | 1.0 | 1.1 | 1.0 | 1.0 | 0.8 | 1.1 | 1.1 |

Additional compounds were tested, including the following:
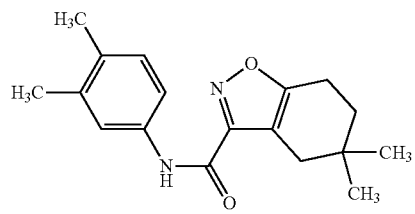
Compound Z1
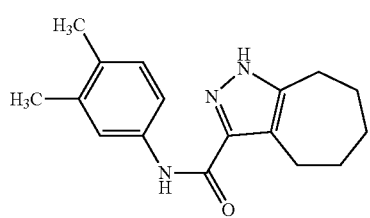
Compound Z2
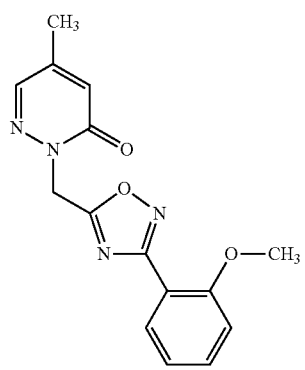
Compound Z150
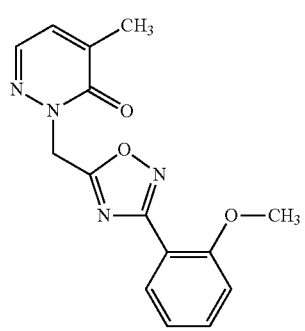
Compound Z151
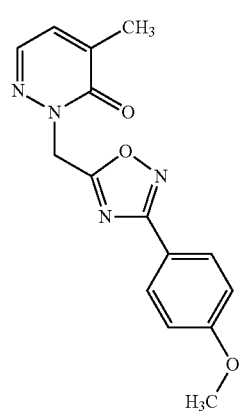
Compound Z153
-continued
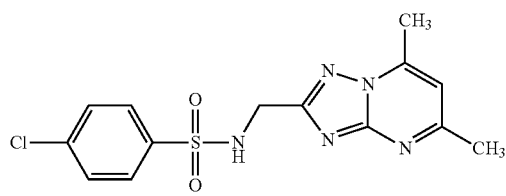
Compound Z91
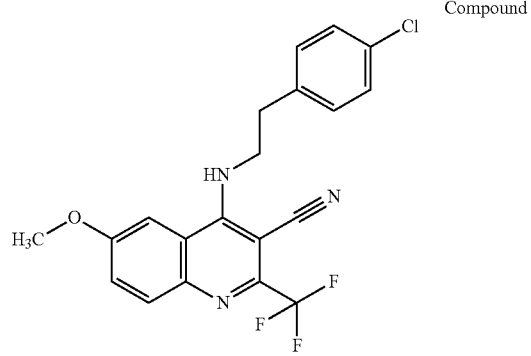
Compound Z39
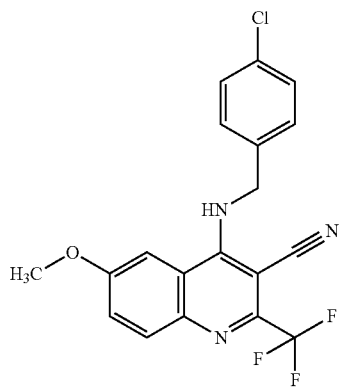
Compound Z38
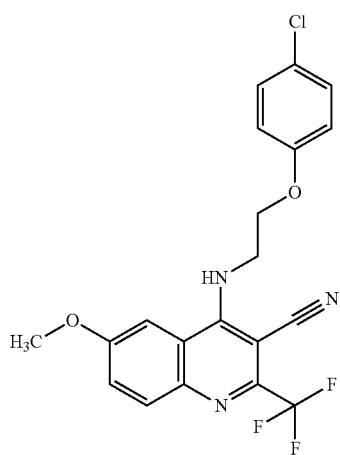
Compound Z40

Compound Z41
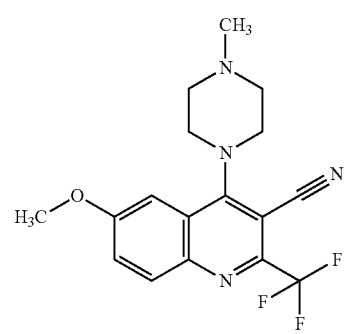
Compound Z42
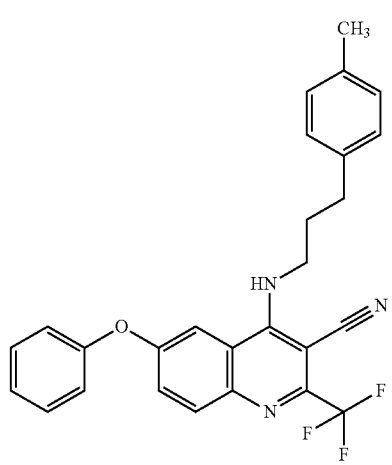
Compound Z43
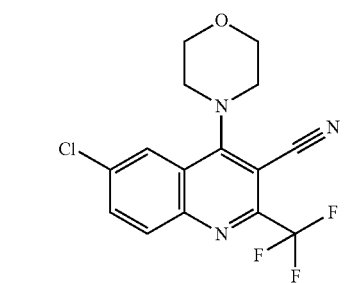
Compound Z44
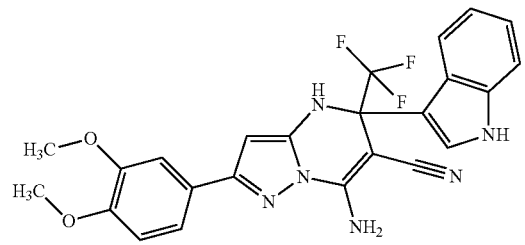
Compound Z45
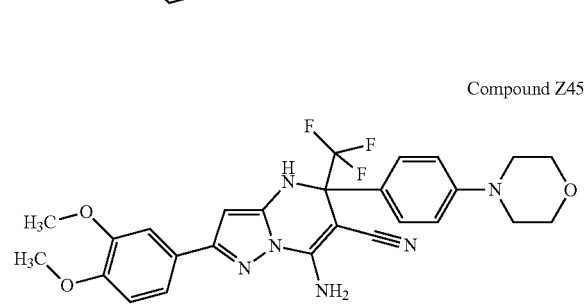
Compound Z46
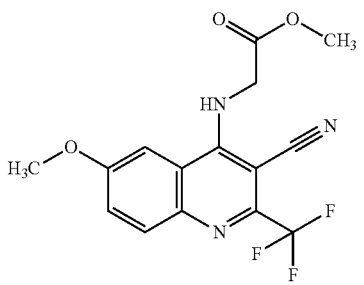
Compound Z47
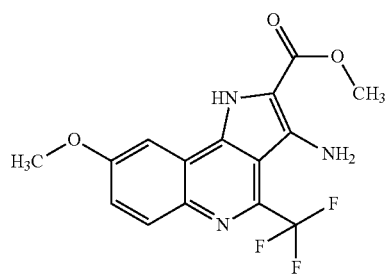
Compound Z48
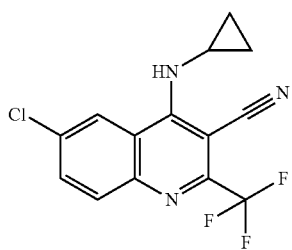
Compound Z49
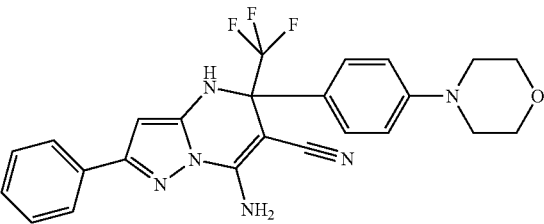
Compound Z50
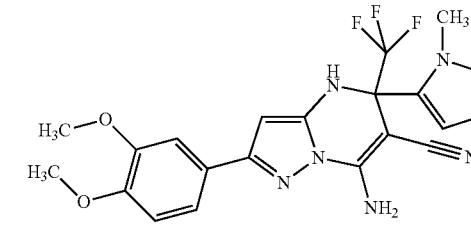
Compound Z51

Compound Z52

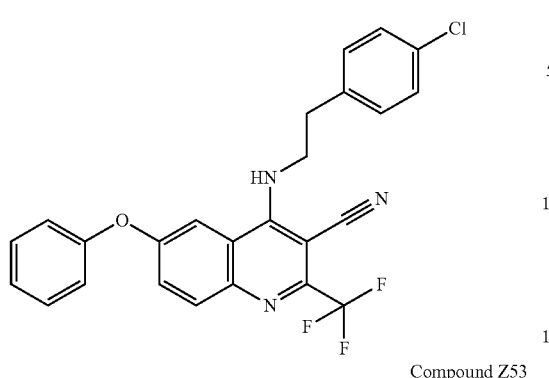

Compound Z53

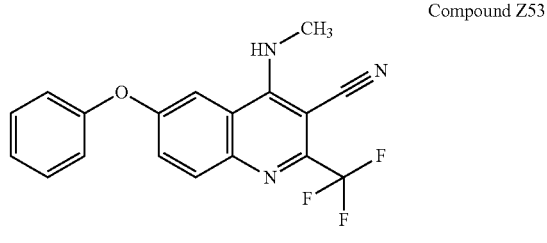

Compounds Z54, Z55 and Z56 were found to have particularly good activity:

Compound Z54

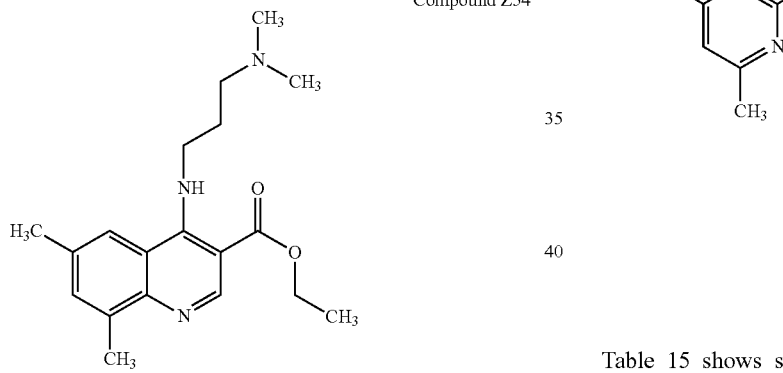

Compound Z55

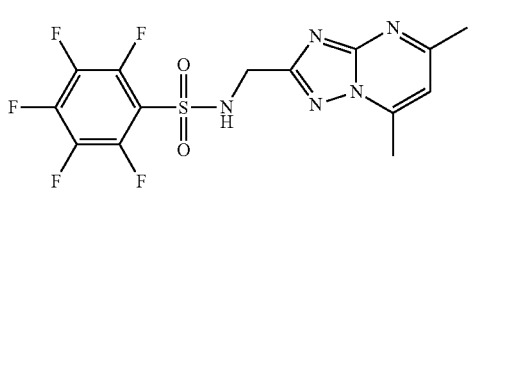

Compound Z56

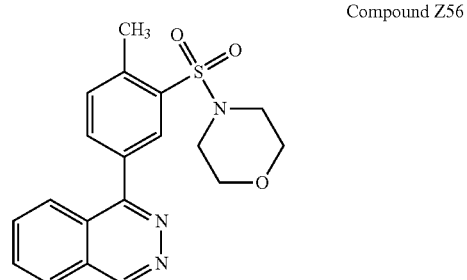

Table 15 shows screening results from another set of compounds.

TABLE 15

| Compound ID | Firefly | | | | | | Renilla | | | | | |
|---|---|---|---|---|---|---|---|---|---|---|---|---|
| | F4, cmpd/DMSO (mean) | | | ERalpha transient, cmpd/DMSO (mean) | | | F4, cmpd/DMSO (mean) | | | ERalpha transient, cmpd/DMSO (mean) | | |
| | 40 uM | 10 uM | 2 uM | 40 uM | 10 uM | 2 uM | 40 uM | 10 uM | 2 uM | 40 uM | 10 uM | 2 uM |
| Z1 | 0.8 | 1.8 | 1.9 | 0.9 | 2.2 | 2.4 | 0.8 | 1.6 | 1.3 | 0.7 | 1.0 | 1.1 |
| Z2 | 0.6 | 1.9 | 1.4 | 0.7 | 1.1 | 1.6 | 1.2 | 1.8 | 1.2 | 1.0 | 1.1 | 1.2 |
| Z3 | 1.6 | 1.1 | 1.5 | 1.7 | 2.6 | 2.2 | 0.9 | 1.4 | 1.5 | 0.9 | 1.0 | 1.1 |
| Z4 | 0.8 | 1.2 | 1.5 | 0.8 | 1.4 | 1.5 | 1.4 | 1.6 | 1.1 | 0.8 | 1.1 | 1.2 |
| Z5 | 1.2 | 0.9 | 1.5 | 2.4 | 2.5 | 2.4 | 1.2 | 0.9 | 1.0 | 1.0 | 1.0 | 1.0 |
| Z6 | 1.1 | 1.4 | 1.4 | 1.1 | 2.2 | 2.0 | 0.9 | 1.1 | 1.1 | 0.9 | 1.1 | 1.1 |
| Z7 | 1.0 | 1.2 | 0.9 | 1.5 | 2.0 | 1.3 | 1.1 | 1.1 | 1.3 | 1.0 | 1.1 | 1.1 |
| Z8 | 0.7 | 4.0 | 2.6 | 0.4 | 2.4 | 2.2 | 0.2 | 9.1 | 2.7 | 0.1 | 1.4 | 1.4 |
| Z9 | 1.2 | 6.7 | 2.5 | 0.5 | 2.7 | 2.2 | 0.3 | 4.9 | 2.1 | 0.2 | 0.8 | 1.3 |
| Z10 | 0.7 | 1.6 | 5.8 | 0.5 | 1.5 | 4.2 | 0.3 | 3.3 | 3.4 | 0.2 | 0.8 | 1.3 |
| Z11 | 0.5 | 1.2 | 3.5 | 0.6 | 1.6 | 2.1 | 0.3 | 2.6 | 2.9 | 0.2 | 0.8 | 1.4 |
| Z12 | 0.4 | 1.8 | 3.9 | 0.4 | 1.3 | 2.4 | 0.4 | 2.7 | 2.7 | 0.2 | 0.7 | 1.3 |
| Z13 | 1.6 | 0.9 | 1.0 | 1.1 | 1.7 | 1.2 | 0.4 | 0.7 | 0.8 | 0.4 | 0.6 | 0.8 |
| Z14 | 1.2 | 0.8 | 1.2 | 1.0 | 1.2 | 1.0 | 1.0 | 0.9 | 0.8 | 1.0 | 1.1 | 1.1 |
| Z15 | 0.9 | 0.5 | 1.0 | 1.1 | 1.1 | 0.9 | 1.0 | 1.1 | 0.8 | 0.9 | 1.0 | 1.0 |
| Z58 | 0.8 | 4.5 | 0.9 | 0.8 | 6.5 | 1.5 | 0.8 | 1.2 | 1.3 | 0.7 | 1.1 | 1.2 |

TABLE 15-continued

| | Firefly | | | | | | Renilla | | | | | |
| | F4, cmpd/DMSO (mean) | | | ERalpha transient, cmpd/DMSO (mean) | | | F4, cmpd/DMSO (mean) | | | ERalpha transient, cmpd/DMSO (mean) | | |
| Compound ID | 40 uM | 10 uM | 2 uM | 40 uM | 10 uM | 2 uM | 40 uM | 10 uM | 2 uM | 40 uM | 10 uM | 2 uM |
| --- | --- | --- | --- | --- | --- | --- | --- | --- | --- | --- | --- | --- |
| Z17 | 0.6 | 6.5 | 1.5 | 2.9 | 9.5 | 1.7 | 0.6 | 1.1 | 1.2 | 0.6 | 1.1 | 1.3 |
| Z61 | 0.8 | 2.5 | 1.7 | 0.7 | 9.1 | 3.0 | 0.6 | 0.5 | 1.3 | 0.7 | 0.8 | 1.4 |
| Z19 | 0.7 | 6.3 | 1.3 | 0.7 | 12.7 | 1.9 | 0.7 | 0.9 | 1.1 | 0.6 | 1.0 | 1.5 |
| Z67 | 0.7 | 0.5 | 1.3 | 0.5 | 1.4 | 1.4 | 0.6 | 1.0 | 1.2 | 0.6 | 1.0 | 1.1 |
| Z68 | 1.2 | 1.1 | 1.5 | 0.7 | 1.5 | 1.1 | 0.6 | 1.0 | 0.9 | 0.6 | 0.9 | 1.1 |
| Z70 | 1.0 | 1.0 | 1.1 | 1.5 | 1.1 | 0.9 | 1.3 | 1.3 | 0.8 | 1.2 | 1.0 | 1.1 |
| Z71 | 0.8 | 1.0 | 0.8 | 0.4 | 1.0 | 1.4 | 0.4 | 0.9 | 1.1 | 0.5 | 1.0 | 1.0 |
| Z75 | 0.8 | 1.2 | 0.9 | 0.9 | 1.9 | 1.1 | 0.8 | 1.0 | 1.1 | 0.7 | 0.9 | 1.0 |
| Z76 | 0.8 | 1.8 | 0.8 | 0.7 | 1.9 | 1.3 | 0.5 | 0.8 | 1.0 | 0.4 | 0.8 | 1.1 |
| Z78 | 1.6 | 1.5 | 1.4 | 1.1 | 2.4 | 1.5 | 0.8 | 1.0 | 1.1 | 0.6 | 0.9 | 1.0 |

Compounds Z8-Z12, Z17 and Z19 were found to have particularly good activity.

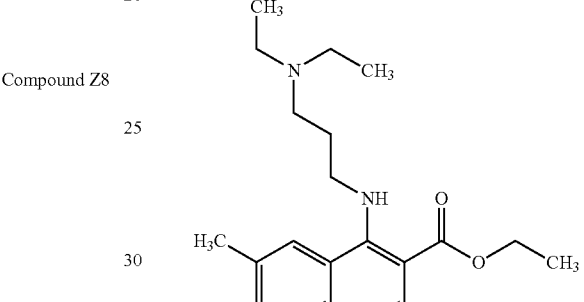

Figure 19A:
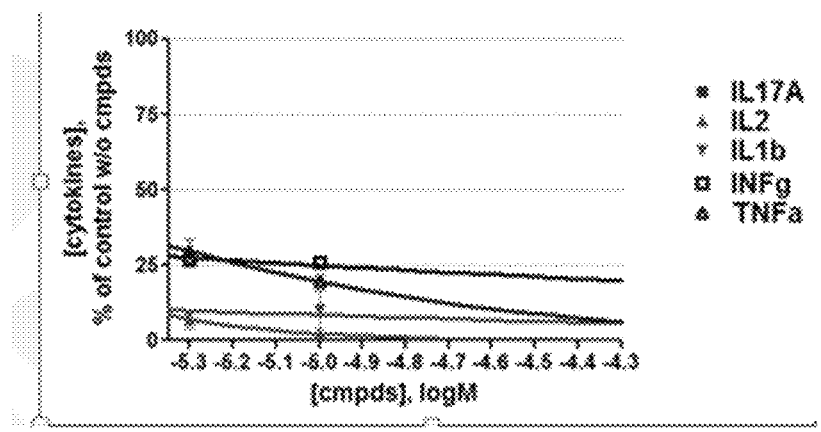
FIGS. 19A and 19B show the results of Dog's PBMC ELISA and cytotoxicity experiments. All compounds were tested at 5, 10, 25 and 50 uM in duplicates on activated by 10 ng/mL PMA+500 ng/mL ionomycin dogs PBMC (1×106 cells/mL). Cell culture supernates were removed and frozen for further ELISA analysis and remained cells were analyzed. Compounds without cytotox were chosen for cytokine release inhibition analysis. Compound Z92 was also analyzed at 5 uM and 10 uM.
Figure 19B:
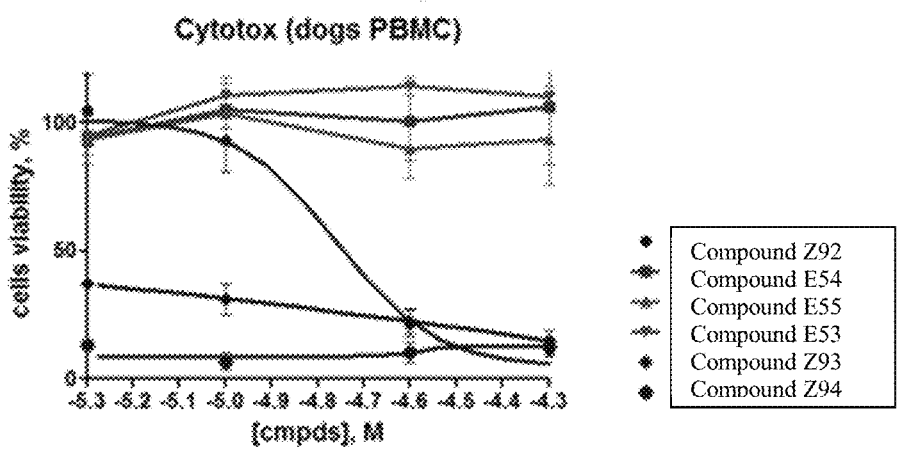

Dog's PMBC ELISA and cytotoxicity experiments were performed on Compound Z92, which also showed good activity. Results are shown in FIGS. 19A and 19B.

Another useful compound is Compound Z95:

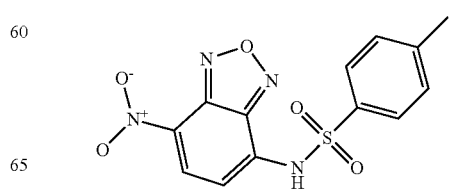

Results of testing done on compound Z95 are shown in Table 16.

TABLE 16

| | NR2F6_full (stable, clone F4), cmpd/DMSO | | | | | | NR2F6_full (transient), cmpd/DMSO | | | | | |
|---|---|---|---|---|---|---|---|---|---|---|---|---|
| | Firefly | | | Renilla | | | Firefly | | | Renilla | | |
| ID | 40 uM | 10 uM | 2 uM | 40 uM | 10 uM | 2 uM | 40 uM | 10 uM | 2 uM | 40 uM | 10 uM | 2 uM |
| Z95 | 3.7 | 2.2 | 1.2 | 0.5 | 0.5 | 1.1 | 2.3 | 1.3 | 1.2 | 0.2 | 0.4 | 1.1 |

Figure 20A:
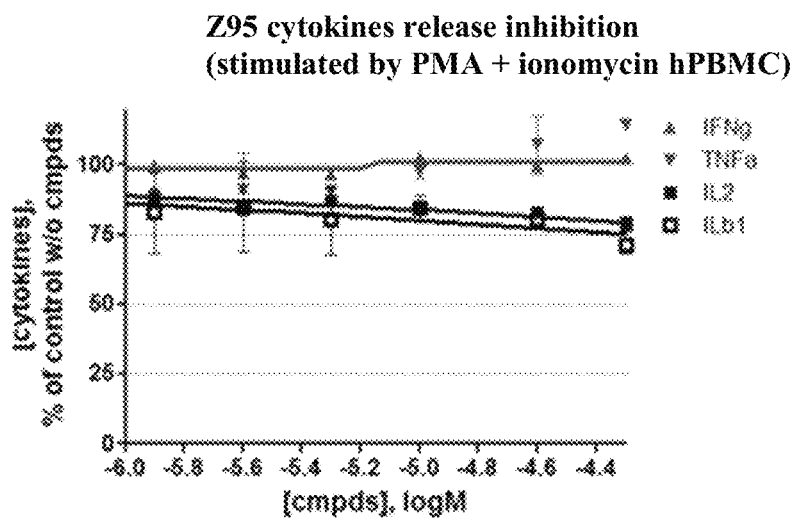
FIGS. 20A and 20B show results of cytokines release by hPBMC and cytotox for Compound Z95. For cytokines release and cytotox on hPBMCs compound was tested at 1.25, 2.5, 5, 10, 25 and 50 uM in duplicates. For cytotox on HEK293, HEK293 pGL4 and HEK293 NR2F6 (full length) compound was tested from 50 uM with dilution step 3.16 in duplicates. Human PBMC were activated by 10 ng/mL PMA+500 ng/mL ionomycin. Data were normalized to controls with (100%) without compounds.
Figure 20B:
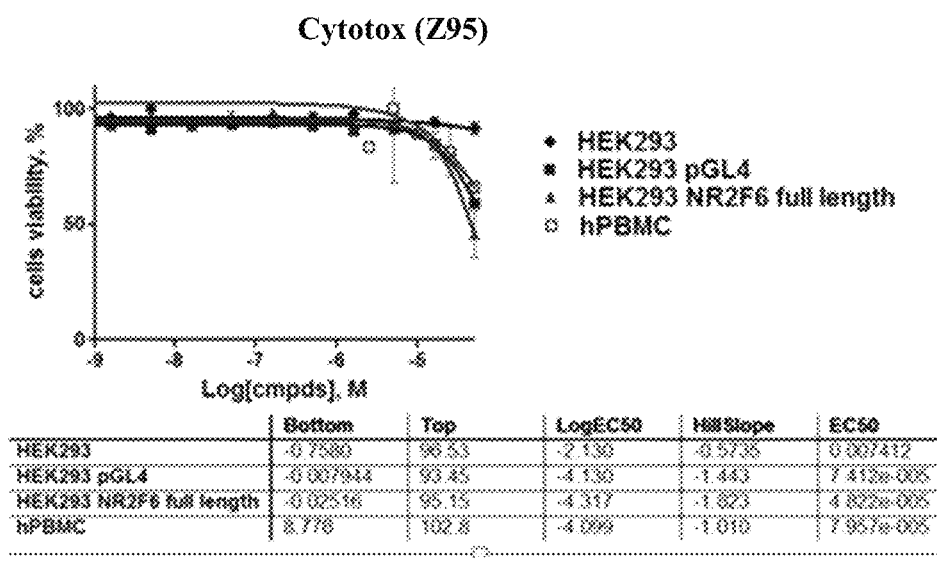
Figure 21A:
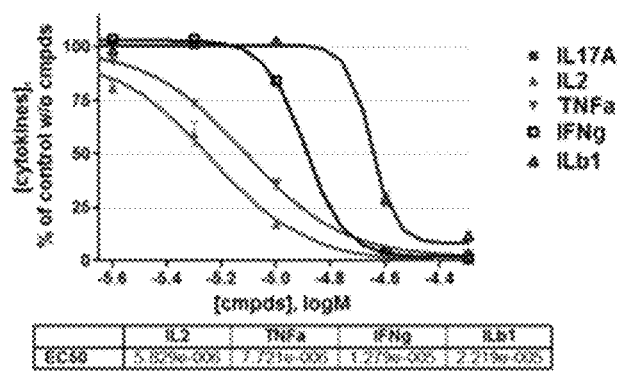
FIGS. 21A-21D show human and dog results of a cytokine release experiment—parent compound for dogs and human PBMC, for Compound D28. All compounds were tested at 5, 10, 25 and 50 uM in duplicates. Dog PBMC (1×106 cells/mL) were activated by 10 ng/mL PMA+500 ng/mL ionomycin. Data were normalized to controls with (100%) without (0%) PMA+ionomycin activation.
Figure 21B:
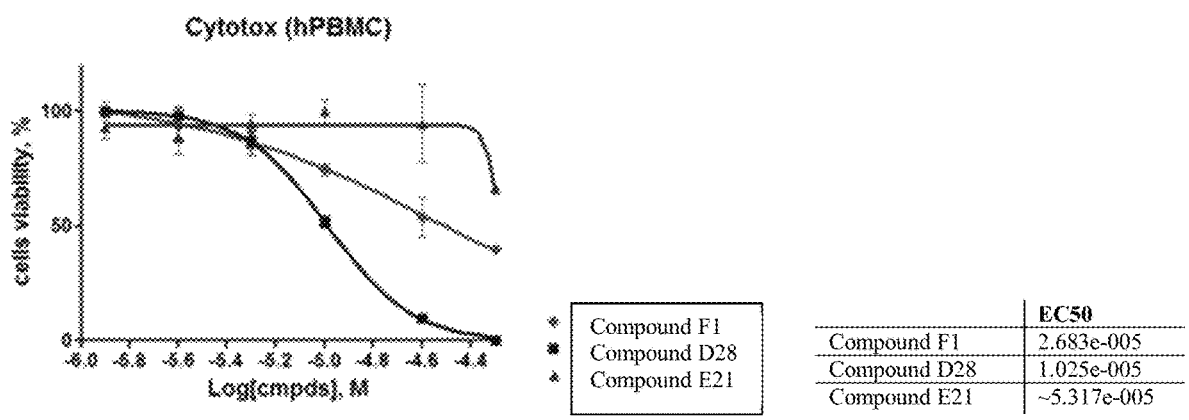
Figure 21C:
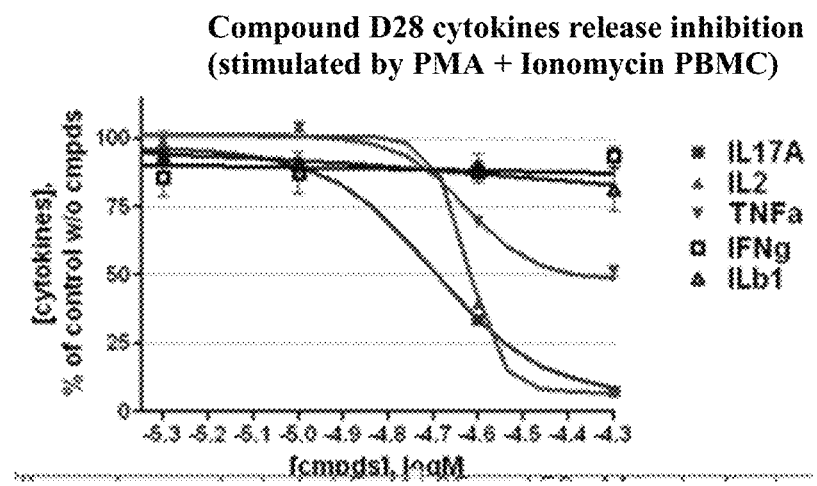
Figure 21D:
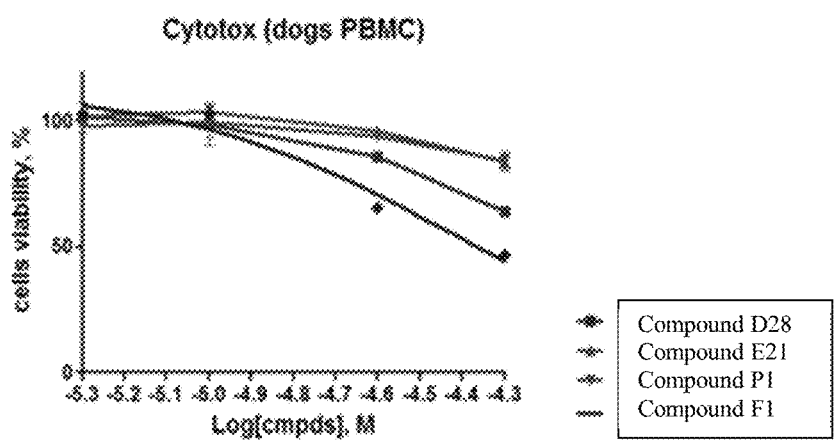

FIGS. 20A and 20B show further results of cytokines release by hPBMC and cytotox on Compound Z95.

Table 17 shows screening results from another set of compounds.

TABLE 17

| | Firefly | | | | | | Renilla | | | | | |
|---|---|---|---|---|---|---|---|---|---|---|---|---|
| Compound | F4, cmpd/DMSO (mean) | | | ERalpha transient, cmpd/DMSO (mean) | | | F4,cmpd/DMSO (mean) | | | ERalpha transient, cmpd/DMSO (mean) | | |
| ID | 40 uM | 10 uM | 2 uM | 40 uM | 10 uM | 2 uM | 40 uM | 10 uM | 2 uM | 40 uM | 10 uM | 2 uM |
| Z27 | 0.7 | 1.3 | 1.3 | 0.5 | 2.1 | 1.3 | 0.9 | 1.2 | 1.2 | 0.8 | 1.2 | 1.2 |
| Z28 | 1.3 | 0.9 | 1.0 | 1.3 | 1.1 | 1.8 | 1.2 | 1.2 | 1.0 | 1.0 | 1.3 | 1.1 |
| Z29 | 1.1 | 1.1 | 1.3 | 6.7 | 1.2 | 1.0 | 0.5 | 0.9 | 0.8 | 0.7 | 1.2 | 0.8 |
| Z30 | 1.2 | 1.1 | 1.4 | 1.4 | 1.1 | 1.4 | 0.7 | 1.1 | 1.1 | 1.6 | 1.1 | 1.1 |
| Z31 | 1.1 | 0.9 | 0.8 | 1.3 | 1.6 | 0.9 | 1.0 | 1.0 | 1.1 | 1.0 | 1.0 | 1.0 |
| Z32 | 1.5 | 0.9 | 1.8 | 1.5 | 0.8 | 1.8 | 1.3 | 1.0 | 1.0 | 0.8 | 1.1 | 1.0 |
| Z33 | 6.6 | 2.0 | 1.7 | 8.8 | 1.8 | 2.1 | 0.6 | 1.0 | 1.1 | 0.9 | 1.5 | 1.0 |
| Z34 | 0.7 | 3.8 | 1.6 | 0.9 | 10.3 | 2.0 | 0.6 | 0.8 | 1.2 | 0.7 | 1.0 | 1.5 |
| Z35 | 1.2 | 1.5 | 1.9 | 7.2 | 2.2 | 2.6 | 0.7 | 2.0 | 1.1 | 0.9 | 1.3 | 1.1 |
| Z36 | 0.7 | 1.8 | 0.7 | 5.8 | 1.6 | 1.2 | 0.6 | 1.8 | 1.0 | 0.8 | 1.6 | 1.2 |
| Z37 | 0.7 | 1.4 | 1.0 | 1.2 | 1.5 | 1.1 | 0.5 | 0.9 | 1.0 | 0.7 | 1.7 | 1.0 |
| Z38 | 0.6 | 0.8 | 0.5 | 0.5 | 0.5 | 0.9 | 0.4 | 0.6 | 0.7 | 0.6 | 0.6 | 0.9 |
| Z39 | 0.7 | 1.0 | 0.8 | 0.8 | 0.5 | 1.2 | 0.5 | 0.5 | 0.7 | 0.6 | 0.6 | 1.1 |
| Z40 | 0.8 | 0.7 | 0.8 | 1.0 | 0.3 | 1.0 | 0.5 | 0.6 | 0.7 | 0.6 | 0.7 | 1.0 |
| Z41 | 1.7 | 1.1 | 1.0 | 1.6 | 1.4 | 0.9 | 0.6 | 0.6 | 0.7 | 0.8 | 1.1 | 1.0 |
| Z42 | 0.6 | 0.9 | 0.9 | 1.1 | 1.8 | 1.5 | 0.7 | 0.9 | 1.2 | 0.7 | 0.9 | 1.1 |
| Z43 | 0.8 | 0.8 | 1.3 | 1.6 | 0.9 | 1.4 | 0.7 | 0.9 | 1.0 | 0.9 | 1.0 | 1.0 |
| Z44 | 0.4 | 0.8 | 0.8 | 1.0 | 1.2 | 1.2 | 0.3 | 1.5 | 1.7 | 0.5 | 0.9 | 1.1 |
| Z45 | 0.5 | 1.2 | 0.8 | 0.7 | 0.6 | 0.8 | 1.1 | 1.2 | 1.2 | 1.0 | 0.8 | 1.1 |
| Z46 | 0.6 | 0.8 | 0.6 | 0.6 | 0.8 | 0.9 | 0.6 | 0.8 | 0.9 | 1.0 | 1.0 | 0.9 |
| Z47 | 2.0 | 1.3 | 0.9 | 1.7 | 1.0 | 0.9 | 1.7 | 1.2 | 1.1 | 1.2 | 1.4 | 1.2 |
| Z48 | 0.7 | 0.5 | 0.9 | 0.5 | 0.3 | 1.5 | 0.6 | 0.6 | 0.8 | 0.6 | 0.8 | 1.1 |
| Z49 | 0.6 | 0.7 | 0.8 | 0.4 | 0.4 | 1.0 | 0.8 | 0.7 | 1.0 | 0.8 | 0.7 | 1.0 |
| Z50 | 0.6 | 0.9 | 0.8 | 0.7 | 0.7 | 1.3 | 0.8 | 2.0 | 1.6 | 0.6 | 0.8 | 1.0 |
| Z51 | 0.7 | 0.6 | 0.6 | 0.4 | 0.8 | 1.3 | 0.3 | 0.7 | 0.8 | 0.3 | 0.9 | 1.1 |
| Z52 | 0.7 | 0.7 | 0.6 | 0.7 | 0.4 | 0.7 | 0.6 | 0.5 | 0.8 | 0.7 | 0.8 | 1.1 |
| Z53 | 0.5 | 0.4 | 0.8 | 0.4 | 0.3 | 1.0 | 0.6 | 0.7 | 0.7 | 0.5 | 0.6 | 1.0 |

Compounds Z33 and Z34 were found to have particularly good activity:

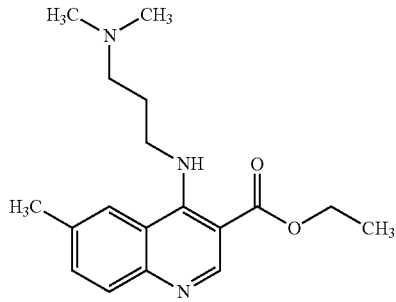

Compound Z33

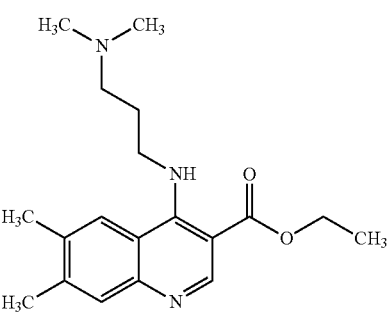

Compound Z34

Other useful compounds are Compound D28 and Compound F1:

Compound D28

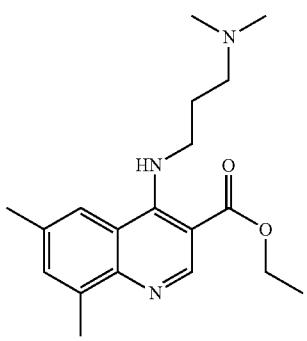

Compound F1

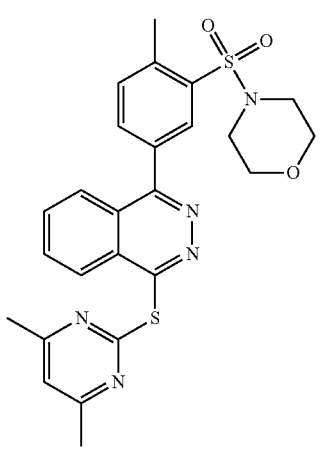

Compound D28 was tested in a cytokine release experiment—parent compound, dog's and human PMBC. Results are shown in FIGS. 21A-21D.

Figure 22A:
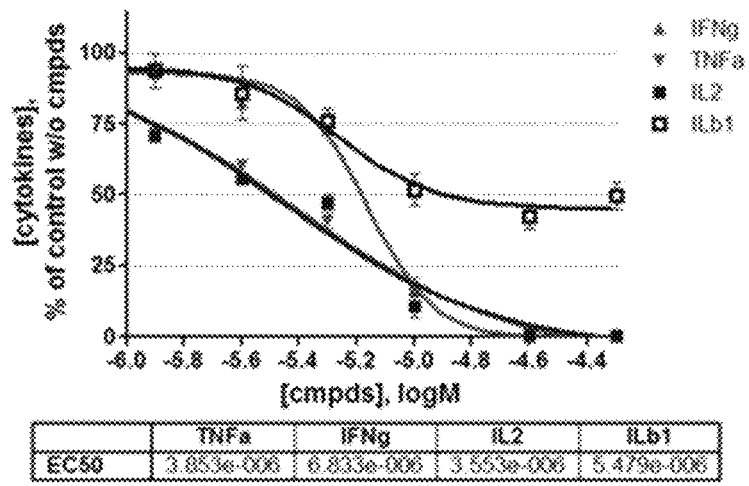
FIGS. 22A and 22B show results of cytokines release by hPBMC and cytotox for Compound Z17. For cytokines release and cytotox on hPBMCs compound was tested at 1.25, 2.5, 5, 10, 25 and 50 uM in duplicates. For cytotox on HEK293, HEK293 pGL4 and HEK293 NR2F6 (full length) compound was tested from 50 uM with dilution step 3.16 in duplicates. Human PBMC were activated by 10 ng/mL PMA+500 ng/mL ionomycin. Data were normalized to controls with (100%) without compounds.
Figure 22B:
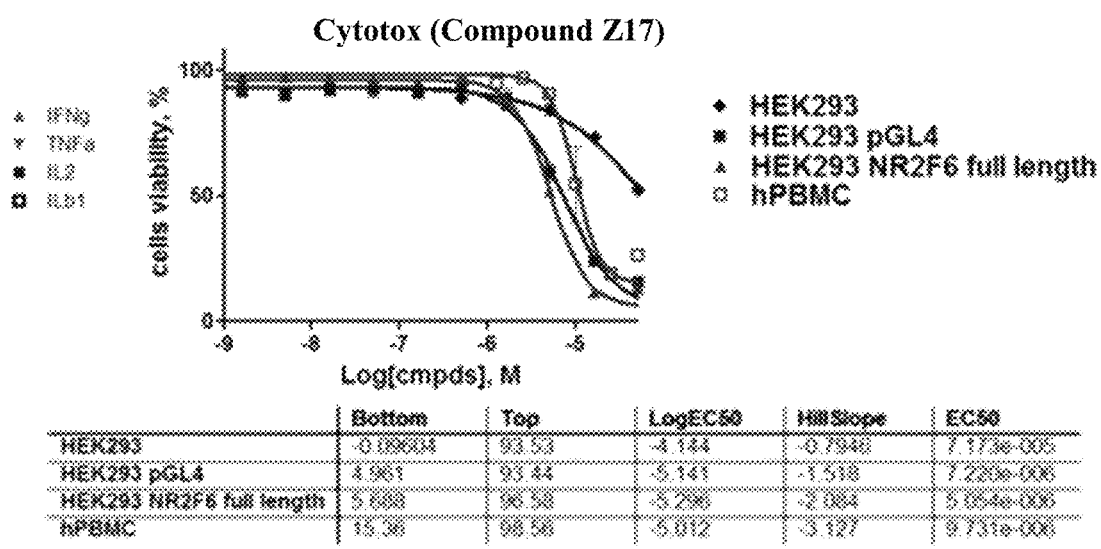

Compound Z17, previously mentioned above, was tested in a cytokine release experiment. Results are shown in FIGS. 22A and 22B.

Figure 23A:
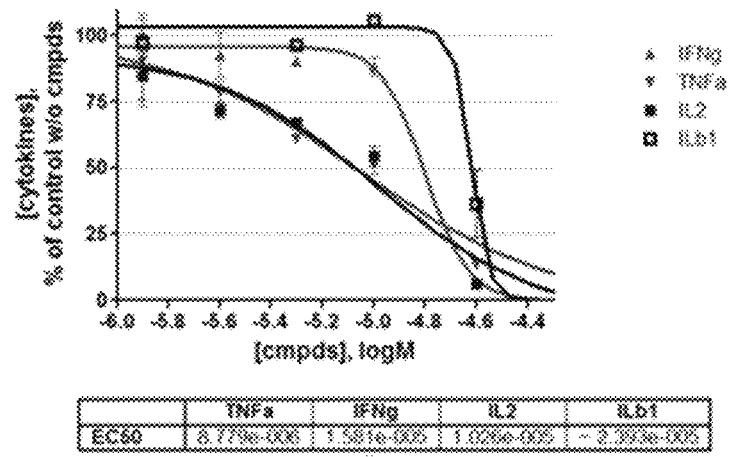
FIGS. 23A and 23B show results of cytokines release by hPBMC and cytotox for Compound Z33. For cytokines release and cytotox on hPBMCs compound was tested at 1.25, 2.5, 5, 10, 25 and 50 uM in duplicates. For cytotox on HEK293, HEK293 pGL4 and HEK293 NR2F6 (full length) compound was tested from 50 uM with dilution step 3.16 in duplicates. Human PBMC were activated by 10 ng/mL PMA+500 ng/mL ionomycin. Data were normalized to controls with (100%) without compounds.
Figure 23B:
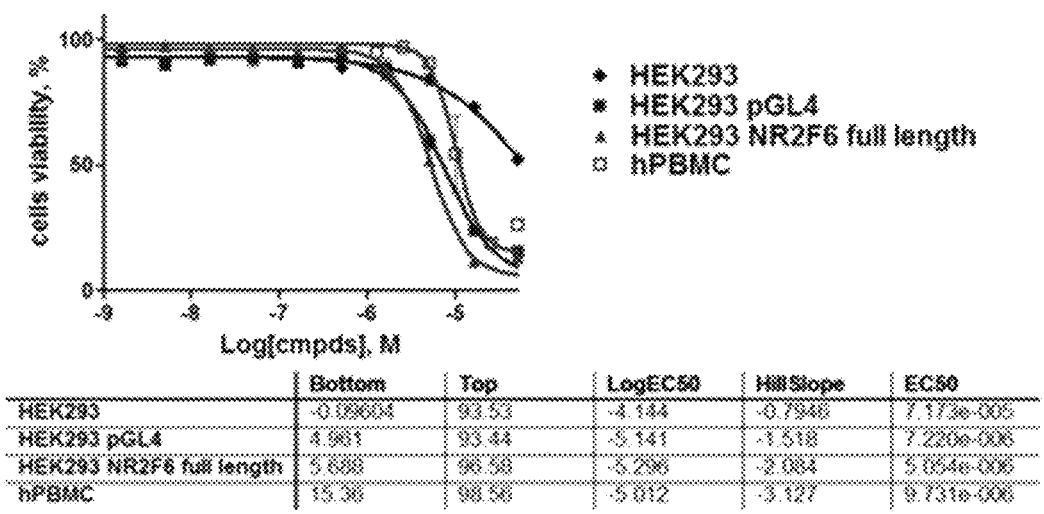

Compound Z33, previously mentioned above, was tested in a cytokine release experiment. Results are shown in FIGS. 23A and 23B.

Another compound found to be useful is Compound E56:

Compound E56

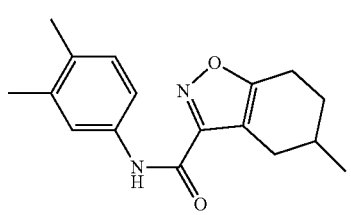

Figure 24:
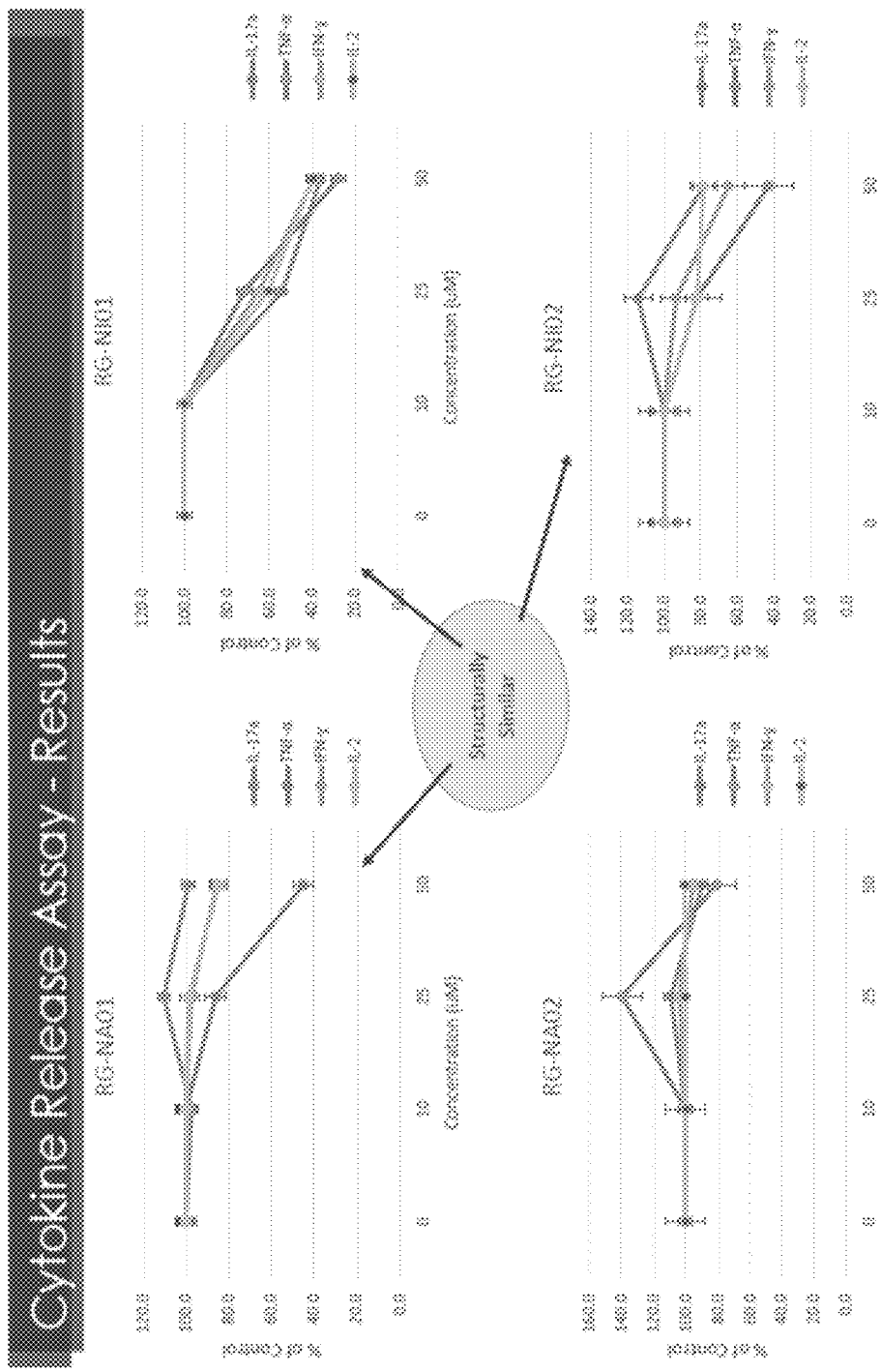
FIG. 24 shows results of a cytokines release by hPBMC for Compound E56.

FIG. 24 shows the results of testing done on Compound E56.

Additional compounds found to be useful are Compounds Z96 and Z97:

Compound Z96

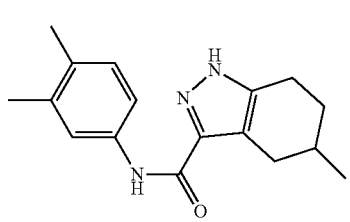

Compound Z97

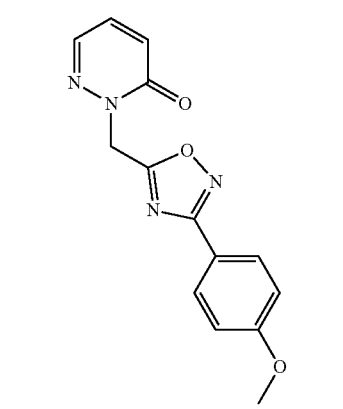

Results of testing done on compounds Z96 and Z97 are shown in Tables 18 and 19, respectively.

TABLE 18

| | NR2F6_full (stable, clone F4), cmpd/DMSO | | | | | | NR2F6_full (transient), cmpd/DMSO | | | | | |
|---|---|---|---|---|---|---|---|---|---|---|---|---|
| | Firefly | | | Renilla | | | Firefly | | | Renilla | | |
| ID | 40 uM | 10 uM | 2 uM | 40 uM | 10 uM | 2 uM | 40 uM | 10 uM | 2 uM | 40 uM | 10 uM | 2 uM |
| Z96 | 2.6 | 2.6 | 2.9 | 1.2 | 1.2 | 1.3 | 2.4 | 2.3 | 2.4 | 0.9 | 1.0 | 1.0 |

TABLE 19

| | NR2F6_full (stable, clone F4), cmpd/DMSO | | | | | | NR2F6_full (transient), cmpd/DMSO | | | | | |
|---|---|---|---|---|---|---|---|---|---|---|---|---|
| | Firefly | | | Renilla | | | Firefly | | | Renilla | | |
| ID | 40 uM | 10 uM | 2 uM | 40 uM | 10 uM | 2 uM | 40 uM | 10 uM | 2 uM | 40 uM | 10 uM | 2 uM |
| Z97 | 1.5 | 2.2 | 2.3 | 1.2 | 1.1 | 1.1 | 2.3 | 2.8 | 2.4 | 1.1 | 1.1 | 1.0 |

Figure 25A:
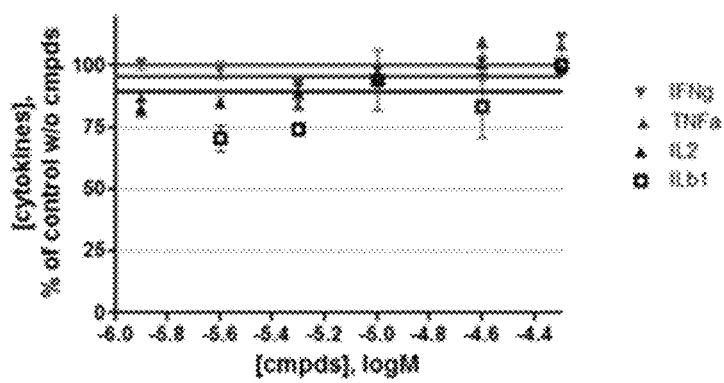
FIGS. 25A and 25B show results of cytokines release by hPBMC and cytotox for Compound Z96. For cytokines release and cytotox on hPBMCs compound was tested at 1.25, 2.5, 5, 10, 25 and 50 uM in duplicates. For cytotox on HEK293, HEK293 pGL4 and HEK293 NR2F6 (full length) compound was tested from 50 uM with dilution step 3.16 in duplicates. Human PBMC were activated by 10 ng/mL PMA+500 ng/mL ionomycin. Data were normalized to controls without (100%) compounds.
Figure 25B:
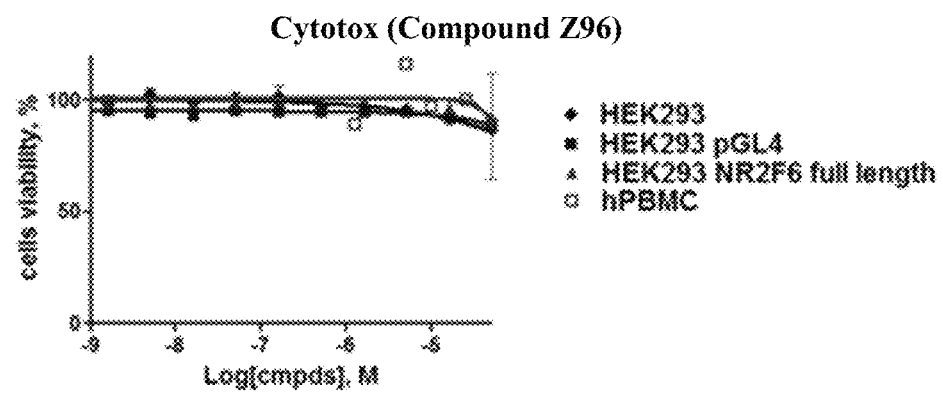
Figure 26A:
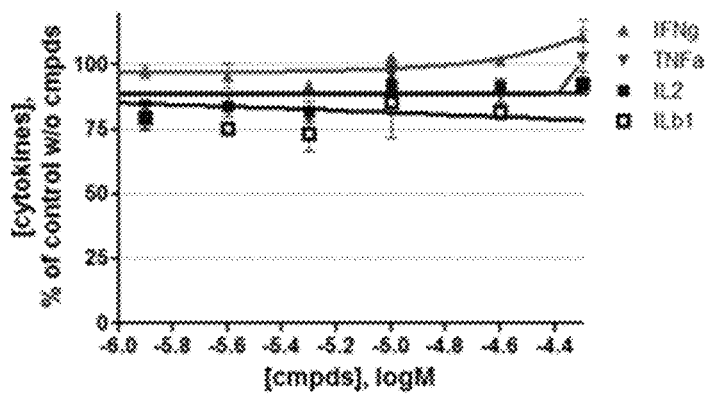
FIGS. 26A and 26B show results of cytokine release by hPBMC and cytotox for Compound Z97.
Figure 26B:
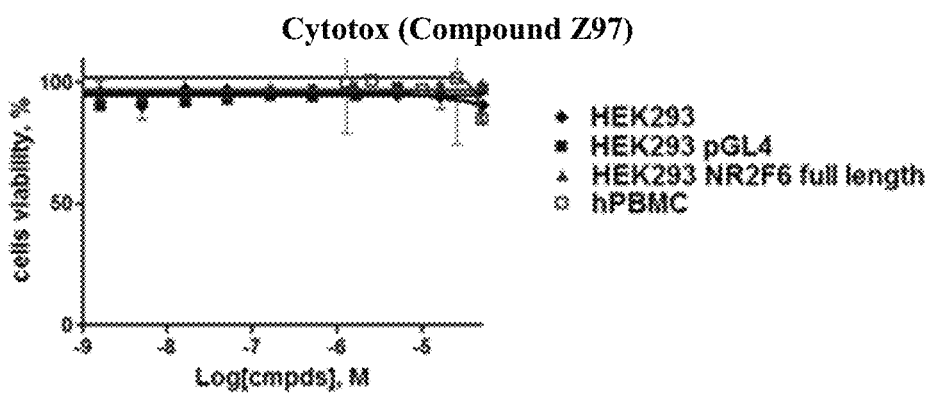

FIGS. 25A and 25B show further results of testing done on Compound Z96. FIGS. 26A and 26B show further results of testing done on Compound Z97.

Additional compounds found to be useful are Compounds Z93 and Z94:

Compound Z93

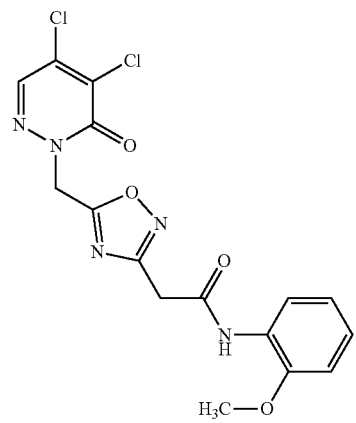

Compound Z94

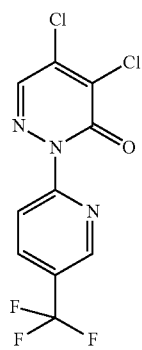

The results of dogs PBMC cytotox for Compounds Z93 and Z94 are included in FIG. 19B, which also shows results for the following Compounds: Z92, E54, E55 and E53.

Additional compounds tested included the following:

Compound 20

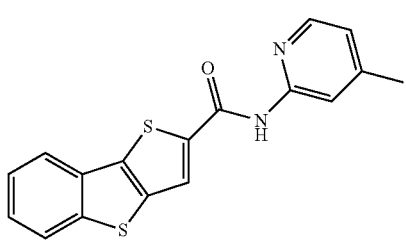

-continued

Compound 21

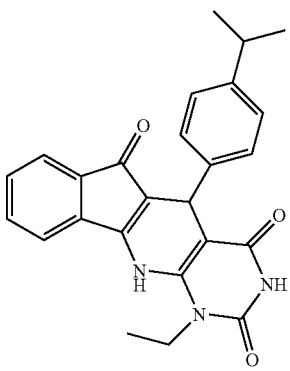

Compound 23

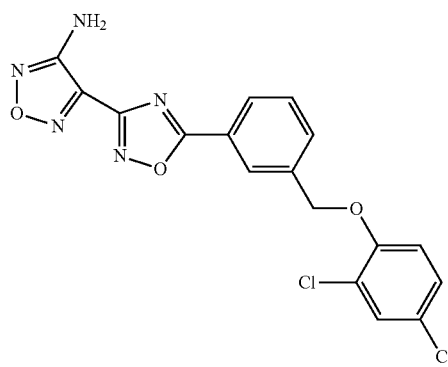

Compound 24

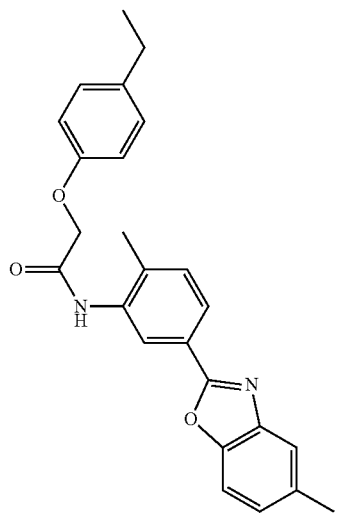

Compound 25

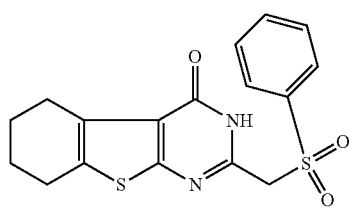

Compound 26
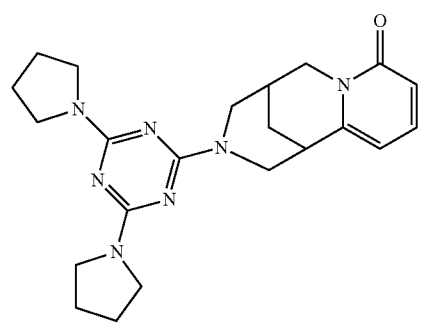
Compound 27
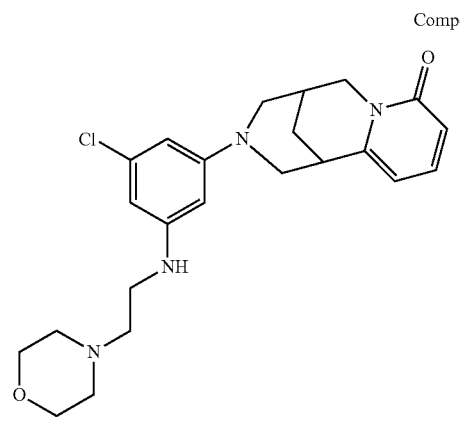
Compound 28
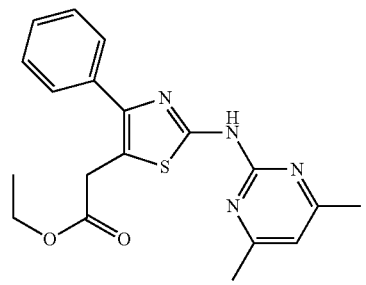
Compound 29
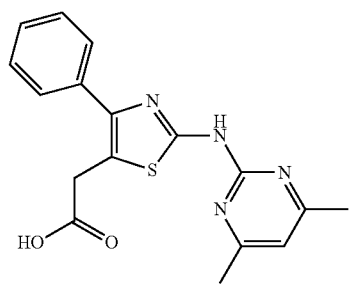
Compound 30
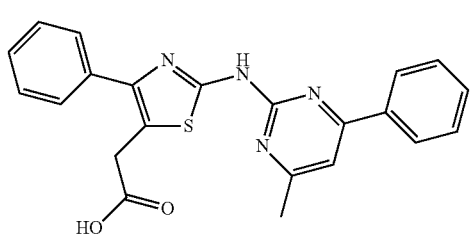
Compound 31
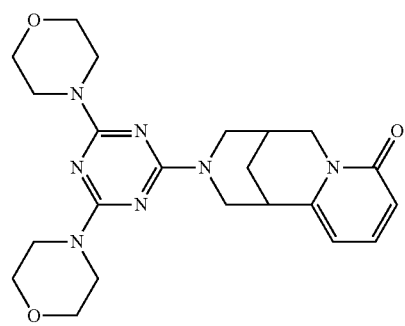
Compound 32
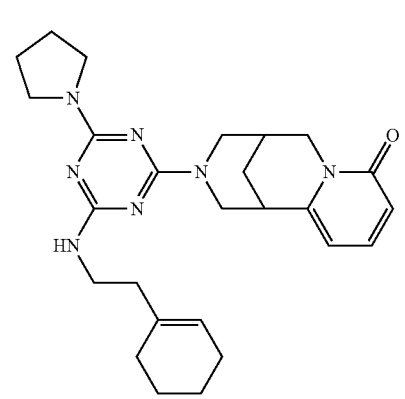
Compound 33
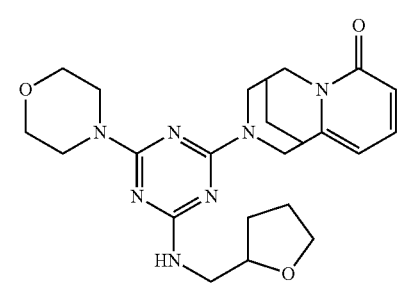
Compound 34
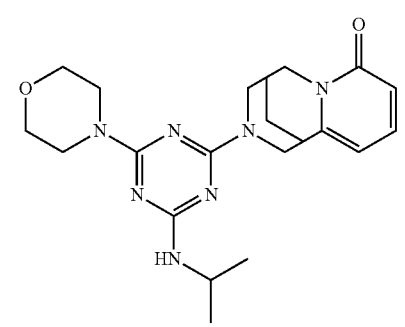
Compound 35
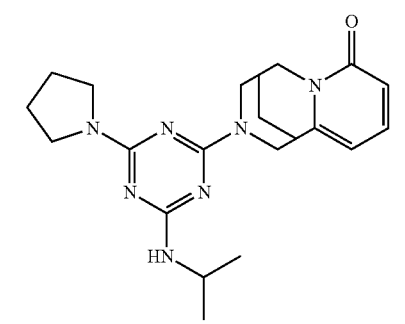

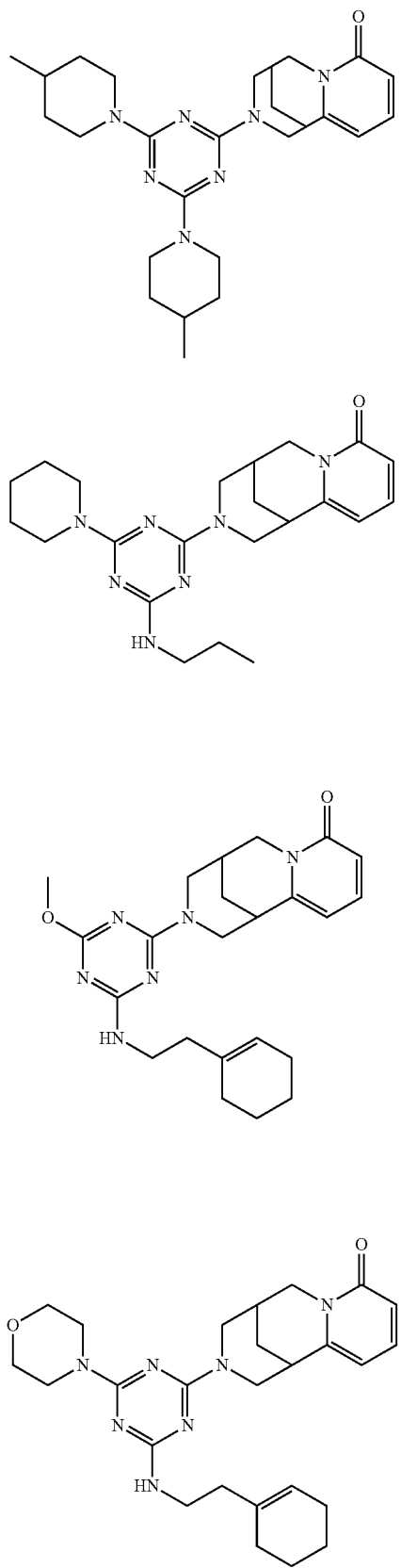
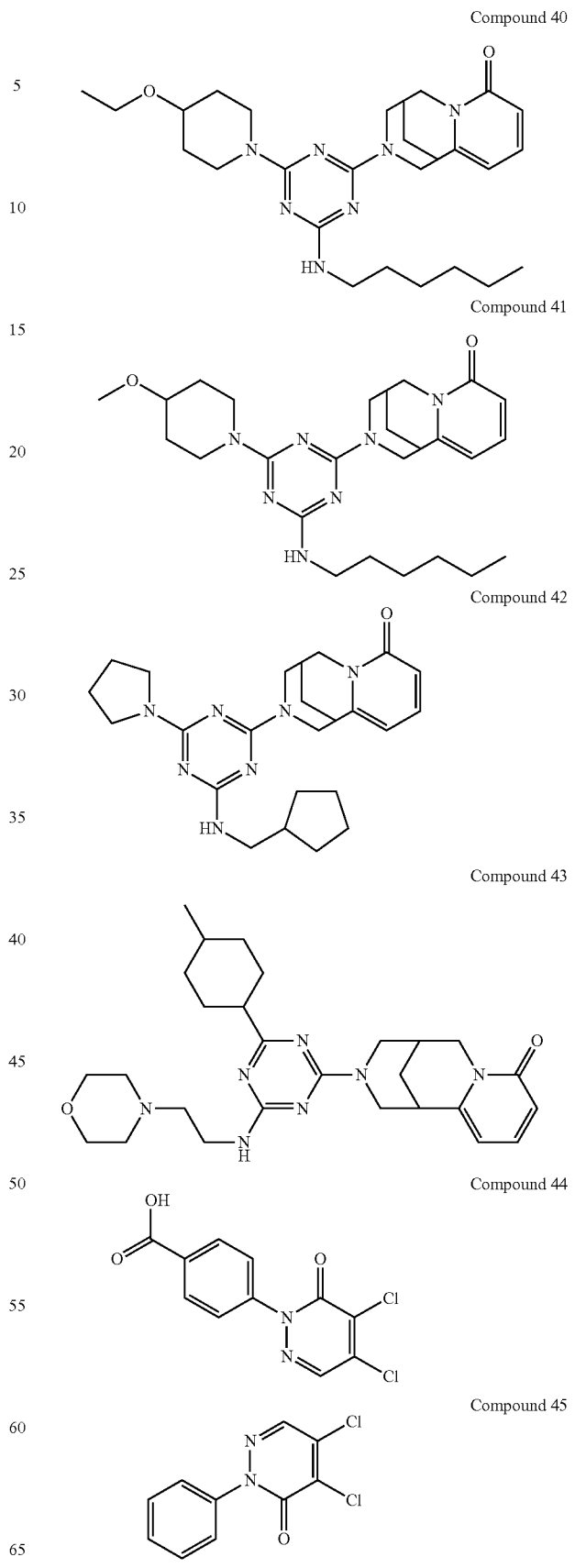

Table 20 shows screening results from another set of compounds.

TABLE 20

| Compound ID | Firefly | | | | | | Renilla | | | | | |
|---|---|---|---|---|---|---|---|---|---|---|---|---|
| | F4, cmpd/DMSO (mean) | | | ERalpha transient, cmpd/DMSO (mean) | | | F4, cmpd/DMSO (mean) | | | ERalpha transient, cmpd/DMSO (mean) | | |
| | 40 uM | 10 uM | 2 uM | 40 uM | 10 uM | 2 uM | 40 uM | 10 uM | 2 uM | 40 uM | 10 uM | 2 uM |
| 26 | 1.3 | 1.1 | 1.0 | 1.1 | 1.3 | 1.0 | 0.7 | 0.7 | 1.0 | 1.0 | 1.0 | 0.9 |
| 27 | 1.0 | 1.0 | 1.0 | 1.2 | 1.2 | 1.2 | 0.8 | 0.9 | 0.9 | 1.2 | 1.1 | 1.1 |
| 28 | 0.6 | 0.9 | 1.2 | 0.6 | 0.5 | 1.0 | 0.6 | 0.8 | 1.1 | 0.7 | 0.8 | 1.2 |
| 29 | 1.5 | 1.4 | 0.9 | 2.2 | 1.7 | 1.2 | 0.8 | 0.9 | 0.8 | 1.1 | 1.0 | 1.1 |
| 30 | 1.8 | 1.6 | 1.5 | 1.3 | 1.5 | 1.1 | 3.4 | 2.3 | 1.2 | 1.0 | 1.2 | 1.2 |
| 31 | 0.9 | 1.0 | 0.8 | 1.0 | 1.2 | 0.8 | 1.0 | 1.0 | 1.0 | 1.1 | 1.1 | 1.0 |
| 32 | 0.8 | 1.3 | 0.8 | 0.7 | 1.2 | 1.2 | 1.0 | 1.4 | 1.2 | 1.1 | 1.3 | 1.2 |
| 33 | 1.1 | 1.0 | 0.8 | 1.4 | 1.3 | 1.3 | 1.4 | 1.3 | 1.2 | 1.3 | 1.1 | 1.2 |
| 34 | 0.9 | 0.8 | 0.9 | 1.2 | 1.2 | 1.1 | 0.9 | 1.1 | 0.9 | 1.1 | 1.1 | 1.0 |
| 35 | 0.8 | 1.0 | 1.1 | 1.3 | 0.9 | 1.0 | 0.9 | 0.9 | 1.1 | 1.1 | 1.0 | 1.0 |
| 36 | 0.9 | 0.6 | 1.3 | 0.4 | 0.8 | 1.1 | 0.5 | 0.8 | 1.2 | 0.3 | 1.1 | 1.2 |
| 37 | 1.3 | 1.1 | 1.3 | 1.2 | 1.4 | 1.1 | 1.3 | 1.2 | 0.9 | 1.1 | 1.1 | 1.1 |
| 38 | 0.7 | 0.8 | 1.2 | 0.5 | 0.9 | 0.8 | 1.3 | 1.1 | 1.1 | 1.1 | 1.1 | 1.2 |
| 39 | 0.9 | 0.9 | 1.1 | 0.9 | 0.6 | 0.9 | 1.0 | 1.4 | 1.2 | 1.2 | 1.2 | 1.1 |
| 40 | 0.8 | 1.0 | 0.9 | 0.7 | 1.0 | 1.0 | 1.0 | 1.3 | 1.1 | 1.1 | 1.2 | 1.2 |
| 41 | 0.9 | 0.9 | 0.8 | 1.4 | 1.5 | 1.5 | 1.1 | 1.1 | 1.1 | 1.1 | 1.2 | 1.2 |
| 42 | 0.9 | 0.8 | 1.6 | 1.0 | 1.0 | 2.3 | 1.1 | 0.8 | 0.7 | 1.0 | 1.0 | 0.9 |
| 43 | 0.8 | 0.9 | 1.0 | 1.2 | 1.4 | 1.4 | 1.1 | 1.1 | 1.0 | 1.0 | 1.0 | 1.1 |
| 44 | 0.7 | 1.5 | 1.3 | 0.5 | 1.3 | 1.5 | 0.3 | 1.1 | 1.1 | 0.3 | 1.2 | 1.3 |
| 45 | 0.7 | 1.2 | 3.2 | 0.6 | 1.6 | 1.8 | 0.2 | 0.8 | 1.6 | 0.2 | 0.8 | 1.6 |

After several rounds of testing, the following compounds were found to be particularly optimal.

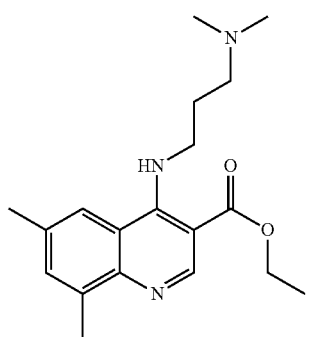

Compound D28

Activity/DMSO: 11/1.5

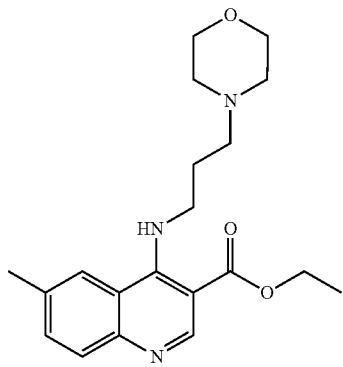

Compound D41

Activity/DMSO: 1.5

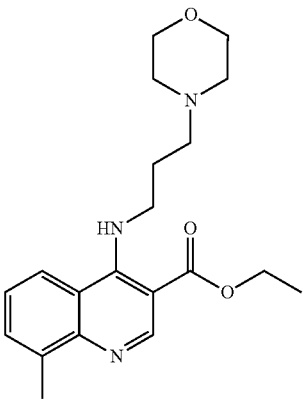

Compound D84

Activity/DMSO: 1.5

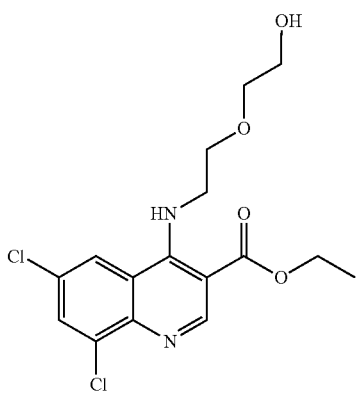

Compound D53

Activity/DMSO: 1.6

Compound D18

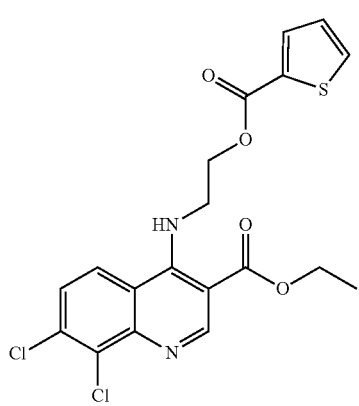

Activity/DMSO: 1.4

Compound D27

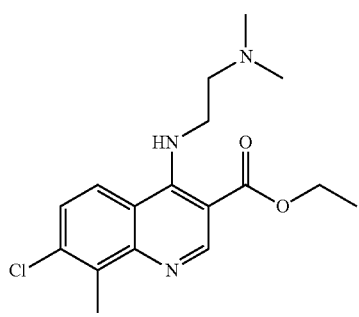

Activity/DMSO: 2.1/1.5

Table 21 shows results of testing on Compound D28.

TABLE 21

| Firefly, cmpd/DMSO | | | Firefly, cmpd | | Firefly, DMSO | | Renilla, cmpd/DMSO | | Renilla, DMSO | |
|---|---|---|---|---|---|---|---|---|---|---|
| repeat 1 | repeat 2 | mean | repeat 1 | repeat 2 | mean plate1 | mean plate2 | repeat 1 | repeat 2 | mean plate1 | mean plate2 |
| 14.1 | 11.7 | 12.8 | 784 | 644 | 56 | 55 | 0.7 | 0.5 | 3237 | 2930 |

Figure 27A:
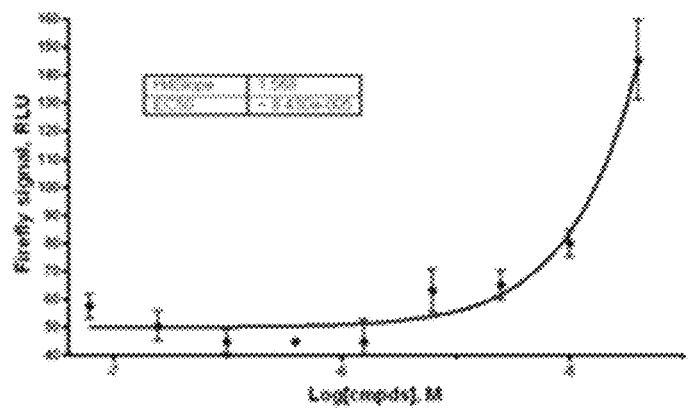
FIGS. 27A-27D show NR2F6 and LBD transient transfection, respectively, for Compound D28.
Figure 27B:
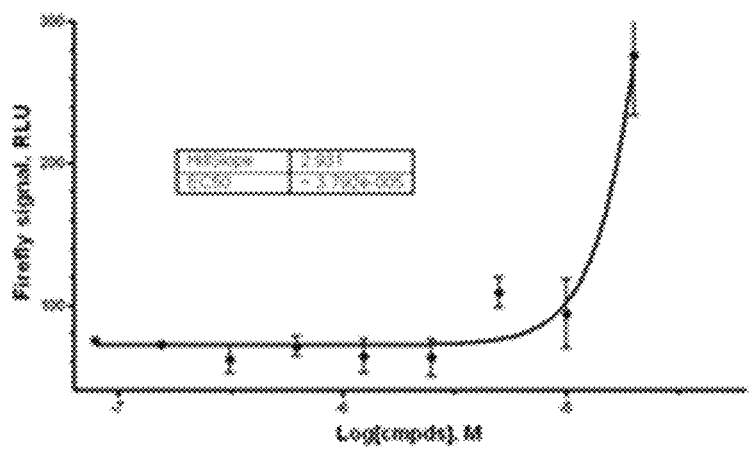
Figure 27C:
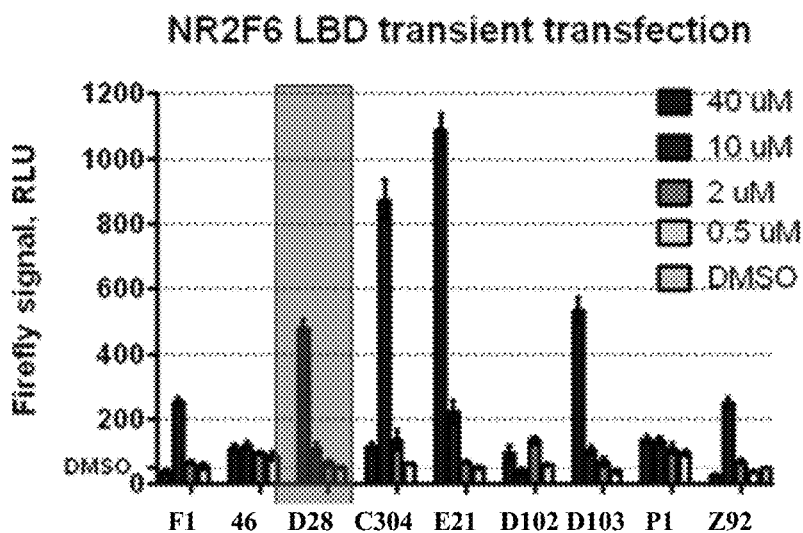
Figure 27D:
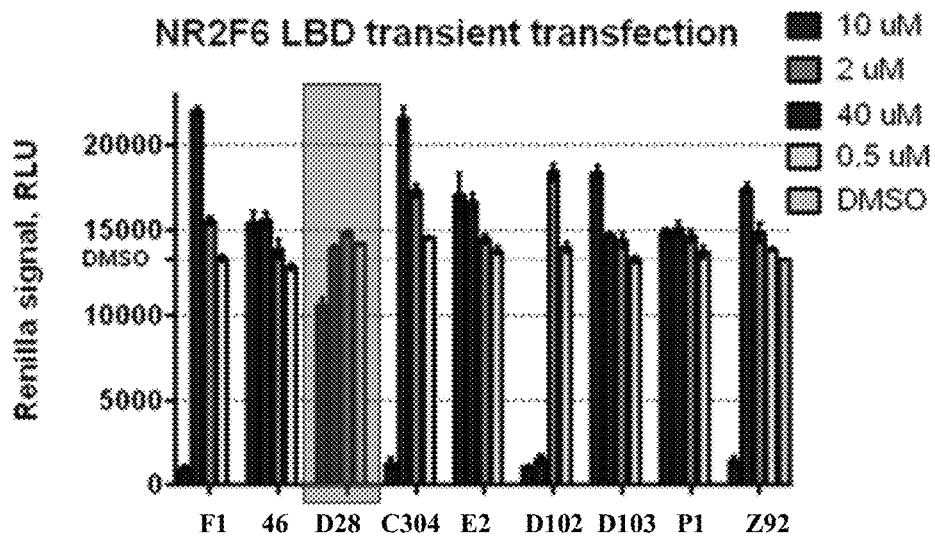
Figure 27E:
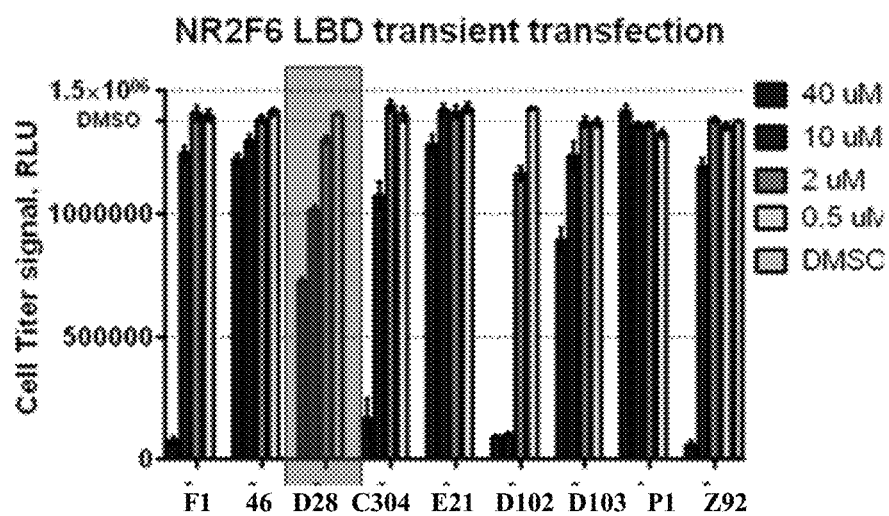
FIGS. 27E and 27F show toxicity of Compound D28.
Figure 27F:
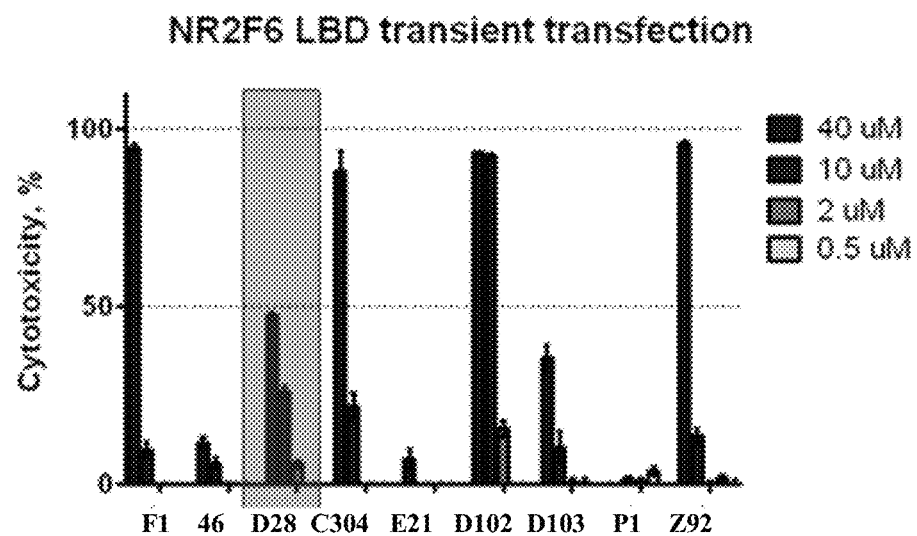
Figure 28A:
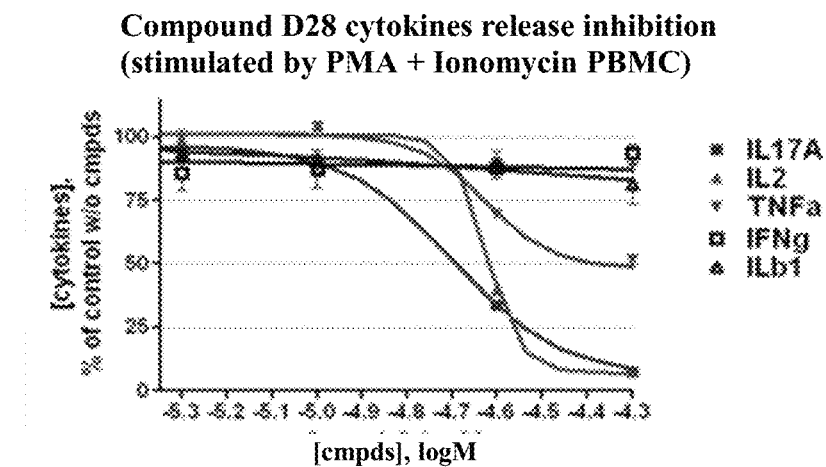
FIGS. 28A-28D show the results of a cytokine release experiment for dog and human PBMC. All compounds were tested at 5, 10, 25 and 50 uM in duplicates. Dog PBMC (1×106 cells/mL) were activated by 10 ng/mL PMA+500 ng/mL ionomycin. Data were normalized to controls with (100%)/without (0%) PMA+ionomycin activation.
Figure 28B:
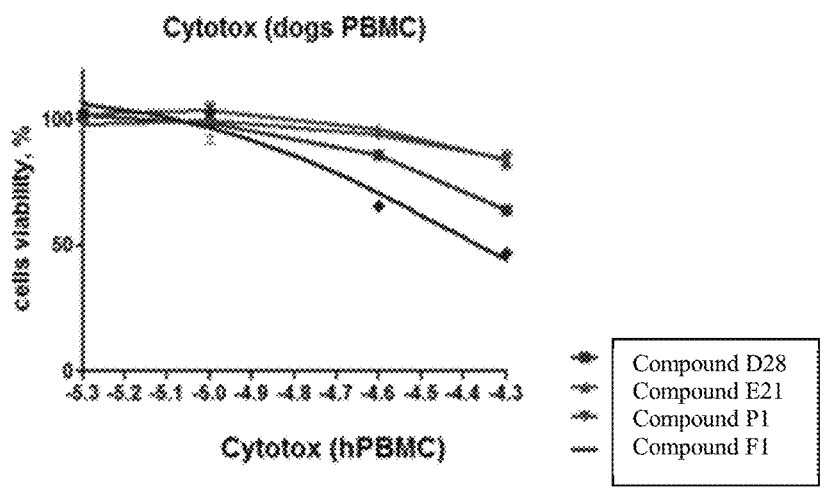
Figure 28C:
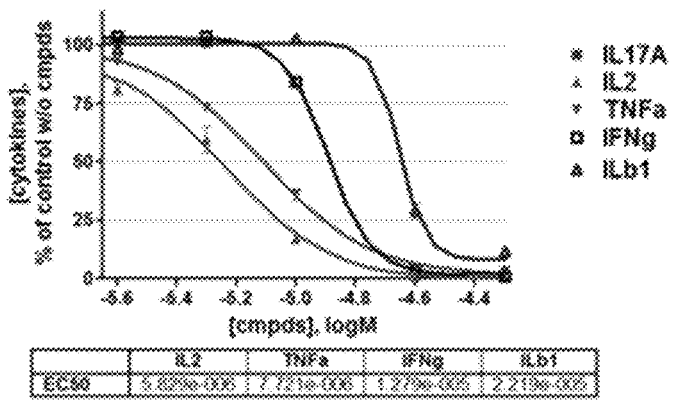
Figure 28D:
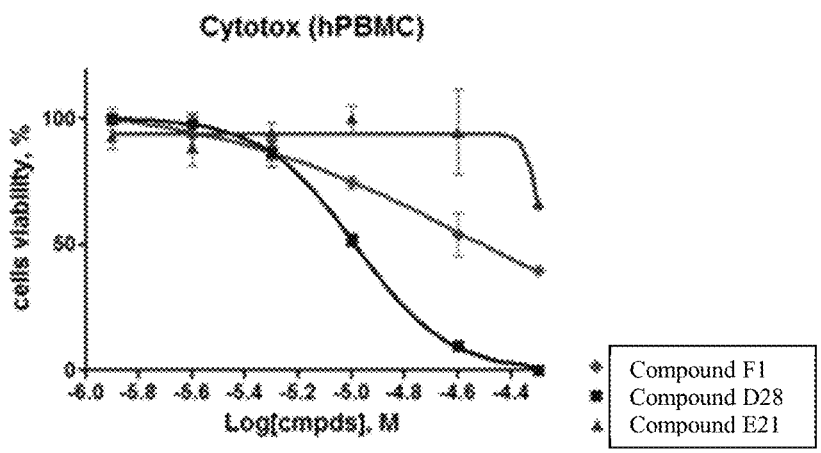
Figure 29:
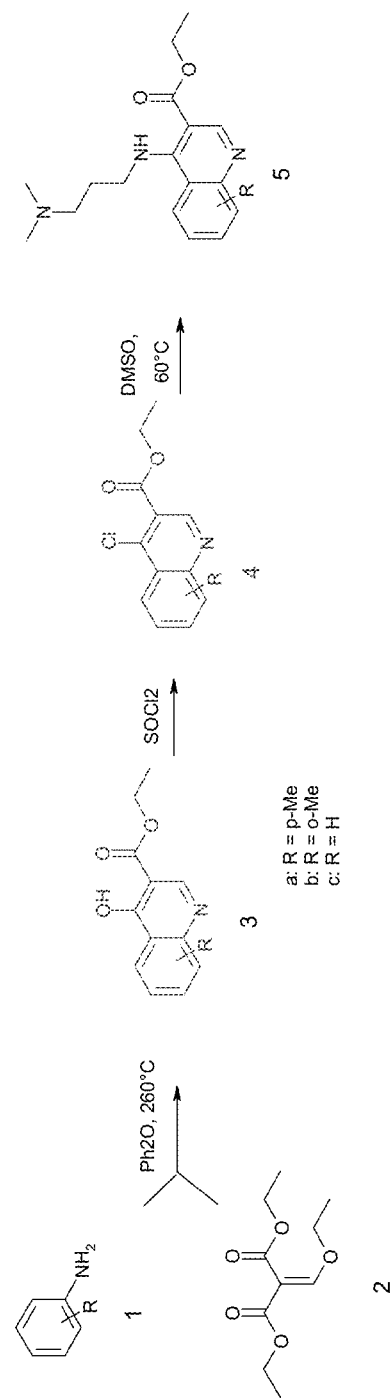
FIGS. 29, 30 31A, 31B and 32 show exemplary methods of formulating the compounds that have been discussed herein.
Figure 30:
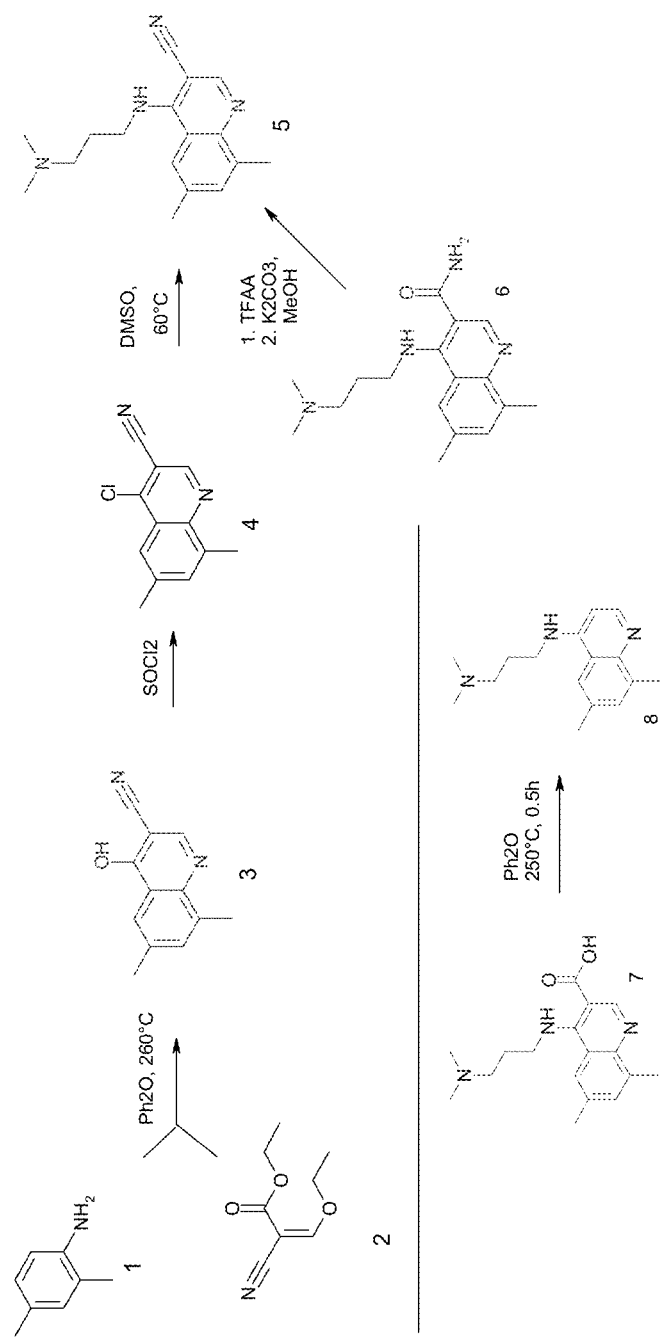

FIGS. 27A and 27B show NR2F6 and LBD transient transfection, respectively, for Compound D28. Higher concentrations were excluded due to lower signal (tox effect). FIGS. 27C and 27D show NR2F6 and LBD transient transfection at different concentrations for different compounds. 9 compounds were tested on LBD transfected cells (40, 10, 2 and 0.5 µM, 4 replicates). FIGS. 27E and 27F show toxicity of Compound D28. 9 compounds were tested for cytotoxicity on LBD transfected cells (40, 10, 2 and 0.5 µM, 4 replicates). Tox effect was found to cause lower signal compared to DMSO. Cytotoxicity normalized to DMSO is shown in FIG. 27F (0% cytotoxicity corresponds to DMSO signal, 100%—zero signal).

FIGS. 28A-D show the results of a cytokind release experiment for dog and human PBMC. All compounds were tested at 5, 10, 25 and 50 uM in duplicates.

Dog PBMC (1×106 cells/mL) were activated by 10 ng/mL PMA+500 ng/mL ionomycin. Data were normalized to controls with (100%)/without (0%) PMA+ionomycin activation.

In further embodiments, the present technology is directed to compounds of Formula (IX):

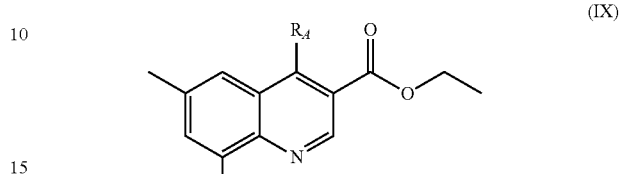

(IX)

wherein $R_A$ is C, H, N, O, S, a halogen, an alkyl group, a substituted alkyl group, a cyclic alkyl group, an aryl group, a substituted aryl group, a heterocyclic group, an ester, an aldehyde, a ketone, a carboxylic acid, an amide, an amine, an ether, a thiol or a nitrile. For example, exemplary but non-limiting compounds are shown below:

Compound Z58

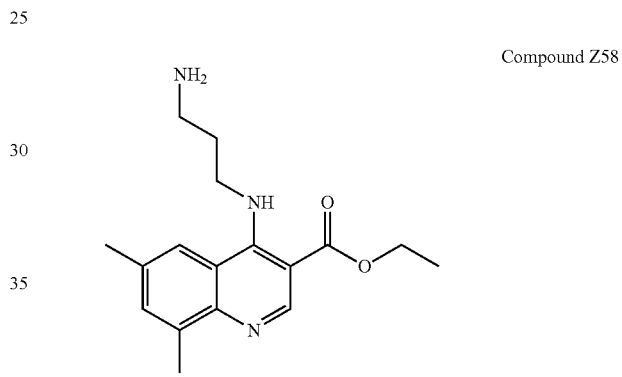

-continued

Compound Z59

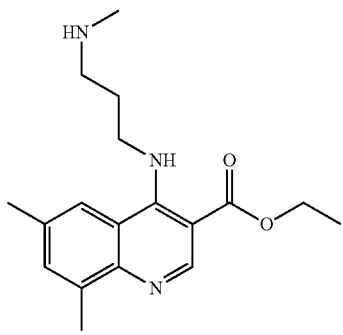

Compound Z17
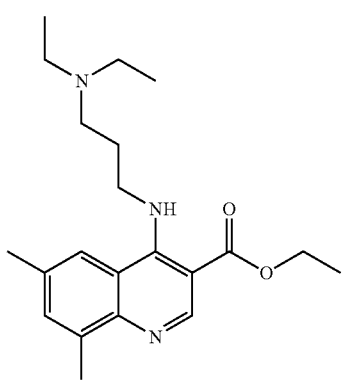
Compound Z63
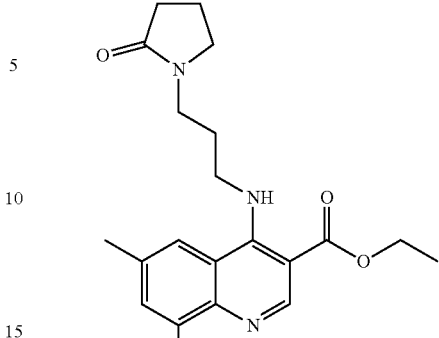
Compound Z60
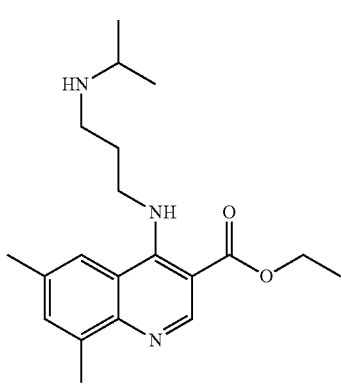
Compound Z19
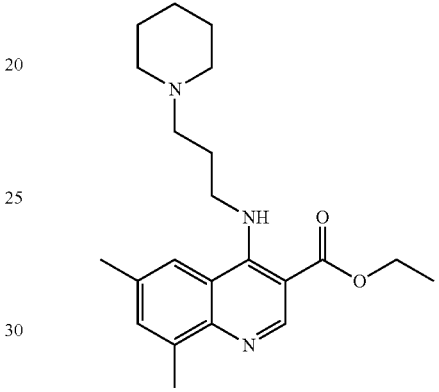
Compound Z61
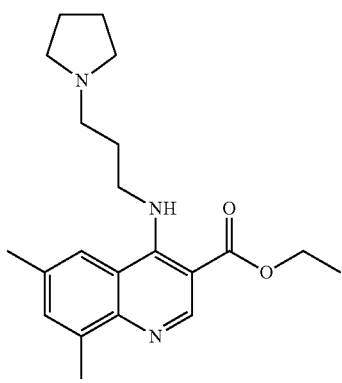
Compound Z64
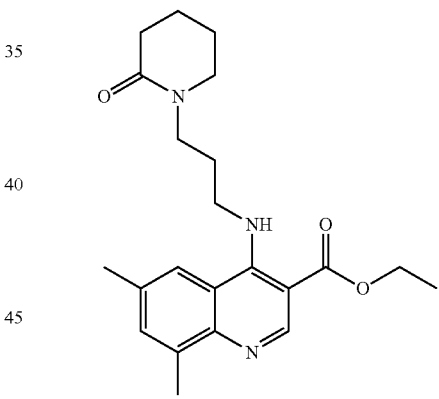
Compound Z62
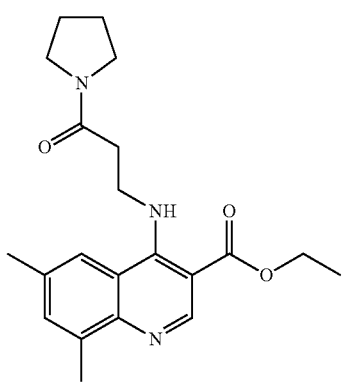
Compound Z65
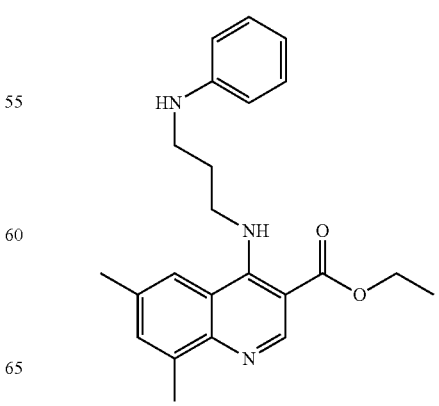

Compound Z66
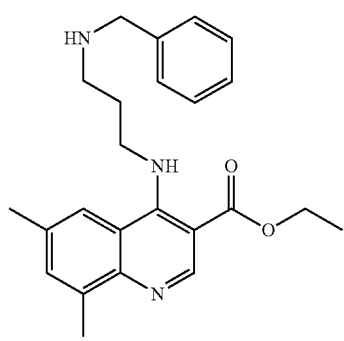
Compound Z70
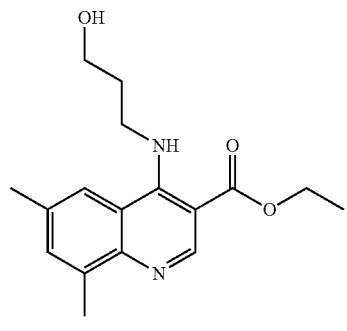
Compound Z67
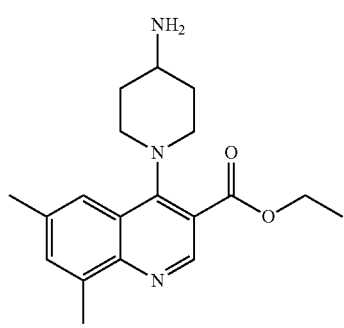
Compound Z71
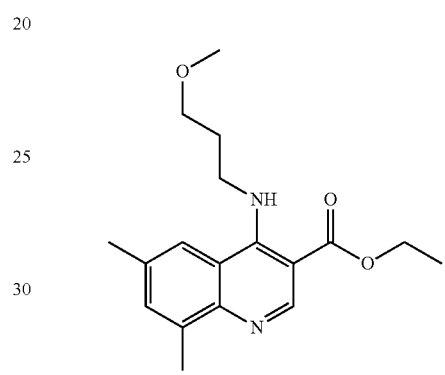
Compound Z68
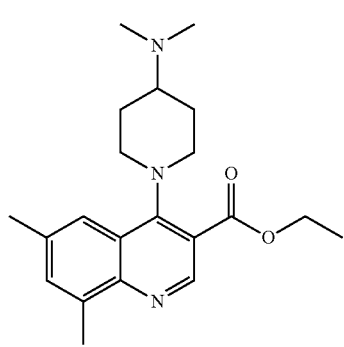
Compound Z72
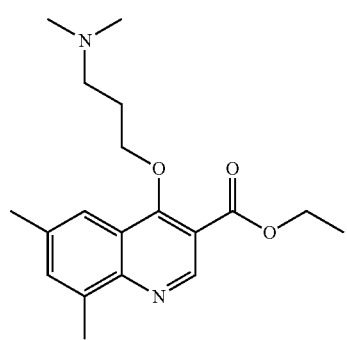
Compound Z69
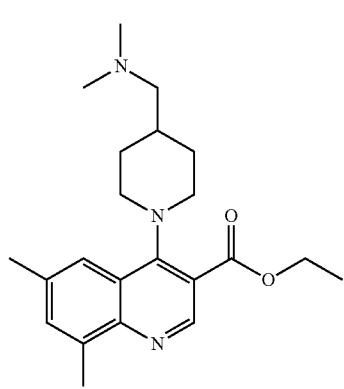
Compound Z73
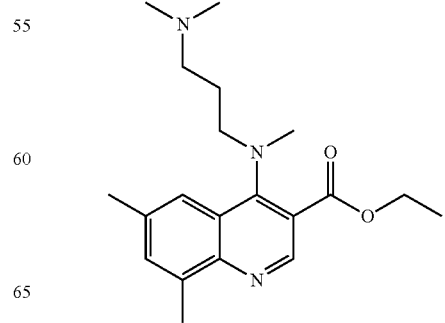

-continued

Compound Z74

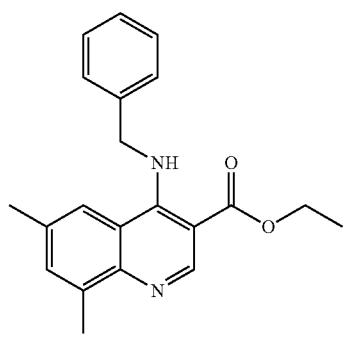

Compound Z75

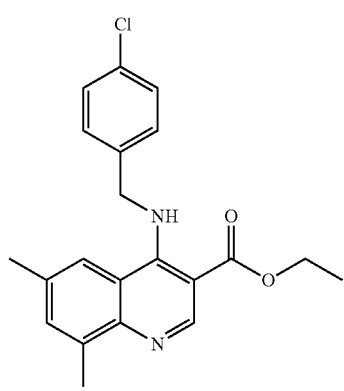

Compound Z76

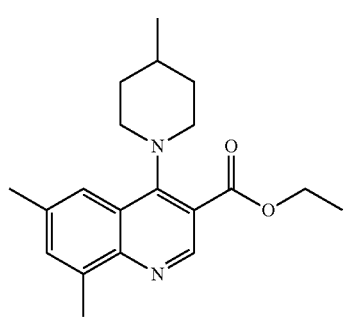

Compound Z77

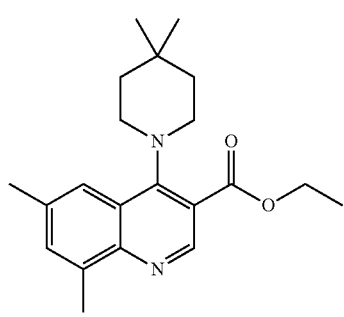

-continued

Compound Z78

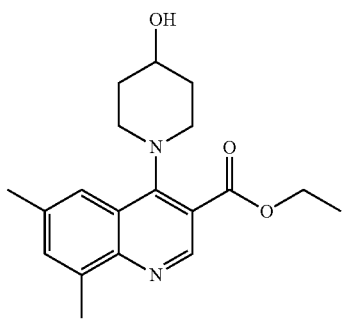

Compound Z79

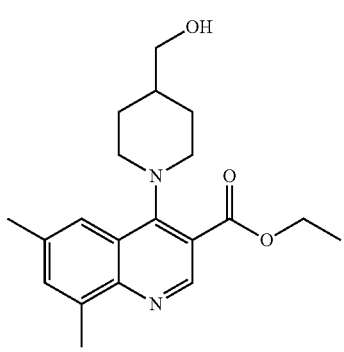

Compound Z80

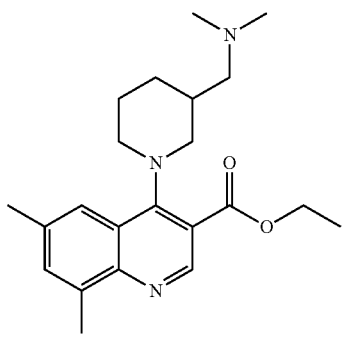

In further embodiments, the present technology is directed to compounds of Formula (X):

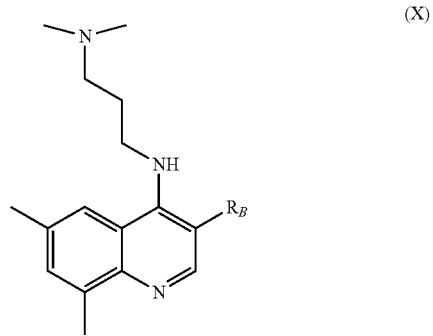

(X)

wherein $R_B$ is C, H, N, O, S, a halogen, an alkyl group, a substituted alkyl group, a cyclic alkyl group, an aryl group, a substituted aryl group, a heterocyclic group, an ester, an aldehyde, a ketone, a carboxylic acid, an amide, an amine, an ether, a thiol or a nitrile. For example, exemplary but non-limiting compounds are shown below:

Compound Z28 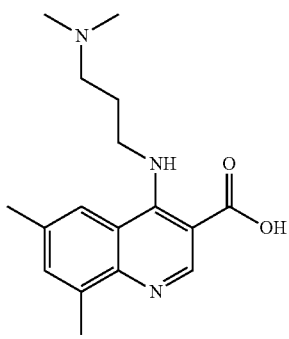
Compound Z81 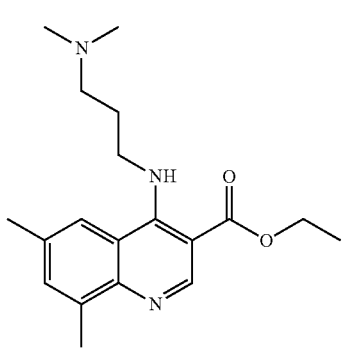
Compound Z29 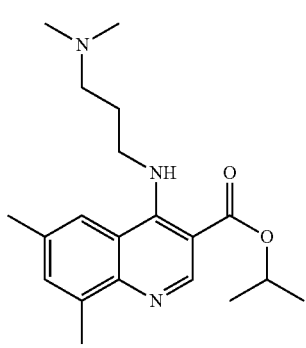
Compound Z82 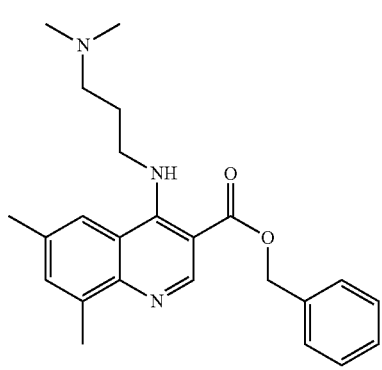
Compound Z83 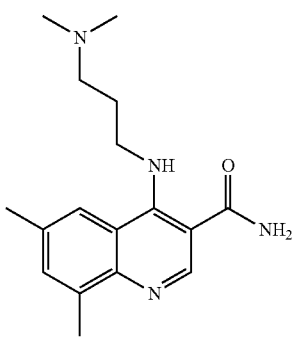
Compound Z30 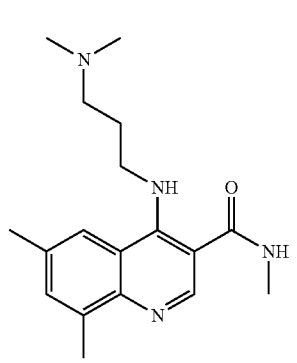
Compound Z31 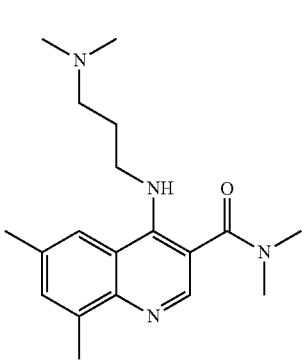
Compound Z32 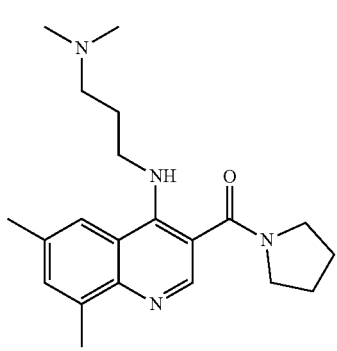

Compound Z84
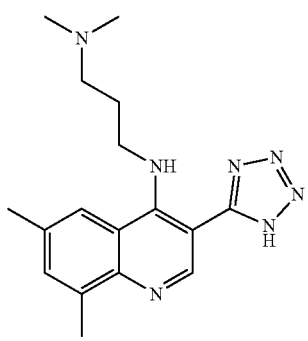

Compound Z85
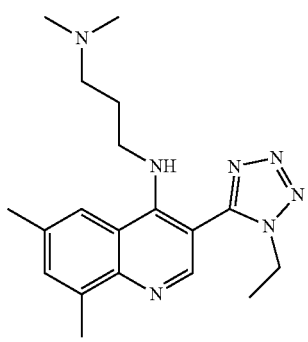

Compound Z86
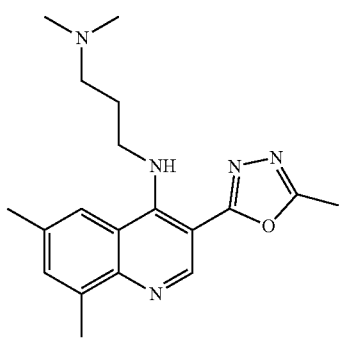

Compound Z87
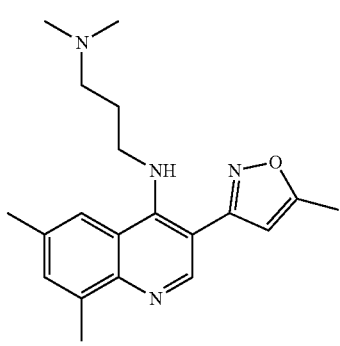

Compound Z88
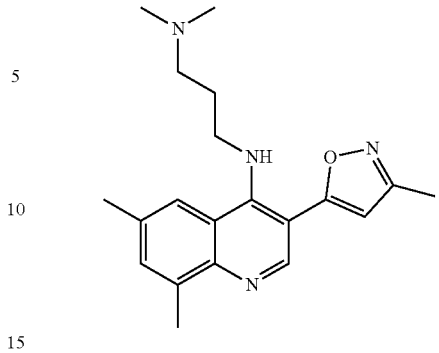

In further embodiments, the present technology is directed to compounds of Formula (XI):

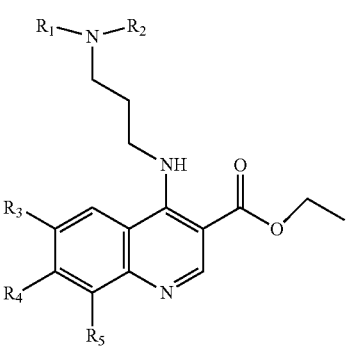

(XI)

wherein any of $R_1$-$R_5$ are C, H, N, O, S, a halogen, an alkyl group, a substituted alkyl group, a cyclic alkyl group, an aryl group, a substituted aryl group, a heterocyclic group, an ester, an aldehyde, a ketone, a carboxylic acid, an amide, an amine, an ether, a thiol or a nitrile. For example, exemplary but non-limiting compounds are shown below:

Compound Z89
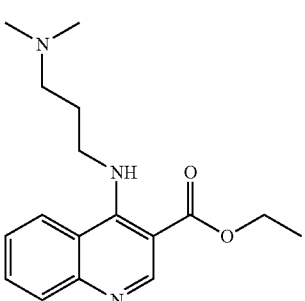

Compound Z33
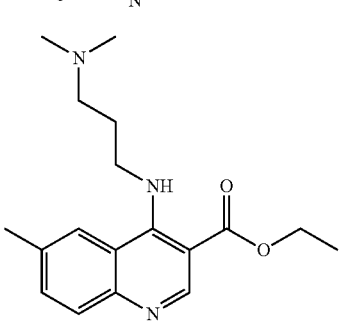

Compound Z90
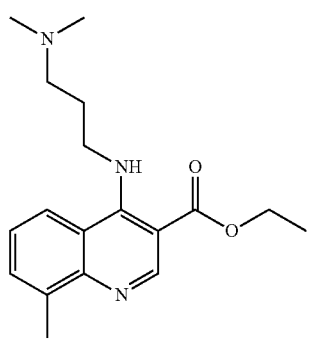
Compound Z37
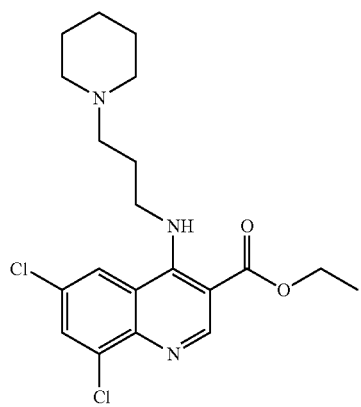
Compound Z34
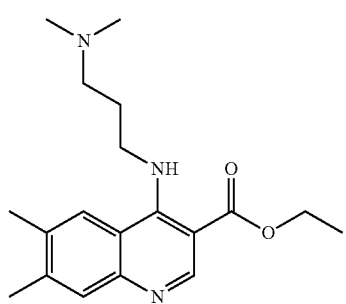
Compound Z98
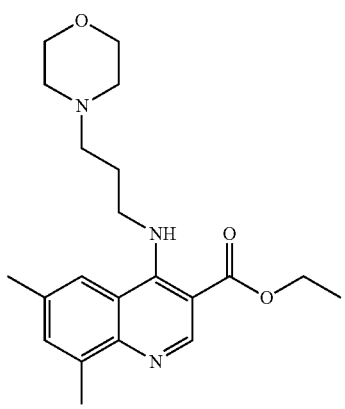
Compound Z35
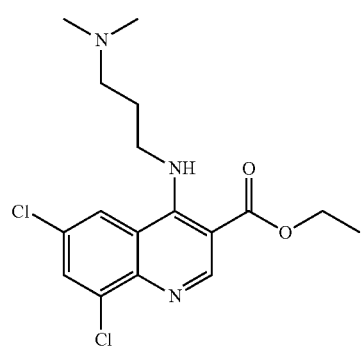
Compound Z36
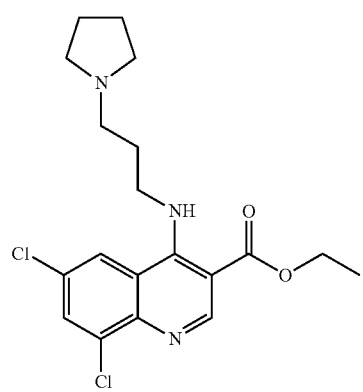
Compound Z99
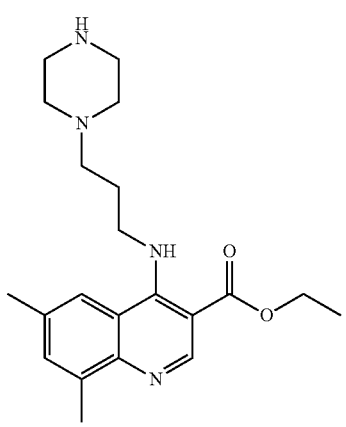

-continued

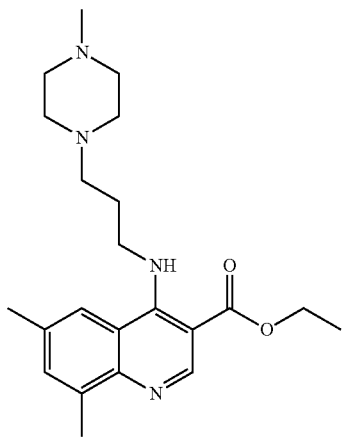
Compound Z100

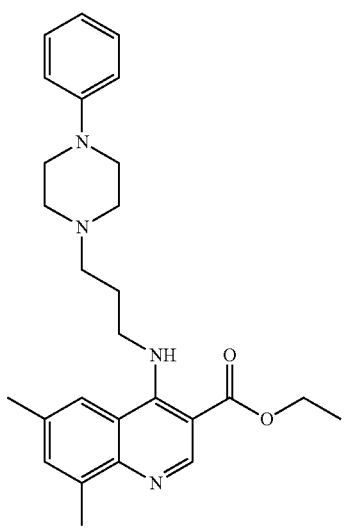
Compound Z101

In various other embodiments, the structure of the Compounds found to be useful have other variations. For example, in certain embodiments, the present technology is directed to compounds of Formula (XII):

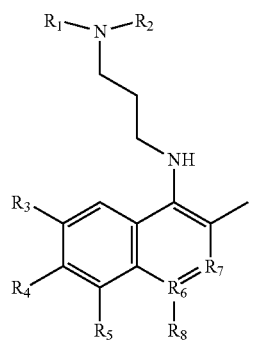
(XII)

wherein any of $R_1$ and $R_8$ is C, H, N, O, S, a halogen, an alkyl group, a substituted alkyl group, a cyclic alkyl group, an aryl group, a substituted aryl group, a heterocyclic group, an ester, an aldehyde, a ketone, a carboxylic acid, an amide, an amine, an ether, or a thiol. Exemplary but non-limiting compounds are shown below:

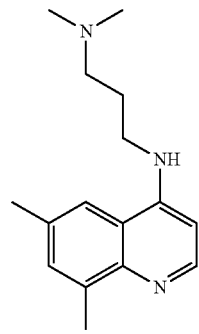
Compound Z102

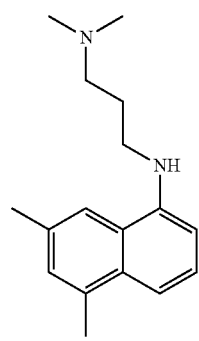
Compound Z103

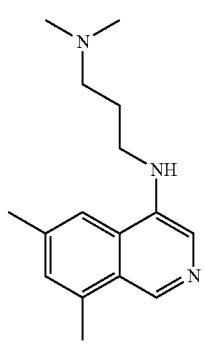
Compound Z104

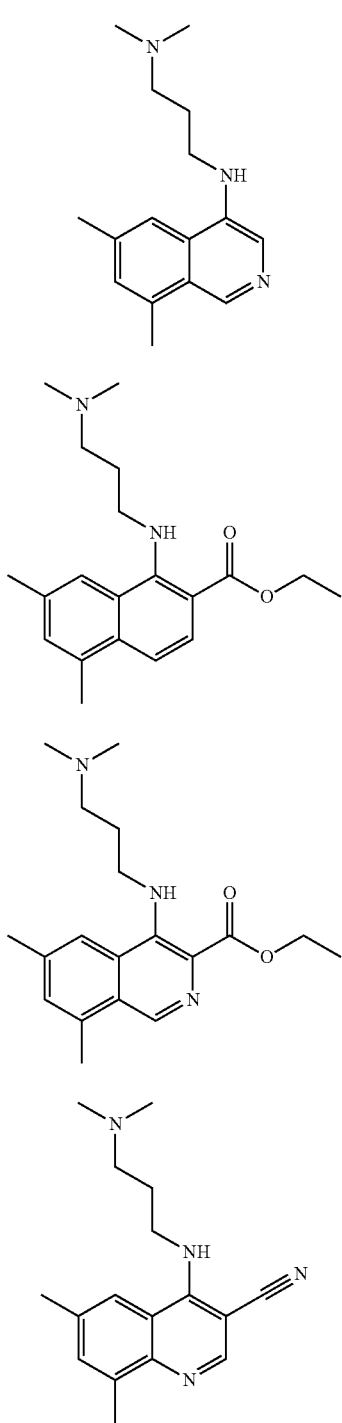

Compound Z105

Compound Z106

Compound Z107

Compound Z108

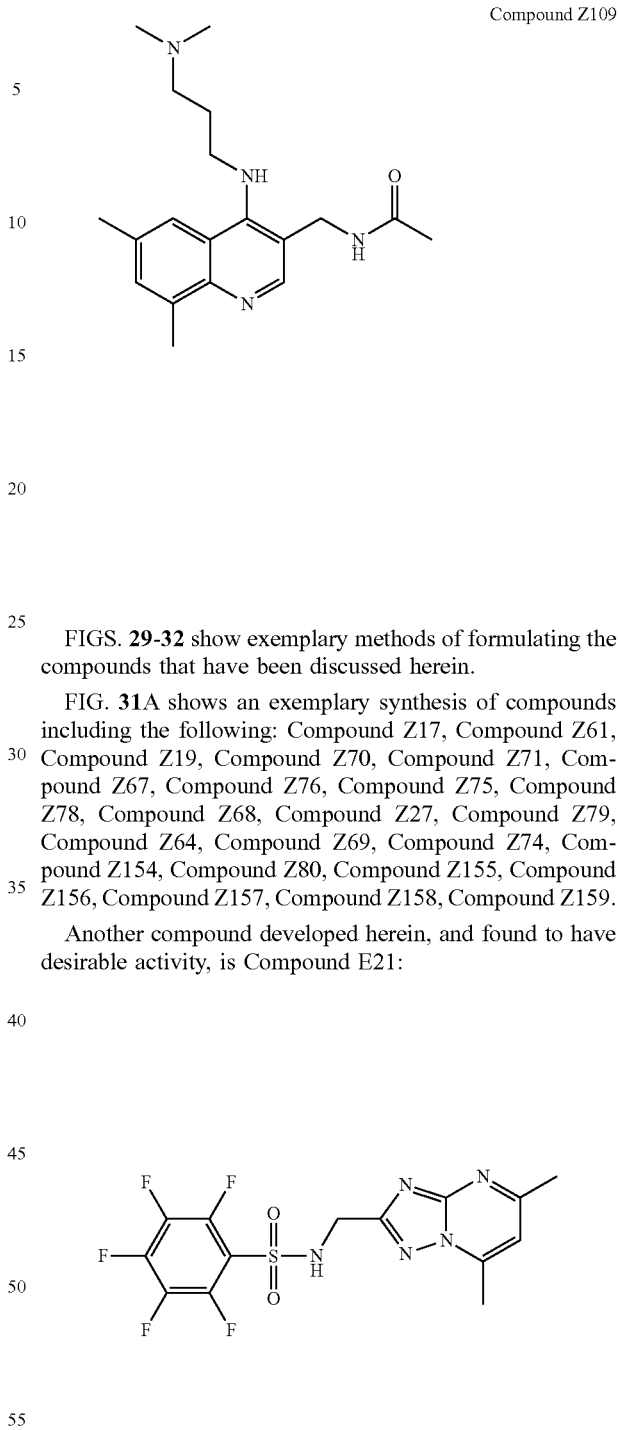

Compound Z109

FIGS. 29-32 show exemplary methods of formulating the compounds that have been discussed herein.

Figure 31A:
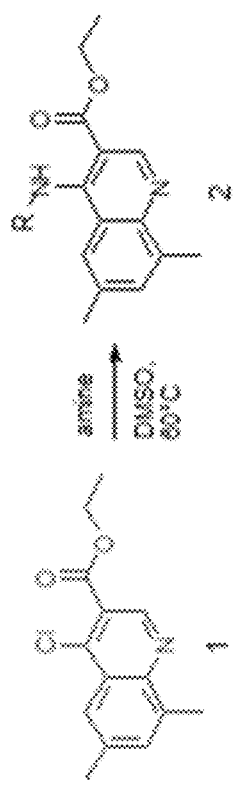
Figure 31B:
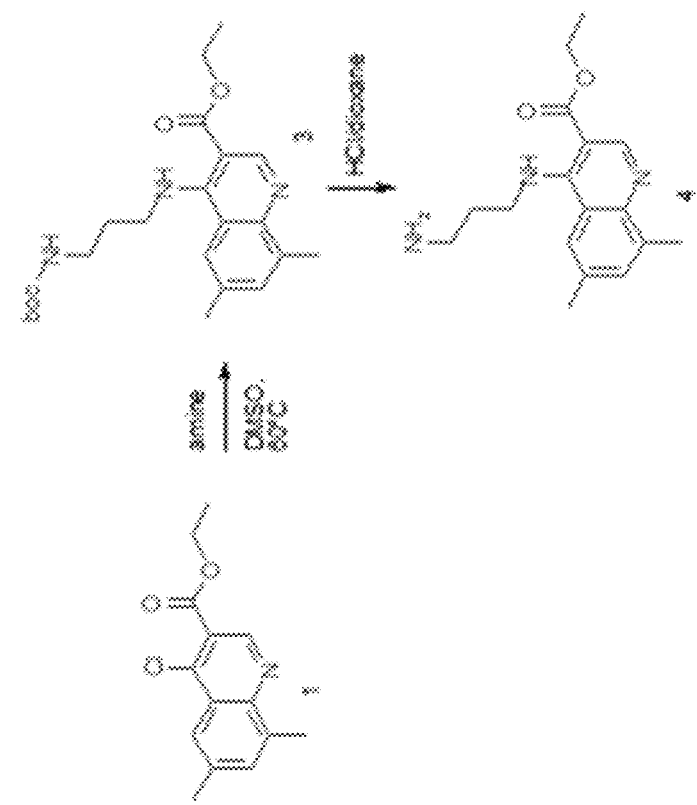
Figure 32:
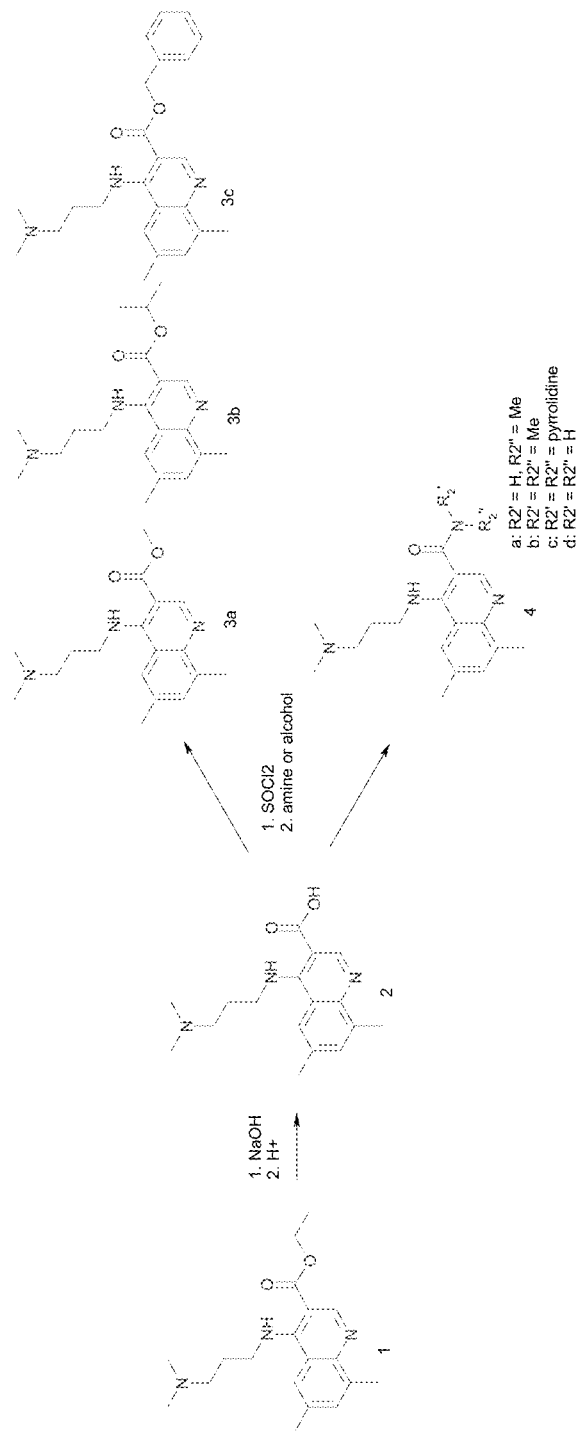

FIG. 31A shows an exemplary synthesis of compounds including the following: Compound Z17, Compound Z61, Compound Z19, Compound Z70, Compound Z71, Compound Z67, Compound Z76, Compound Z75, Compound Z78, Compound Z68, Compound Z27, Compound Z79, Compound Z64, Compound Z69, Compound Z74, Compound Z154, Compound Z80, Compound Z155, Compound Z156, Compound Z157, Compound Z158, Compound Z159.

Another compound developed herein, and found to have desirable activity, is Compound E21:

Table 22 shows results of testing on Compound E21.

TABLE 22

| Firefly, cmpd/DMSO | | | Firefly, cmpd | | Firefly, DMSO | | Renilla, cmpd/DMSO | | Renilla, DMSO | |
|---|---|---|---|---|---|---|---|---|---|---|
| repeat 1 | repeat 2 | mean | repeat 1 | repeat 2 | mean plate1 | mean plate2 | repeat 1 | repeat 2 | mean plate1 | mean plate2 |
| 9.5 | 5.6 | 7.3 | 526 | 306 | 56 | 55 | 0.6 | 0.8 | 3237 | 2930 |

Figure 33A:
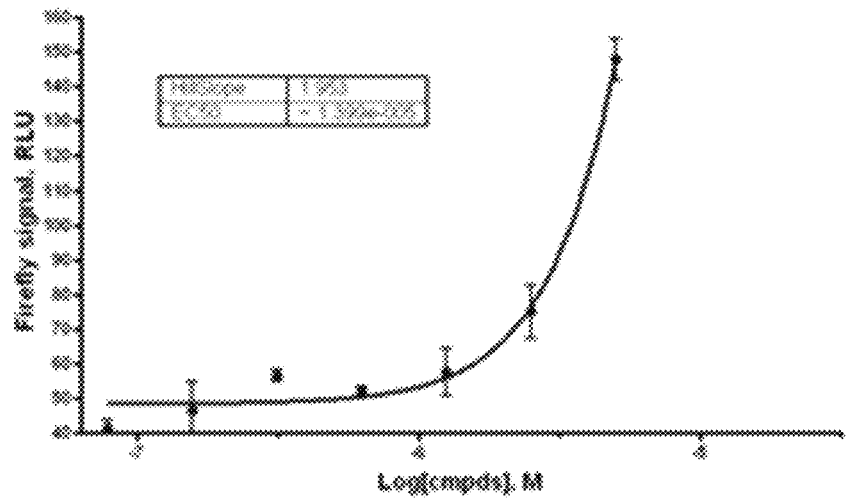
FIGS. 33A and 33B and 34A-34D show NR2F6 and LBD transient transfection, respectively, for Compound E21.
Figure 33B:
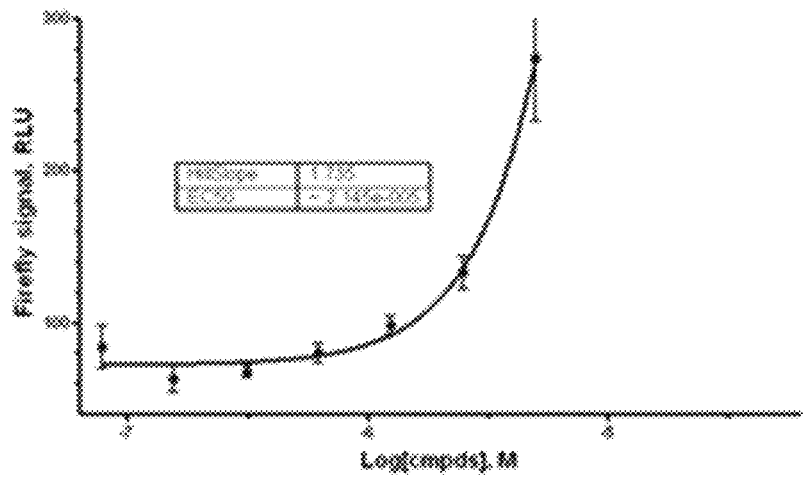

FIGS. 33A and 33B show NR2F6 and LBD transient transfection for Compound E21. Higher concentrations were excluded due to lower signal (tox) effect.

Figure 34A:
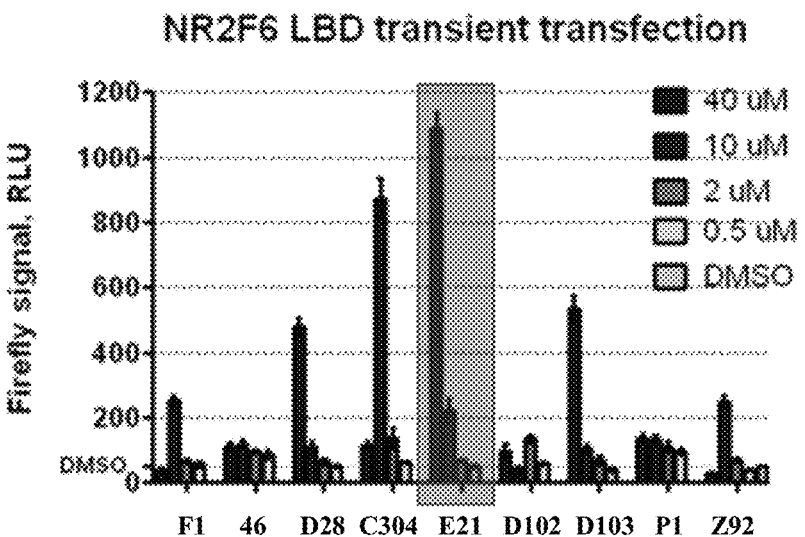
Figure 34B:
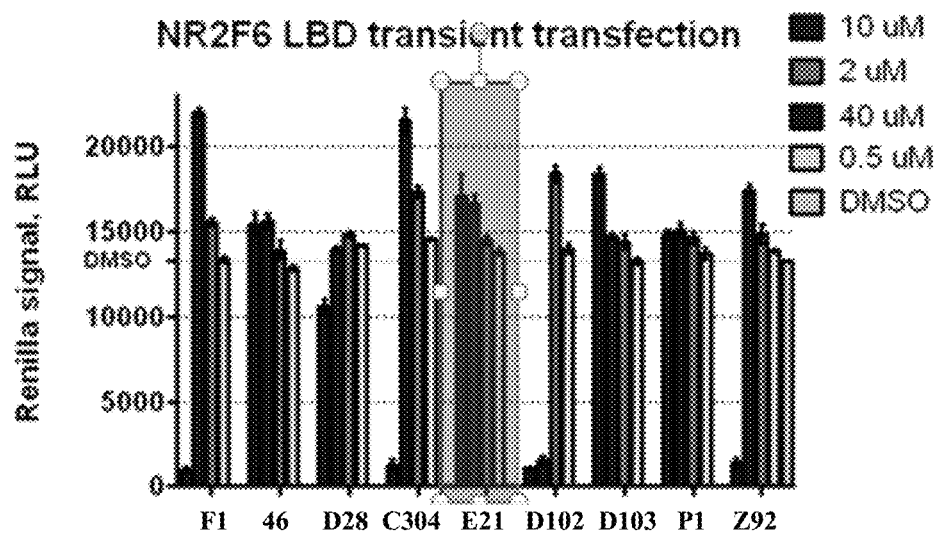
Figure 34C:
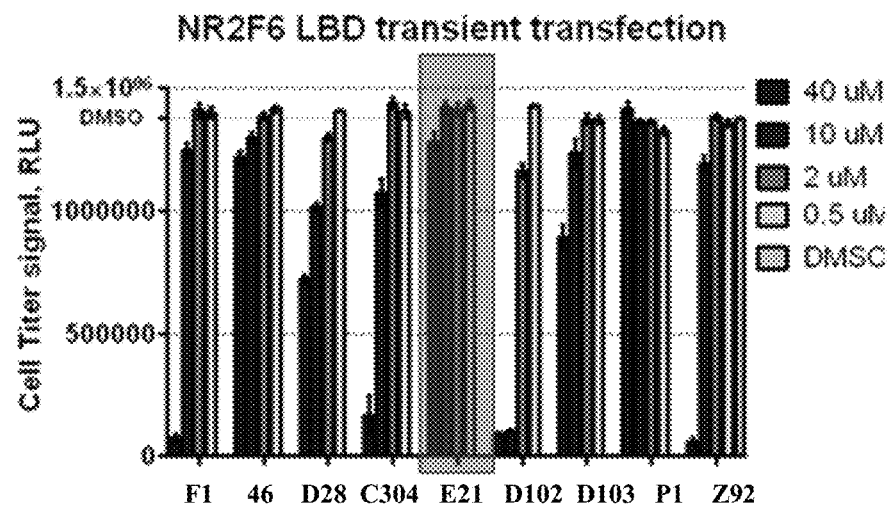
Figure 34D:
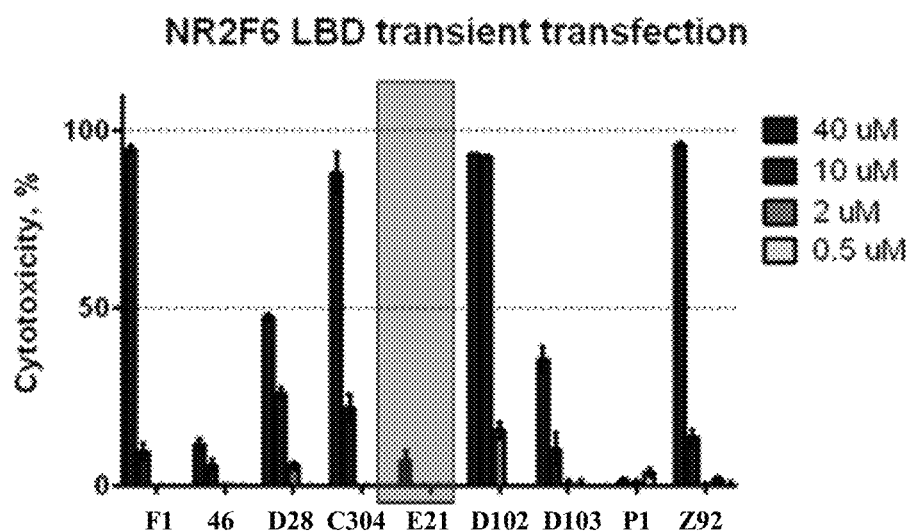
Figure 35A:
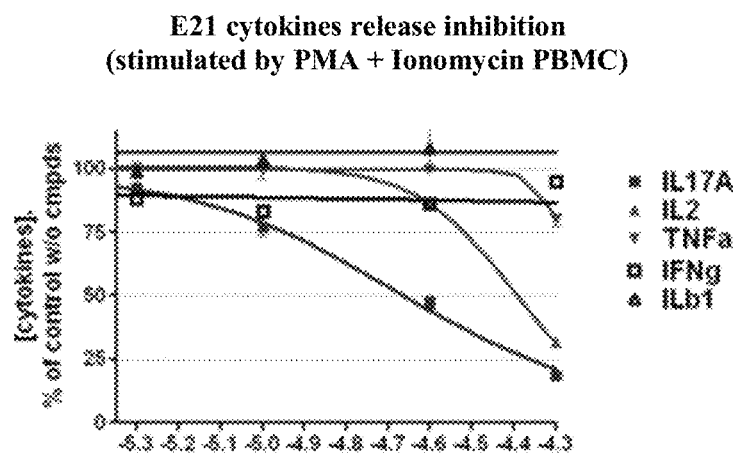
FIGS. 35A to 35D show the results of a cytokine release experiment for dog and human PBMC, for Compound E21.
Figure 35B:
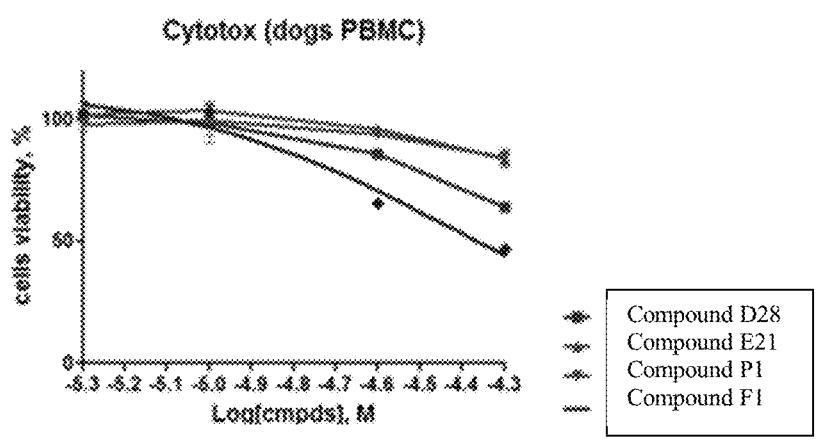
Figure 35C:
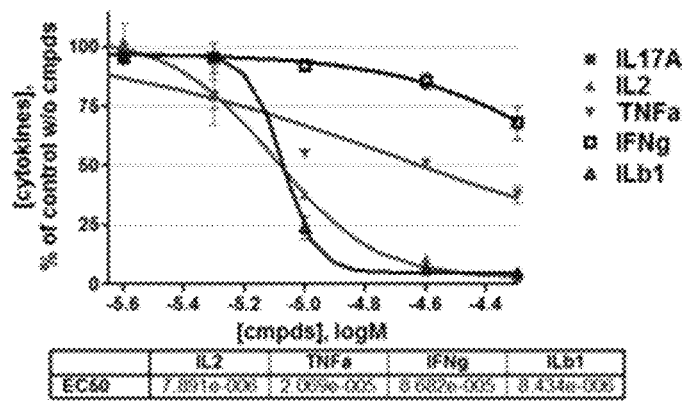
Figure 35D:
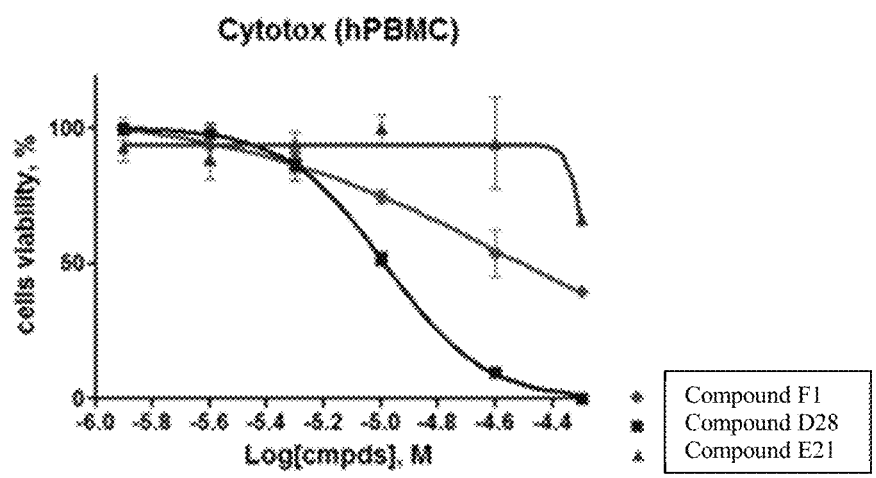

FIGS. 34A and 34B show NR2F6 LBD transient transfection for Compound E21. 9 compounds were tested on LBD transfected cells (40, 10, 2 and 0.5 µM, 4 replicates). FIGS. 34C and 34D show NR2F6 and LBD transient transfection at different concentrations for different compounds. 9 compounds were tested on LBD transfected cells (40, 10, 2 and 0.5 µM, 4 replicates). Tox effect was found to cause lower signal compared to DMSO. Cytotoxicity normalized to DMSO is shown in FIG. 34D (0% cytotoxicity corresponds to DMSO signal, 100%—zero signal). All compounds were tested at 5, 10, 25 and 50 uM in duplicates. Dog PBMC (1×106 cells/mL) were activated by 10 ng/mL PMA+ 500 ng/mL ionomycin. Data were normalized to controls with (100%)/without (0%) PMA+ionomycin activation.

As shown in FIG. 36, related compounds were generated from Compound E21 and tested for activity.

Additional related compounds found to have desirable activity include the following:

Compound E8
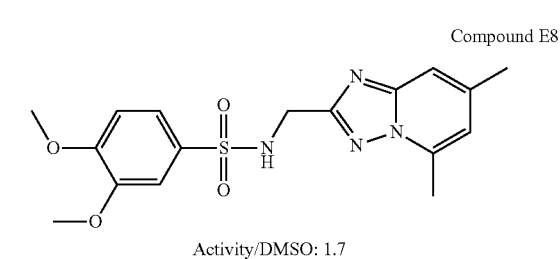
Activity/DMSO: 1.7

Compound E15
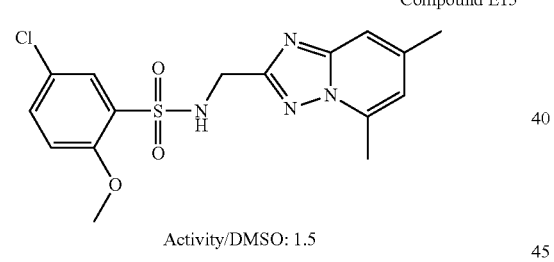
Activity/DMSO: 1.5

Compound E4
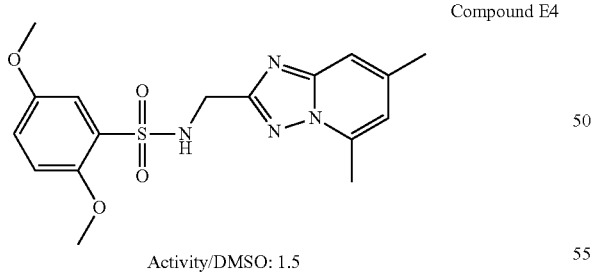
Activity/DMSO: 1.5

Compound E10
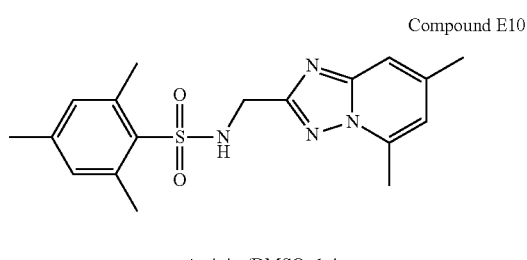
Activity/DMSO: 1.4

Compound E57
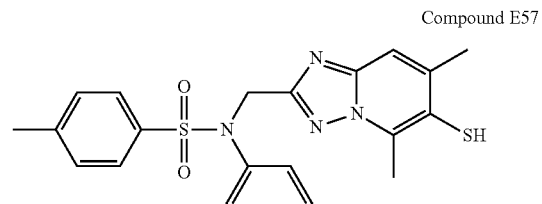
Activity/DMSO: 1.4

Compound E25
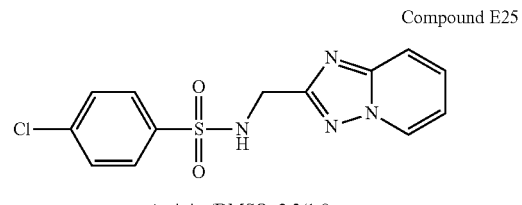
Activity/DMSO: 2.3/1.8

Compound E26
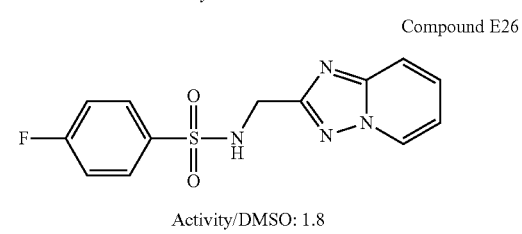
Activity/DMSO: 1.8

Compound E58
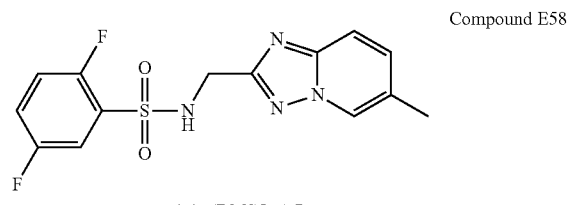
Activity/DMSO: 1.7

Compound E52
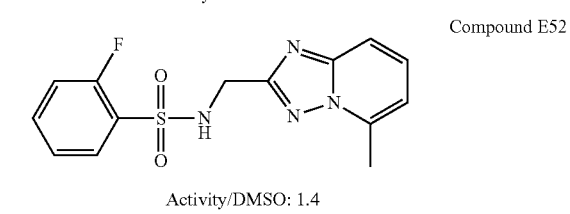
Activity/DMSO: 1.4

Compound E41
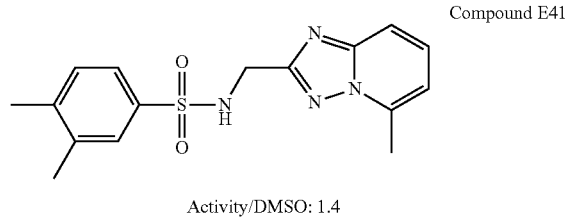
Activity/DMSO: 1.4

Compound E24
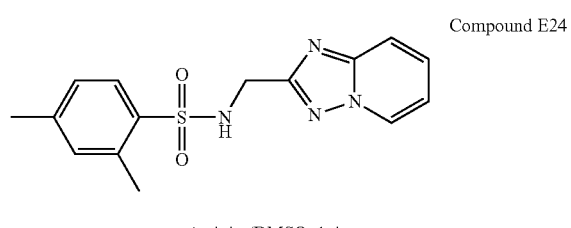
Activity/DMSO: 1.4

Table 23 shows the screening results of certain of the above compounds.

TABLE 23

| | | Firefly | | | | | |
|---|---|---|---|---|---|---|---|
| | | NR2F6 full length, cmpd/DMSO (mean) | | | F4, cmpd/DMSO (mean) | | |
| | | Concentration, mM | | | | | |
| | Compound ID | 40 | 10 | 2 | 40 | 10 | 2 |
| Screening Results | Compound E4 | 1.0 | 1.0 | 1.1 | 0.8 | 0.9 | 0.9 |
| | Compound E8 | 0.9 | 1.2 | 1.2 | 0.7 | 1.0 | 1.0 |
| | Compound E10 | 1.1 | 1.5 | 1.3 | 0.8 | 1.0 | 1.1 |
| | Compound E15 | 1.1 | 0.8 | 1.2 | 0.8 | 1.1 | 1.3 |
| | Compound E57 | 0.9 | 1.2 | 1.3 | 1.3 | 1.3 | 1.0 |
| | Compound E24 | 1.1 | 1.1 | 1.0 | 0.7 | 0.9 | 1.0 |
| | Compound E41 | 0.9 | 1.0 | 1.1 | 0.4 | 0.7 | 0.9 |
| | Compound E52 | 1.4 | 1.3 | 1.0 | 0.7 | 0.9 | 0.7 |

Additional compounds synthesized and found to have desirable activity include the following:

Compound E59
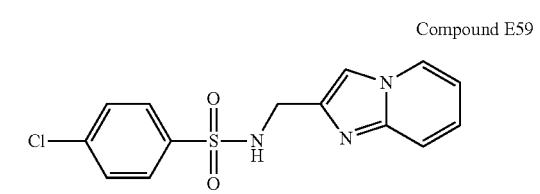

Compound E60
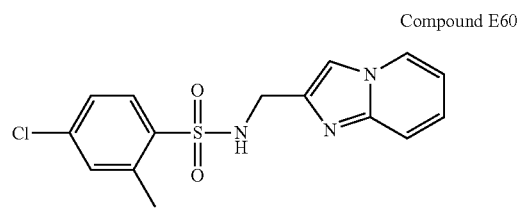

Compound E61
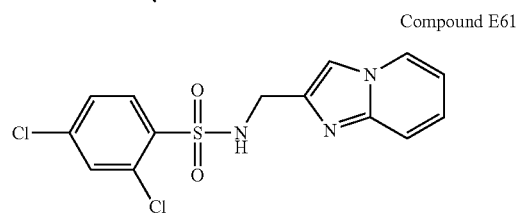

Compound E62
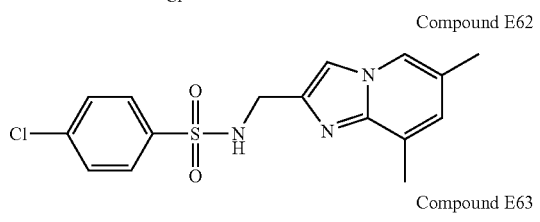

Compound E63
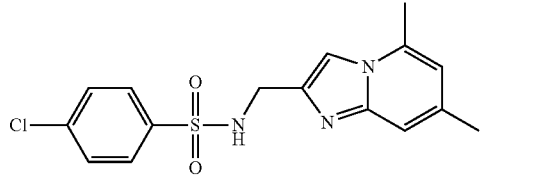

Compound E64
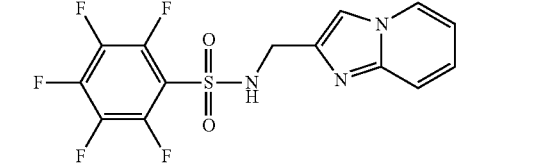

Compound E65
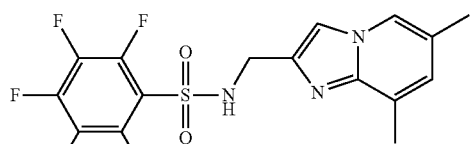

Compound E66
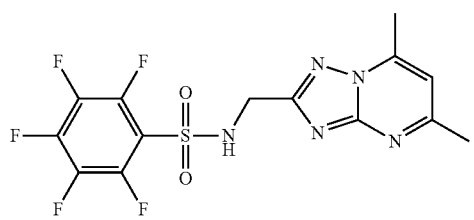

Compound E67
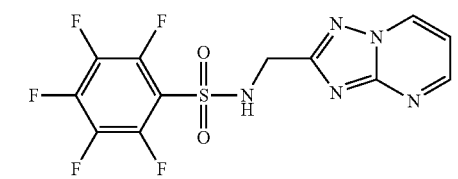

Compound E68
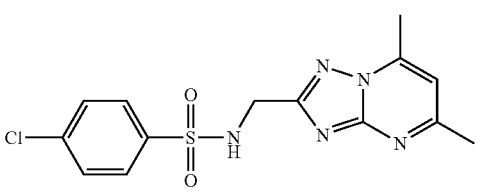

Compound E69
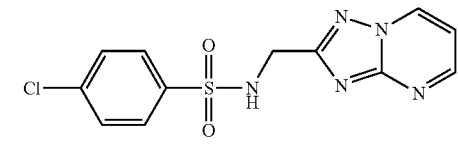

Figure 37:
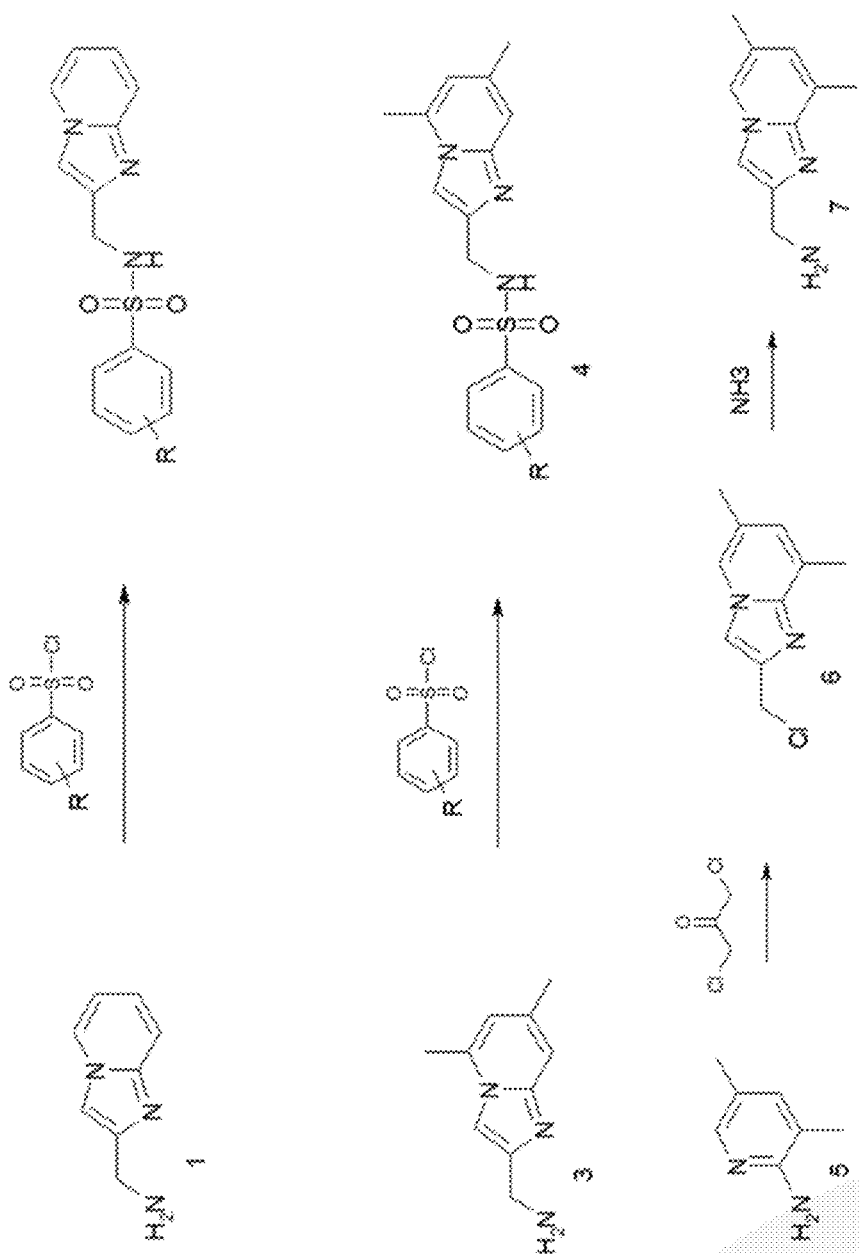
FIG. 37 shows additional compounds that were synthesized and tested according to the present embodiments.

FIG. 37 shows exemplary methods of formulating the compounds that have been discussed herein; specifically, exemplary synthesis of compounds including the following: Compound Z160, Compound Z161, Compound Z162, Compound Z163.

As discussed above, Compound F1 was of particular interest herein:

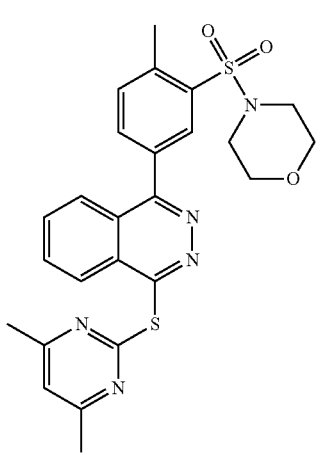

Compound F1

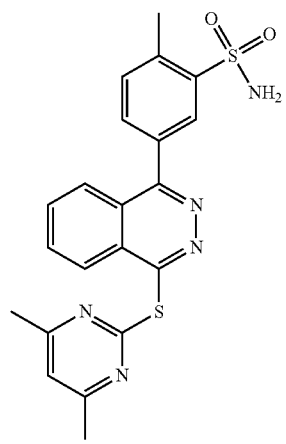

Compound F2

Table 24 shows results of testing on Compound F1.

TABLE 24

| Firefly, cmpd/DMSO | | | Firefly, cmpd | | Firefly, DMSO | | Renilla, cmpd/DMSO | | Renilla, DMSO | |
|---|---|---|---|---|---|---|---|---|---|---|
| repeat 1 | repeat 2 | mean | repeat 1 | repeat 2 | mean plate1 | mean plate2 | repeat 1 | repeat 2 | mean plate1 | mean plate2 |
| 5.6 | 4.6 | 5.1 | 310 | 252 | 56 | 55 | 1.1 | 1.2 | 3237 | 2930 |

Figure 38A:
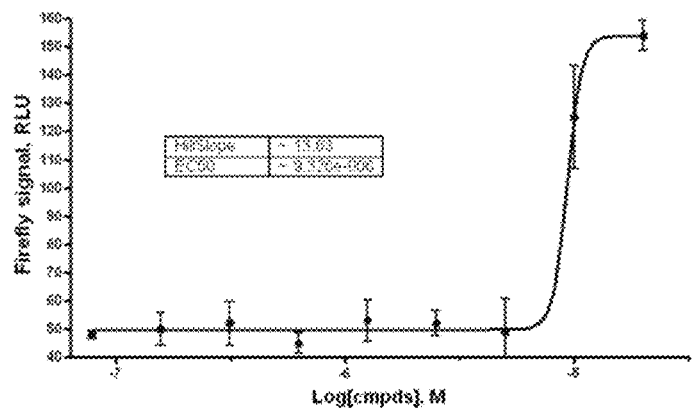
FIGS. 38A and 38B, 39A-39D and 40A-40D show results of testing on Compound F1.
Figure 38B:
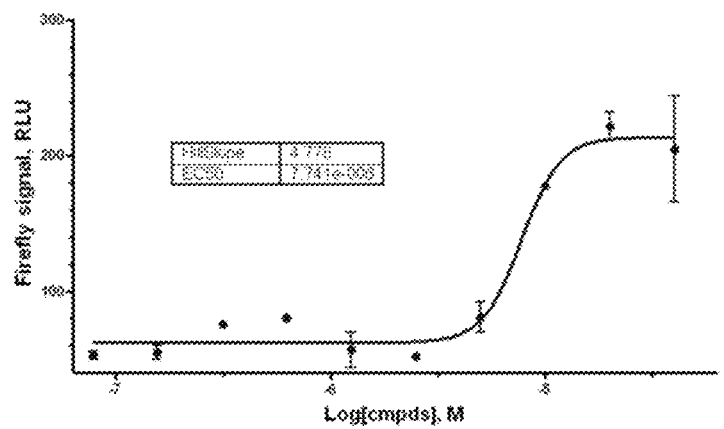

FIGS. 38A and 38B show NR2F6 and LBD transient transfection, respectively, for Compound F1.

Figure 39A:
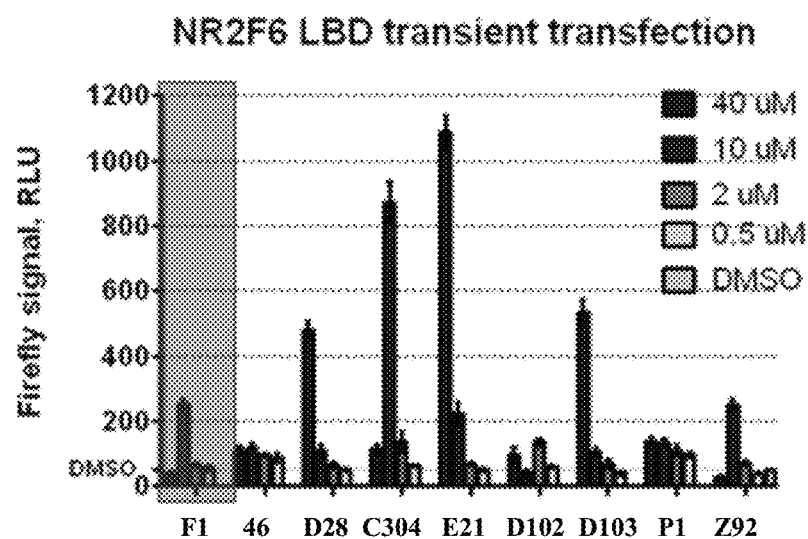
Figure 39B:
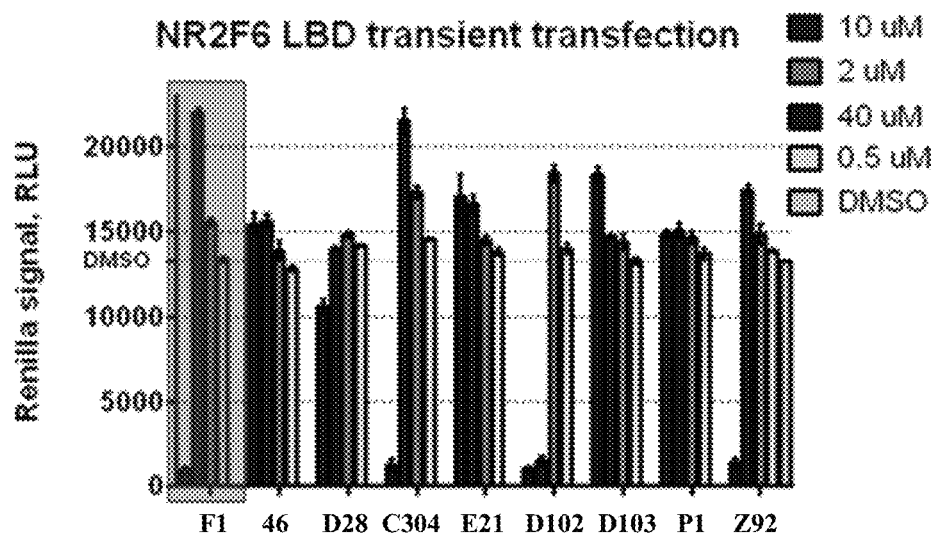
Figure 39C:
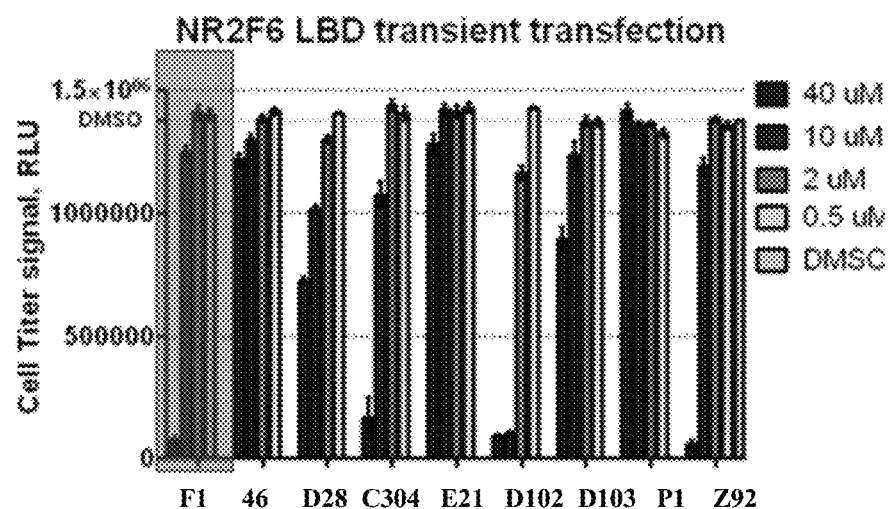
Figure 39D:
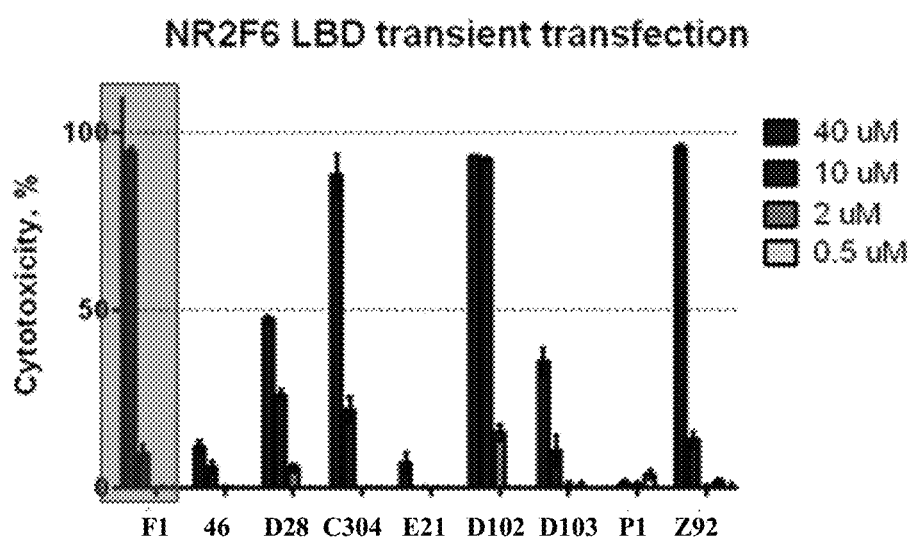
Figure 40A:
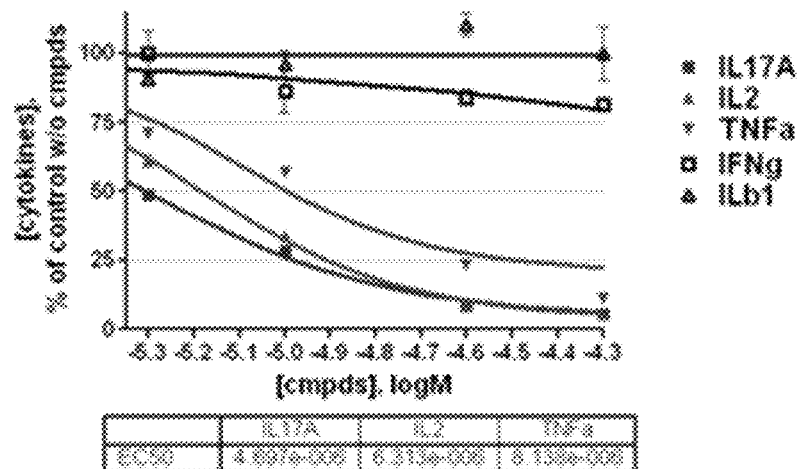
Figure 40B:
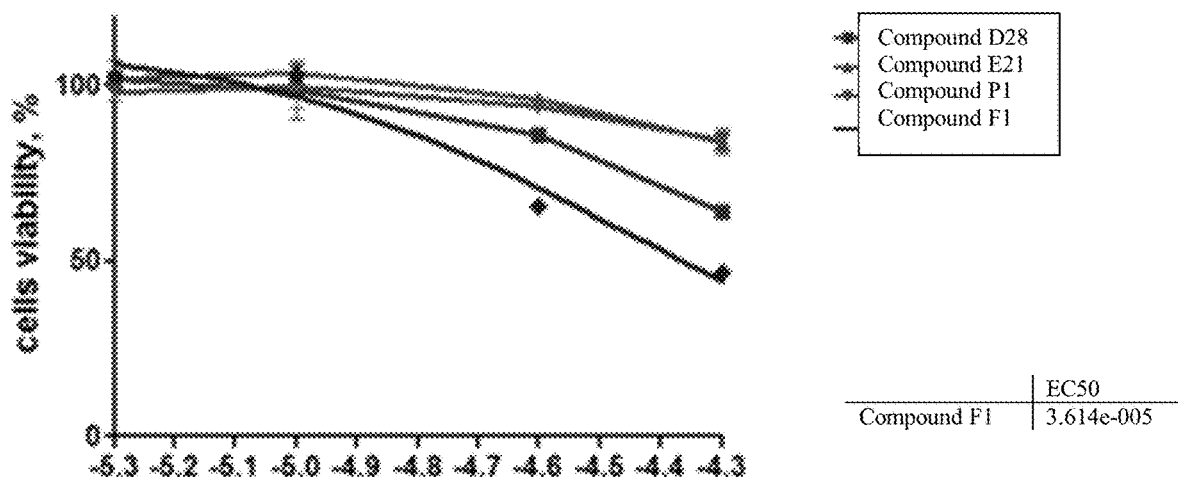
Figure 40C:
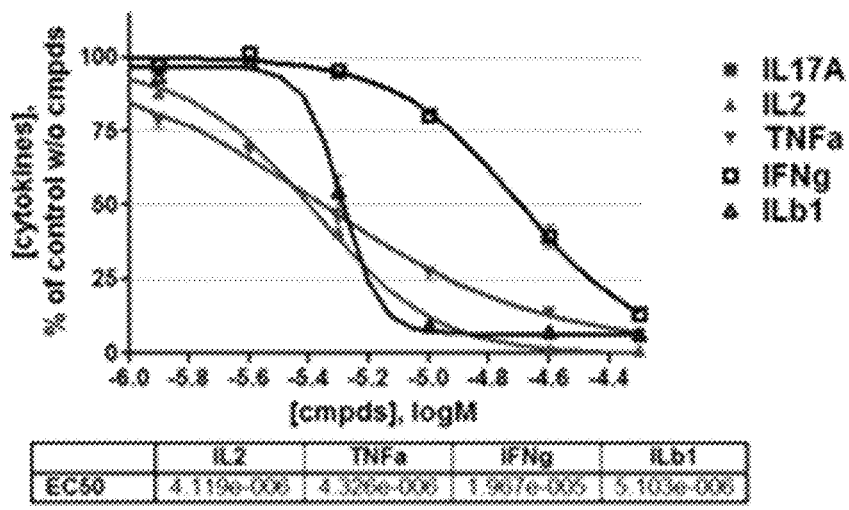
Figure 40D:
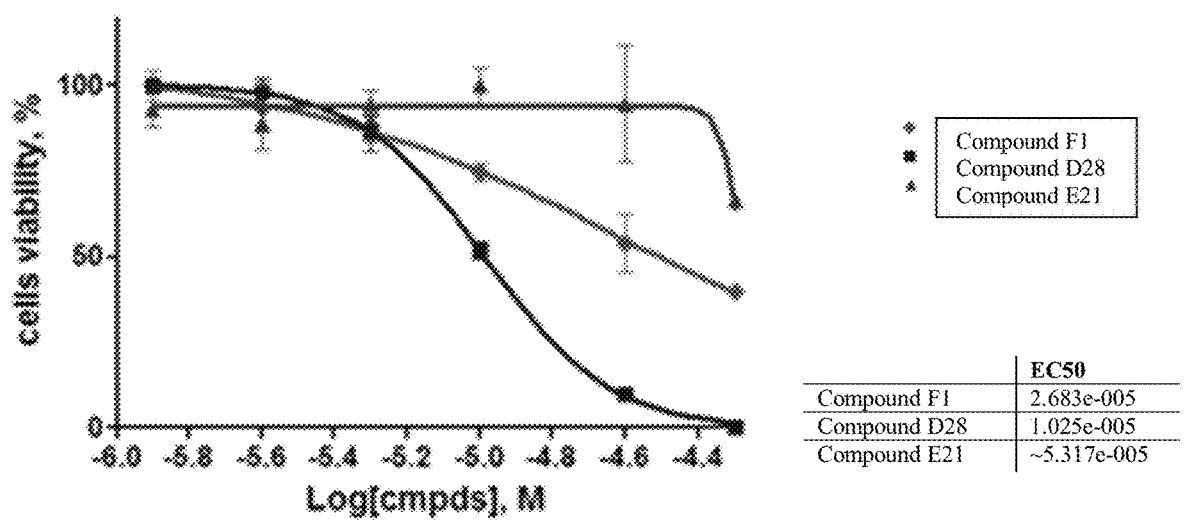

FIGS. 39A and 39B show NR2F6 LBD transient transfection for Compound F1. 9 compounds were tested on LBD transfected cells (40, 10, 2 and 0.5 µM, 4 replicates). FIGS. 39C and 39D show toxicity of NR2F6 LBD transient transfection. 9 compounds were tested for cytotoxicity on LBD transfected cells (40, 10, 2 and 0.5 µM, 4 replicates). Tox effect causes lower signal compared to DMSO. Cytotoxicity normalized to DMSO is shown in FIG. 39D (0% cytotoxicity corresponds to DMSO signal, 100%—zero signal).

FIGS. 40A-D show the results of cytokine release experiment for dogs and human PBMC. All compounds were tested at 5, 10, 25 and 50 uM in duplicates.

Dog PBMC (1×106 cells/mL) were activated by 10 ng/mL PMA+500 ng/mL ionomycin. Data were normalized to controls with (100%)/without (0%) PMA+ionomycin activation.

Figure 41:
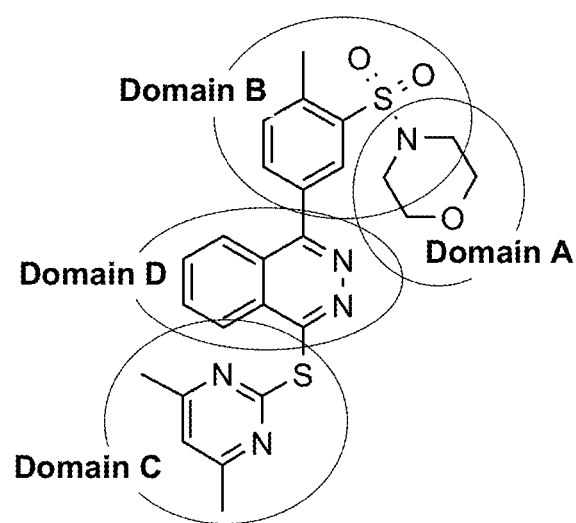
FIG. 41 shows the general SAR strategy for testing Compound F1 and compounds related to it in structure; by dividing the active molecule into four domains (Domains A through D), and evaluating each domain independently to establish SAR trends.

FIG. 41 shows the general SAR strategy for testing Compound F1 and compounds related to it in structure. Formally, the active molecule was divided into four domains (Domains A through D). Each domain was evaluated independently to establish SAR trends. Combinations of optimized domains evaluated additive or synergistic effect. 4 related analogs were available.

For example, compounds were tested with varying values of Domain A. Exemplary compounds found to be useful are listed as follows:

-continued

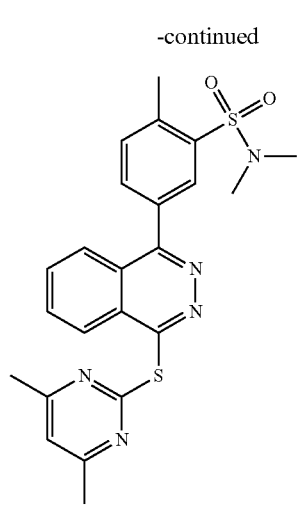

Compound F3

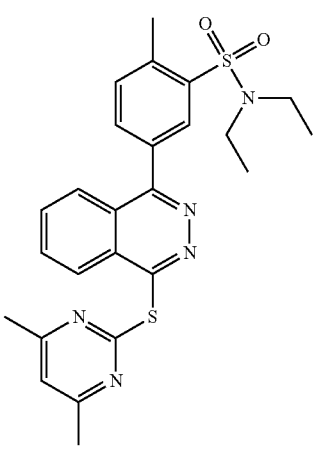

Compound F4

-continued

Compound F5
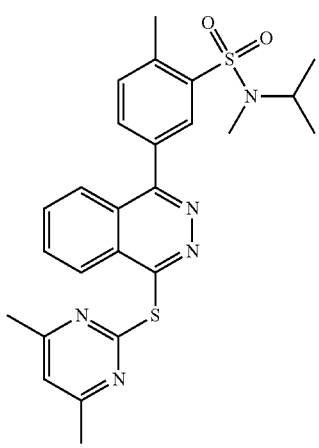

Compound F6
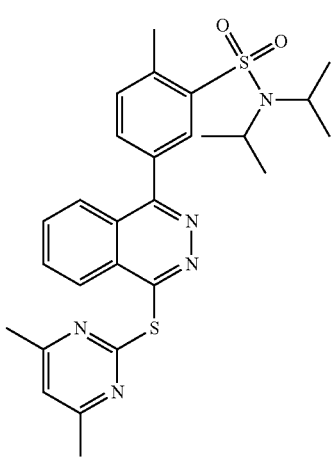

In certain embodiments, a compound herein has Formula (XIII):

(XIII)
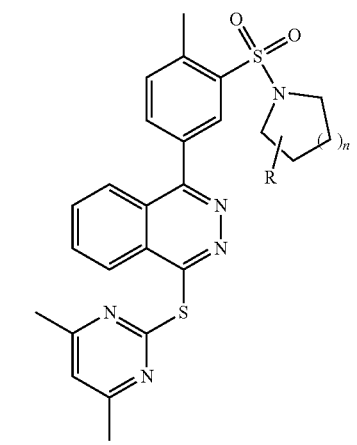

n = 1, 2, 3
R = all available wherein n is an integer 1, 2, or 3, and R is any other moiety mentioned in the present disclosure (e.g., C, H, N, O, S, a halogen, an alkyl group, a substituted alkyl group, a cyclic alkyl group, an aryl group, a substituted aryl group, a heterocyclic group, an ester, an aldehyde, a ketone, a carboxylic acid, an amide, an amine, an ether, a thiol or a nitrile).

Similarly, compounds were tested with varying values of Domain C. Exemplary compounds found to be useful are listed as follows:

Compound F7
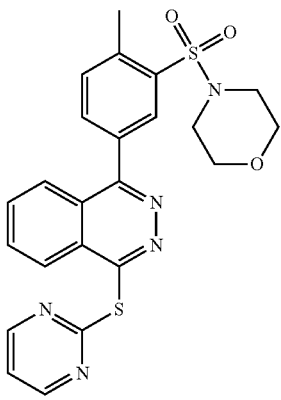

Compoudn F8
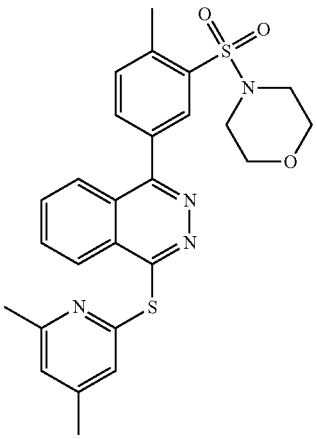

Compound F9
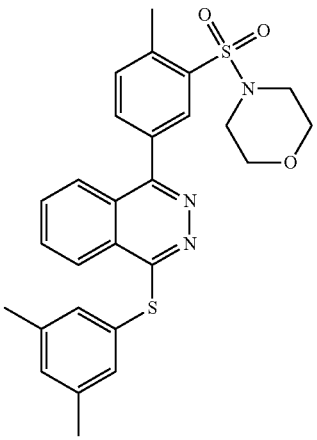

Compound F10

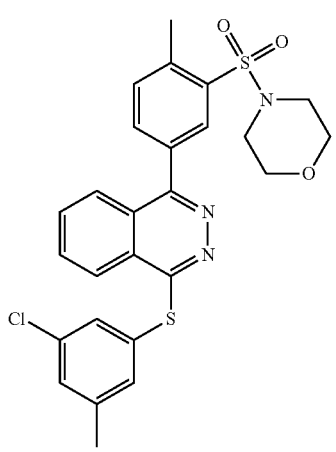

Compound F11

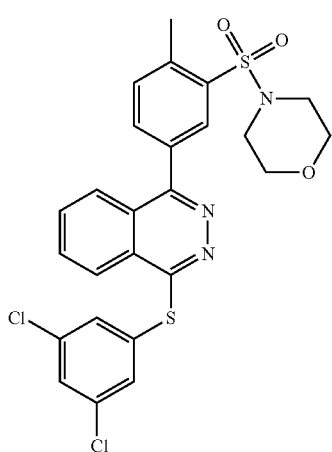

In certain embodiments, a compound herein has Formula (XIV):

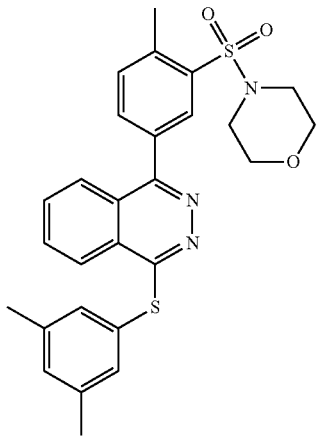

X = any possible wherein X is C, H, N, O, S, a halogen, an alkyl group, a substituted alkyl group, a cyclic alkyl group, an aryl group, a substituted aryl group, a heterocyclic group, an ester, an aldehyde, a ketone, a carboxylic acid, an amide, an amine, an ether, a thiol, a nitrile or any other moiety mentioned herein.

Figure 42:
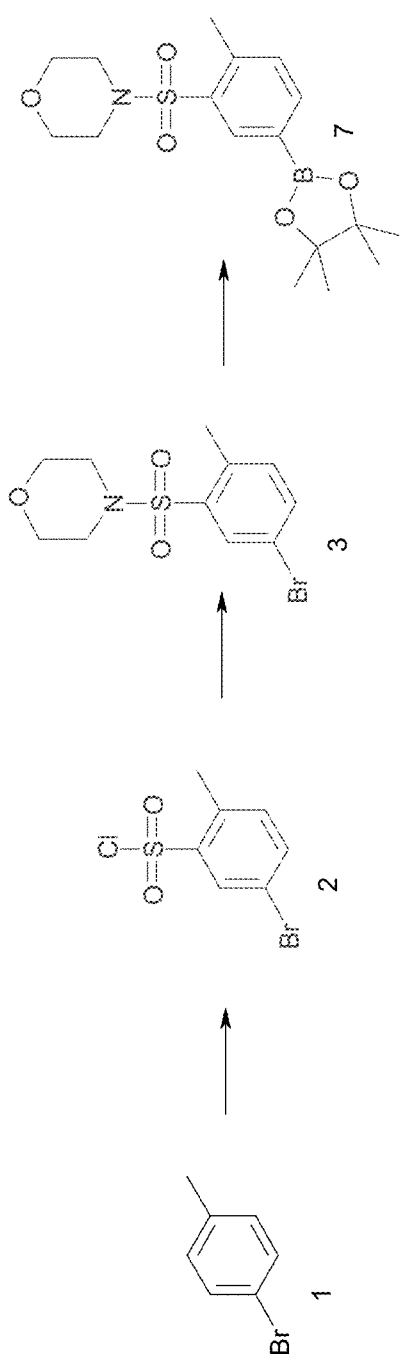
FIG. 42 shows an exemplary synthesis of a boronate compound, and the results of other exemplary syntheses of compounds comprising boronate, and the relative proportions of resultant compounds.

In other embodiments, the present technology is directed to compounds comprising a boronate, and synthesis of such compounds. For example, FIG. 42 shows an exemplary synthesis of a boronate compound. In various embodiments, the synthesis achieved a yield of at least about 95%, at least about 90% and at least about 85%; with at least about 85% purity. In various embodiments, a regioisomer was present in the yield, in amounts of about 10 to about 20%, or about 12 to about 18%. In various embodiments, the regioisomers could be separated.

FIG. 42 shows the results of other exemplary syntheses of compounds comprising boronate, and the relative proportions of resultant compounds.

Another compound found to have good activity is Compound P1:

Compound P1

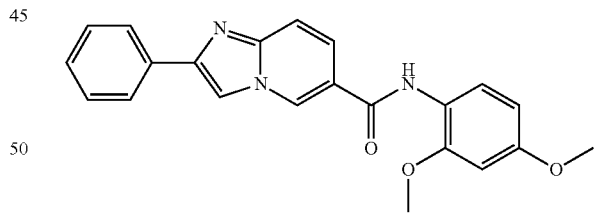

Table 25 shows results of testing on Compound P1.

TABLE 25

| Firefly, cmpd/DMSO | | | Firefly, cmpd | | Firefly, DMSO | | Renilla, cmpd/DMSO | | Renilla, DMSO | |
|---|---|---|---|---|---|---|---|---|---|---|
| repeat 1 | repeat 2 | mean | repeat 1 | repeat 2 | mean plate1 | mean plate2 | repeat 1 | repeat 2 | mean plate1 | mean plate2 |
| 4.0 | 3.0 | 3.5 | 236 | 166 | 59 | 56 | 1.0 | 0.9 | 3030 | 3118 |

Figure 44A:
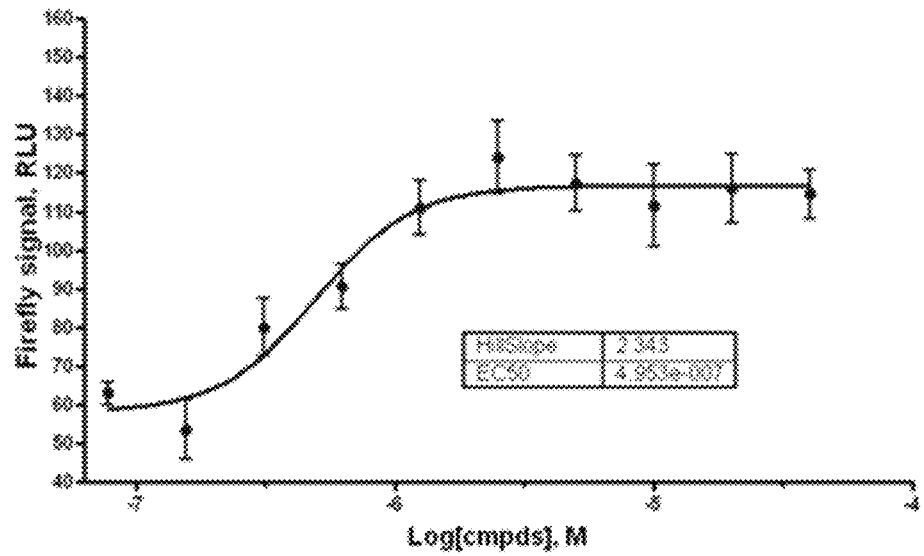
FIGS. 44A and 44B and 45A-D show NR2F6 and LBD transient transfection, respectively, for Compound P1.
Figure 44B:
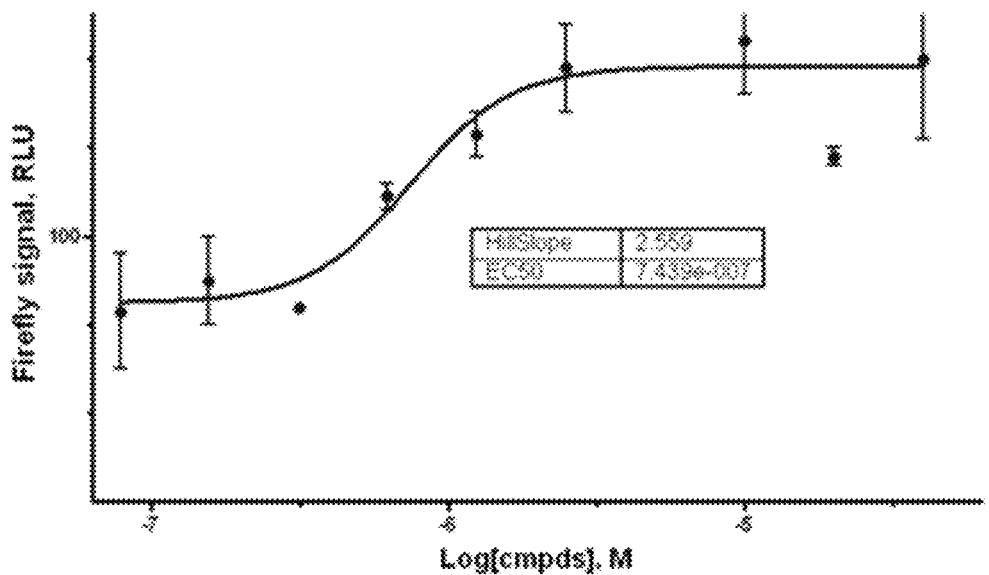
Figure 45A:
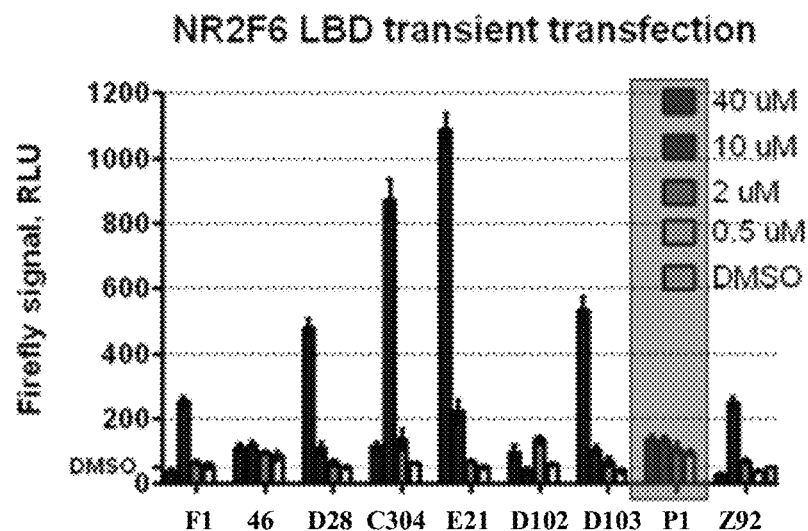
Figure 45B:
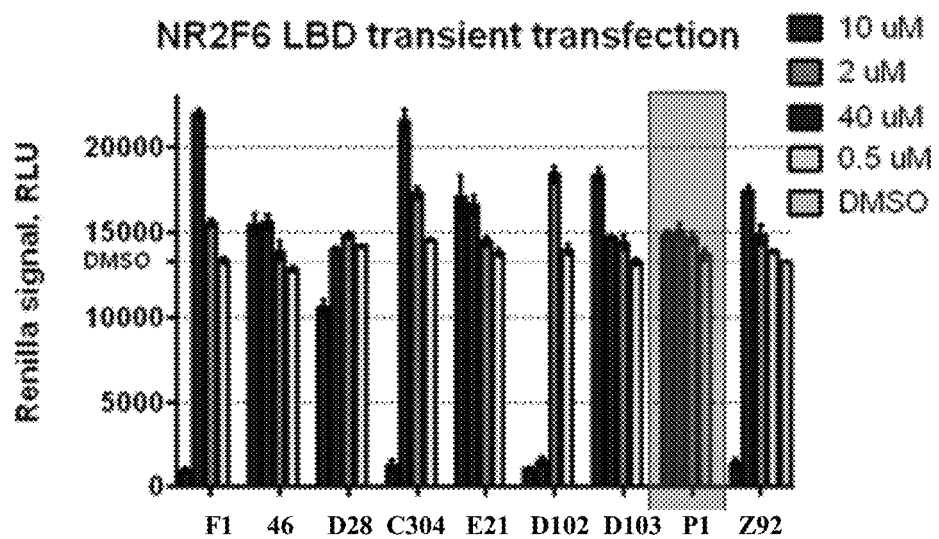
Figure 45C:
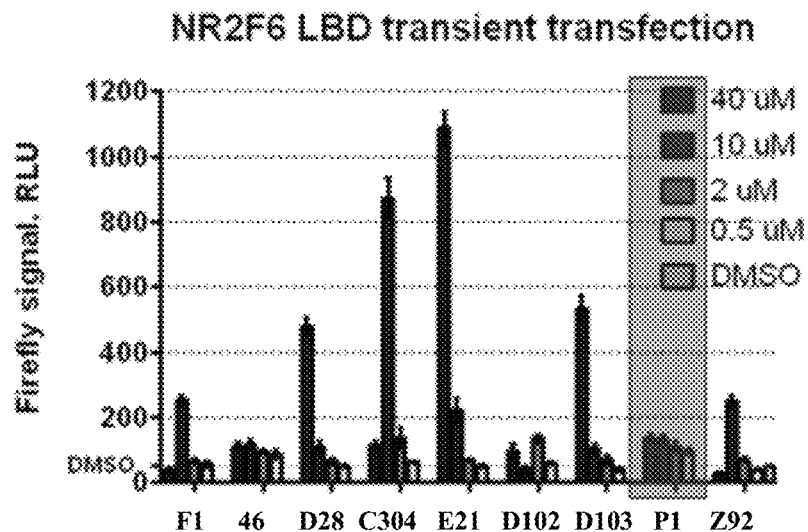
Figure 45D:
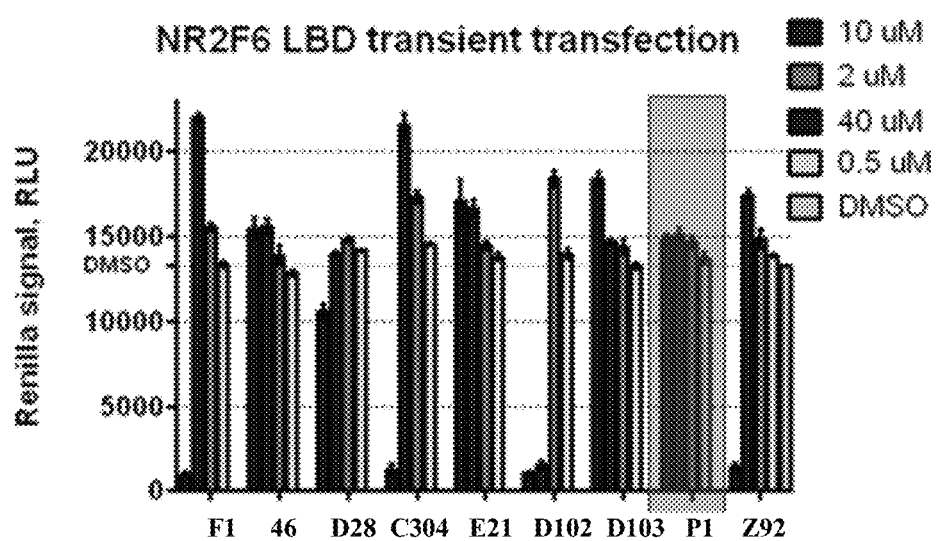

FIGS. 44A and 44B show NRdF6 and LBD transient transfection of Compound P1.

FIGS. 45A-D show NR2F6 LBD transient transfection for 9 different compounds, including Compound P1.

Figure 46A:
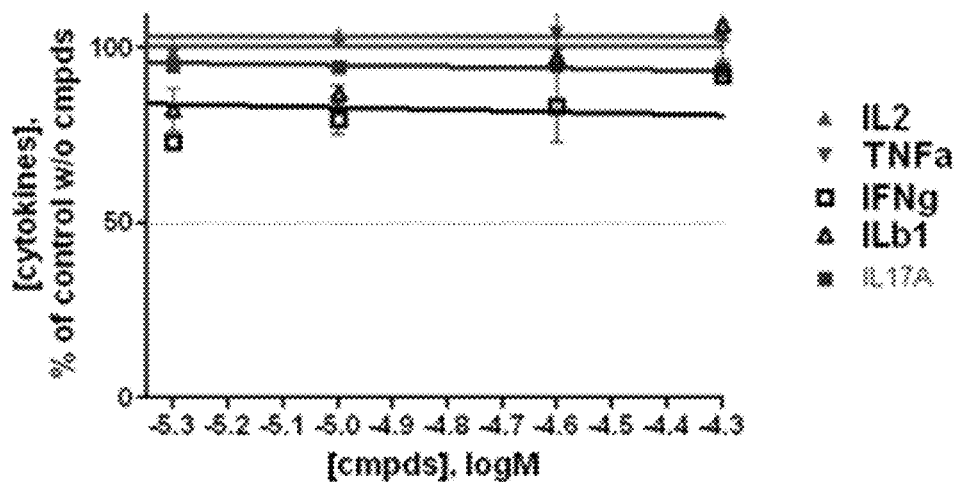
FIGS. 46A and 46B show the results of a cytokine release experiment for dog and human PBMC, for Compound P1.
Figure 46B:
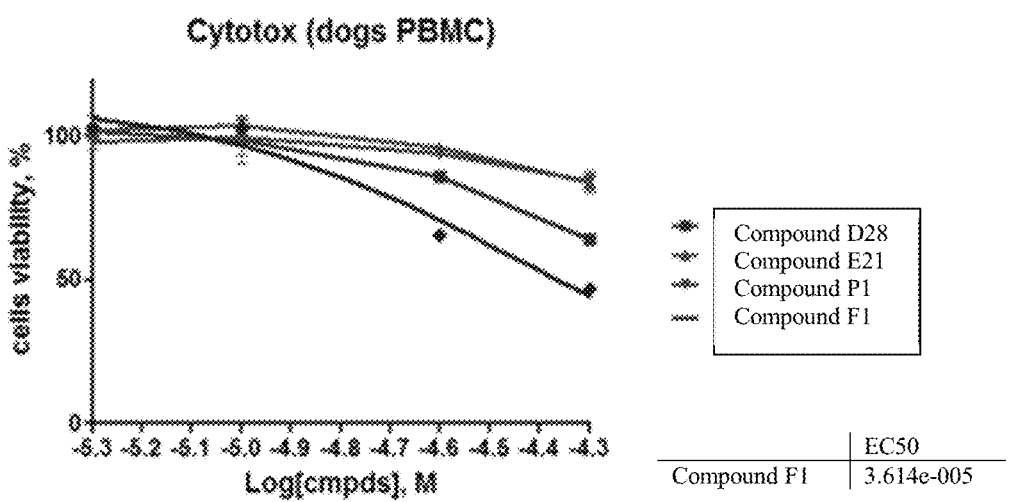

FIGS. 46A and 46B show the results of the cytokine release experiment with dogs PBMC.

Figure 47A:
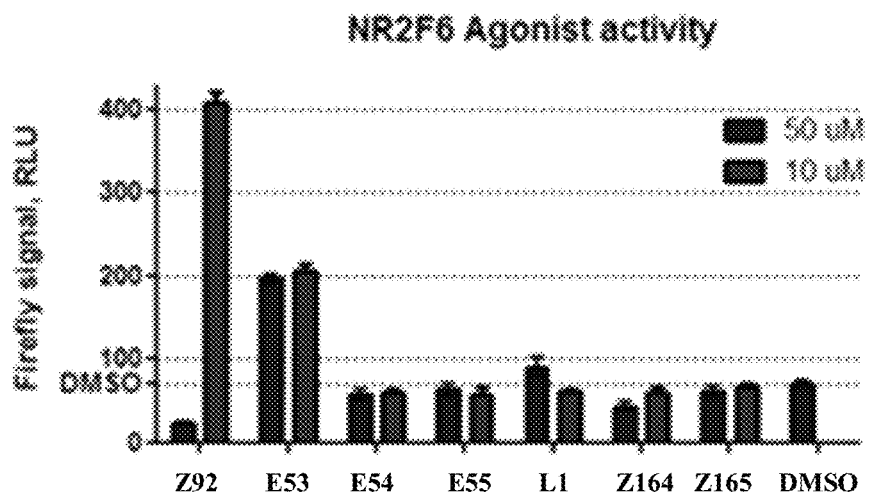
FIGS. 47A and 47B show NR2F6 agonist activity of various compounds discussed herein.
Figure 47B:
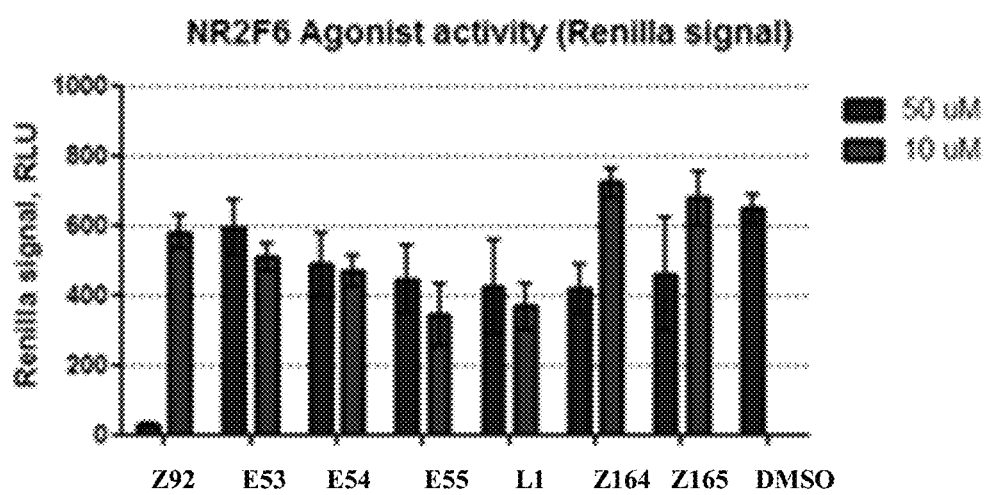
Figure 48:
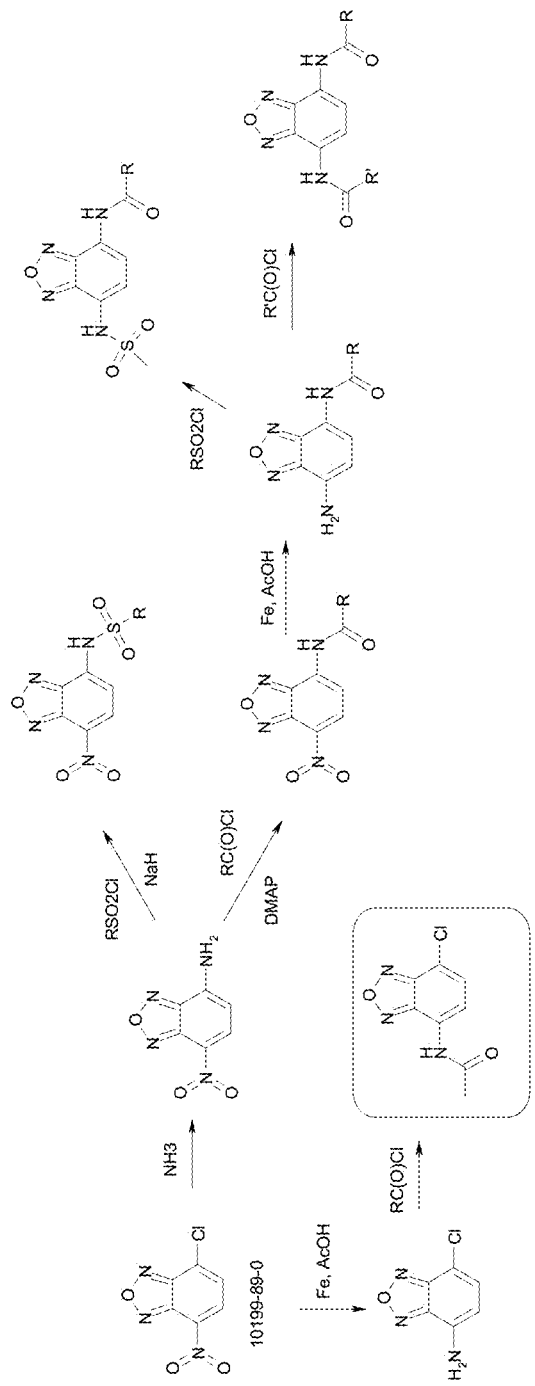
FIGS. 48-51 show synthesis of various additional compounds discussed herein.
Figure 49:
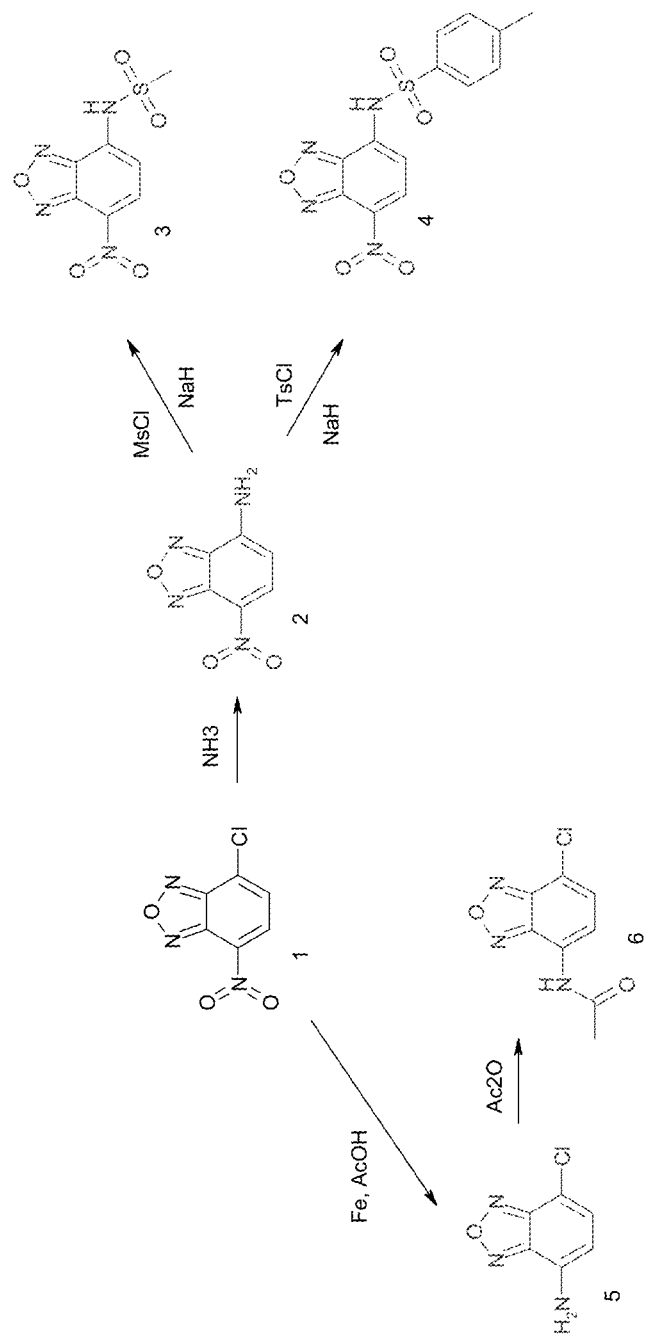
Figure 50:
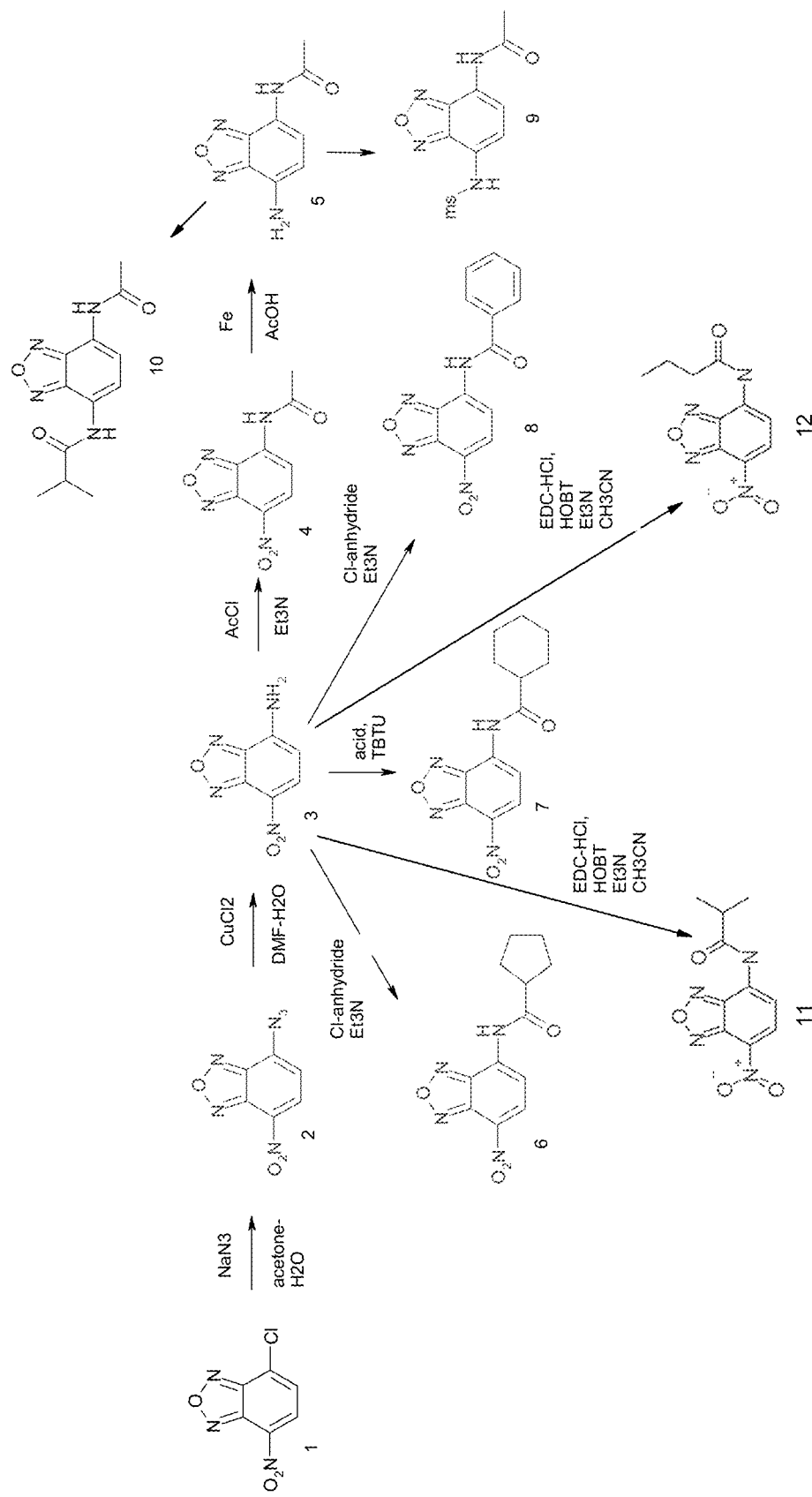
Figure 51:
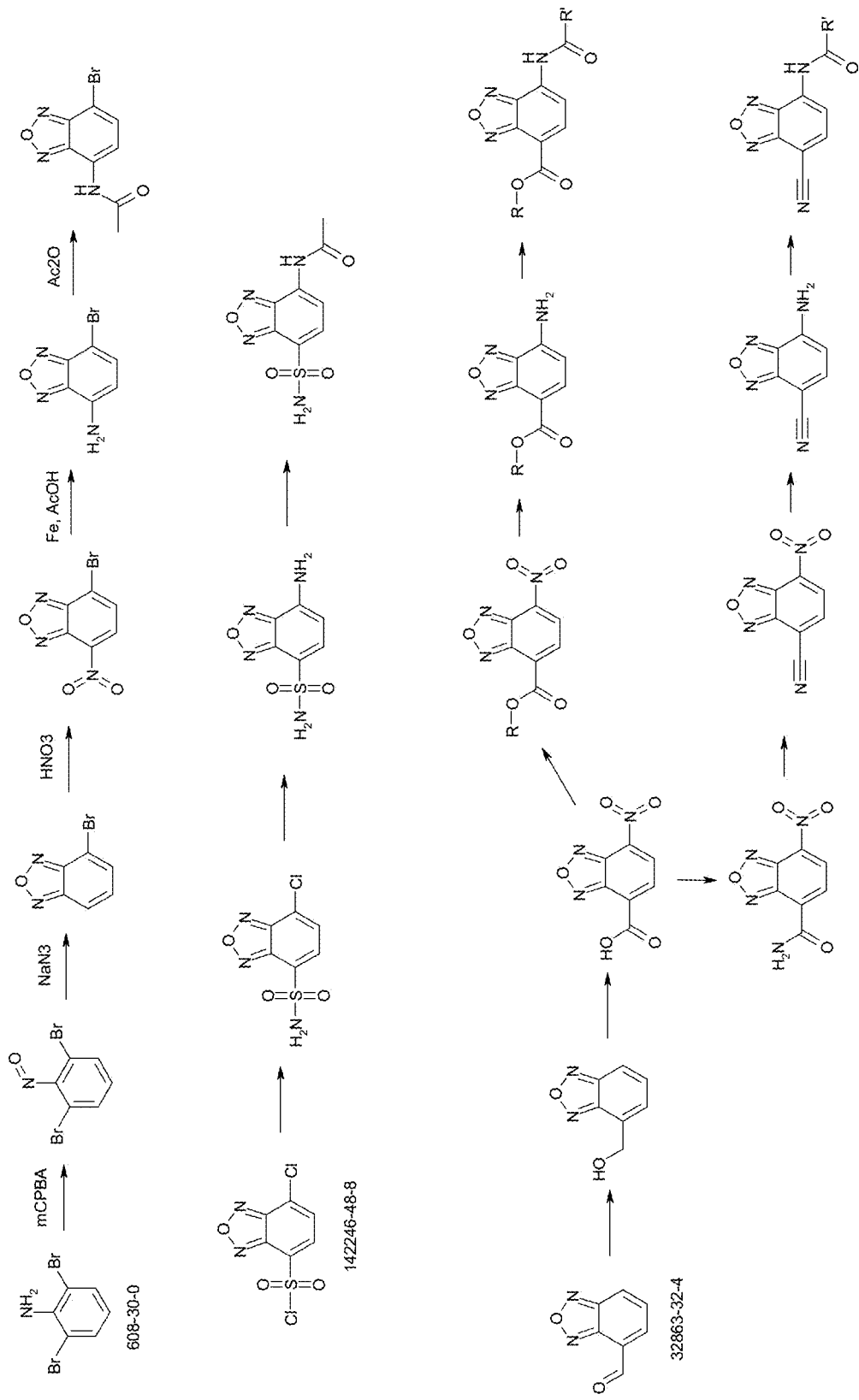
Figure 52A:
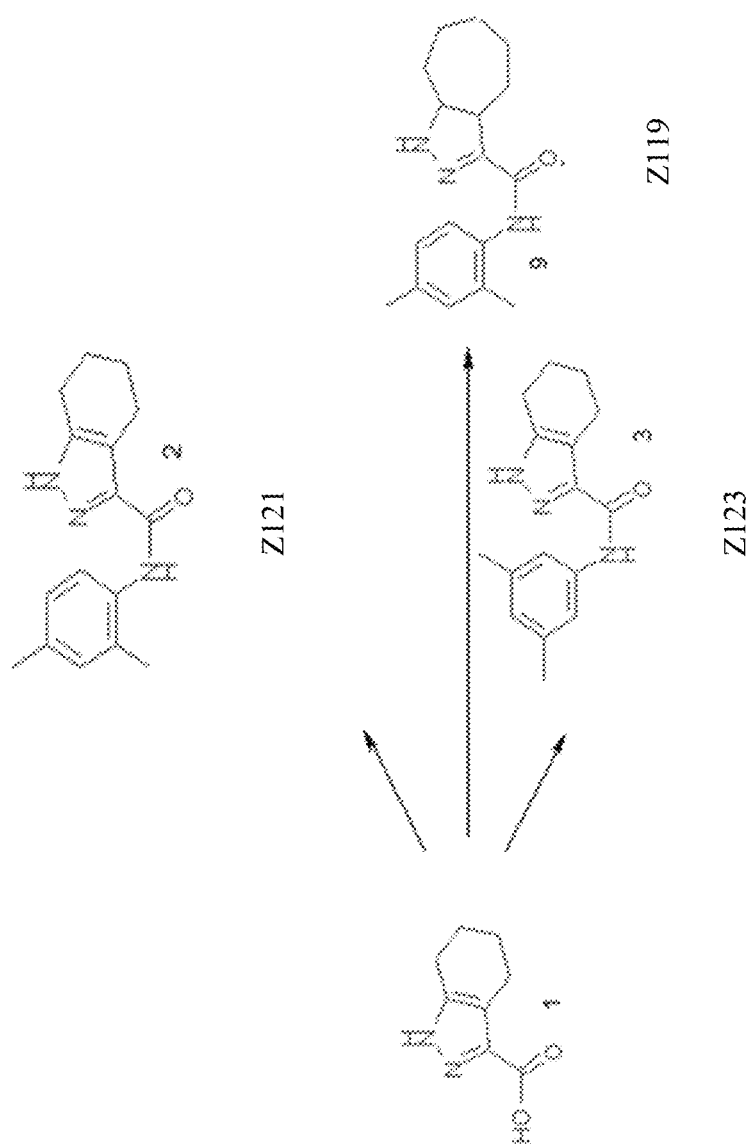
FIGS. 52A and 52B show synthesis of Compounds Z119, Z120, Z121 and Z123.
Figure 52B:
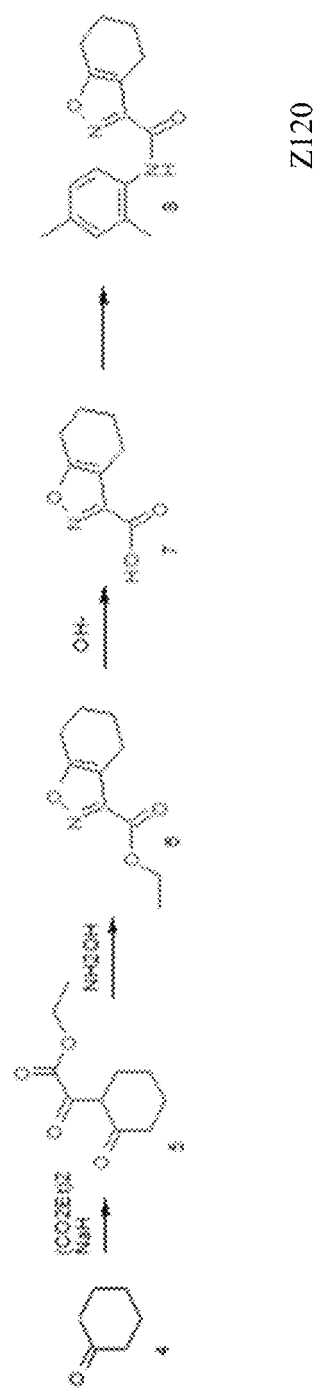
Figure 53:
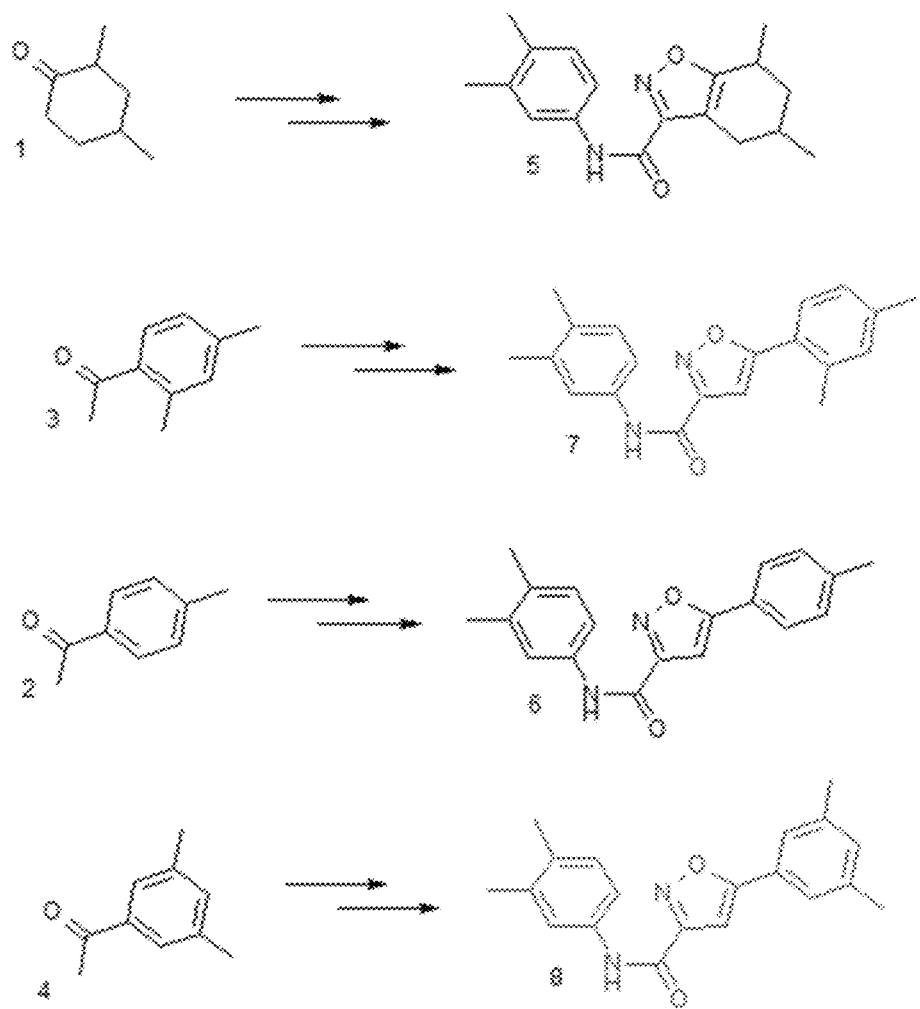
FIG. 53-55 shows synthesis of additional compounds herein.
Figure 54:
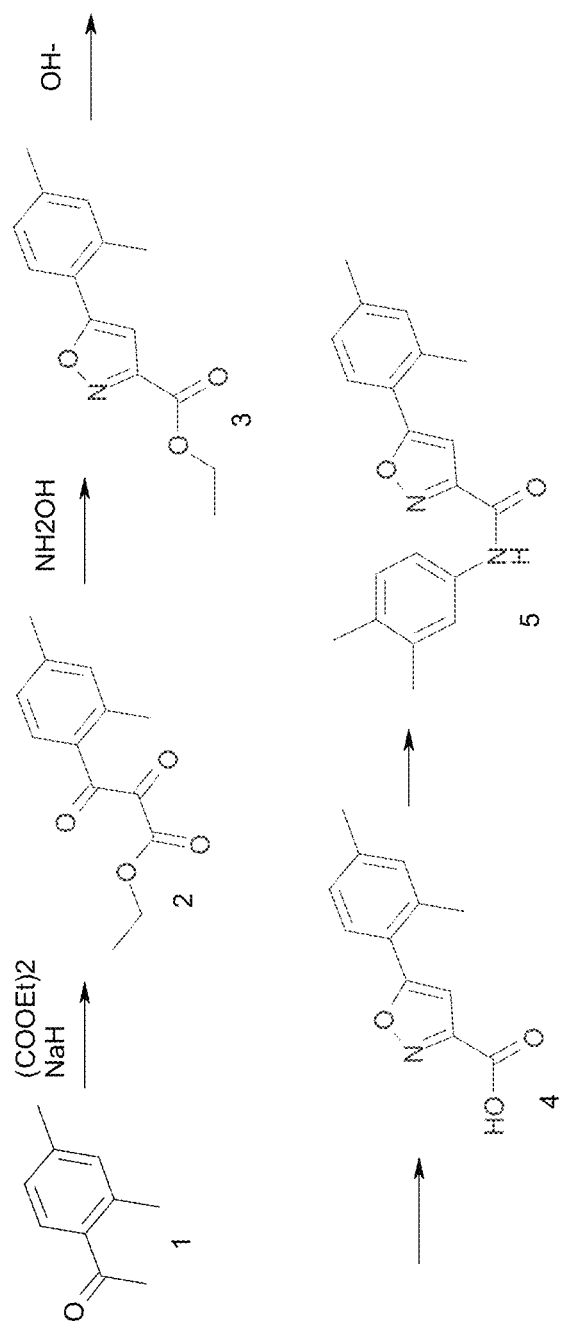
Figure 55:
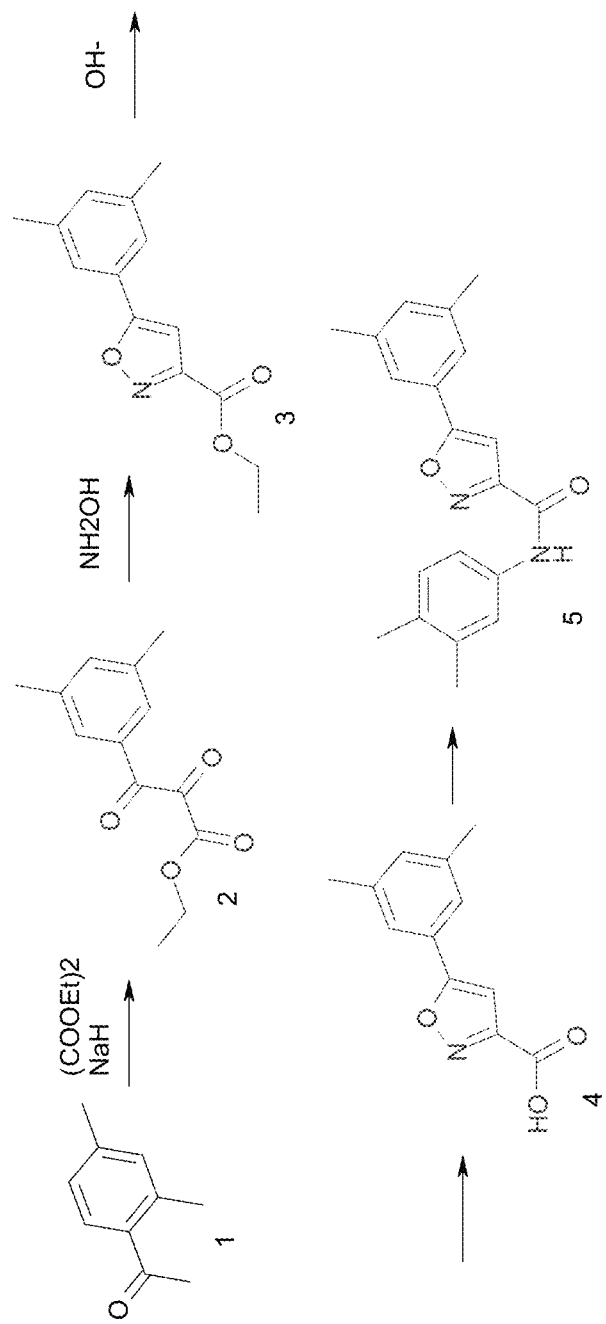

FIGS. 47A and 47B show NR2F6 agonist activity and NR2F6 agonist activity (Renilla signal) for 7 compounds along with a DMSO control. The conclusion is that Compound Z92 shown similar slight activity (~3 times firefly signal over DMSO level) at 10 uM and 50 uM. Compound E53 increases firefly activity in 6 times at 10 uM and appeared to show strong cytotox effect (great decreasing both renilla and firefly activity). Both Compounds Z92 and E53 will be tested on greater concentration range for confirmation on both cell line with double stable transfection (clone F1-pGL4) and cell line with transient transfection.

In certain embodiments, the present technology is directed to compounds of Formula (XV):

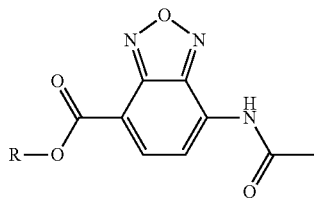

(XV)

wherein R is C, H, N, O, S, an alkyl group, a substituted alkyl group, a cyclic alkyl group, an aryl group, a substituted aryl group, a heterocyclic group, an ester, an aldehyde, a ketone, a carboxylic acid, an amide, an amine, an ether, a thiol or a nitrile. In certain embodiments, R is H or an alkyl group.

In certain embodiments, the present technology is directed to compounds of Formula (XVI):

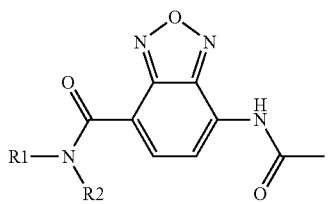

(XVI)

wherein any of R1 and R2 are C, H, N, O, S, a halogen, an alkyl group, a substituted alkyl group, a cyclic alkyl group, an aryl group, a substituted aryl group, a heterocyclic group, an ester, an aldehyde, a ketone, a carboxylic acid, an amide, an amine, an ether, a thiol or a nitrile. In certain embodiments, either or both of R1 and R2 are H, alkyl, phenyl, piperidine, or pyrrolidine.

Exemplary compounds include the following:

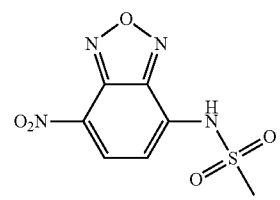

Compound Z13

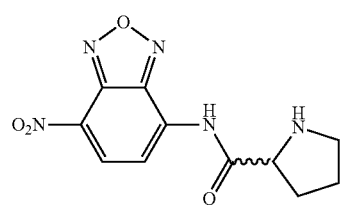

Compound Z102

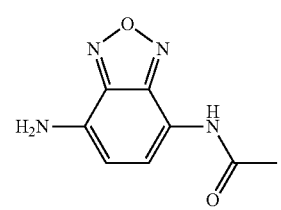

Compound 111

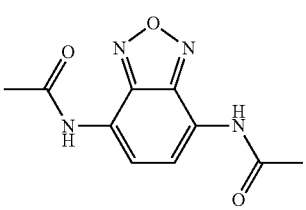

Compound Z112

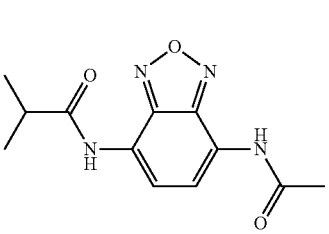

Compound Z14

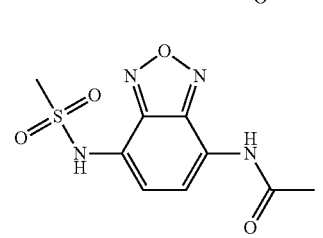

Compound Z15

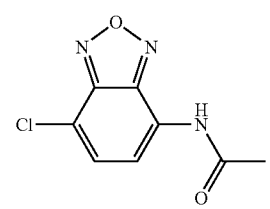

Compound Z113

-continued

Compound Z114

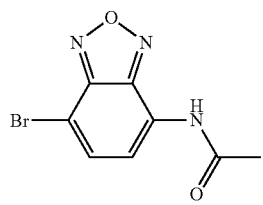

Compound Z115

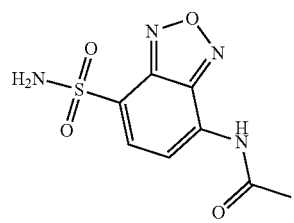

Compound Z116

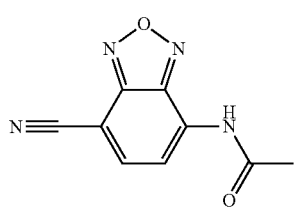

Table 26 shows activity results for two exemplary compounds, Compound Z95 and Compound Z113.

TABLE 26

| | Firefly, cmpd/DMSO (mean) | | | F4, cmpd/DMSO (mean) | | |
| --- | --- | --- | --- | --- | --- | --- |
| | Concentration | | | | | |
| ID | 40 | 10 | 2 | 40 | 10 | 2 |
| Z95 | 2.3 | 1.3 | 1.2 | 3.7 | 2.2 | 1.2 |
| Z113 | 0.9 | 1.1 | 1.3 | 1.2 | 1.5 | 1.2 |

FIGS. 48-51 show embodiments of a synthetic methods of formulating a compound according to the present technology.

Further compounds found to have good activity include the following:

Compound Z117

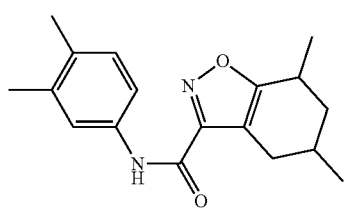

Compound Z118

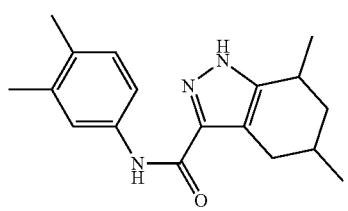

-continued

Compound Z119

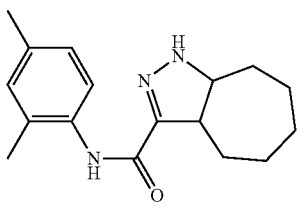

Compound Z120

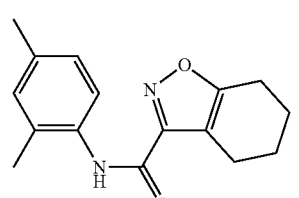

Compound Z121

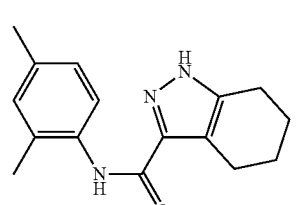

Compound Z122

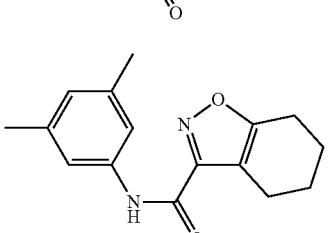

Compound Z123

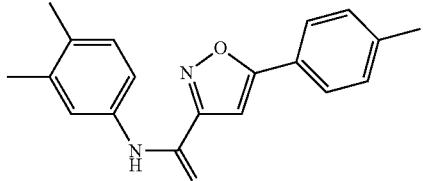

Compound Z124

Compound Z125

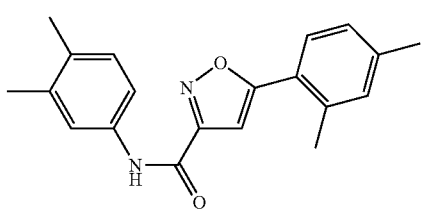

Compound Z126

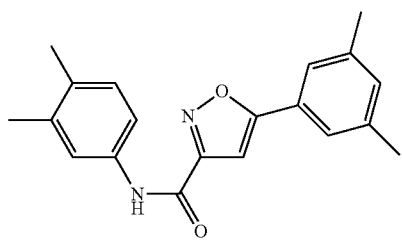

FIGS. 52-55 illustrate syntheses of various compounds discussed herein.

Figure 56A:
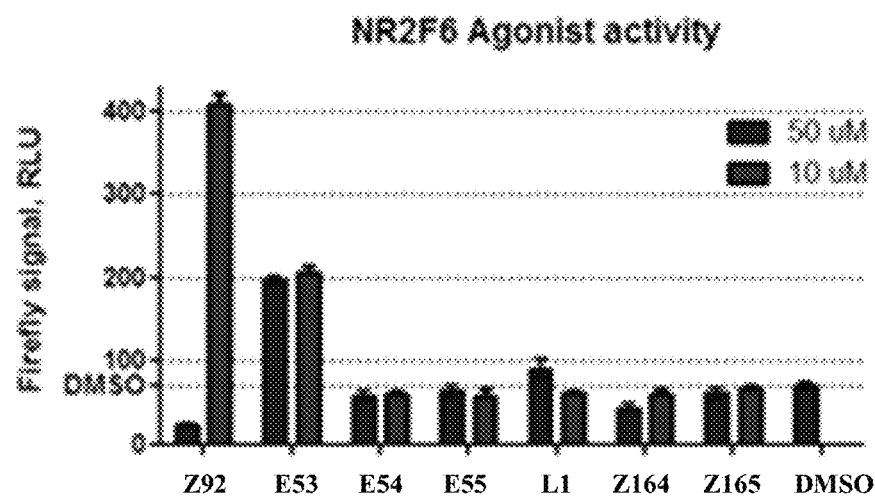
FIGS. 56A and 56B show Nr2F6 agonist activity for various compounds discussed herein.
Figure 56B:
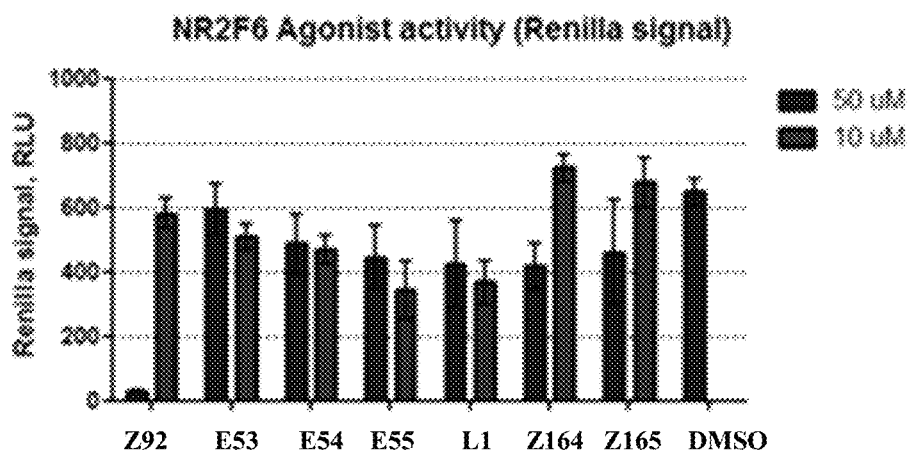

FIGS. 56A and 56B show HTS activity confirmation for various compounds. Compound E53 shown similar slight activity (~3 times firefly signal over DMSO level) at 10 uM and 50 uM. 8010-3060 increase firefly activity in 6 times at 10 uM and It seems it shown strong cytotox effect (great decreasing both renilla and firefly activity). Both Compound Z92 and Compound E53 will be further tested on greater concentration range for confirmation on both cell line with double stable transfection (clone F1-pGL4) and cell line with transient transfection.

Further compounds found to have good activity include the following:

Compound Z127

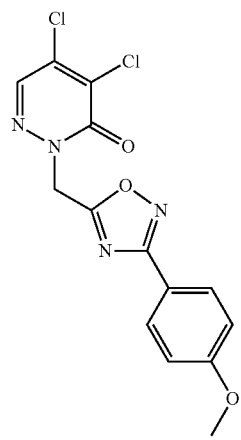

Compound Z128

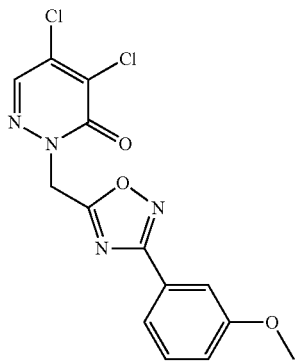

Compound Z159

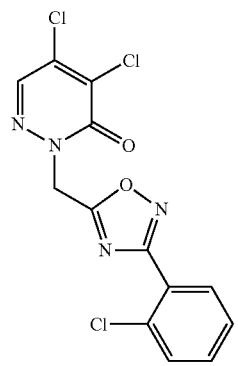

Compound Z130

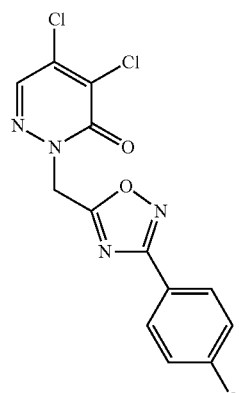

Compound Z131

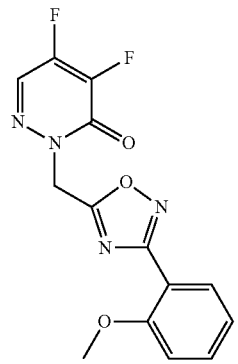

Compound Z132

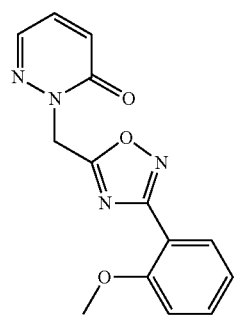

Compound Z133
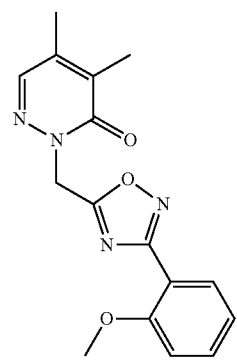
Compound Z134
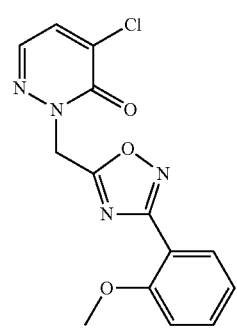
Compound Z135
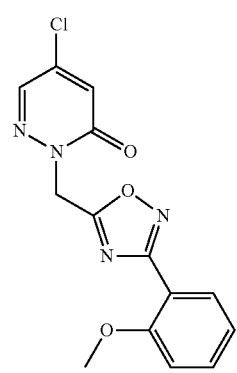
Compound Z136
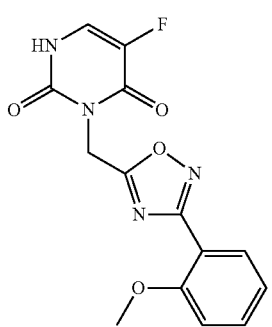
Compound Z137
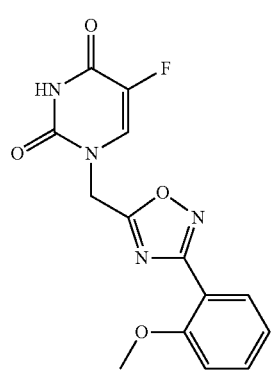
Compound Z138
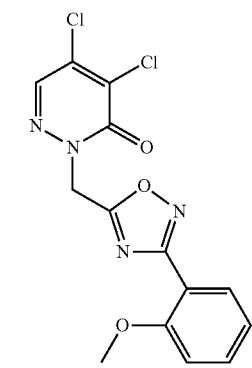
Compound Z139
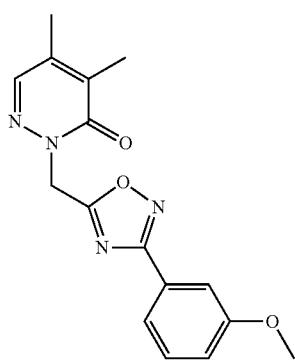
Compound Z140
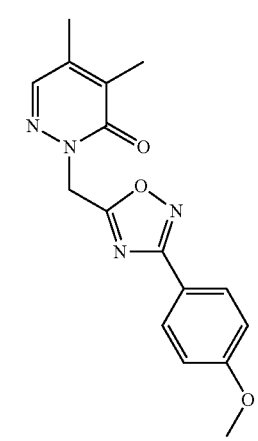

Compound Z23
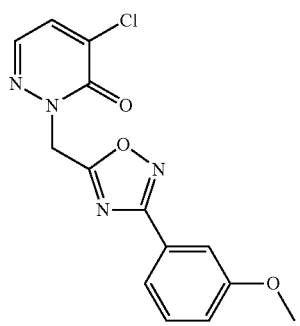
Compound Z141
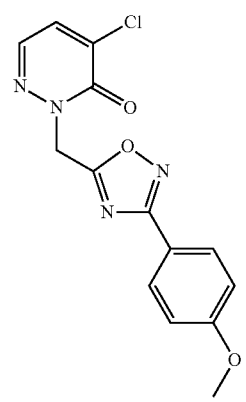
Compound Z142
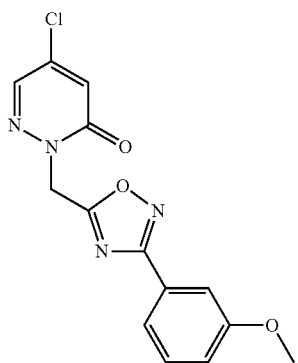
Compound Z142
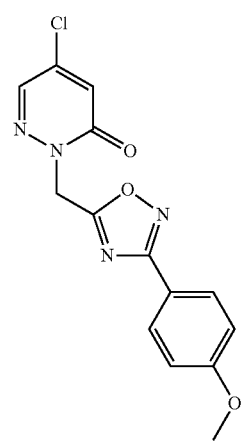
Compound Z25
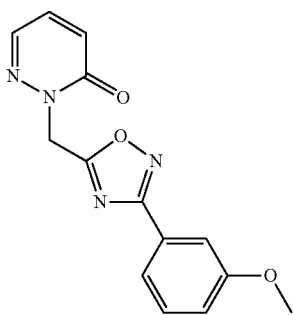
Compound Z97
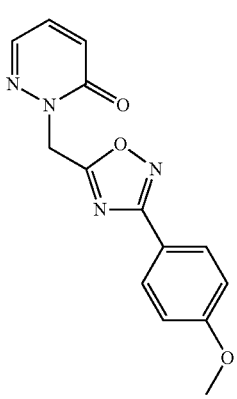
Compound Z6
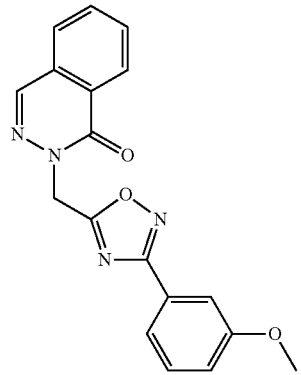
Compound Z7
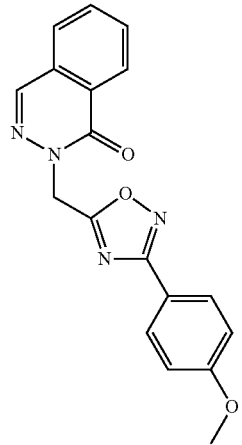

Figure 57:
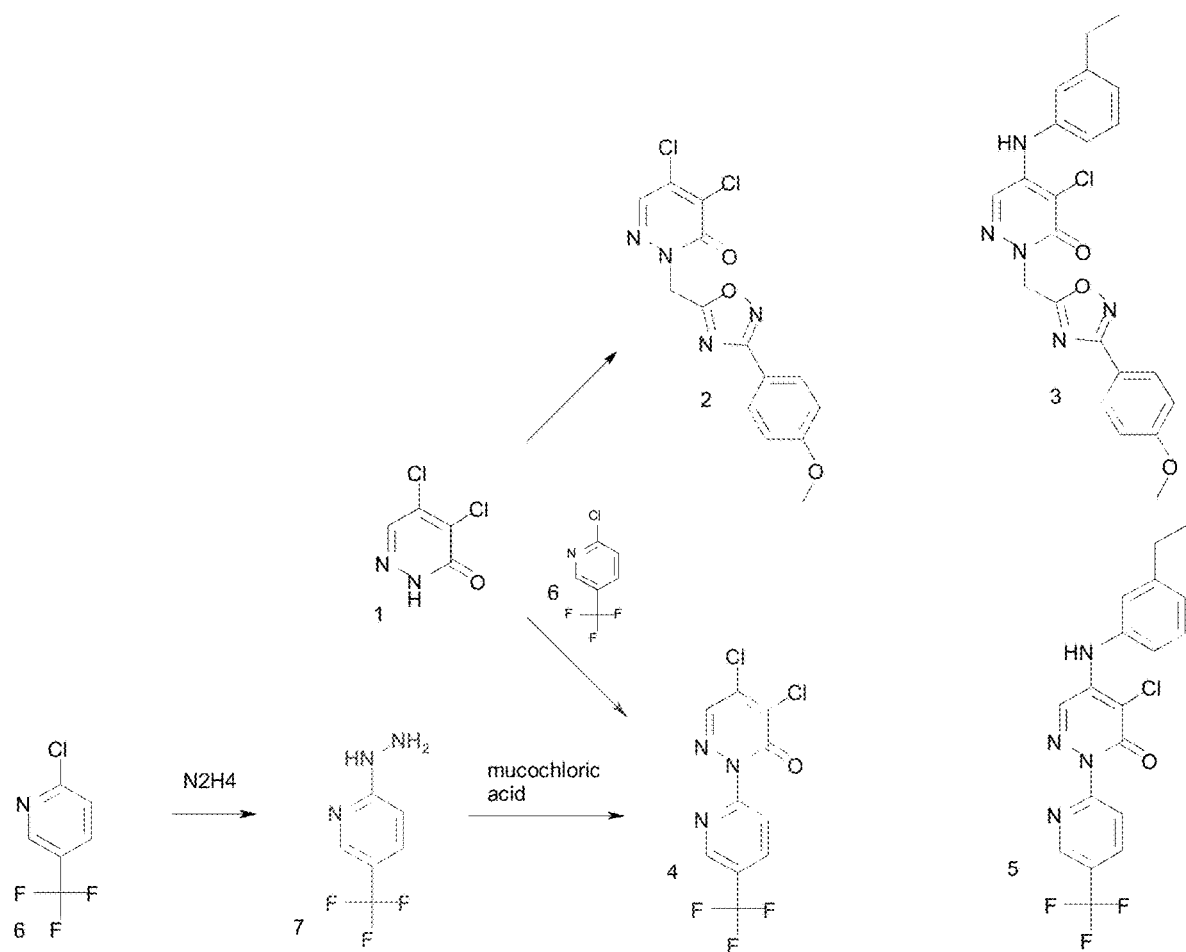
FIGS. 57 and 58 show synthesis of various compounds discussed herein.
Figure 58:
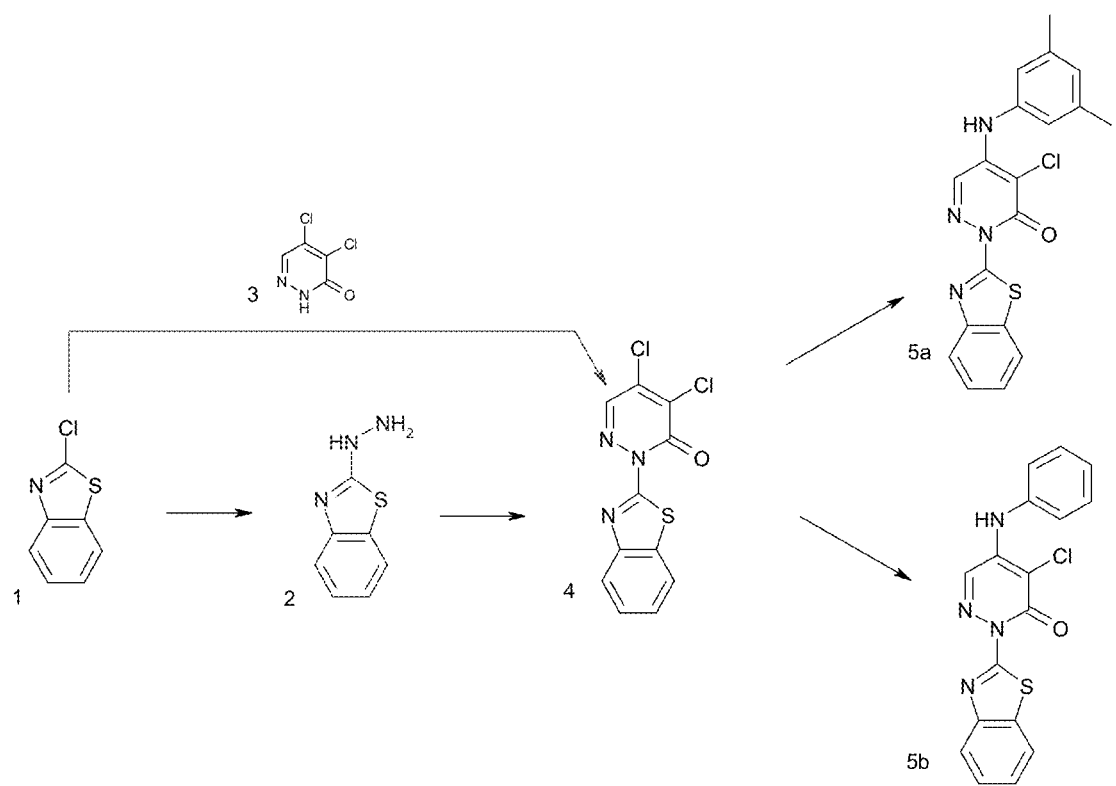

Compound Z143
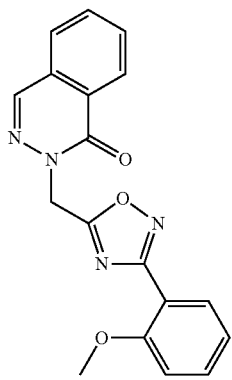
Compound Z144
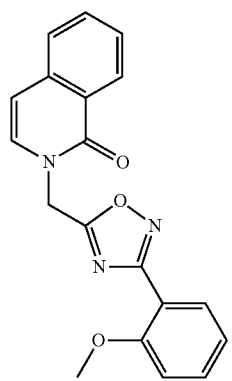
Compound Z145
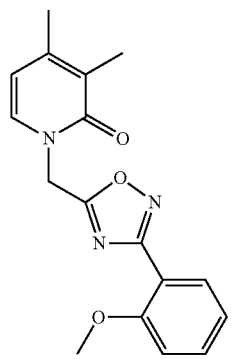
Compound Z146
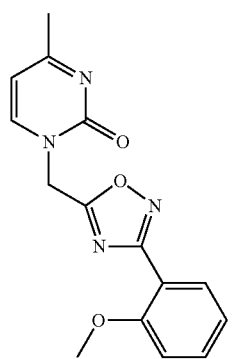
Compound Z147
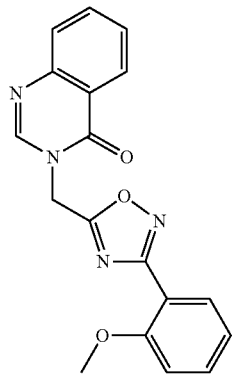
Compound Z148
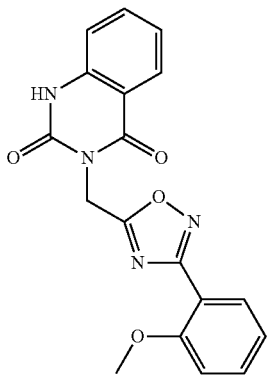
Compound Z149
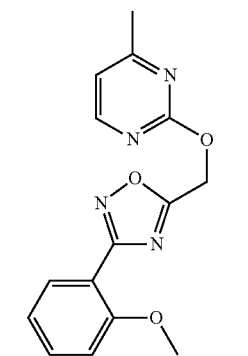
FIGS. 57 and 58 show syntheses of exemplary compositions found to be useful.
Table 27 shows the activity of various compounds discussed herein.
TABLE 27
| ID | Firefly, cmpd/DMSO (mean) | *Renilla*, cmpd/DMSO (mean) |
|---|---|---|
| Z134 | 1.1 | 0.9 |
| Z135 | 1.0 | 1.0 |
| Z152 | 1.6 | 1.0 |
| Z153 | 2.0 | 1.1 |
| Z150 | 1.0 | 0.9 |
| Z151 | 1.1 | 1.0 |
| Z149 | 1.5 | 1.0 |
| Z139 | 1.5 | 1.1 |
| Z140 | 1.2 | 1.0 |
| Z141 | 1.8 | 0.9 |
| Z142 | 1.1 | 0.9 |

TABLE 27-continued

| ID | Firefly, cmpd/DMSO (mean) | Renilla, cmpd/DMSO (mean) |
|---|---|---|
| Z97 | 2.1 | 1.0 |
| Z113 | 1.0 | 0.9 |

The present technology is directed to a composition according to any of the compounds described herein, substantially free of impurities. As used herein, the term "substantially free of impurities" means that the compound contains no significant amount of extraneous matter, including starting materials, residual solvents, or any other impurities that may result from the preparation or isolation of the compounds herein. In various embodiments, at least about 95%, at least about 97% or at least about 98% by weight of a compound herein is present in a dosage form herein.

Although the present technology has been described in relation to particular embodiments thereof, these embodiments and examples are merely exemplary and not intended to be limiting. Many other variations and modifications and other uses will become apparent to those skilled in the art. The present technology should, therefore, not be limited by the specific disclosure herein, and can be embodied in other forms not explicitly described here, without departing from the spirit thereof

We claim:

1. A pharmaceutical composition comprising a pharmaceutical compound in solid form, or a pharmaceutically acceptable salt thereof, together with a pharmaceutically acceptable excipient, diluent, or carrier, wherein the pharmaceutical compound has a structure of Formula (II),

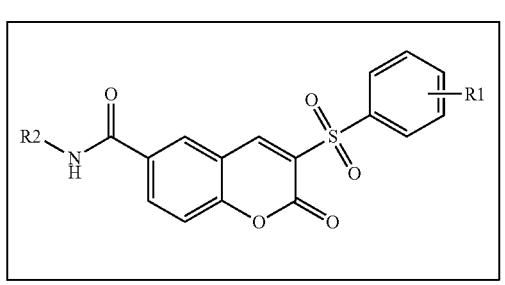

(II)

wherein R2 is a halogen, an alkyl group, a substituted alkyl group, a cyclic alkyl group, an aryl group, a substituted aryl group, a heterocyclic group, an ester, an aldehyde, a ketone, a carboxylic acid, an amide, an amine, an ether, or a nitrile, and R1 is H, a halogen, an alkyl group, a substituted alkyl group, a cyclic alkyl group, an aryl group, a substituted aryl group, a heterocyclic group, an ester, an aldehyde, a ketone, a carboxylic acid, an amide, an amine, an ether, or a nitrile.

2. The pharmaceutical composition of claim 1, wherein the pharmaceutical compound having a structure of Formula (II) is selected from the group consisting of:

Compound C134 wherein R1 is 4-Me, R2 is 2,-3-di-MeC6H3,
Compound C161 wherein R1 is H, R2 is 4-Me-C6H4,
Compound C164 wherein R1 is H, R2 is 2,-4-di-MeC6H3,
Compound C180 wherein R1 is 4-Cl, R2 is 4-MeOC6H4,
Compound C111 wherein R1 is H, R2 is PhCH2CH2,
Compound C126 wherein R1 is 4-CH3, R2 is 3-MeOC6H4,
Compound C127 wherein R1 is 4-F, R2 is 3-MeOC6H4, and
Compound C172 wherein R1 is 4-F, R2 is 3-MeC6H4.

3. The pharmaceutical composition of claim 1 in an oral dosage form.

* * * * *